United States Patent
Sikes Johnson et al.

(10) Patent No.: US 11,740,236 B2
(45) Date of Patent: Aug. 29, 2023

(54) PROTEIN FOR RAPID, EFFICIENT CAPTURE OF ANTIGENS

(71) Applicant: Massachusetts Institute of Technology, Cambridge, MA (US)

(72) Inventors: Hadley Sikes Johnson, Arlington, MA (US); Eric Alexander Miller, Cambridge, MA (US); Ki-Joo Sung, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 493 days.

(21) Appl. No.: 16/158,506

(22) Filed: Oct. 12, 2018

(65) Prior Publication Data
US 2019/0113512 A1    Apr. 18, 2019

Related U.S. Application Data

(60) Provisional application No. 62/572,392, filed on Oct. 13, 2017.

(51) Int. Cl.
| | |
|---|---|
| *G01N 33/566* | (2006.01) |
| *C07K 14/33* | (2006.01) |
| *G01N 33/569* | (2006.01) |
| *C07K 14/195* | (2006.01) |
| *C07K 16/06* | (2006.01) |
| *C07K 16/28* | (2006.01) |

(52) U.S. Cl.
CPC ......... *G01N 33/566* (2013.01); *C07K 14/195* (2013.01); *C07K 14/33* (2013.01); *C07K 16/065* (2013.01); *C07K 16/28* (2013.01); *G01N 33/56911* (2013.01); *C07K 2319/20* (2013.01); *C07K 2319/24* (2013.01); *C07K 2319/60* (2013.01); *G01N 2400/26* (2013.01)

(58) Field of Classification Search
CPC .......... G01N 33/566; G01N 33/56911; G01N 2400/26; C07K 14/195; C07K 14/33; C07K 16/065; C07K 16/28
See application file for complete search history.

(56) References Cited

U.S. PATENT DOCUMENTS

| | | | | |
|---|---|---|---|---|
| 5,856,201 A | * | 1/1999 | Shoseyov | C07K 16/065 |
| | | | | 436/503 |
| 2005/0118729 A1 | * | 6/2005 | Morag | G01N 33/6842 |
| | | | | 436/518 |
| 2017/0252417 A1 | * | 9/2017 | Irvine | A61K 39/0011 |

FOREIGN PATENT DOCUMENTS

| | | |
|---|---|---|
| CN | 102392000 A | 3/2012 |
| WO | 2008/141436 | 11/2008 |

OTHER PUBLICATIONS

Hirabayashi et al. J. Biol. Chem. 266: 23648-23653, 1991.*
Miller et al. "Activity-based assessment of an engineered hyperthermophilic protein as a capture agent in paper-based diagnostic tests" Supporting Information, Jun. 29, 2016, Molecular Systems Design & Engineering, vol. 1 No. 4, p. 377-381. (Year: 2016).*

(Continued)

*Primary Examiner* — Gary B Nickol
*Assistant Examiner* — Amelia Nicole Dickens
(74) *Attorney, Agent, or Firm* — Wolf, Greenfield & Sacks, P.C.

(57) ABSTRACT

The present disclosure relates to proteins comprising a target-binding domain for detection of a target of interest, methods, compositions and kits thereof.

7 Claims, 108 Drawing Sheets
Specification includes a Sequence Listing.

(56) References Cited

OTHER PUBLICATIONS

Kozak, "Initiation of translation in prokaryotes and eukaryotes", 1999, Gene, vol. 234, p. 187-208. (Year: 1999).*
Ryu et al. "Translation initiation mediated by nuclear cap-binding protein complex", Apr. 30, 2017, BMB Reports, vol. 50 No. 4, p. 186-193. (Year: 2017).*
Kosugi et al. "Hydrophilic Domains of Scaffolding Protein CbpA Promote Glycosyl Hydrolase Activity and Localization of Cellulosomes to the Cell Surface of Clostridium cellulovorans", Oct. 2004, Journal of Bacteriology, vol. 186 No. 16, p. 6351-6359. (Year: 2004).*
Sabathe et al. "Characterization of the CipA scaffolding protein and in vivo production of a minicellulosome in Clostridium acetobutylicum", Feb. 2003, Journal of Bacteriology, vol. 185 No. 3, p. 1092-1096. (Year: 2003).*
Zhao et al. "Hyperthermostable binding molecules on phage: Assay components for point-of-care diagnostics for active tuberculosis infection", Jan. 3, 2017, Analytical Biochemistry, vol. 521, p. 59-71. (Year: 2017).*
Almieda et al. "A biomolecular recognition approach for the functionalization of cellulose with gold nanoparticles", Apr. 17, 2017, Journal of Molecular Recognition, vol. 30, p. 1-7. (Year: 2017).*
Miller et al. "Activity-based assessment of an engineered hyperthermophilic protein as a capture agent in paper-based diagnostic tests" Supporting Information, Jun. 29, 2016, Molecular Systems Design & Engineering, vol. 1 No. 4, p. 377-381. Made of record in PTO-892 mailed Sep. 26, 2022. (Year: 2016).*
International Search Report and Written Opinion for PCT/US2018/055582, dated Mar. 14, 2019.
International Preliminary Report on Patentability for PCT/US2018/055582, dated Apr. 23, 2020.
Invitation to Pay Additional Fees for PCT/US2018/055582 dated Jan. 15, 2019.
Miller et al., Activity-based assessment of an engineered hyperthermophilic protein as a capture agent in paper-based diagnostic tests. Mol Syst Des Eng. Dec. 1, 2016;1(4):377-381. doi: 10.1039/C6ME00032K. Epub Jun. 29, 2016. PMID: 28451464; PMCID: PMC5403157.
Miller et al., Paper-based diagnostics in the antigen-depletion regime: High-density immobilization of rcSso7d-cellulose-binding domain fusion proteins for efficient target capture. Biosens Bioelectron. Apr. 15, 2018; 102:456-463. doi: 10.1016/j.bios.2017.11.050. Epub Nov. 20, 2017. PMID: 29182928; PMCID: PMC5983361.
Traxlmayr et al., Strong Enrichment of Aromatic Residues in Binding Sites from a Charge-neutralized Hyperthermostable Sso7d Scaffold Library. J Biol Chem. Oct. 21, 2016;291(43):22496-22508. doi: 10.1074/jbc.M116.741314. Epub Aug. 30, 2016. PMID: 27582495.
Ackerman et al., Highly avid magnetic bead capture: an efficient selection method for de novo protein engineering utilizing yeast surface display. Biotechnol Prog. May-Jun. 2009;25(3):774-83. doi: 10.1002/btpr.174. PMID: 19363813; PMCID: PMC2837102.
Care et al., Solid-binding peptides for immobilisation of thermostable enzymes to hydrolyse biomass polysaccharides. Biotechnol Biofuels. Feb. 2, 2017;10:29. doi: 10.1186/s13068-017-0715-2. PMID: 28184244; PMCID: PMC5289021.
Dai et al., A colorimetric paper sensor for lactate assay using a cellulose-binding recombinant enzyme. Sensors Act B Chem. 2017;238:138-144.
Holstein et al., Immobilizing affinity proteins to nitrocellulose: a toolbox for paper-based assay developers. Anal Bioanal Chem. Feb. 2016;408(5): 1335-46. doi: 10.1007/s00216-015-9052-0. Epub Oct. 1, 2015. PMID: 26427504.
Hussack et al., Multivalent anchoring and oriented display of single-domain antibodies on cellulose. Sensors (Basel). 2009;9(7):5351-67. doi: 10.3390/s90705351. Epub Jul. 7, 2009.
Hyre et al., Cooperative hydrogen bond interactions in the streptavidin-biotin system. Protein Sci. Mar. 2006;15(3):459-67. doi: 10.1110/ps.051970306. Epub Feb. 1, 2006. PMID: 16452627.
Kelley et al., Advancing the speed, sensitivity and accuracy of biomolecular detection using multi-length-scale engineering. Nat Nanotechnol. Dec. 2014;9(12):969-80. doi: 10.1038/nnano.2014.261. PMID: 25466541; PMCID: PMC4472305.
McBee, The characteristics of Clostridium thermocellum. J Bacteriol. Apr. 1954;67(4):505-6. doi: 10.1128/jb.67.4.505-506.1954. PMID: 13152068; PMCID: PMC357262.
Napolitano et al., Identification of *Mycobacterium tuberculosis* ornithine carboamyltransferase in urine as a possible molecular marker of active pulmonary tuberculosis. Clin Vaccine Immunol. Apr. 2008;15(4):638-43. doi: 10.1128/CVI.00010-08. Epub Feb. 27, 2008. PMID: 18305107.
Ricci et al., Using Nature's "Tricks" To Rationally Tune the Binding Properties of Biomolecular Receptors. Acc Chem Res. Sep. 20, 2016;49(9): 1884-92. doi: 10.1021/acs.accounts.6b00276. Epub Aug. 26, 2016. PMID: 27564548; PMCID: PMC5660318.
Seker et al., Material binding peptides for nanotechnology. Molecules. Feb. 9, 2011;16(2):1426-51. doi: 10.3390/molecules16021426. PMID: 21307821; PMCID: PMC6259601.
Shen et al., Site-selective orientated immobilization of antibodies and conjugates for immunodiagnostics development. Methods. Mar. 1, 2017;116:95-111. doi: 10.1016Zj.ymeth.2016.i1.010. Epub Nov. 19, 2016. PMID: 27876681; PMCID: PMC5374010.
Yaniv et al., Structure of a family 3a carbohydrate-binding module from the cellulosomal scaffoldin CipA of Clostridium thermocellum with flanking linkers: implications for cellulosome structure. Acta Crystallogr Sect F Struct Biol Cryst Commun. Jul. 2013;69(Pt 7):733-7. doi: 10.1107/S174430911301614X. Epub Jun. 27, 2013. PMID: 23832198; PMCID: PMC3702315.
Yu et al., Biofunctional paper via the covalent modification of cellulose. Langmuir. Jul. 31, 2012;28(30): 11265-73. doi: 10.1021/la301661x. Epub Jul. 20, 2012. PMID: 22708701; PMCID.
Zhu et al., Cellulose paper sensors modified with zwitterionic poly(carboxybetaine) for sensing and detection in complex media. Anal Chem. Mar. 18, 2014;86(6):2871-5. doi: 10.1021/ac500467c. Epub Mar. 5, 2014. PMID: 24571794.

* cited by examiner

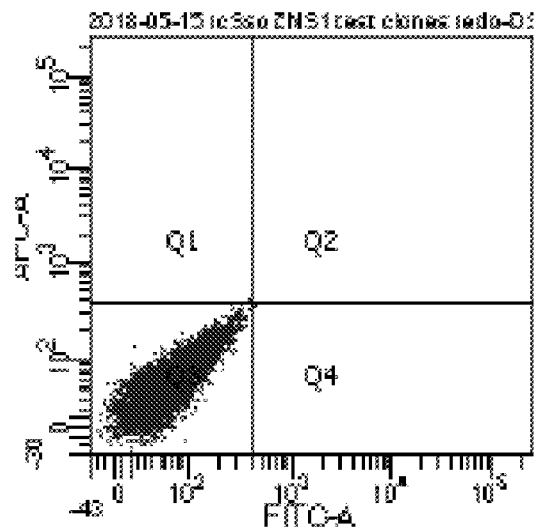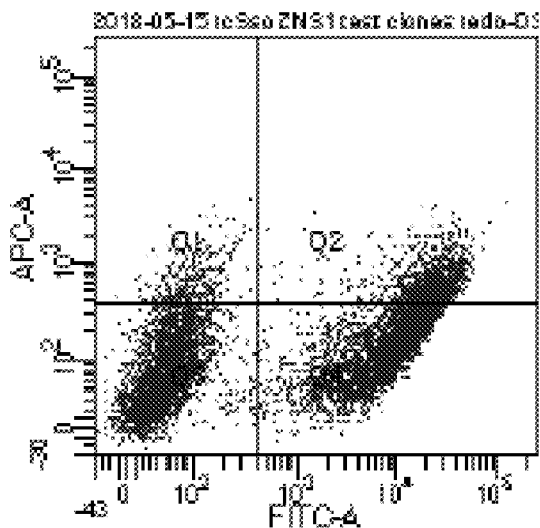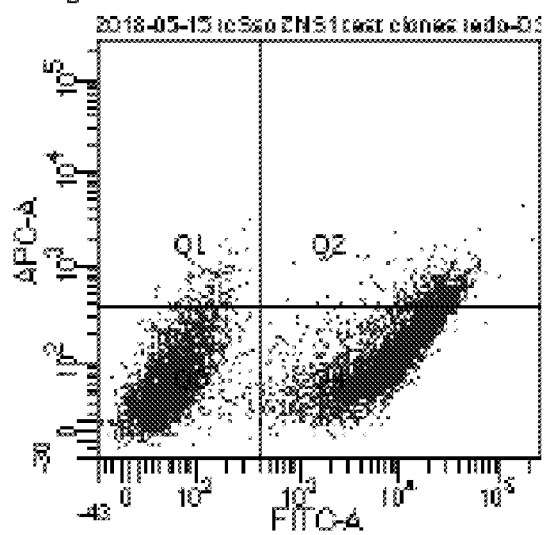
FIG. 20

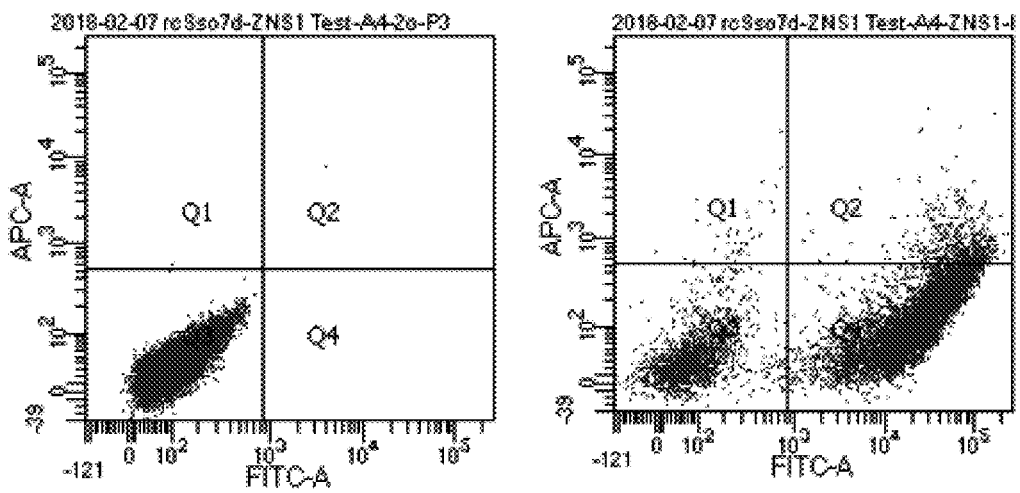
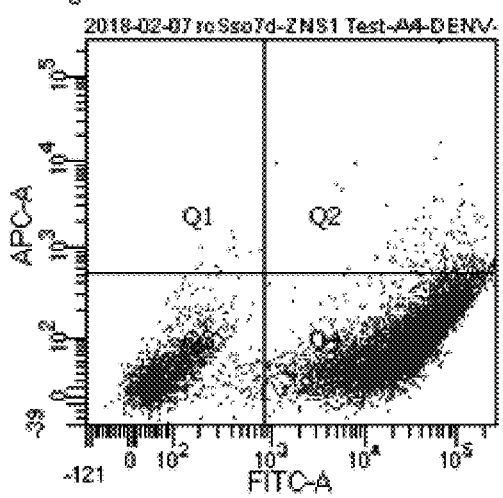
FIG. 21 rcSso7d.NS1.3
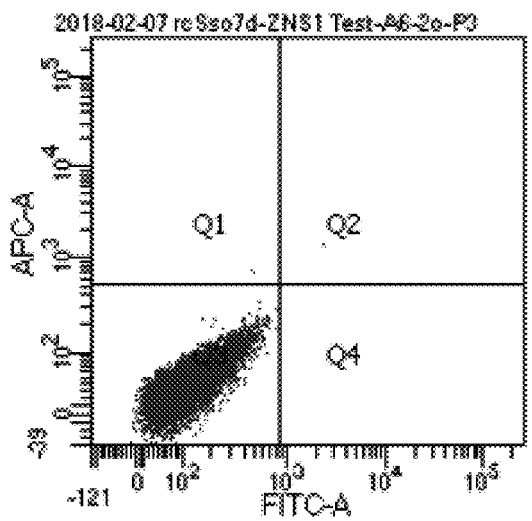
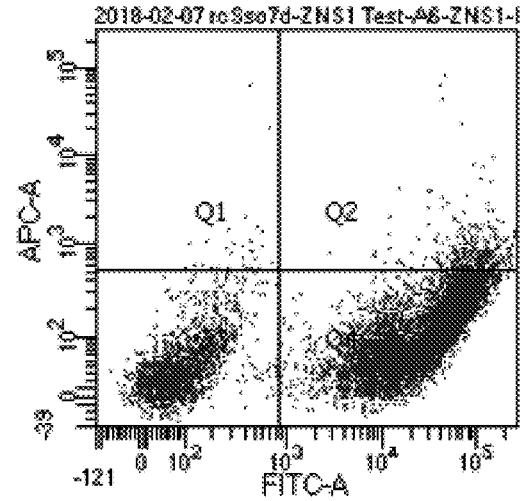
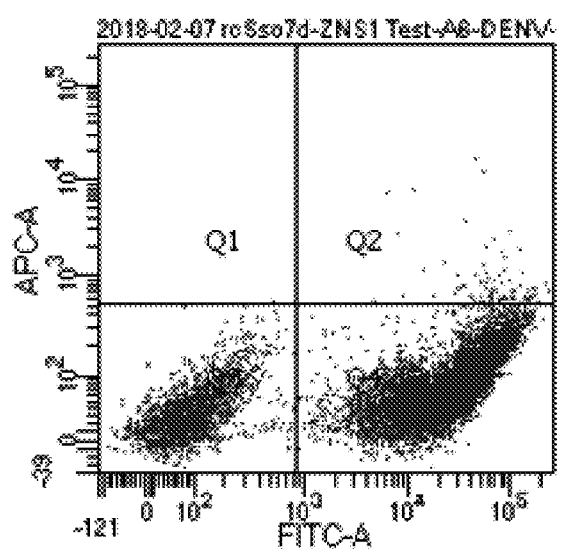
FIG. 22 rcSso7d.NS1.4

Condition: Secondary control
Antigen (Ag): N/A
Ag pre-treatment: N/A
Detection reagent: Mouse anti-His/ goat anti-mouse AF647

Condition: Baseline binding
Antigen (Ag): 200 nM ZIKV NS1
Ag pre-treatment: 0.1% BSA, 4°C
Detection reagent: Mouse anti-His/ goat anti-mouse AF647

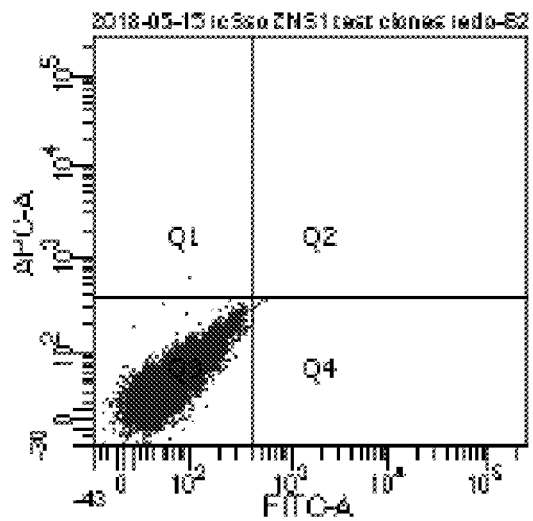
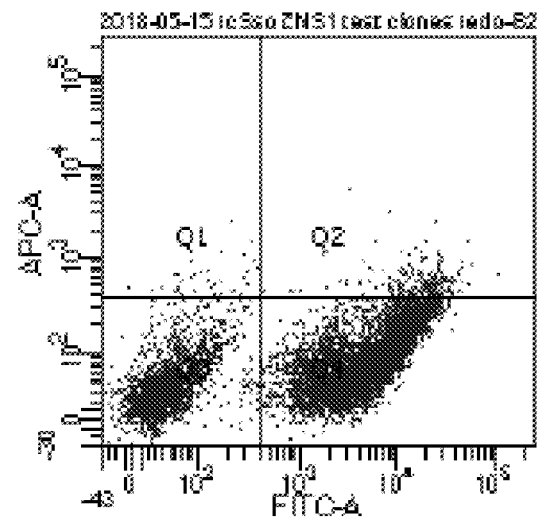

Condition: Condition: Baseline binding
Antigen (Ag): 200 nM DENV2 NS1
Ag pre-treatment: 0.1% BSA, 4°C
Detection reagent: Mouse anti-His/ goat anti-mouse AF647

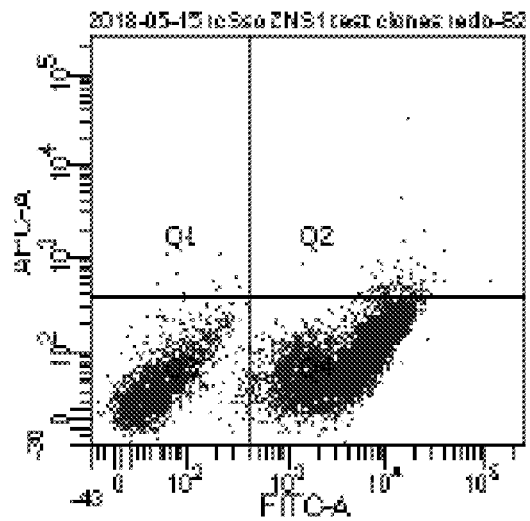

FIG. 23 rcSso7d.NS1.5

Condition: Secondary control
Antigen (Ag): N/A
Ag pre-treatment: N/A
Detection reagent: Mouse anti-His/
goat anti-mouse AF647

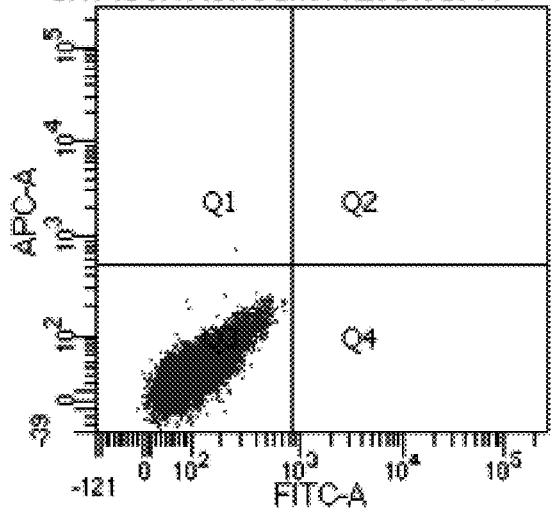

Condition: Baseline binding
Antigen (Ag): 200 nM ZIKV NS1
Ag pre-treatment: 0.1% BSA, 4°C
Detection reagent: Mouse anti-His/
goat anti-mouse AF647

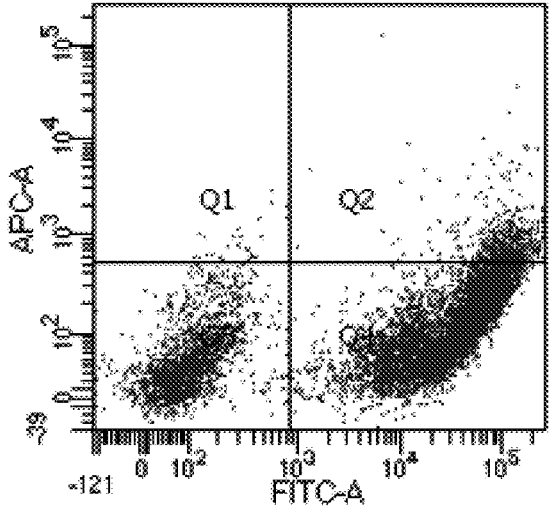

Condition: Condition: Baseline binding
Antigen (Ag): 200 nM DENV2 NS1
Ag pre-treatment: 0.1% BSA, 4°C
Detection reagent: Mouse anti-His/
goat anti-mouse AF647

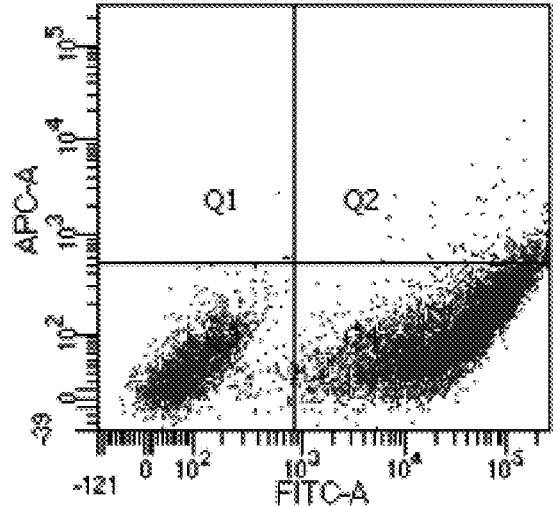

FIG. 24 rcSso7d.NS1.6

Condition: Secondary control
Antigen (Ag): N/A
Ag pre-treatment: N/A
Detection reagent: Mouse anti-His/
goat anti-mouse AF647

Condition: Baseline binding
Antigen (Ag): 200 nM ZIKV NS1
Ag pre-treatment: 0.1% BSA, 4°C
Detection reagent: Mouse anti-His/
goat anti-mouse AF647

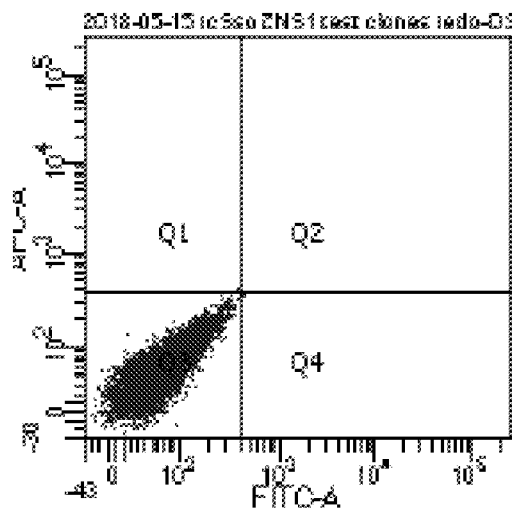
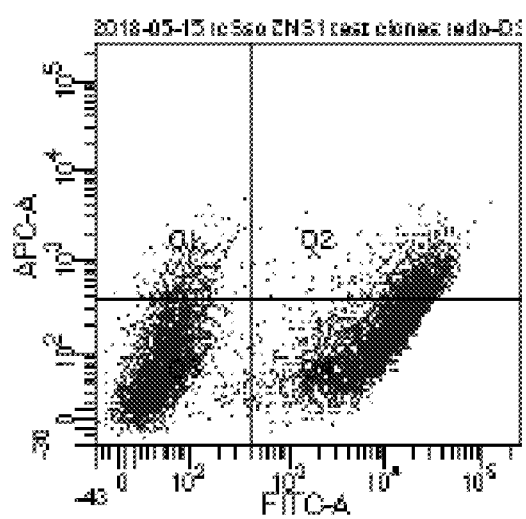

Condition: Condition: Baseline binding
Antigen (Ag): 200 nM DENV2 NS1
Ag pre-treatment: 0.1% BSA, 4°C
Detection reagent: Mouse anti-His/
goat anti-mouse AF647

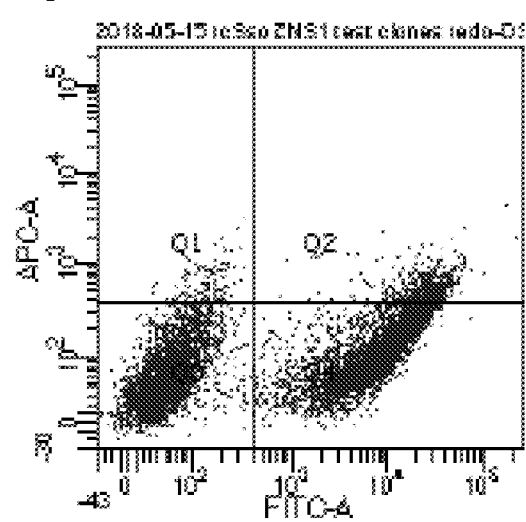

FIG. 25 rcSso7d.IL6.2
Condition: Three-component negative control (antigen absent)
Antigen (Ag): N/A
Ag pre-treatment: N/A
Detection reagent: Mouse anti-His/ goat anti-mouse AF647
Condition: Baseline binding
Antigen (Ag): 0.25 nM human IL-6
Ag pre-treatment: 0.1% BSA, 4°C
Detection reagent: Mouse anti-His/ goat anti-mouse AF647
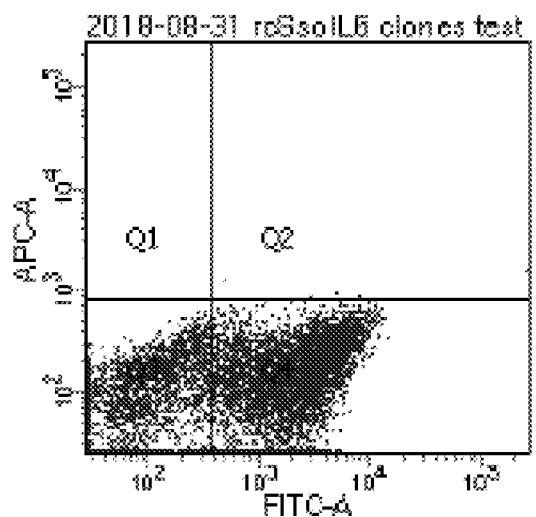 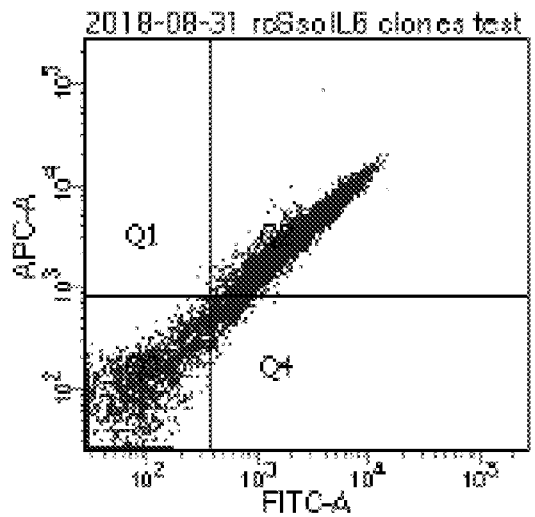
FIG. 27 rcSso7d.IL6.6
Condition: Three-component negative control (antigen absent)
Antigen (Ag): N/A
Ag pre-treatment: N/A
Detection reagent: Mouse anti-His/ goat anti-mouse AF647
Condition: Baseline binding
Antigen (Ag): 0.25 nM human IL-6
Ag pre-treatment: 0.1% BSA, 4°C
Detection reagent: Mouse anti-His/ goat anti-mouse AF647
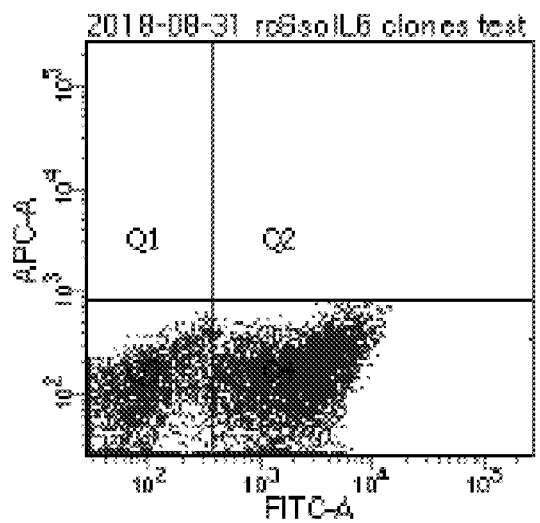 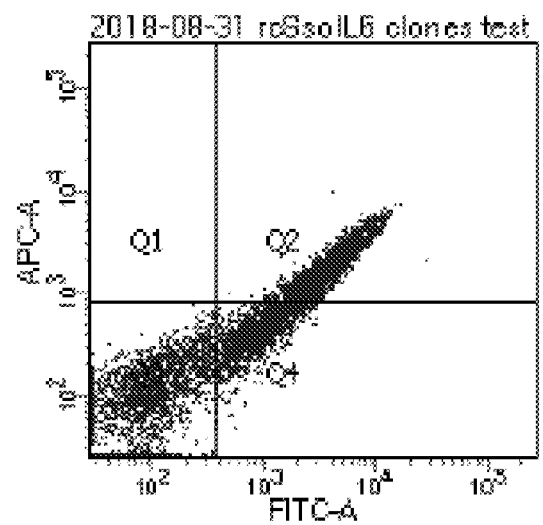
FIG. 31

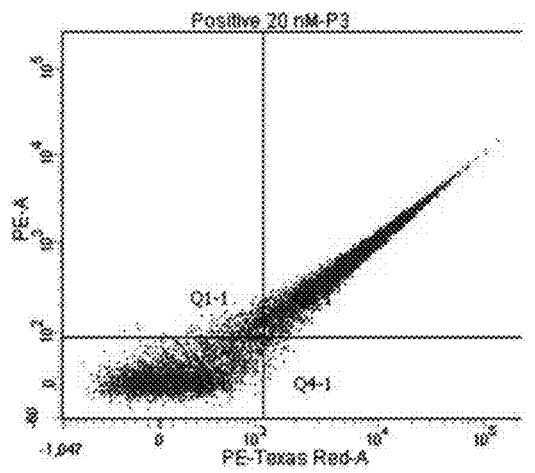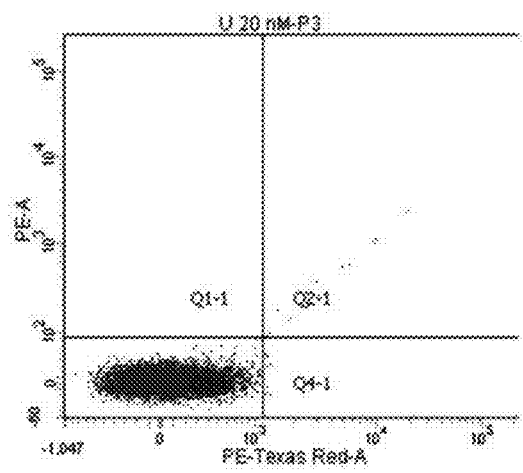
FIG. 39

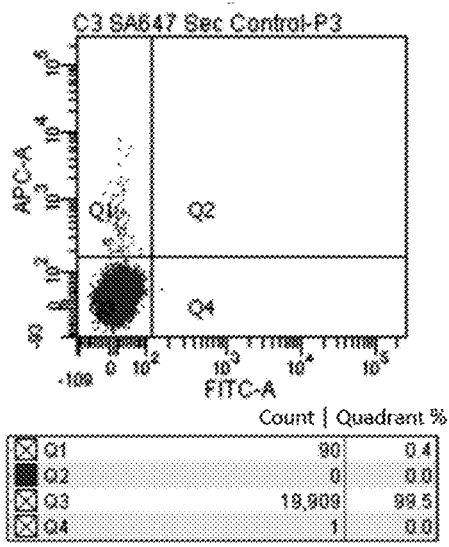
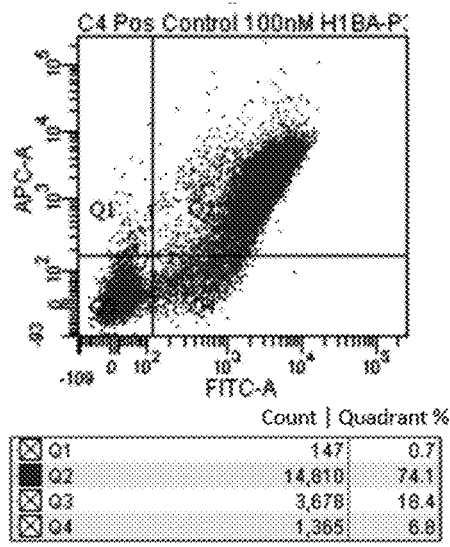
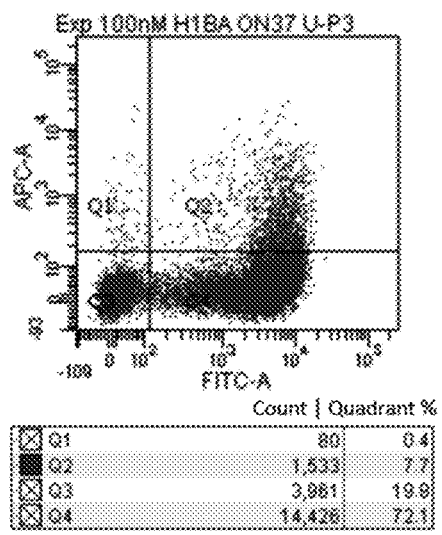
FIG. 40A rcSso7d.H1BA.3
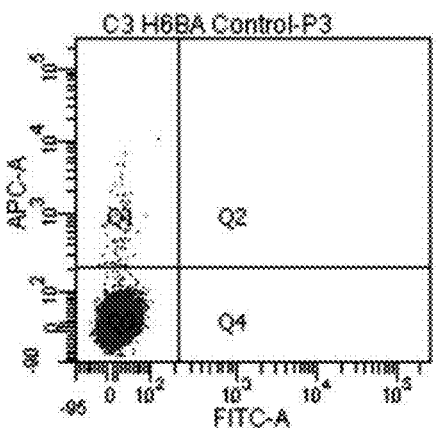
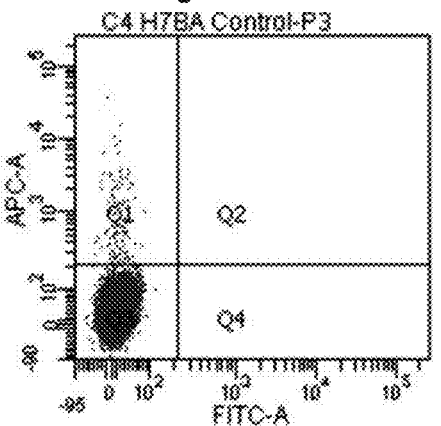
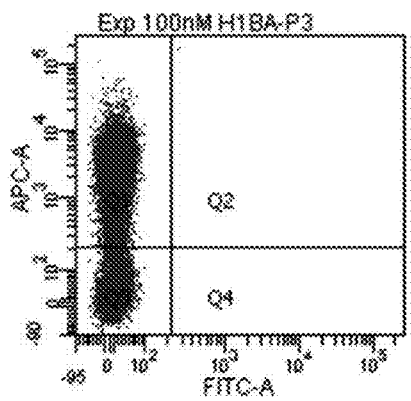
FIG. 40C rcSso7d.H1BA.4
Condition: Secondary control
Antigen (Ag): N/A
Ag pre-treatment: 0.1% BSA, 4°C
Pre-treatment time: N/A
Detection reagent: SA AF647
Condition: Baseline binding
Antigen (Ag): 100 nM H1bx
Ag pre-treatment: 0.1% BSA, 4°C
Pre-treatment time: N/A
Detection reagent: SA AF647
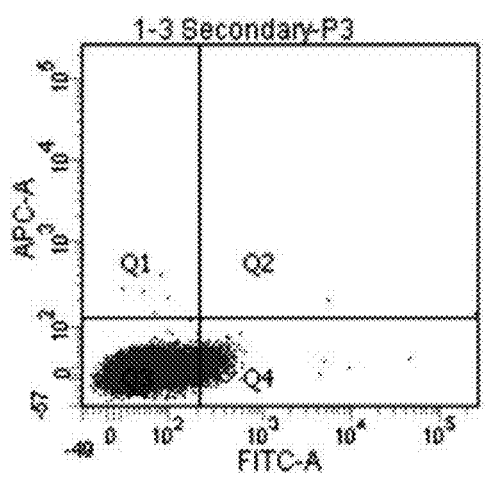
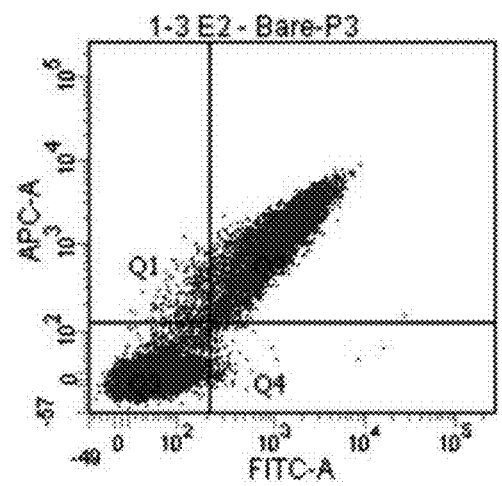
| | Count | Quadrant % |
|---|---|---|
| Q1 | 5 | 0.0 |
| Q2 | 2 | 0.0 |
| Q3 | 19,071 | 95.4 |
| Q4 | 922 | 4.6 |
| | Count | Quadrant % |
|---|---|---|
| Q1 | 355 | 1.8 |
| Q2 | 5,914 | 29.6 |
| Q3 | 13,562 | 67.8 |
| Q4 | 169 | 0.8 |
FIG. 41 rcSso7d.H1BA.5
Condition: Secondary control
Antigen (Ag): N/A
Ag pre-treatment: 0.1% BSA, 4°C
Pre-treatment time: N/A
Detection reagent: SA AF647
Condition: Baseline binding
Antigen (Ag): 100 nM H1BA
Ag pre-treatment: 0.1% BSA, 4°C
Pre-treatment time: N/A
Detection reagent: SA AF647
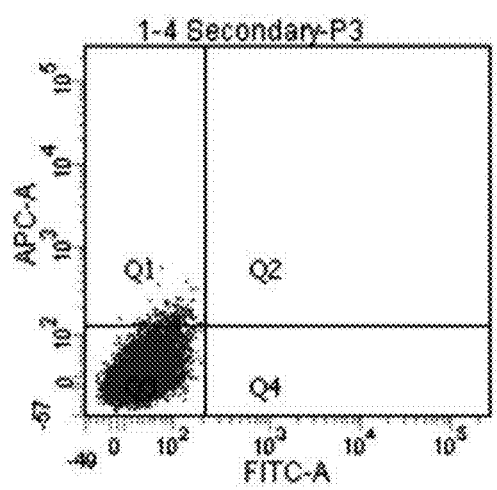
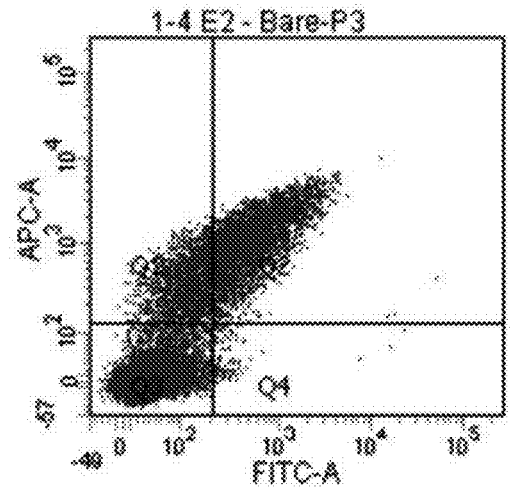
FIG. 42

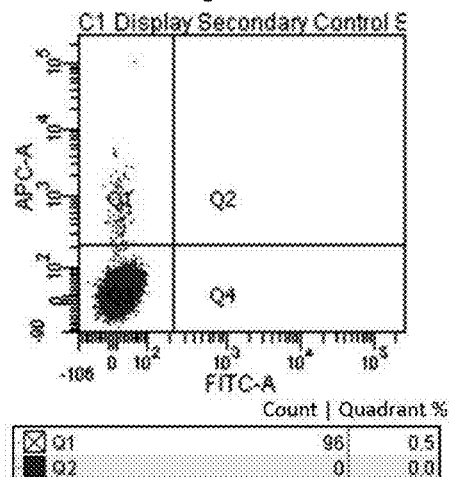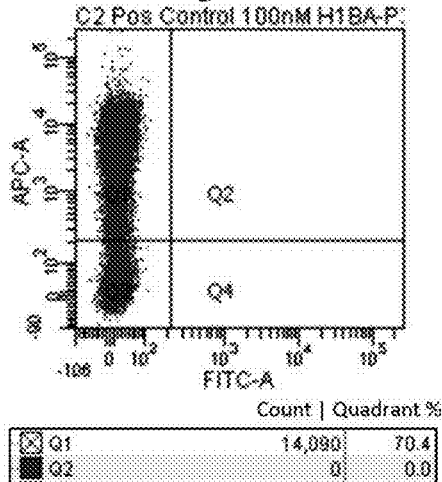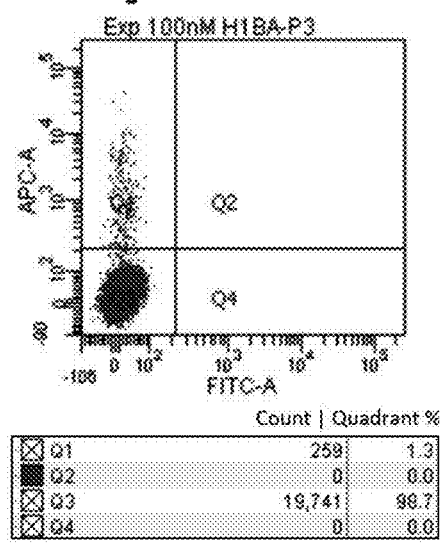
FIG. 43

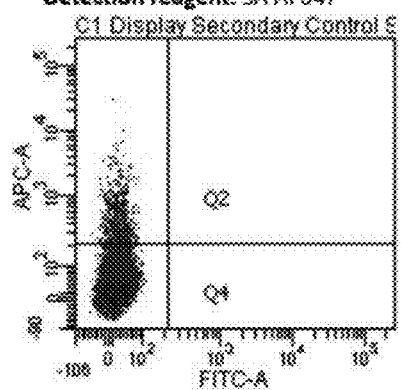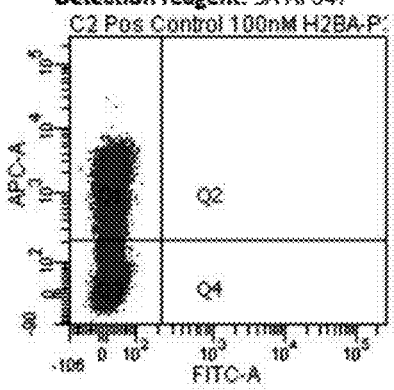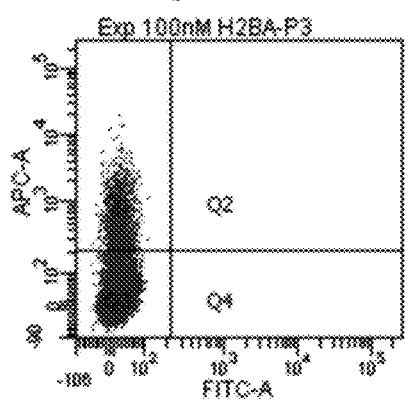
FIG. 45 rcSso7d.H4.1

Condition: Secondary control
Antigen (Ag): N/A
Ag pre-treatment: N/A
Pre-treatment time: N/A
Detection reagent: Mouse anti-His/ goat anti-mouse AF647

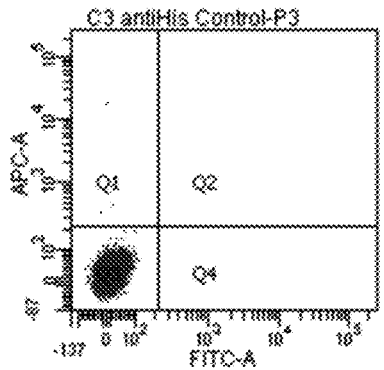

Condition: Baseline binding
Antigen (Ag): 100 nM H4
Ag pre-treatment: 0.1% BSA, 4°C
Pre-treatment time: N/A
Detection reagent: Mouse anti-His/ goat anti-mouse AF647

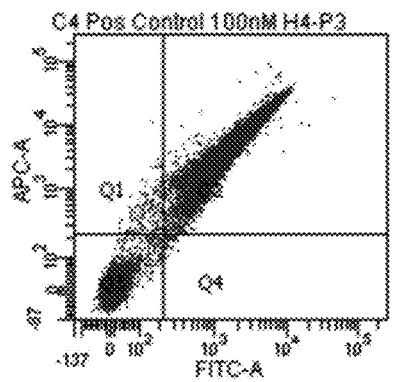

Condition: Condition: Overnight heat/ urine inactivation
Antigen (Ag): 100 nM H4
Ag pre-treatment: Urine, 37°C
Pre-treatment time: Overnight
Detection reagent: Mouse anti-His/ goat anti-mouse AF647

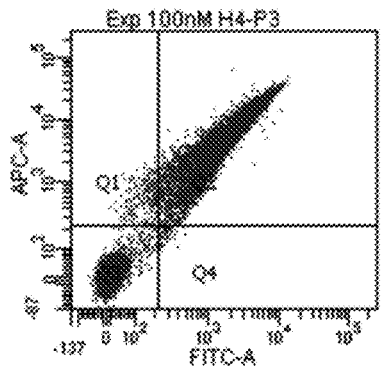

FIG. 47 rcSso7d.H4.2
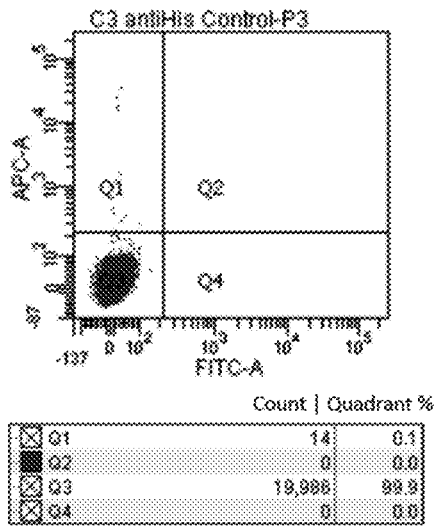
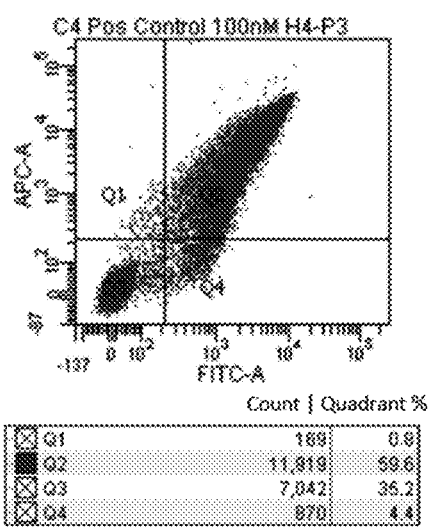
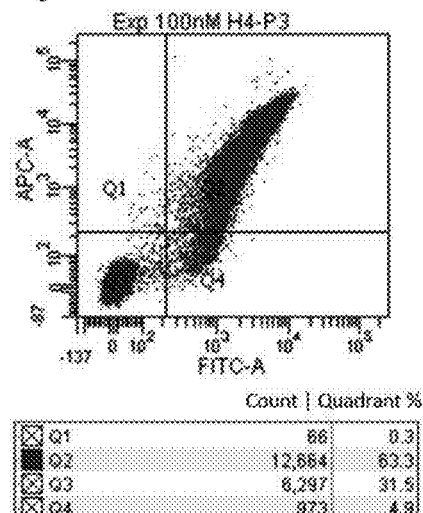
FIG. 48 rcSso7d.H4.3
Condition: Secondary control
Antigen (Ag): N/A
Ag pre-treatment: N/A
Pre-treatment time: N/A
Detection reagent: Mouse anti-His/ goat anti-mouse AF647
Condition: Baseline binding
Antigen (Ag): 100 nM H4
Ag pre-treatment: 0.1% BSA, 4°C
Pre-treatment time: N/A
Detection reagent: Mouse anti-His/ goat anti-mouse AF647
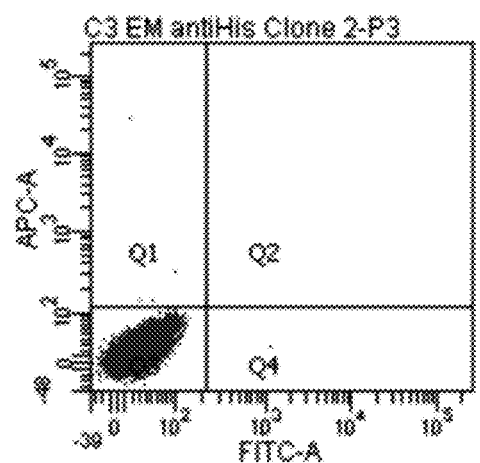
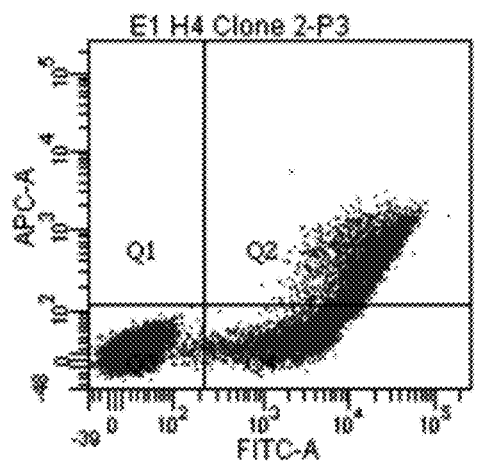
FIG. 49 rcSso7d.H4.4
Condition: Secondary control
Antigen (Ag): N/A
Ag pre-treatment: N/A
Pre-treatment time: N/A
Detection reagent: Mouse anti-His/ goat anti-mouse AF647
Condition: Baseline binding
Antigen (Ag): 100 nM H4
Ag pre-treatment: 0.1% BSA, 4°C
Pre-treatment time: N/A
Detection reagent: Mouse anti-His/ goat anti-mouse AF647
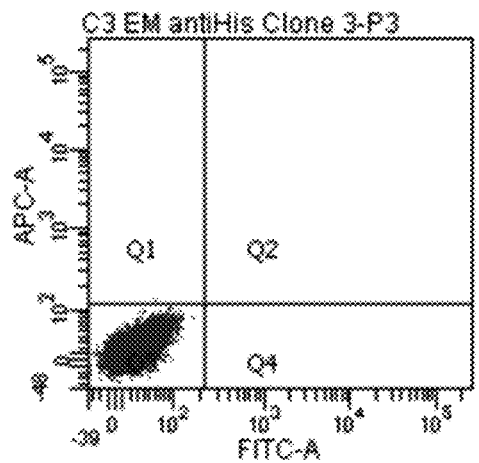
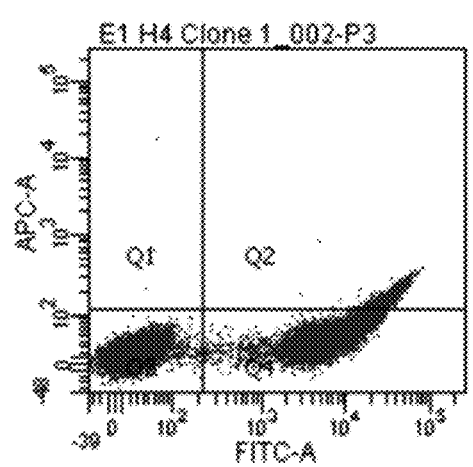
FIG. 50 rcSso7d.H4.5
Condition: Secondary control
Antigen (Ag): N/A
Ag pre-treatment: N/A
Pre-treatment time: N/A
Detection reagent: Mouse anti-His/ goat anti-mouse AF647
Condition: Baseline binding
Antigen (Ag): 100 nM H4
Ag pre-treatment: 0.1% BSA, 4°C
Pre-treatment time: N/A
Detection reagent: Mouse anti-His/ goat anti-mouse AF647
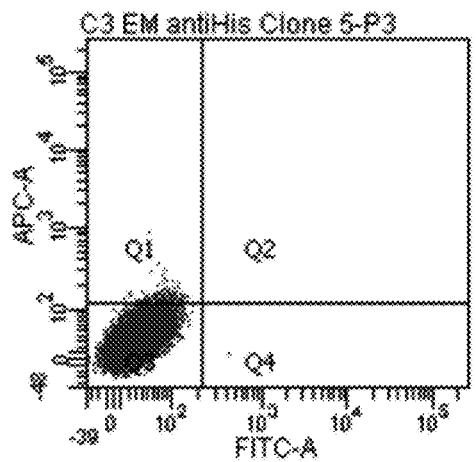
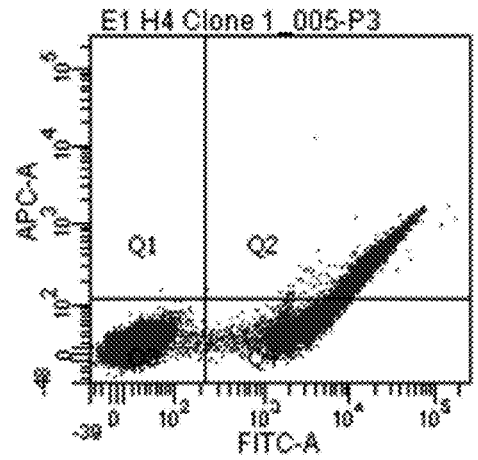
FIG. 51 rcSso7d.H4.6
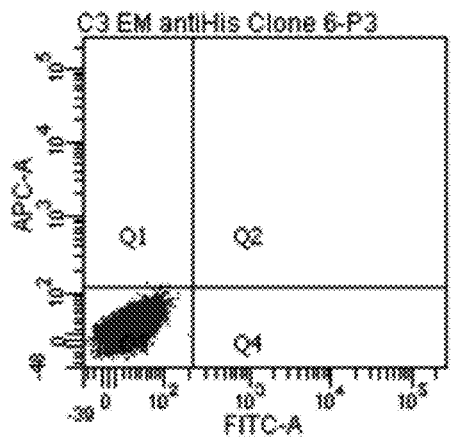
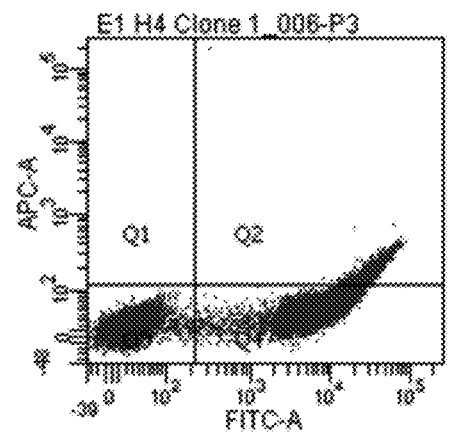
FIG. 52 rcSso7d.H4.7
Condition: Secondary control
Antigen (Ag): N/A
Ag pre-treatment: N/A
Pre-treatment time: N/A
Detection reagent: Mouse anti-His/ goat anti-mouse AF647
Condition: Baseline binding
Antigen (Ag): 100 nM H4
Ag pre-treatment: 0.1% BSA, 4°C
Pre-treatment time: N/A
Detection reagent: Mouse anti-His/ goat anti-mouse AF647
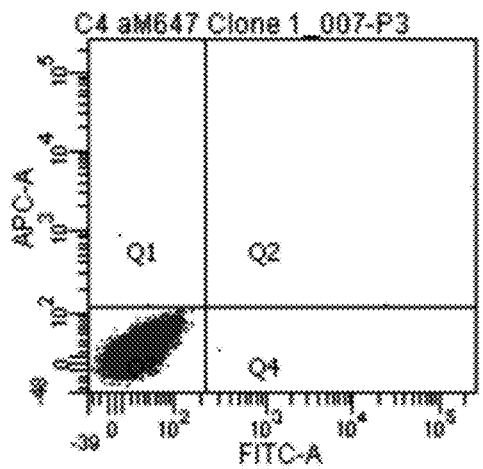
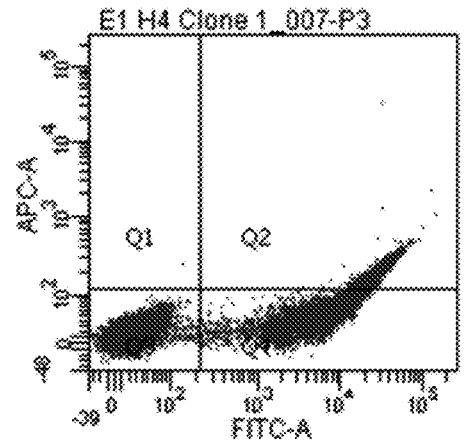
FIG. 53 rcSso7d.H4.8
Condition: Secondary control
Antigen (Ag): N/A
Ag pre-treatment: N/A
Pre-treatment time: N/A
Detection reagent: Mouse anti-His/ goat anti-mouse AF647
Condition: Baseline binding
Antigen (Ag): 100 nM H4
Ag pre-treatment: 0.1% BSA, 4°C
Pre-treatment time: N/A
Detection reagent: Mouse anti-His/ goat anti-mouse AF647
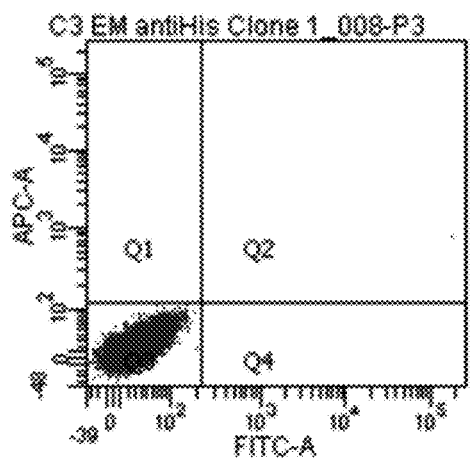
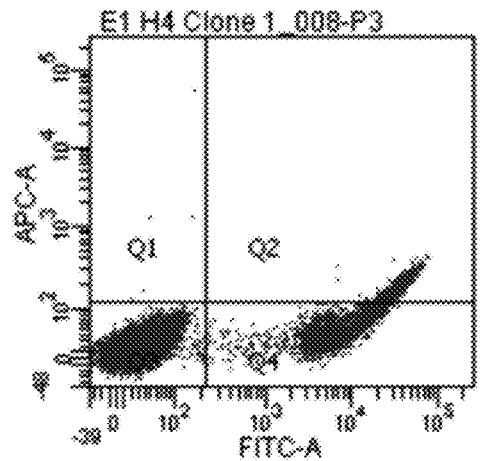
FIG. 54 rcSso7d.H4.9
Condition: Secondary control
Antigen (Ag): N/A
Ag pre-treatment: N/A
Pre-treatment time: N/A
Detection reagent: Mouse anti-His/ goat anti-mouse AF647
Condition: Baseline binding
Antigen (Ag): 100 nM H4
Ag pre-treatment: 0.1% BSA, 4°C
Pre-treatment time: N/A
Detection reagent: Mouse anti-His/ goat anti-mouse AF647
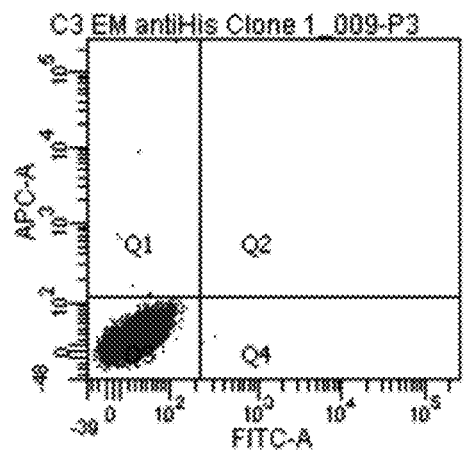
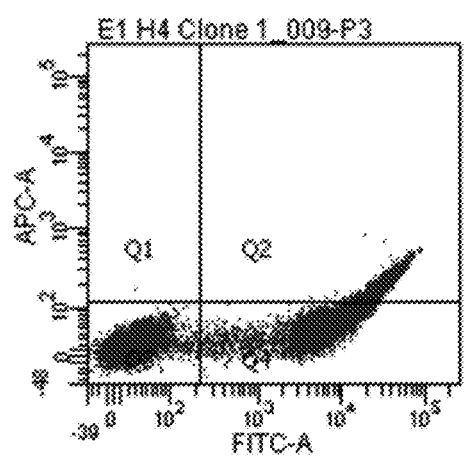
FIG. 55 rcSso7d.H4.2/H4/BA-MBP-rcSso7d.H4.1
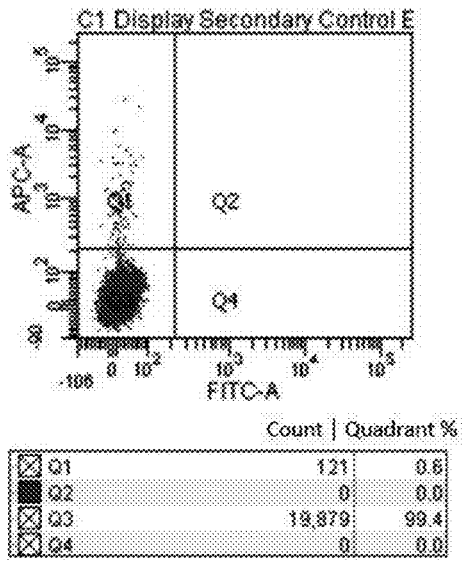
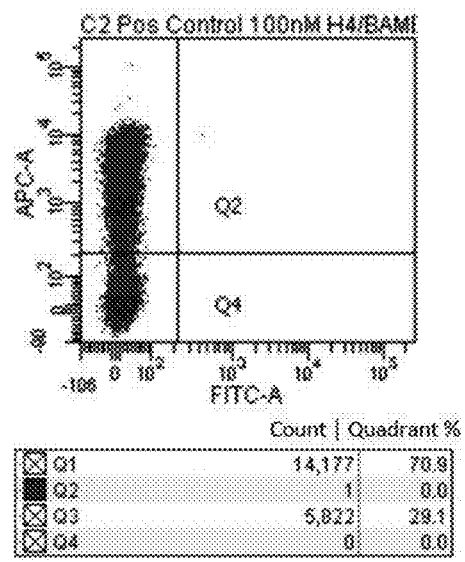
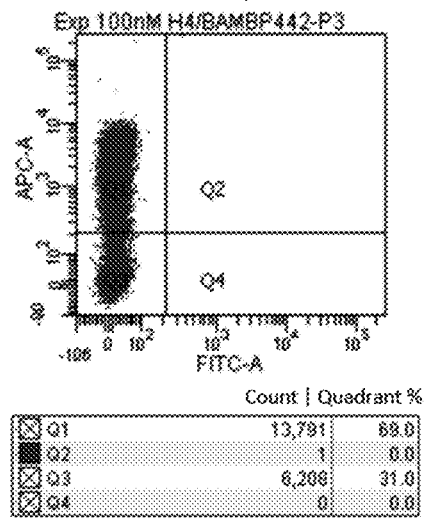
FIG. 56A rcSso7d.H4.2/H4/BA-MBP-rcSso7d.H4.1

Condition: Secondary control
Antigen (Ag): N/A
Ag pre-treatment: N/A
Pre-treatment time: N/A
Detection reagent: Avidin-purified BA-MBP-rcSso7d.H4.2/SA AF647

Condition: Baseline binding
Antigen (Ag): 100 nM H4
Ag pre-treatment: 0.1% BSA, 4°C
Pre-treatment time: N/A
Detection reagent: Avidin-purified BA-MBP-rcSso7d.H4.2/SA AF647

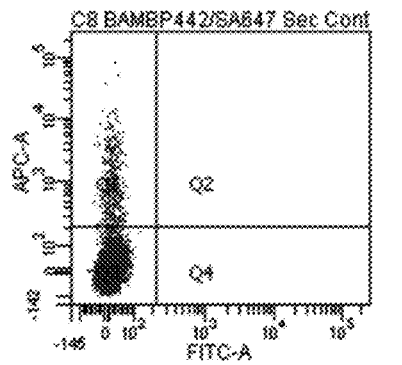
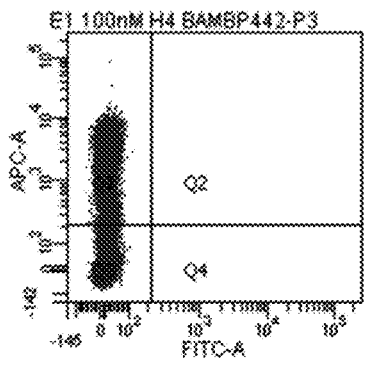

Condition: Condition: Weeklong heat/urine inactivation
Antigen (Ag): 100 nM H4
Ag pre-treatment: Urine, 37°C
Pre-treatment time: 1 week
Detection reagent: Avidin-purified BA-MBP-rcSso7d.H4.2/SA AF647

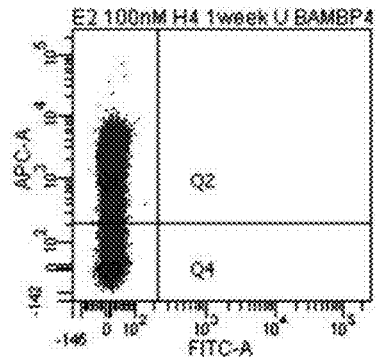

FIG. 56B

H6BA
38.1 kDa rcSso7d.H6BA.1

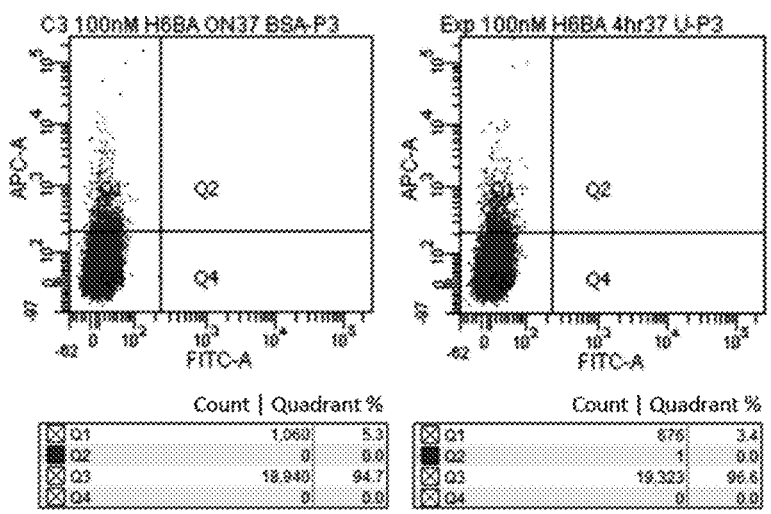
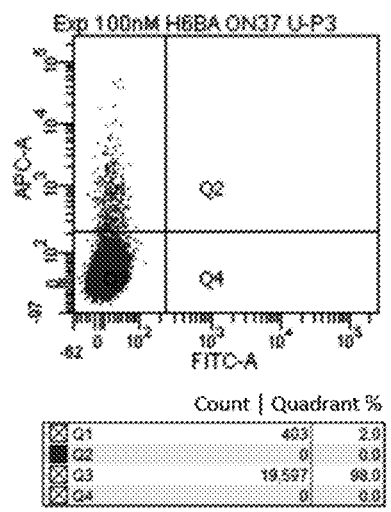
FIG. 58B

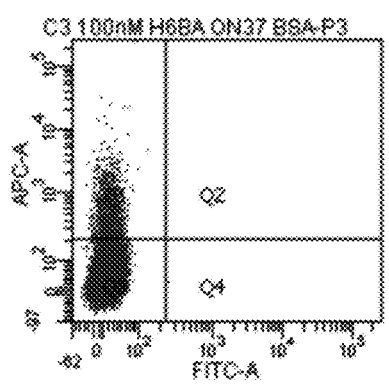
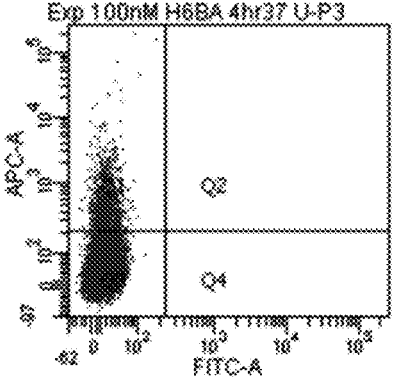
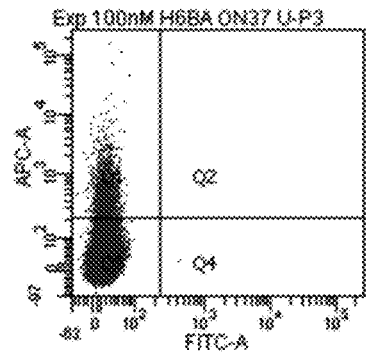
FIG. 59B

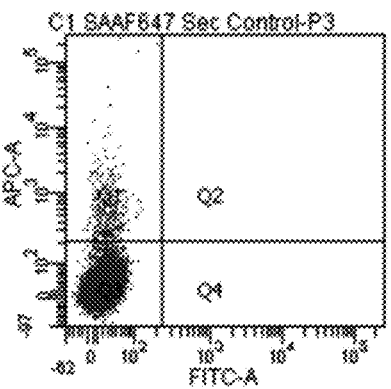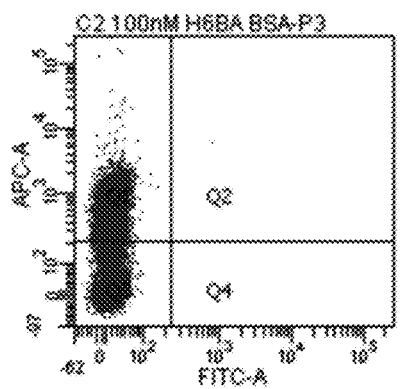
FIG. 60A rcSso7d.H6BA.3
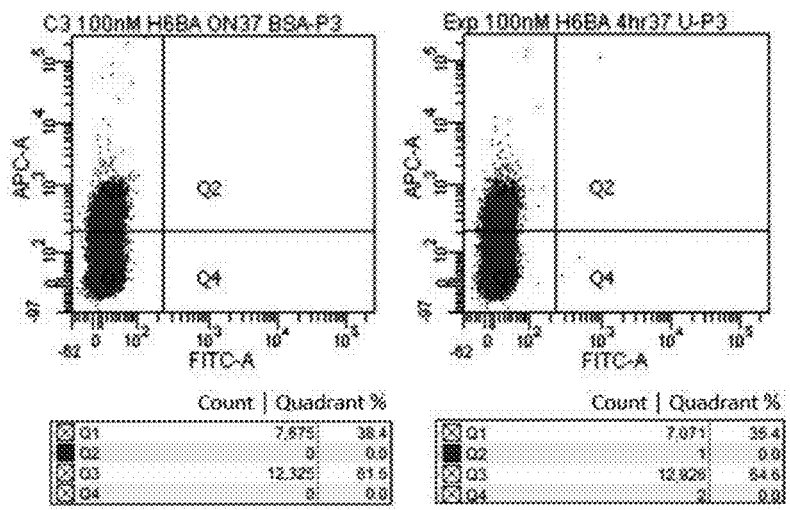
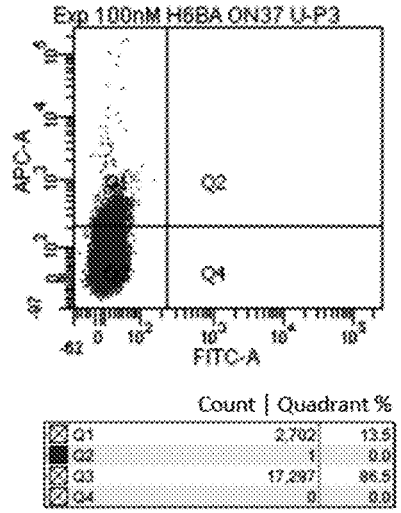
FIG. 60B rcSso7d.H7.1

Condition: Secondary control
Antigen (Ag): N/A
Ag pre-treatment: N/A
Pre-treatment time: N/A
Detection reagent: Mouse anti-His/ goat anti-mouse AF647

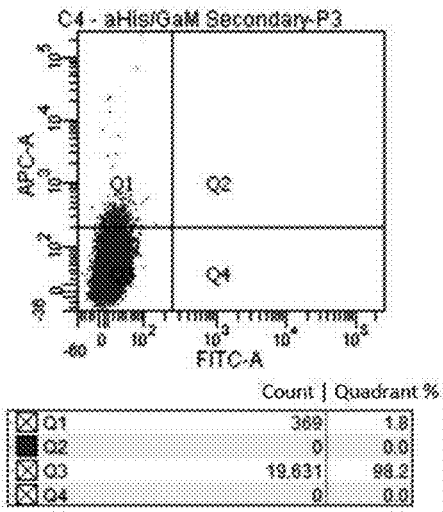

Condition: Baseline binding
Antigen (Ag): 100 nM H7
Ag pre-treatment: 0.1% BSA, 4°C
Pre-treatment time: N/A
Detection reagent: Mouse anti-His/ goat anti-mouse AF647

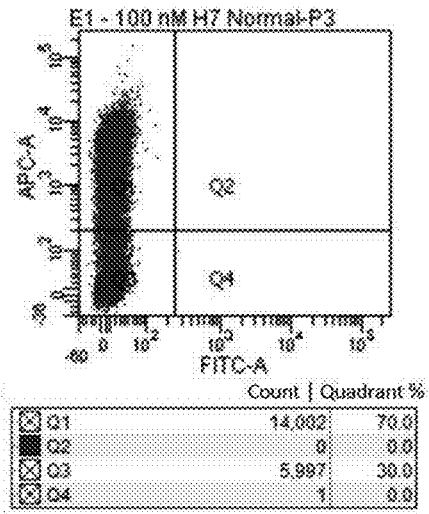

Condition: Short-term heat/ urine inactivation
Antigen (Ag): 100 nM H7
Ag pre-treatment: Urine, 37°C
Pre-treatment time: 4 hours
Detection reagent: Mouse anti-His/ goat anti-mouse AF647

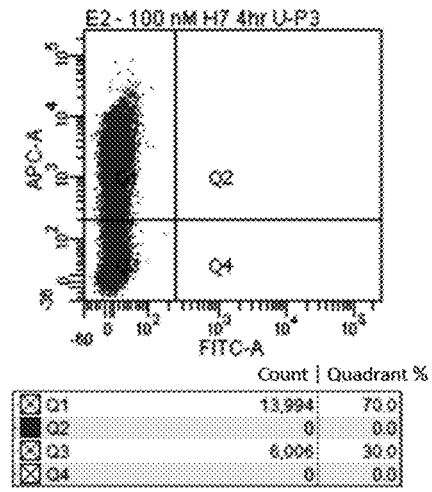

Condition: Overnight heat/ urine inactivation
Antigen (Ag): 100 nM H7
Ag pre-treatment: Urine, 37°C
Pre-treatment time: Overnight
Detection reagent: Mouse anti-His/ goat anti-mouse AF647

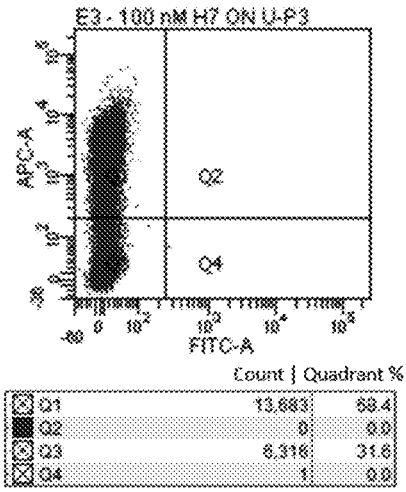

FIG. 62 rcSso7d.H4.5-CBD
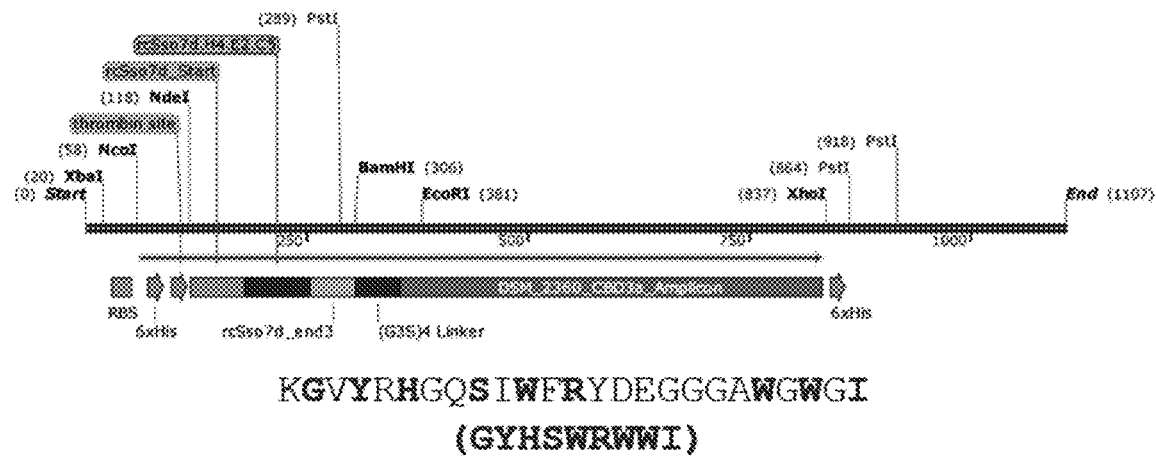
KGVYRHGQSIWFRYDEGGGAWGWGI
(GYHSWRWWI)
FIG. 65A rcSso7d.H4.9-CBD
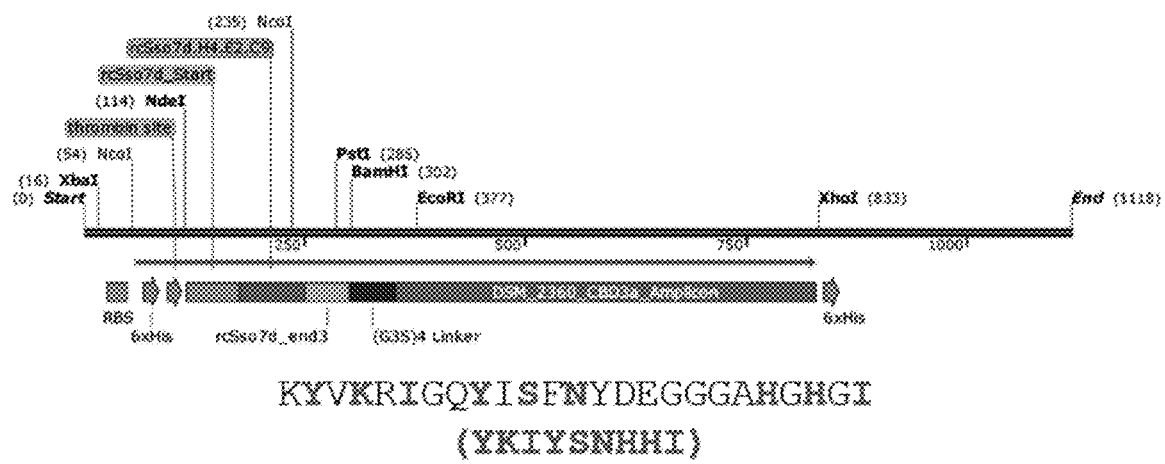
KYVKRIGQYISFNYDEGGGAHGHGI
(YKIYSNHHI)
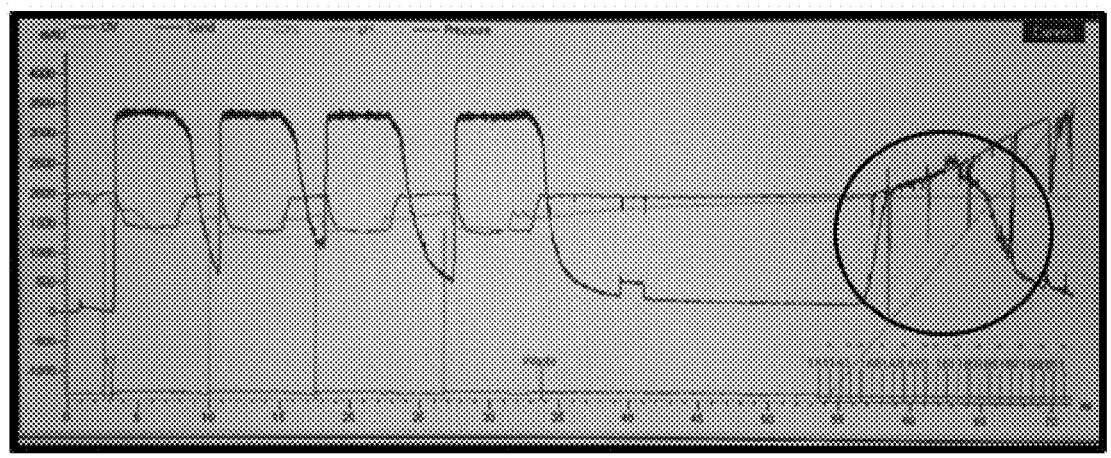
FIG. 65B rcSso7d.SA-CBD
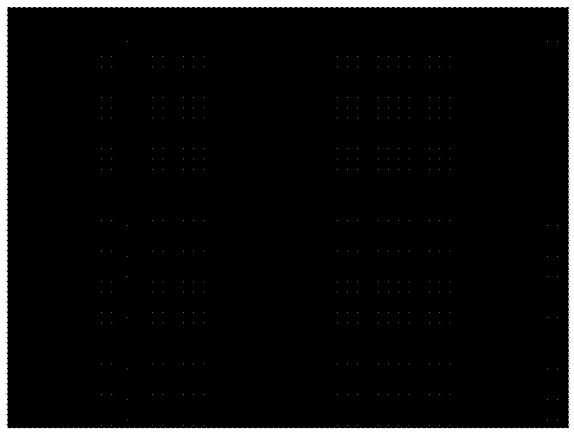
Negative control
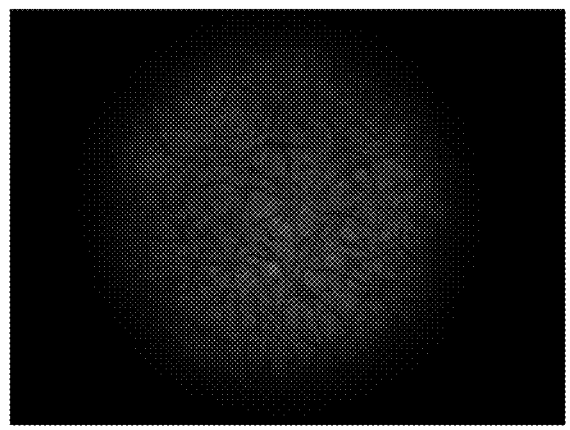
Positive control
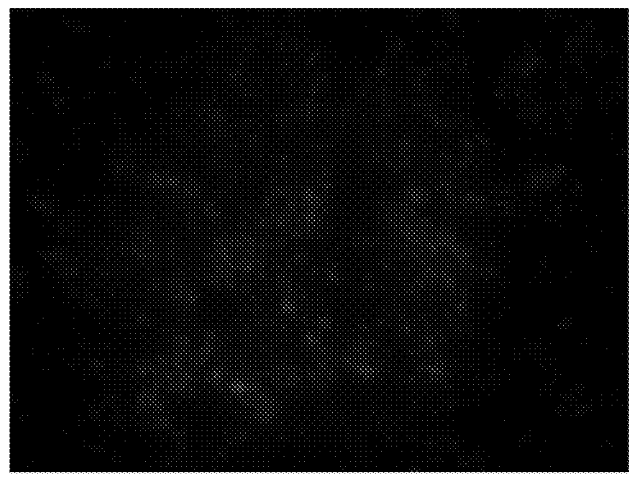
Experimental sample
FIG. 69

_US 11,740,236 B2_

PROTEIN FOR RAPID, EFFICIENT CAPTURE OF ANTIGENS

RELATED APPLICATION

This application claims priority under 35 U.S.C. § 119(e) to U.S. Provisional Application No. 62/572,392, filed Oct. 13, 2017, which is incorporated herein by reference in its entirety.

GOVERNMENT SUPPORT

This invention was made with Government support under Grant No. P30 CCA14051 awarded by the National Institutes of Health. The Government has certain rights in the invention.

FIELD

Methods and compositions for detecting targets of interest are disclosed herein.

BACKGROUND

Under the antigen-dilute conditions of a typical diagnostic assay, every target molecule that goes uncaptured represents a loss in potential binding signal, and directly diminishes diagnostic sensitivity. (Kelley et al., 2014; Rissin et al., 2013) Given that the signal-to-noise ratio for an immunoassay is directly proportional to the molar abundance of bound analyte, general strategies must be developed to enhance the efficiency of target capture, in order to boost the maximum achievable sensitivity for any given diagnostic platform.

SUMMARY

In some aspects, the present disclosure relates to the development of a general strategy for enhancing the efficiency of target capture in immunoassays, using a bifunctional fusion protein construct which incorporates a substrate-anchoring moiety (e.g., a cellulose binding domain (CBD)) for the high-abundance immobilization of an antigen-binding protein (e.g., Sso7d, reduced charge Sso7d (rcSso7d)). The approach utilizes a pseudo first-order rate constant model and was tested in a paper-based assay format using a fusion construct consisting of an rcSso7d binding protein and a CBD (rcSso7d-CBD fusion protein). The rcSso7d-CBD fusion proteins described herein enable oriented, high-density, and rapid adsorption of the antigen-binding protein (e.g., rcSso7d) to a cellulose-containing substrate.

According to some aspects, a bifunctional fusion protein including a cellulose binding domain (CBD) or a carbohydrate-binding module (CBM) and an engineered reduced-charge Sso7d (rcSso7d) antigen-binding protein is provided herein.

In some embodiments, the C-terminus of the engineered rcSso7d antigen-binding protein is linked to the N-terminus of the CBD.

In some embodiments, the engineered rcSso7d antigen-binding protein is linked to the CBD through a linker. In some embodiments, the linker is a Gly-Ser linker.

In some embodiments, the engineered rcSso7d antigen-binding protein comprises a streptavidin-binding domain. In some embodiments, the rcSso7d antigen-binding protein comprises a tuberculosis antigen-binding domain, a Flavivirus non-structural 1 (NS1) binding domain, an interleukin-6 (IL-6) binding domain, or a fluorophore binding domain. In some embodiments, the tuberculosis antigen-binding domain comprises a Rv1656-binding domain.

In some embodiments, the rcSso7d antigen-binding protein comprises at least 85% of the amino acid sequence of SEQ ID NO: 3 from _Sulfolobus solfataricus_.

In some embodiments, the CBD is a type 3a CBD or a type 1 dimerized cellulose binding domain (dCBD). In some embodiments, the type 3a CBD is a domain of the protein CipA from _Clostridium thermocellum_.

According to some aspects, a method for detecting an antigen of interest is provided herein. In some embodiments, the method includes contacting any of the bifunctional fusion proteins described herein with a cellulose-containing substrate for a time sufficient for the bifunctional fusion protein to bind the cellulose-containing substrate; contacting the bifunctional fusion protein bound to the cellulose-containing substrate with a sample that includes an antigen of interest; and detecting the antigen of interest bound by the engineered rcSso7d antigen-binding protein.

In some embodiments, the bifunctional fusion protein is in solution. In some embodiments, the solution comprises a buffer.

In some embodiments, the sample is a biological sample.

In some embodiments, the bifunctional fusion protein is in molar excess of the antigen of interest. In some embodiments, the bifunctional fusion protein is in at least 10-fold molar excess of the antigen of interest. In some embodiments, the antigen of interest is a tuberculosis antigen. In some embodiments, the antigen of interest is Rv1656 or streptavidin.

In some embodiments, at least 50% of the antigen of interest is depleted from the sample.

In some embodiments, the cellulose-containing substrate is paper or nitrocellulose. In some embodiments, the cellulose-containing substrate is chromatography paper. In some embodiments, the chromatography paper is unmodified.

In some embodiments, the method further includes rinsing the cellulose-containing substrate with a buffer solution before detecting the antigen of interest bound by the engineered rcSso7d antigen-binding protein.

In some embodiments, the sample is a biological sample from a subject. In some embodiments, the subject is a mammal. In some embodiments, the subject is a human.

In some embodiments, the CBD is bound to the cellulose-containing substrate.

In some embodiments, the engineered rcSso7d antigen-binding protein binds to a tuberculosis antigen. In some embodiments, the engineered rcSso7d antigen-binding protein binds to Rv1656 or binds to streptavidin.

According to some aspects, methods for detecting an antigen of interest are provided herein. In some embodiments, the method includes contacting any of the bifunctional fusion proteins described herein with a sample including an antigen of interest, wherein the antigen of interest binds to the bifunctional fusion protein and forms a complex; contacting the complex with a cellulose-containing substrate for a time sufficient for the complex to bind to the cellulose-containing substrate; and detecting the antigen of interest bound by the engineered rcSso7d antigen-binding protein.

In some embodiments, the bifunctional fusion protein is in solution. In some embodiments, the solution comprises a buffer.

In some embodiments, the sample is a biological sample.

In some embodiments, the bifunctional fusion protein is in molar excess of the antigen of interest. In some embodiments, the bifunctional fusion protein is in at least 10-fold molar excess of the antigen of interest. In some embodiments, the antigen of interest is a tuberculosis antigen. In some embodiments, the antigen of interest is Rv1656 or streptavidin.

In some embodiments, at least 50% of the antigen of interest is depleted from the sample.

In some embodiments, the cellulose-containing substrate is paper or nitrocellulose. In some embodiments, the cellulose-containing substrate is chromatography paper. In some embodiments, the chromatography paper is unmodified.

In some embodiments, the method further includes rinsing the cellulose-containing substrate with a buffer solution before detecting the antigen of interest bound by the engineered rcSso7d antigen-binding protein.

In some embodiments, the sample is a biological sample from a subject. In some embodiments, the subject is a mammal. In some embodiments, the subject is a human.

In some embodiments, the CBD is bound to the cellulose-containing substrate.

In some embodiments, the engineered rcSso7d antigen-binding protein binds to a tuberculosis antigen. In some embodiments, the engineered rcSso7d antigen-binding protein binds to Rv1656 or binds to streptavidin.

According to some aspects, methods for assessing the presence or amount of an antigen of interest is a sample are provided herein. In some embodiments, the method includes contacting the sample with any of the bifunctional fusion proteins described herein and measuring the presence or amount of the antigen of interest in the sample.

In some embodiments, the bifunctional fusion protein is in solution. In some embodiments, the solution comprises a buffer.

In some embodiments, the sample is a biological sample.

In some embodiments, the bifunctional fusion protein is in molar excess of the antigen of interest. In some embodiments, the bifunctional fusion protein is in at least 10-fold molar excess of the antigen of interest. In some embodiments, the antigen of interest is a tuberculosis antigen. In some embodiments, the antigen of interest is Rv1656 or streptavidin.

In some embodiments, at least 50% of the antigen of interest is depleted from the sample.

In some embodiments, the bifunctional fusion protein is bound to a cellulose-containing substrate. In some embodiments, the cellulose-containing substrate is paper or nitrocellulose. In some embodiments, the cellulose-containing substrate is chromatography paper. In some embodiments, the chromatography paper is unmodified.

In some embodiments, the sample is a biological sample from a subject. In some embodiments, the subject is a mammal. In some embodiments, the subject is a human.

In some embodiments, the CBD is bound to the cellulose-containing substrate.

In some embodiments, the engineered rcSso7d antigen-binding protein binds to a tuberculosis antigen. In some embodiments, the engineered rcSso7d antigen-binding protein binds to Rv1656 or binds to streptavidin.

According to some aspects, compositions are provided herein. In some embodiments, the composition includes any of the bifunctional fusion proteins described herein bound to a cellulose-containing substrate.

In some embodiments, the cellulose-containing substrate is paper, nitrocellulose or cellulose powder. In some embodiments, the cellulose-containing substrate is chromatography paper. In some embodiments, the chromatography paper is unmodified.

According to some aspects, kits for assessing a presence or amount of an antigen are provided herein. In some embodiments, the kit includes a container containing any of the bifunctional fusion proteins described herein. In some embodiments, the kit includes a container containing any of the target binding proteins or domains disclosed herein, wherein the target binding protein or domain is not part of a bifunctional fusion protein disclosed herein.

In some embodiments, the kit further includes a cellulose-containing substrate.

In some embodiments, the bifunctional fusion protein is bound to the cellulose-containing substrate. In some embodiments, the bifunctional fusion protein is not bound to the cellulose-containing substrate. In some embodiments, the cellulose-containing substrate is paper, nitrocellulose or cellulose powder. In some embodiments, the cellulose-containing substrate is chromatography paper. In some embodiments, the chromatography paper is unmodified.

According to some aspects, methods for assaying an antigen of interest are provided herein. In some embodiments, the method includes contacting an antigen with any of the bifunctional fusion proteins described herein bound to a cellulose-containing substrate, wherein the bifunctional fusion protein is bound to the cellulose-containing substrate at an at least 10-fold or greater molar excess or at an at least 10-fold or greater volume-average concentration excess to the antigen of interest. In some embodiments, the bifunctional fusion protein is in at least 60-fold molar excess of the antigen of interest.

In some embodiments, the antigen of interest is a tuberculosis antigen. In some embodiments, the antigen of interest is Rv1656 or streptavidin.

In some embodiments, the cellulose-containing substrate is paper or nitrocellulose. In some embodiments, the cellulose-containing substrate is chromatography paper. In some embodiments, the chromatography paper is unmodified.

In some embodiments, the CBD is bound to the cellulose-containing substrate.

In some embodiments, the engineered rcSso7d antigen-binding protein binds to a tuberculosis antigen. In some embodiments, the engineered rcSso7d antigen-binding protein binds to Rv1656 or binds to streptavidin.

In some embodiments, any of the bifunctional fusion proteins disclosed herein comprise at least 2, 3, 4, 5, 6, 7, 8, 9 or 10 rcSso7d antigen-binding proteins or antigen-binding domains. In some embodiments, the at least 2, 3, 4, 5, 6, 7, 8, 9 or 10 rcSso7d antigen-binding proteins are genetically fused together. In some embodiments, the at least 2, 3, 4, 5, 6, 7, 8, 9 or 10 rcSso7d antigen-binding proteins are directly or indirectly linked to the CBM or CBD.

In some embodiments, the cellulose powder is in solution to capture a soluble analyte, antigen or antigen of interest.

According to another aspect, engineered reduced-charge Sso7d (rcSso7d) antigen-binding proteins or domains are contemplated herein.

In some embodiments, the rcSso7d antigen-binding protein is directly or indirectly linked to a maltose binding protein (MBP).

In some embodiments, the rcSso7d further comprises a biotin acceptor.

According to another aspect, methods for detecting an antigen of interest are contemplated herein.

In some embodiments, the method includes contacting an antigen of interest with an oxidized cellulose substrate for a time sufficient for the antigen of interest to bind to the oxidized cellulose substrate, contacting the antigen of interest bound to the oxidized cellulose substrate of with an engineered rcSso7d antigen-binding protein disclosed herein for a time sufficient for the antigen of interest to bind to an engineered rcSso7d antigen-binding protein disclosed herein, and detecting the antigen of interest bound to the engineered rcSso7d antigen-binding protein.

In some embodiments, the antigen of interest is detected with a streptavidin conjugated to a fluorophore.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

(FIG. 5A) SA-E titration curves for various applied soluble concentrations of rcSso7d.SA-CBD. Sets of non-functionalized cellulose test zones were prepared with a range of soluble rcSso7d.SA-CBD concentrations. All test zones were contacted for 30s and washed, and were then treated for 30 minutes with a serial dilution of SA-E ranging from 256 nM to 0.25 nM. Samples were imaged in the TEXAS RED@ channel using an exposure time of 1000 ms. Datasets were fit with a second-order polynomial. Error bars represent the standard deviation of four independent replicates. (FIG. 5B) Limits of detection for various applied concentrations of rcSso7d.SA-CBD. The measured MFI values for all negative control samples (with [SA-E] ranging from 256 nM to 0.25 nM) were averaged to calculate a conservative three-sigma detection threshold of 167.8 AU. Second-order polynomial lines of best fit were used to calculate the antigen concentration corresponding to this LOD for each sample set treated with a different applied rcSso7d.SA-CBD concentration. Second-order polynomial lines of best fit were also used to plot the upper and lower bounds of each data point (determined by the standard deviation), and these bounding trendlines were used to generate bounds on the limits of detection, represented by the error bars.

(FIG. 11A) Performance of dry incubation samples over time; (FIG. 11B) performance of dry incubation samples after four months' incubation at 40° C.

FIG. 19. SA-E titration for rcSso7d-CBD Types 1 and 3a.

FIG. 20 shows flow cytometry data indicating the specific binding activity of Flavivirus NS1 protein binder rcSso7d.NS1.1.

FIG. 21 shows flow cytometry data indicating the specific binding activity of Flavivirus NS1 protein binder rcSso7d.NS1.2.

FIG. 22 shows flow cytometry data indicating the specific binding activity of Flavivirus NS1 protein binder rcSso7d.NS1.3.

FIG. 23 shows flow cytometry data indicating the specific binding activity of Flavivirus NS1 protein binder rcSso7d.NS1.4.

FIG. 24 shows flow cytometry data indicating the specific binding activity of Flavivirus NS1 protein binder rcSso7d.NS1.5.

FIG. 25 shows flow cytometry data indicating the specific binding activity of Flavivirus NS1 protein binder rcSso7d.NS1.6.

FIG. 27 shows flow cytometry data indicating the specific binding activity of Human IL-6 protein binder rcSso7d.IL6.2.

FIG. 31 shows flow cytometry data indicating the specific binding activity of Human IL-6 protein binder rcSso7d.IL6.6.

FIG. 33A shows a schematic representation of the rcSso7d.NS1.1-CBD construct immobilized to cellulose following with incubations of Zika virus NS1 (at various concentrations), biotinylated anti-Zika virus NS1 antibody, and streptavidin-AF 647.

FIG. 33B shows binder performance of rcSso7d.NS1.1-CBD in cellulose paper-based assay.

FIG. 39 shows flow cytometry data indicating the specific binding activity of H1 binder rcSso7d.H1BA.2.

FIGS. 40A-40C show flow cytometry data indicating the specific binding activity of H1 binder rcSso7d.H1BA.3.

FIG. 41 shows flow cytometry data indicating the specific binding activity of binder rcSso7d.H1BA.4 (1.E2.3).

FIG. 42 shows flow cytometry data indicating the specific binding activity of H1 binder rcSso7d.H1BA.5 (1.E2.4).

FIG. 43 shows flow cytometry data indicating the specific binding activity of H1 binder rcSso7d.H1BA.6.

FIG. 45 shows flow cytometry data indicating the specific binding activity of H2 binder rcSso7d.H2BA.1.

FIG. 47 shows flow cytometry data indicating the specific binding activity of H4 binder rcSso7d.H4.1.

FIG. 48 shows flow cytometry data indicating the specific binding activity of H4 binder rcSso7d.H4.2.

FIG. 49 shows flow cytometry data indicating the specific binding activity of H4 binder rcSso7d.H4.3.

FIG. 50 shows flow cytometry data indicating the specific binding activity of H4 binder rcSso7d.H4.4.

FIG. 51 shows flow cytometry data indicating the specific binding activity of H4 binder rcSso7d.H4.5.

FIG. 52 shows flow cytometry data indicating the specific binding activity of H4 binder rcSso7d.H4.6.

FIG. 53 shows flow cytometry data indicating the specific binding activity of H4 binder rcSso7d.H4.7.

FIG. 54 shows flow cytometry data indicating the specific binding activity of H4 binder rcSso7d.H4.8.

FIG. 55 shows flow cytometry data indicating the specific binding activity of H4 binder rcSso7d.H4.9.

FIGS. 56A-56B show flow cytometry data indicating the specific binding activity of H4 binders rcSso7d.H4.2/H4/BA-MBP-rcSso7d.H4.1.

FIGS. 58A-58B show flow cytometry data indicating the specific binding activity of H6 binder rcSso7d.H6BA.1.

FIGS. 59A-59B show flow cytometry data indicating the specific binding activity of H6 binder rcSso7d.H6BA.2.

FIGS. 60A-60B show flow cytometry data indicating the specific binding activity of H6 binder rcSso7d.H6BA.3.

FIG. 62 shows flow cytometry data indicating the specific binding activity of H7 binder rcSso7d.H7.1.

FIGS. 65A-65B show cloning and purification data of rcSso7d.H4.5-CBD (FIG. 65A) and rcSso7d.H4.9-CBD (FIG. 65B). The sequences is FIG. 65A correspond to SEQ ID NOs: 122 and 98, top to bottom. The sequences is FIG. 65B correspond to SEQ ID NOs: 123 and 102, top to bottom.

FIGS. 66A-66B show H4 binding activity of selected clones. FIG. 66C shows positive rcSso7d.H4.E1-BA controls. FIG. 66D shows schematic representations of the constructs in the assay rcSso7d.H4.2-CBD Full (1) and rcSso7d.H4.2-CBD with pre-incubation of the rcSso7d.H4.E1-BA and SA-AF647 species (4).

FIG. 68A is a multimer schematic. FIG. 68B shows a 12% SDS-PAGE demonstrating the purity of the 1x-, 2x-, and 3x-CBD variants following purification with immobilized metal affinity chromatography. FIG. 68C shows binder performance of the immobilized rcSso7d-CBD variants in antigen-capture assays, using streptavidin ALEXA FLUOR@ 647 as the analyte.

FIG. 69 shows the immobilization of rcSso7d.SA-CBD on cellulose powder for combing through large volumes. Images show the results of the negative control, positive control, and experimental sample.

$$y = \frac{A - B}{\left(1 + \left(\frac{x}{C}\right)^D\right)^E} + B \quad \text{(Eq. S10)}$$

Figure 74A:
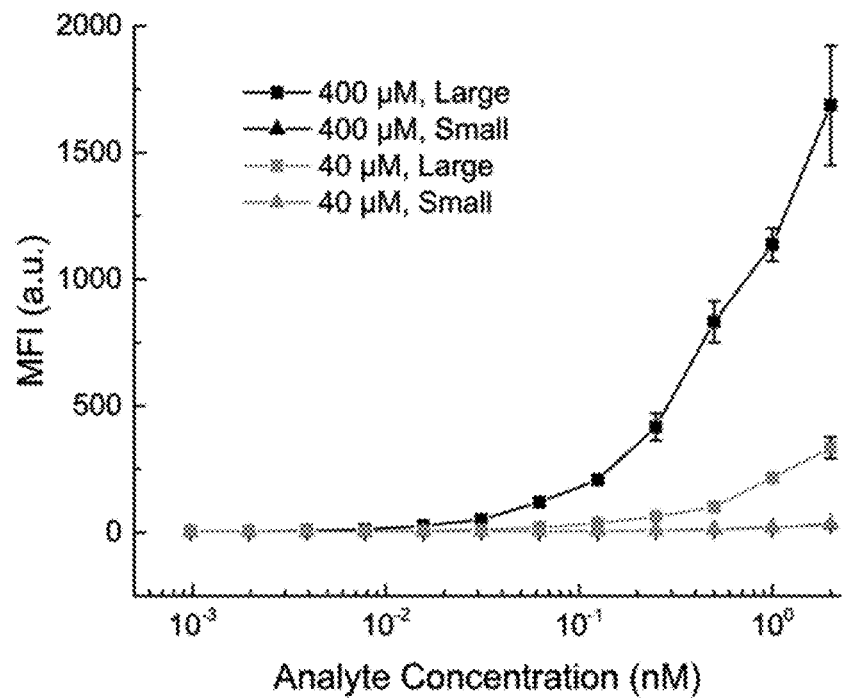
Figure 74B:
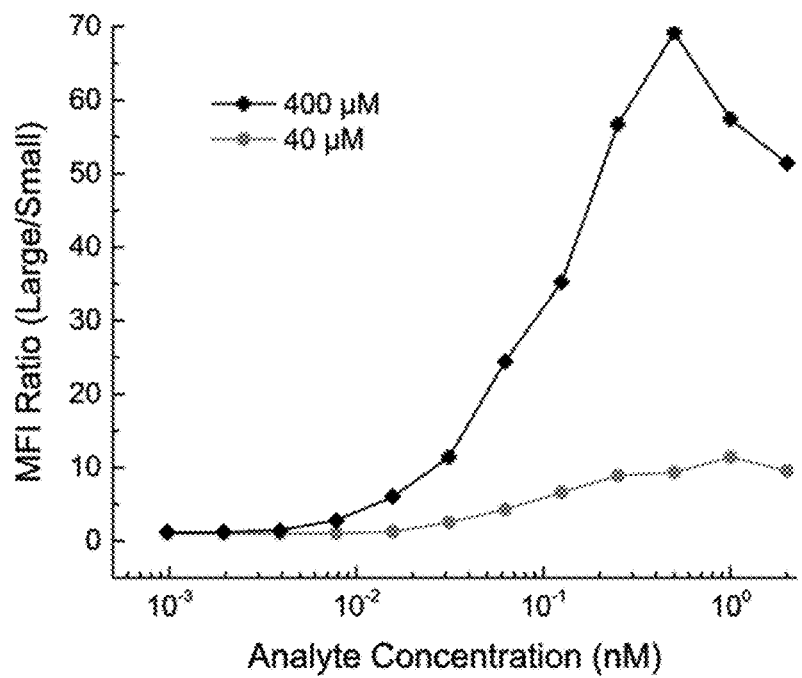
Figure 87:
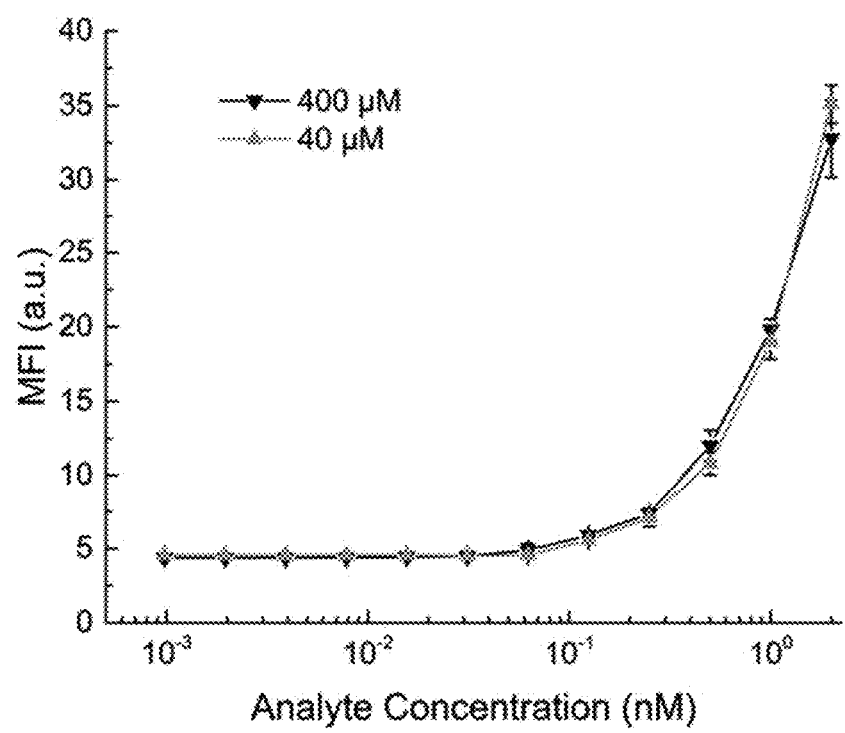

FIGS. 74A-74B show a comparison between analyte titration curves for rcSso7d-CBD at varying local concentrations. FIG. 74A shows mean fluorescence intensity (MFI) observed at varying analyte concentrations for large- (10 mL) and small-volume (10 µL) samples using test zones with local rcSso7d-CBD concentrations of 400 and 40 µM. Data points corresponding to the 400 µM/10 µL samples directly overlap with those corresponding to the M/10 µL samples (FIG. 87). FIG. 74B shows fluorescence ratios comparing the corresponding large- and small-volume samples at local rcSso7d-CBD concentrations of 400 and 40 µM. Large-volume samples consist of 10 mL of analyte solution (5 mL min-1, 20 recirculations). Small-volume samples consisted of 10 µL incubated on the test zones for an equivalent 40 min period. Error bars represent the standard deviation of three (large- volume) or four (small-volume) independent replicates.

Figure 75A:
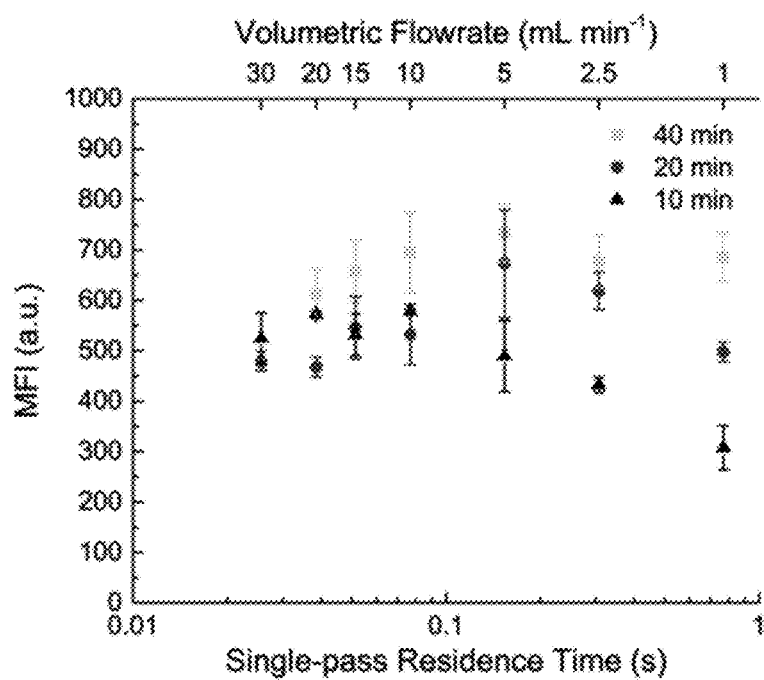
Figure 75B:
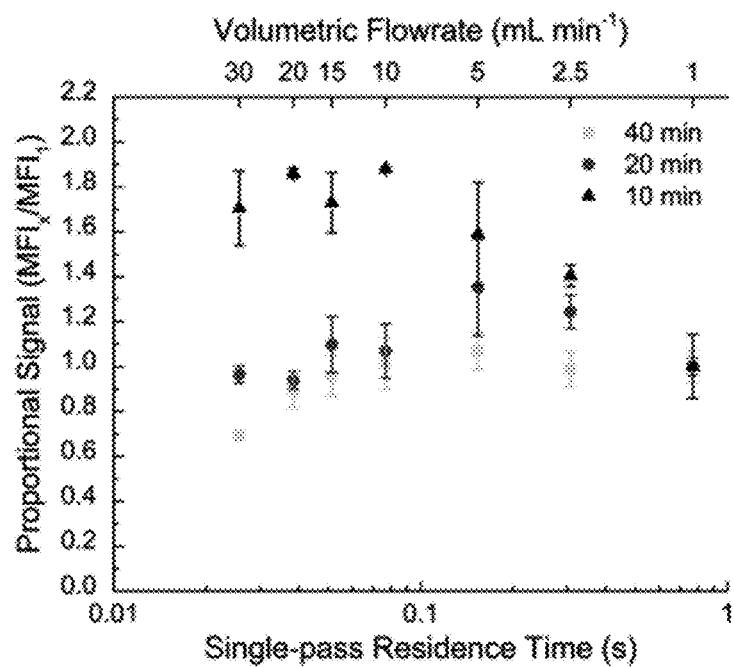
Figure 75C:
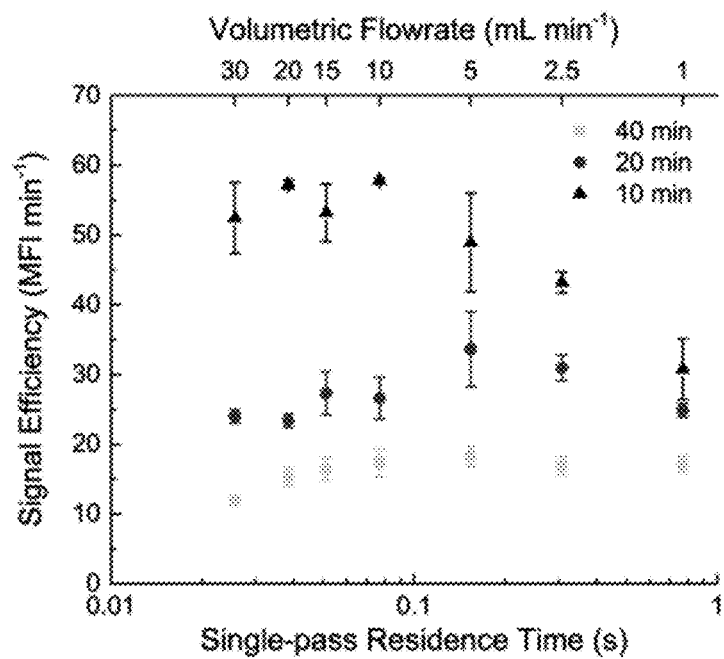
Figure 75D:
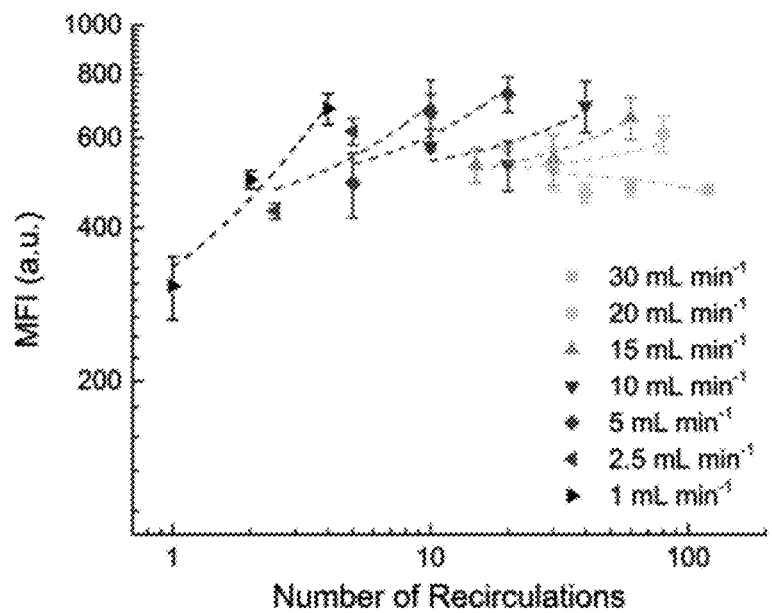

FIGS. 75A-75D show assay performance for varying flow rates and total processing times. FIG. 75A shows absolute mean fluorescence intensity (MFI), FIG. 75B shows proportional MFI (relative to samples processed for the same period of time at 1 mL min-1), and FIG. 75C shows signal development efficiency (MFI min-1) for varying single-pass residence times and total processing times. FIG. 75D shows signal development as a function of the number of recirculations. Linear trend lines indicate the performance of samples produced using a common volumetric flow rate (denoted in the legend). Sample specifications: 10 mL and 1 nM SA-AF647. Error bars represent the standard deviation of three independent replicates.

Figure 76:
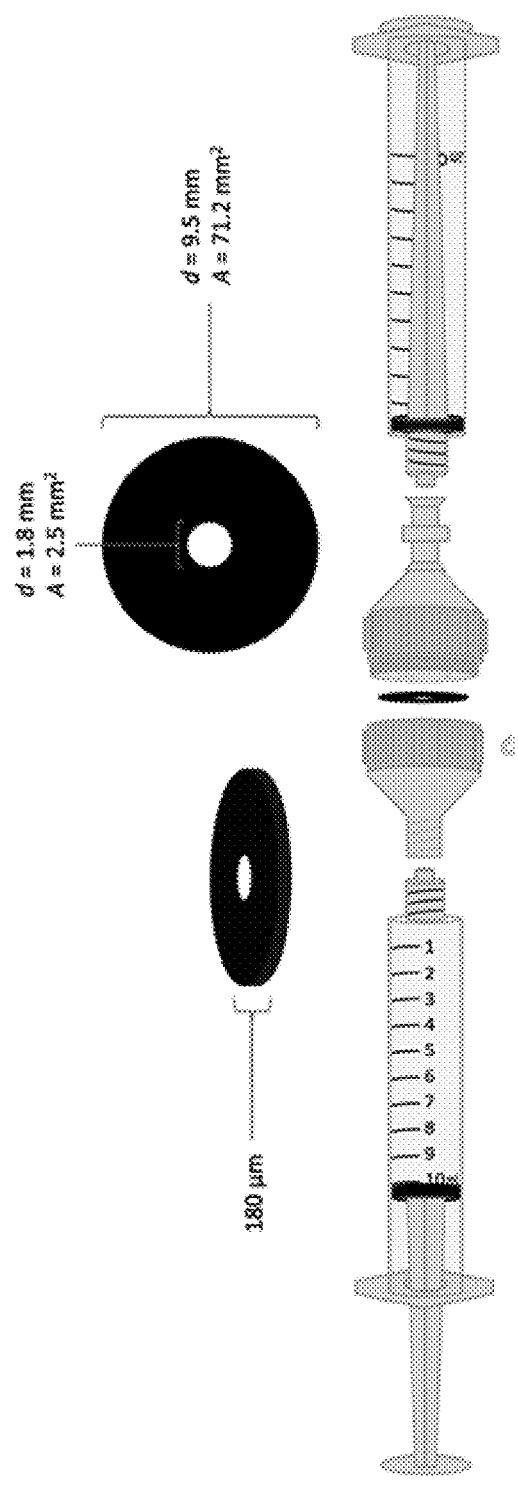

FIG. 76 shows a syringe-based assay format. Paper samples are excised and secured in a 13 mm Swinnex filter holder. A 10-mL syringe is connected upstream and used to pre-fill the filter holder with the analyte solution. A Qosina Female-to-Female Luer-Lok connector is used to join this cassette to a second syringe downstream, and any remaining air is bled from the system. In all cases, the top of the test zone (the surface to which the rcSso7d.SA-CBD solution was applied) is oriented so as to be the first side contacted by the analyte solution.

Figure 77A:
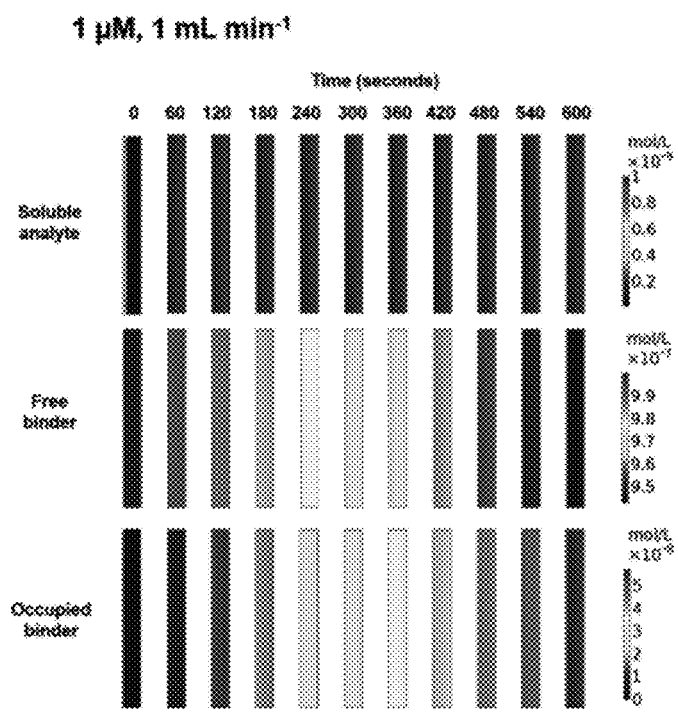
Figure 77B:
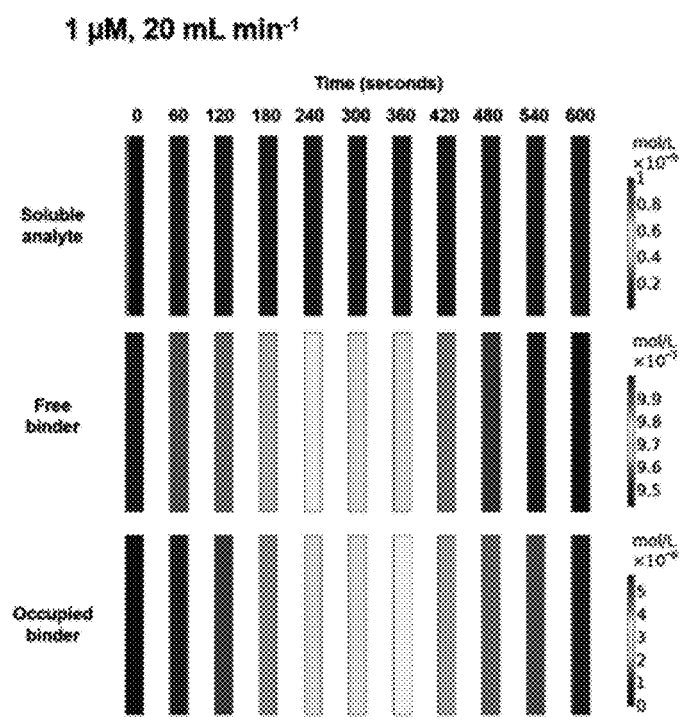
Figure 77C:
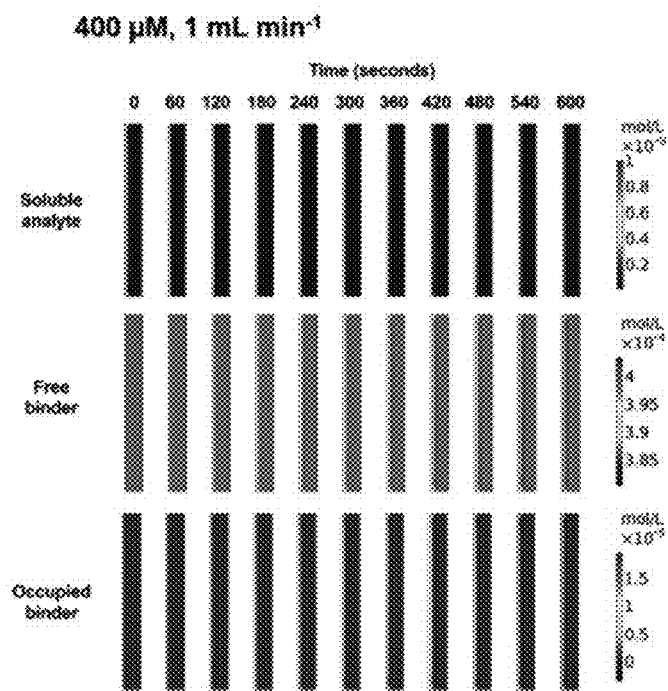
Figure 77D:
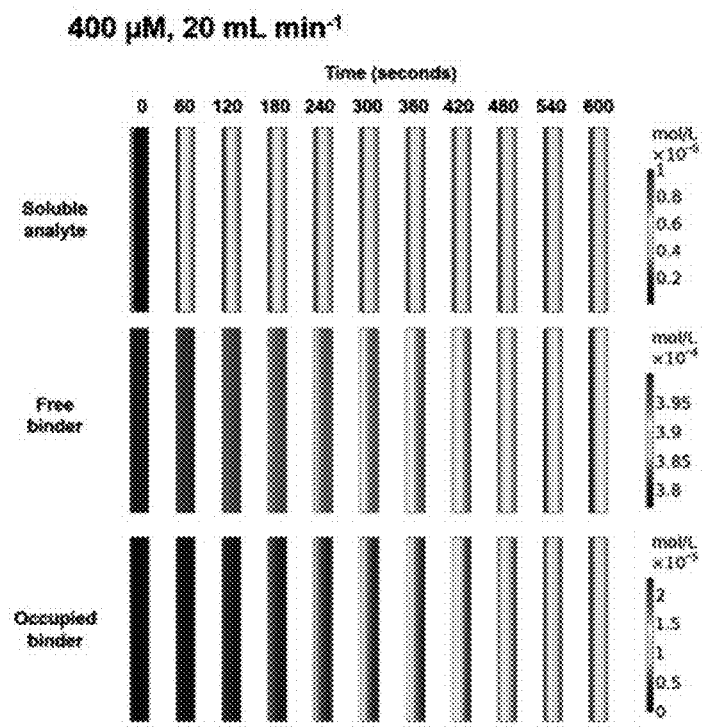

FIGS. 77A-77D show a set-up of COMSOL proportional analyte capture model. The test zone is modeled as a two dimensional reactor volume, throughout which the immobilized binder is homogeneously distributed. Depth=L=180 µm; width=2rtz=1.8 mm. Analyte concentration at the inlet (at left) is 1 nM. The binder concentration and volumetric flow rate for the sample sets are varied across the different subfigures: 1 µM, 1 mL min-1 (FIG. 77A), 1 µM, 20 mL min-1 (FIG. 77B), 400 µM, 1 mL min-1 (FIG. 77C), and 400 µM, 20 mL min1 (FIG. 77D). Within each sub-figure, the rows of test snapshots correspond to the soluble analyte, free binder, and the occupied binder (from top to bottom). Test zone snapshots are captured every sixty seconds, at time-points denoted along the top of each sub-figure. Legends at right denote the concentrations of the relevant species for the corresponding row of cross-sectional snapshots. In order to capture system dynamics, color-bars are scaled relative to the relevant species for each set of operating conditions, rather than representing a universal concentration scale.

Figure 78:
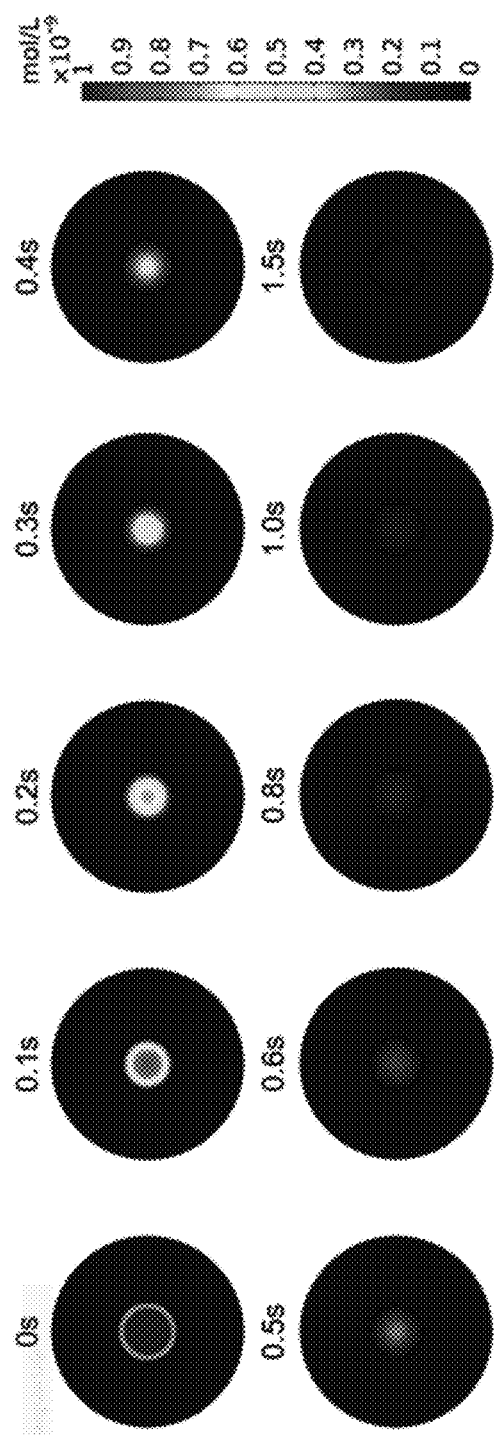

FIG. 78 shows a set-up of COMSOL diffusion model. An idealized circular pore (r=5.5 µm) is initialized with an analyte concentration of 1 nM. The surrounding matrix represents a binder-functionalized fibrous network, at an average binder concentration of 40 mM. Analyte diffusion and capture is allowed to proceed over the course of 2 seconds, to model diffusive capture over a range of different sample residence times. Each snapshot represents a different time-point, denoted above the pore image, and the color-bar represents the concentration of the soluble analyte.

Figure 79:
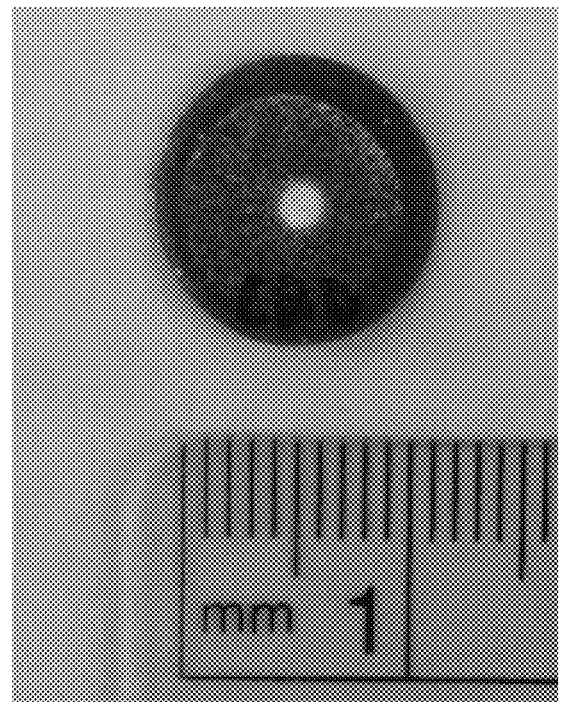

FIG. 79 shows the confirmation of fluid flow across the entire assay cross-sectional area. Insoluble cellulose powder (50 µm diameter) was added to the sample volume in order to track the fluid flow as the sample was recirculated across the test zone. Rather than focusing solely within the hydrophilic region, the powder distributes across the entire cross-sectional area, indicating that the hydrophobic region permits fluid flow once it becomes sufficiently wetted. Thus, the relevant flow volume is 12.81 µL, rather than that associated strictly with the binder-functionalized region (0.45 µL).

Figure 80:
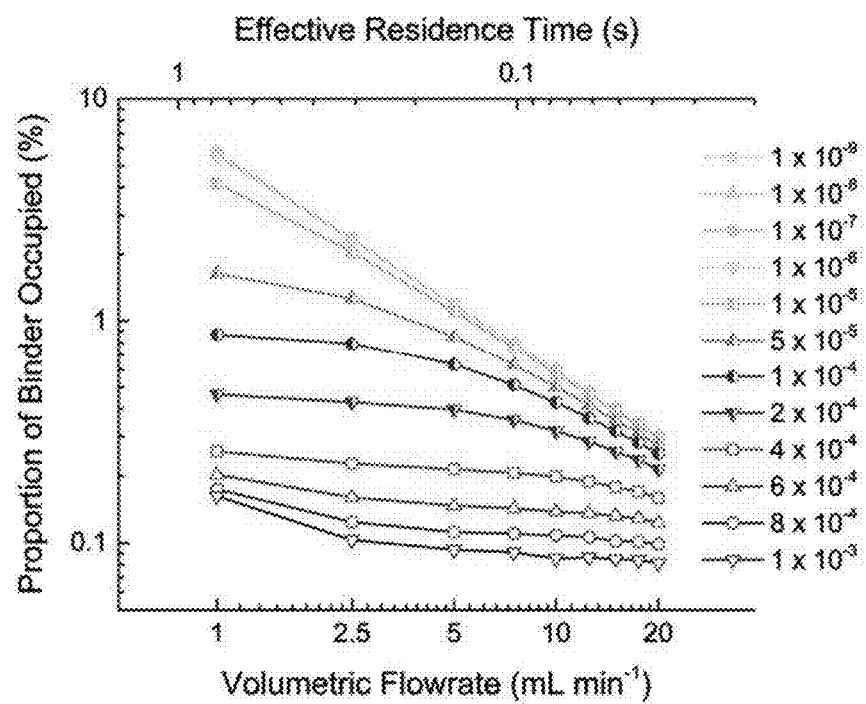

FIG. 80 shows proportional binder occupancy at varying concentrations and volumetric flow rates. Each line plot represents operation at a different local binder concentration (denoted in the legend). For all data sets, analyte was introduced at a concentration of 1 nM, and data was collected immediately following a single simulated 10-mL recirculation.

Figure 81A:
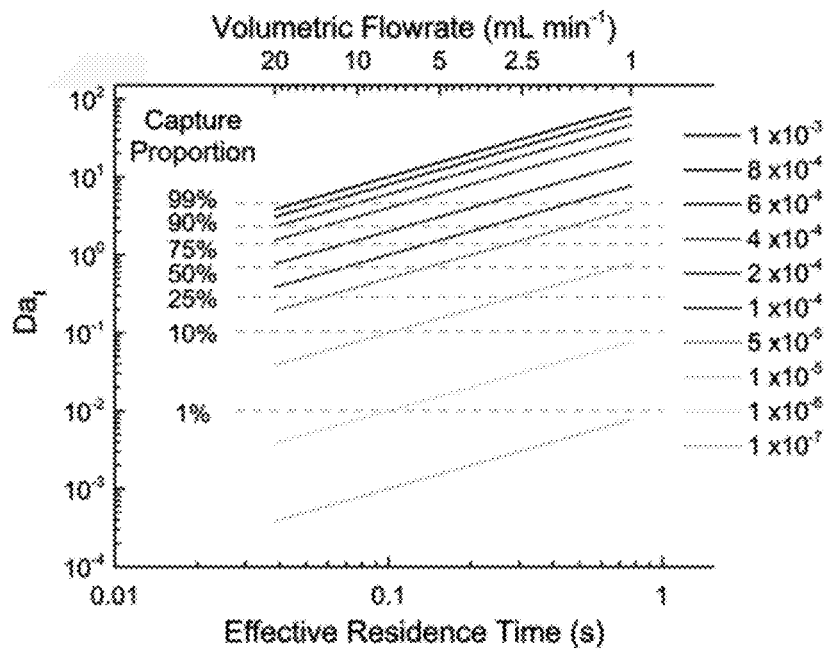
Figure 81B:
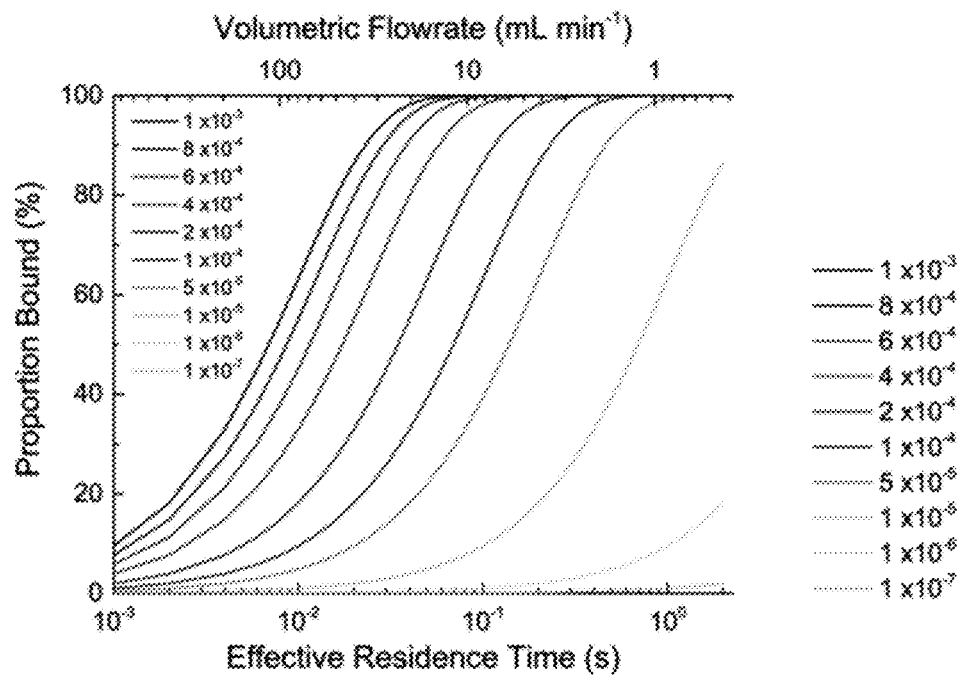

FIGS. 81A-81B show the correlation of flow rate, binder concentration, analyte capture, and DaI. FIG. 81A shows standard curves correlating volumetric flow rate, binder concentration (mol $L^{-1}$), and Damköhler number, as well as rates of proportional analyte capture predicted by the pseudo first-order rate model. FIG. 81B shows predicted proportional binding curves for varying local concentrations of immobilized binder.

Figure 82A:
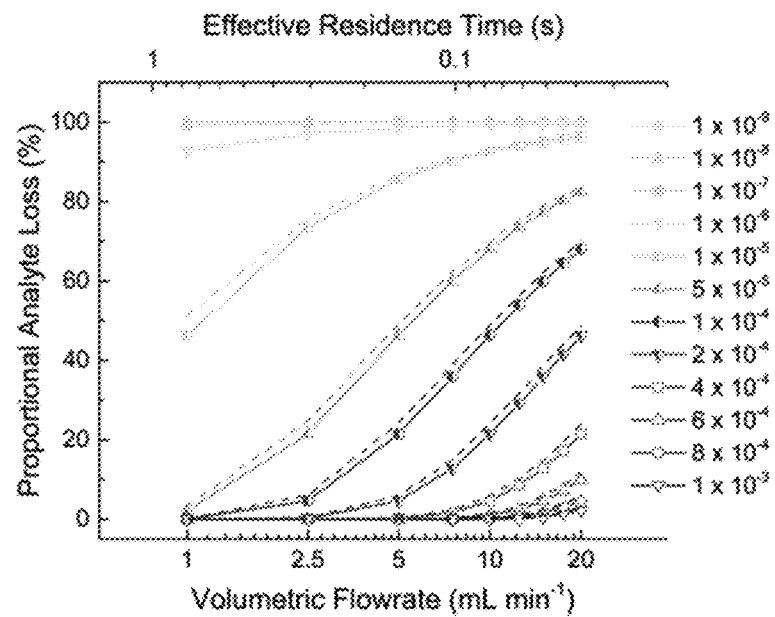
Figure 82B:
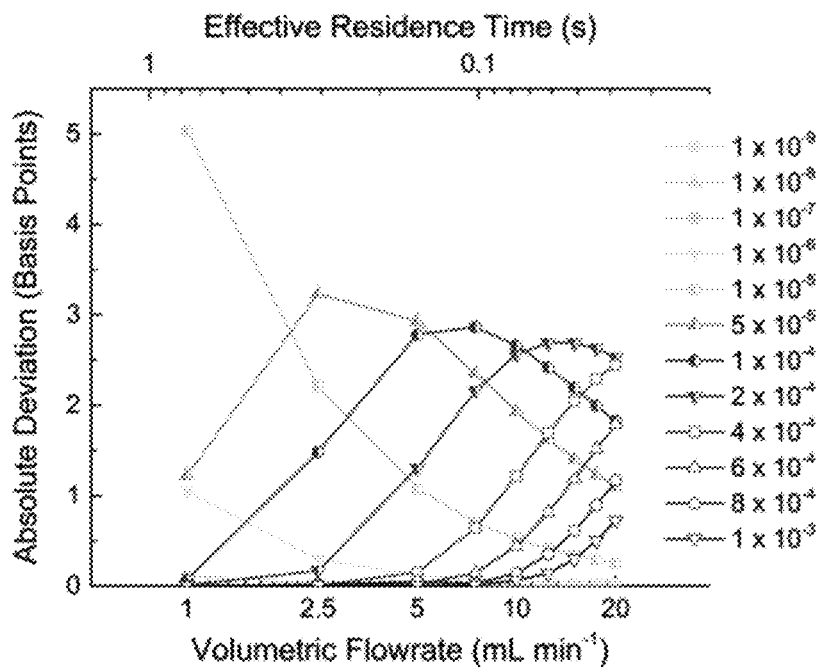

FIGS. 82A-82B show deviation between finite-element analysis and PFORC model. FIG. 82A shows a comparison of the finite element model of analyte binding in the non-diffusive limit (dashed lines) and the pseudo first-order rate constant model (solid lines). FIG. 82B shows the absolute basis point deviation between the FEA model and PFORC model for all processing conditions. The greatest deviation between the predictive models is observed in regions of dynamic signal change.

Figure 83:
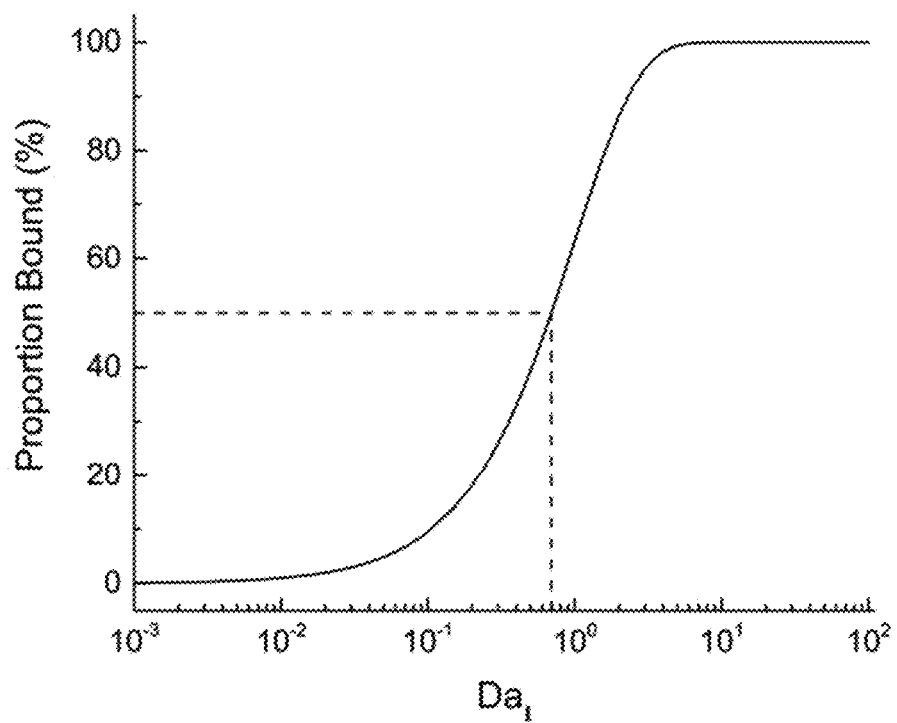

FIG. 83 shows a Damköhler master curve. All dimensional binding curves generated via the pseudo first-order rate model collapse onto a single dimensionless binding curve describing system performance. This relation is valid for all cases in which the immobilized binder is in significant molar excess (>10x) of the soluble analyte. Dashed lines highlight the value of the Damköhler number at which 50% of the analyte is captured.

Figure 84:
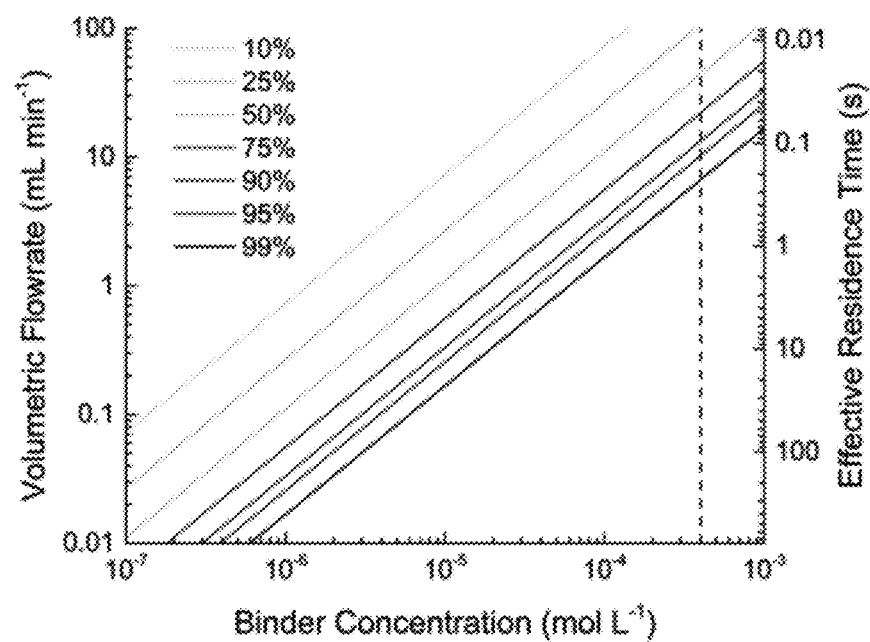

FIG. 84 shows binding isotherms. Curves denote the theoretical proportional analyte capture observed for a given volumetric flow rate (or residence time) at varying concentrations of immobilized binder. The dashed line indicates the operating regime of the standard rcSso7d-CBD system (CB=400 µM).

Figure 85:
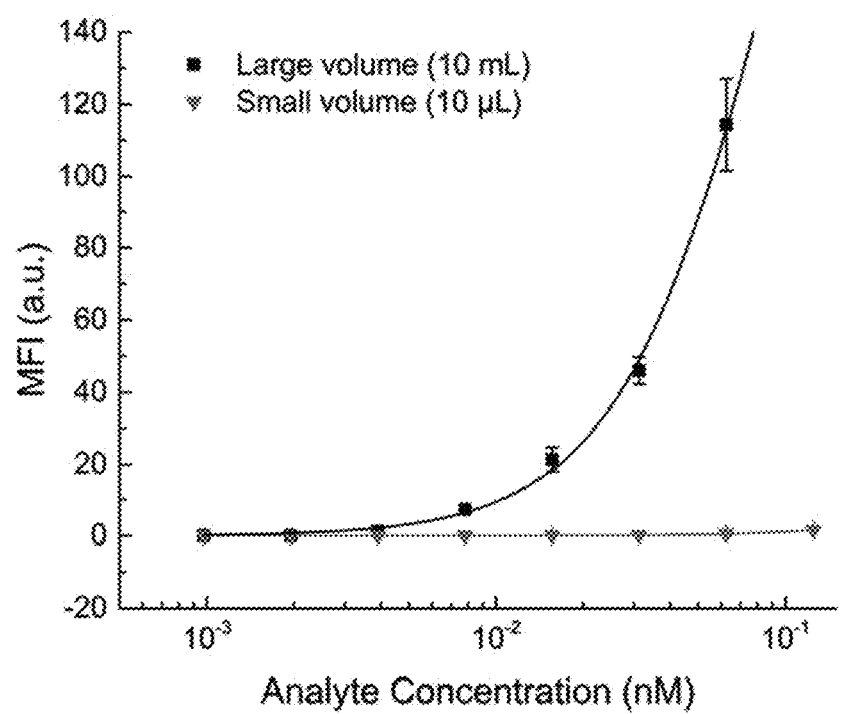

FIG. 85 shows titration curves near the point of signal onset. All large-volume samples consisted of 10 mL sample volumes, driven across the test zone at 5 mL min-1 for 20 recirculations. All small-volume samples consisted of 10 µL sample volumes, applied directly to the test zones and allowed to incubate for an equivalent 40-minute period. Dataset is identical to that seen in FIG. 73. Error bars represent the standard deviation of three (large-volume) or four (small-volume) independent replicates.

Figure 86A:
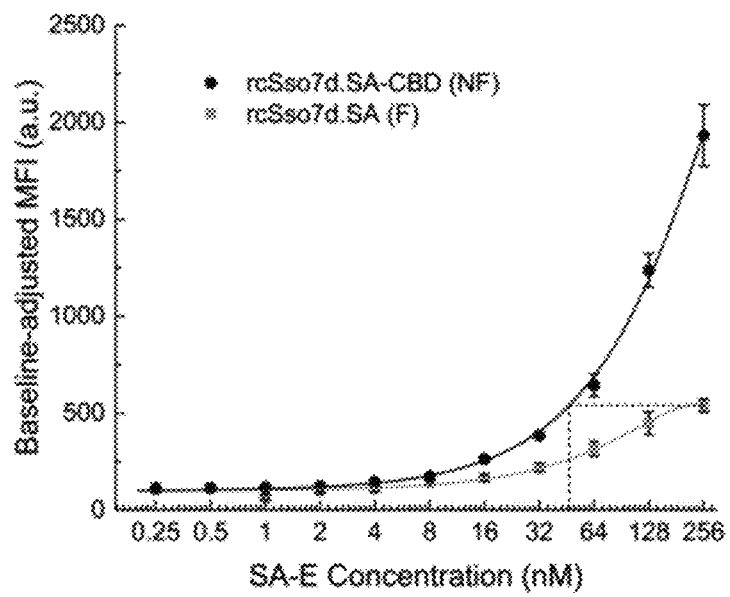
Figure 86B:
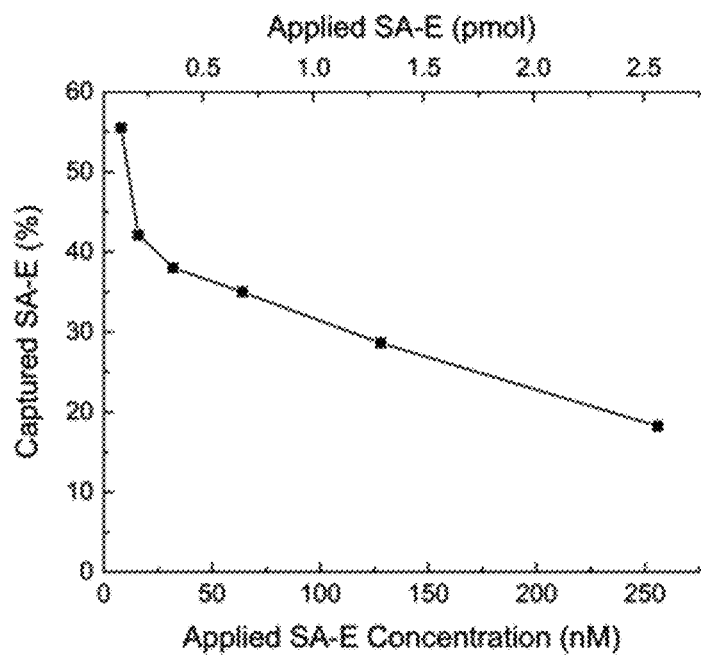

FIGS. 86A-86B show the calculation of immobilized protein abundance on functionalized paper. FIG. 86A shows titration data for rcSso7d.SA-CBD applied to non-functionalized paper (black) and rcSso7d.SA applied to aldehyde-functionalized paper (red), for streptavidin-eosin (SA-E) concentrations ranging from 0.25 nM to 256 nM and 10 µL sample volumes. FIG. 86B shows proportional analyte capture at varying applied analyte concentrations. Analysis is conducted for all applied concentrations wherein there is an appreciable difference between signals observed for the functionalized and non-functionalized samples. All tests were incubated with the analyte solution for thirty minutes. Error bars represent the standard deviation of four independent replicates.

FIG. 87 shows the comparison between small-volume titration curves for rcSso7d-CBD at local concentrations of 400 µM and 40 µM. Dataset is identical to that seen in FIG. 74A. Small-volume samples consisted of 10 µL incubated on the test zones for a 40-minute period. Error bars represent the standard deviation of four independent replicates.

Figure 88:
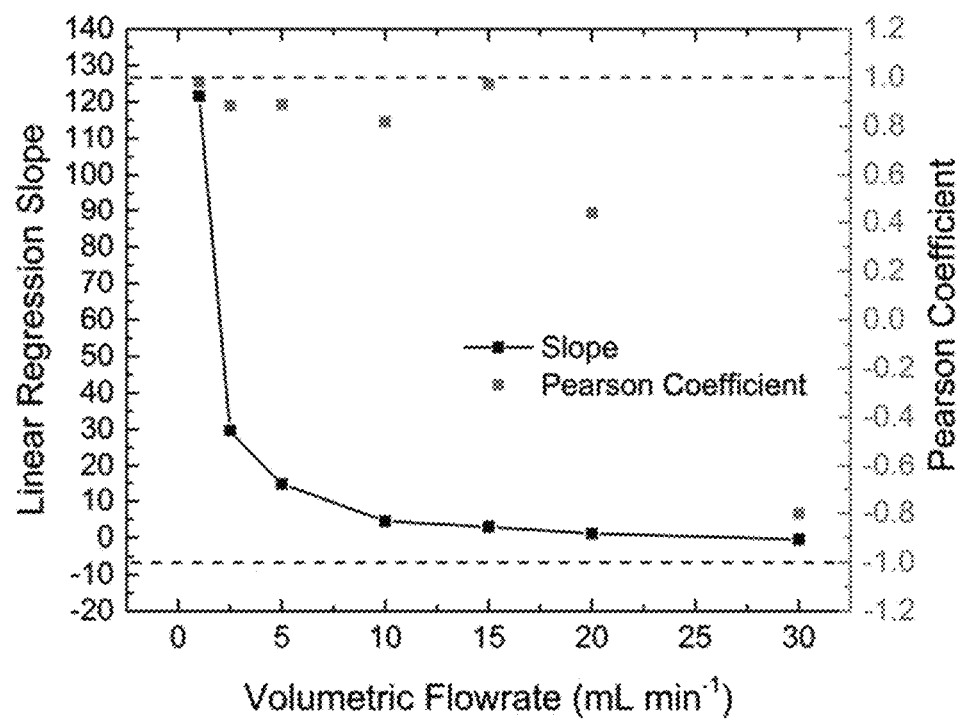

FIG. 88 shows linear regression slopes, which correlate the number of recirculations and the degree of signal development, decline with increasing volumetric flow rate. In nearly all cases, linear regression curves are observed to correlate well with the experimental data, as indicated by Pearson coefficients near ±1.

Figure 89:
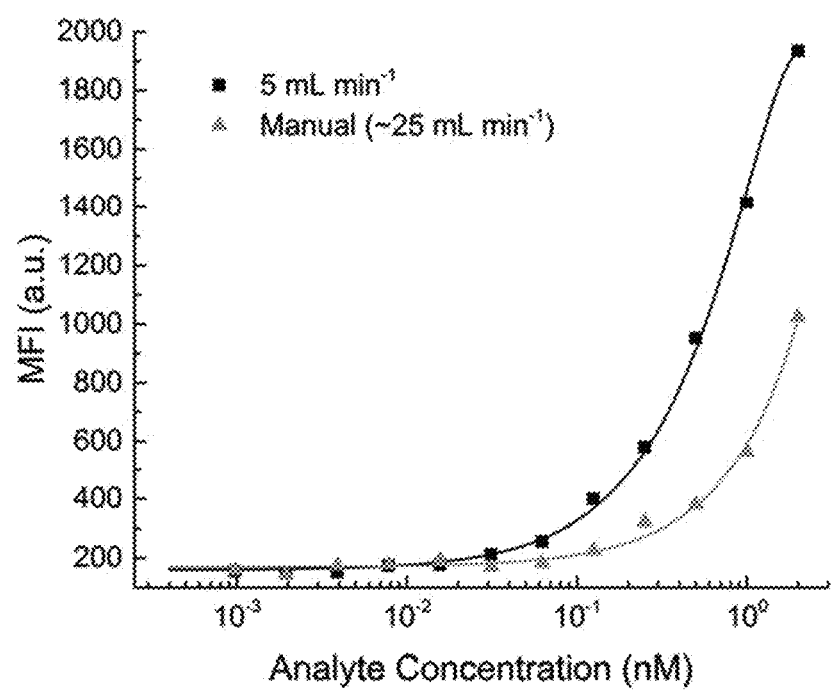

FIG. 89 shows a representative manual titration curve using streptavidin-eosin as the soluble analyte. Samples were processed for 20 recirculations each. Each data point represents a single assay replicate. Manual samples were processed at a flow rate that could be sustained without physical discomfort (~25 mL min-1). Samples were exposed for 1000 ms using a TXRED®-4040C filter set. Streptavidin-eosin was prepared as described in Reference 3.

Figure 90:
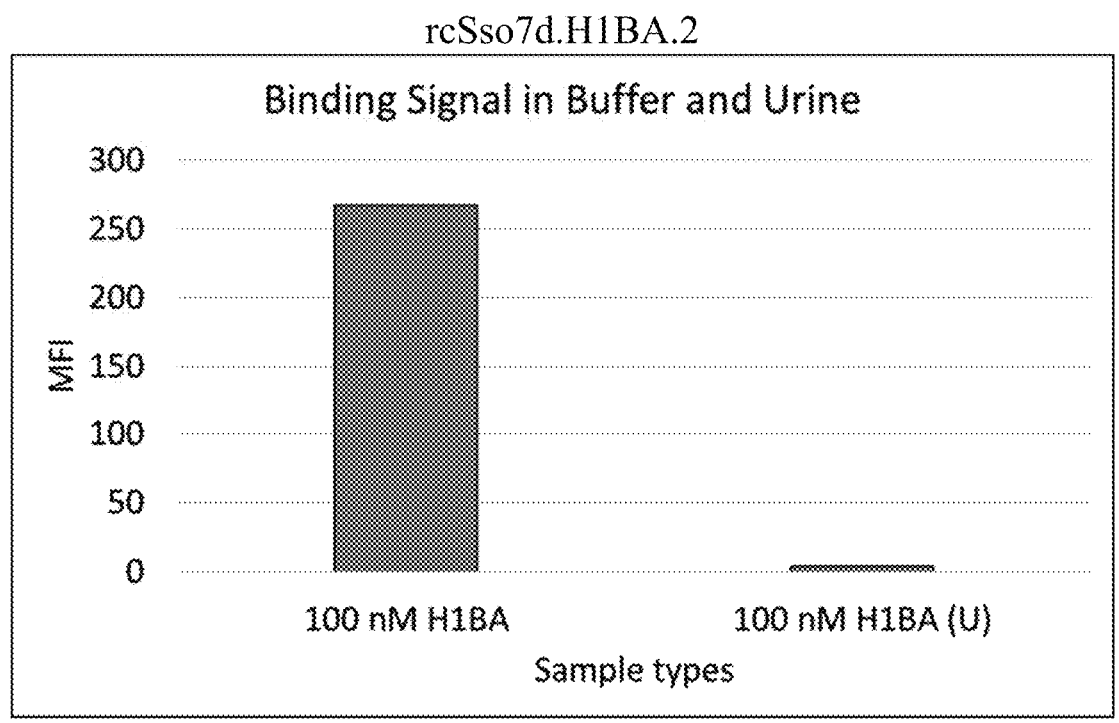

FIG. 90 shows the binding activity of rcSso7d.H1BA.2 binder against urine-treated analytes, quantified using the geometric mean fluorescence intensity, rather than population proportions.

Figure 91:
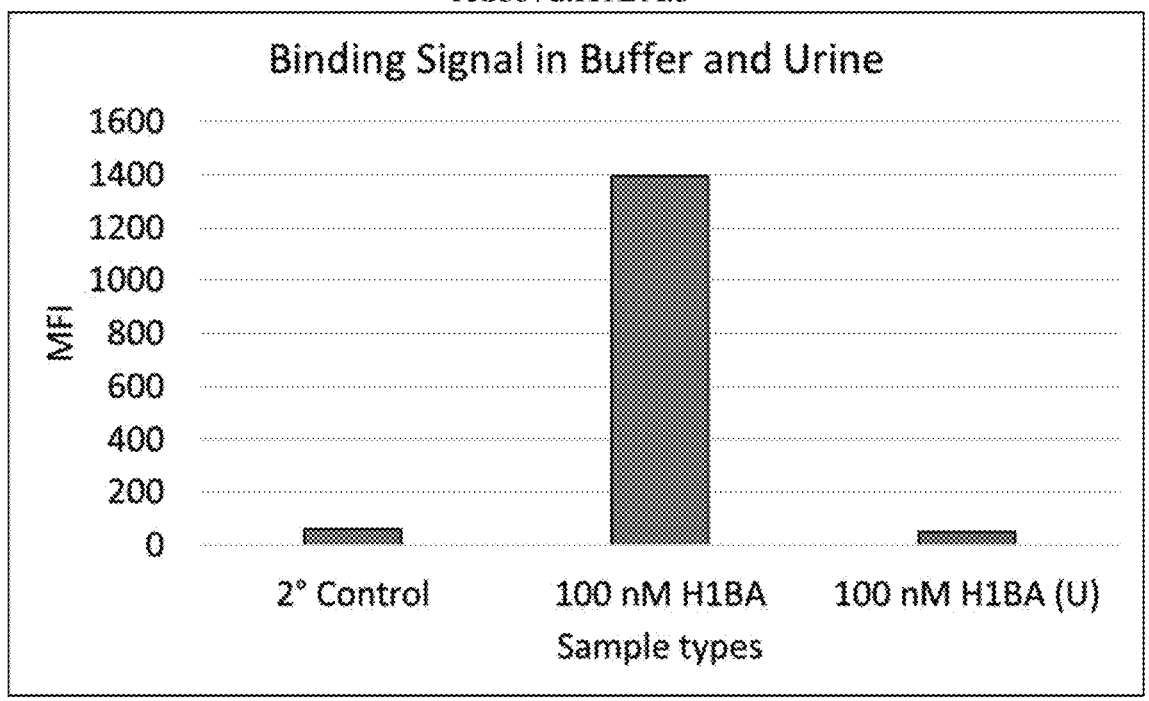

FIG. 91 shows the binding activity of rcSso7d.H1BA.3 binder against urine-treated analytes, quantified using the geometric mean fluorescence intensity, rather than population proportions.

Figure 92:
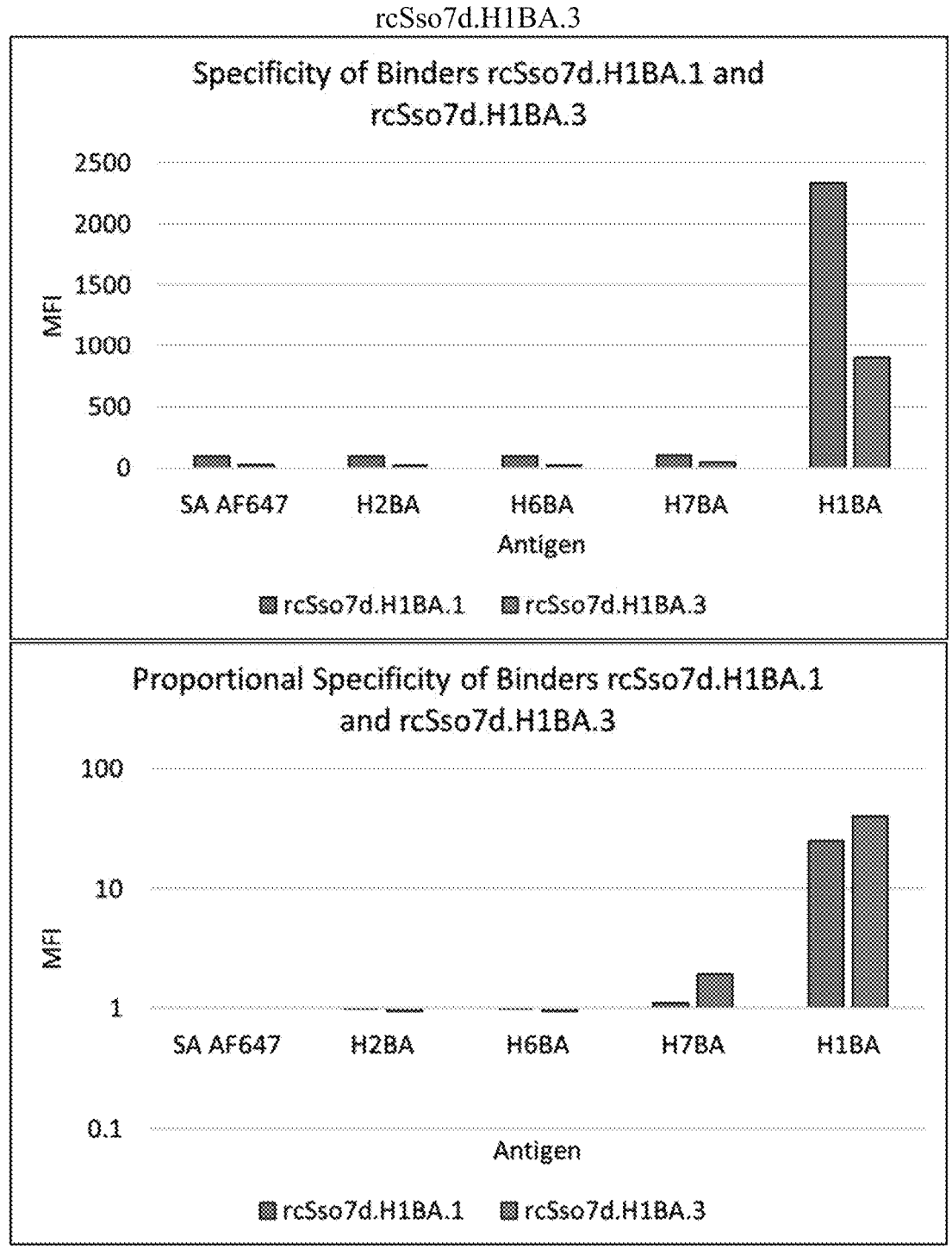

FIG. 92 shows the specificity and proportional specificity of binders rcSso7d.H1BA.1 and rcSso7d.H1BA.3.

Figure 93:
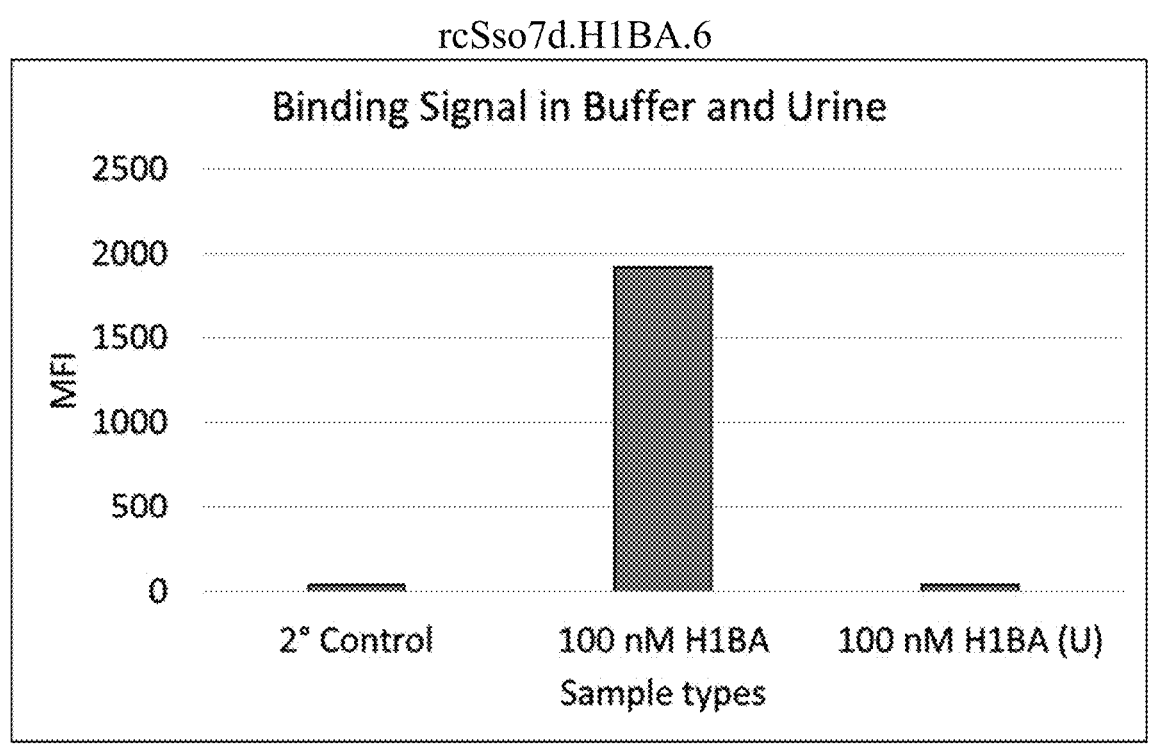

FIG. 93 shows the binding activity of rcSso7d.H1BA.6 binder against urine-treated analytes, quantified using the geometric mean fluorescence intensity, rather than population proportions.

Figure 94:
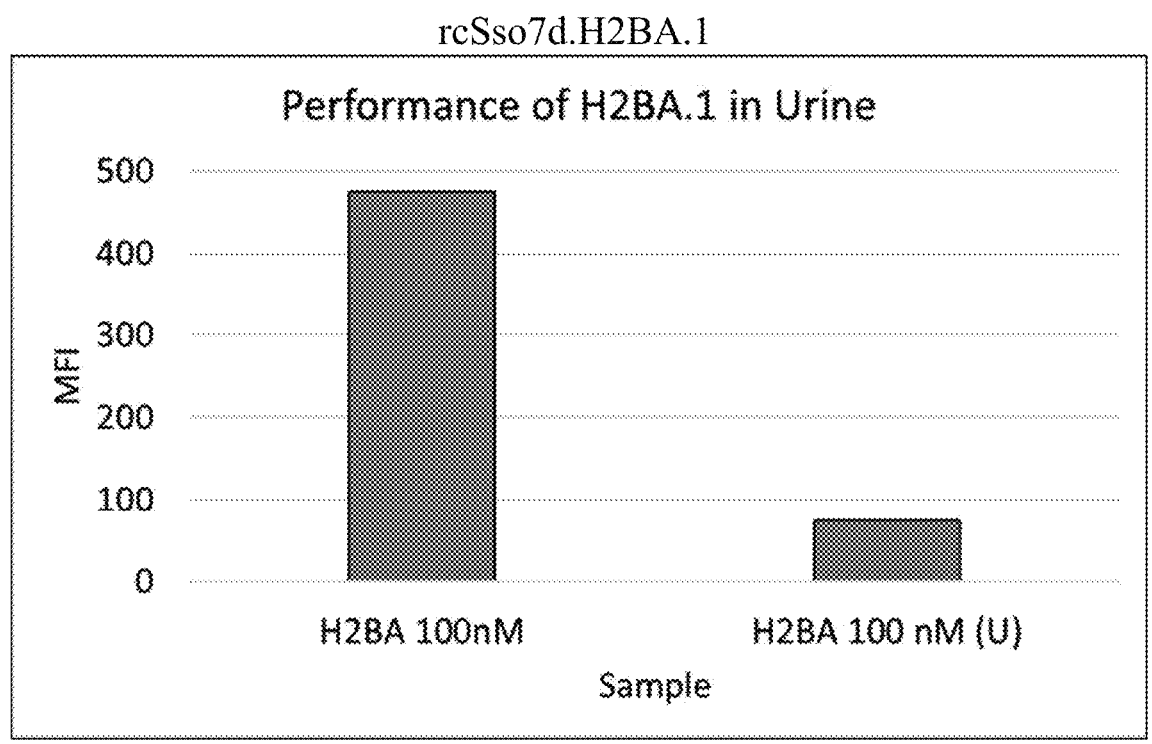

FIG. 94 shows the binding activity of rcSso7d.H2BA.1 binder against urine-treated analytes, quantified using the geometric mean fluorescence intensity, rather than population proportions.

Figure 95A:
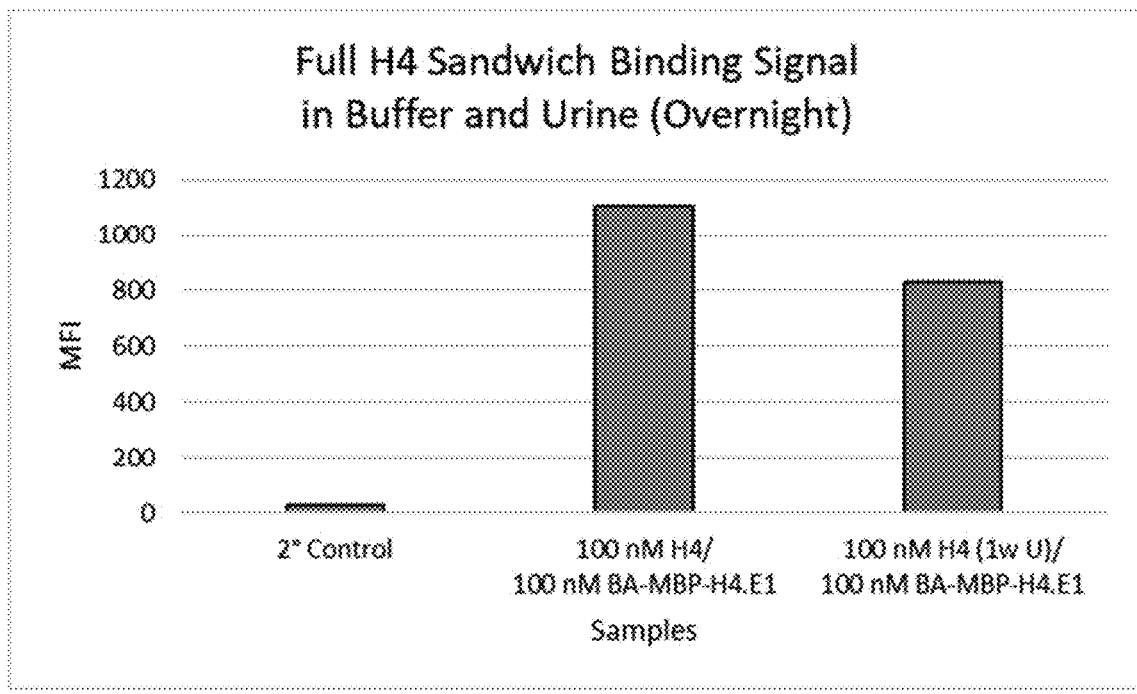
Figure 95B:
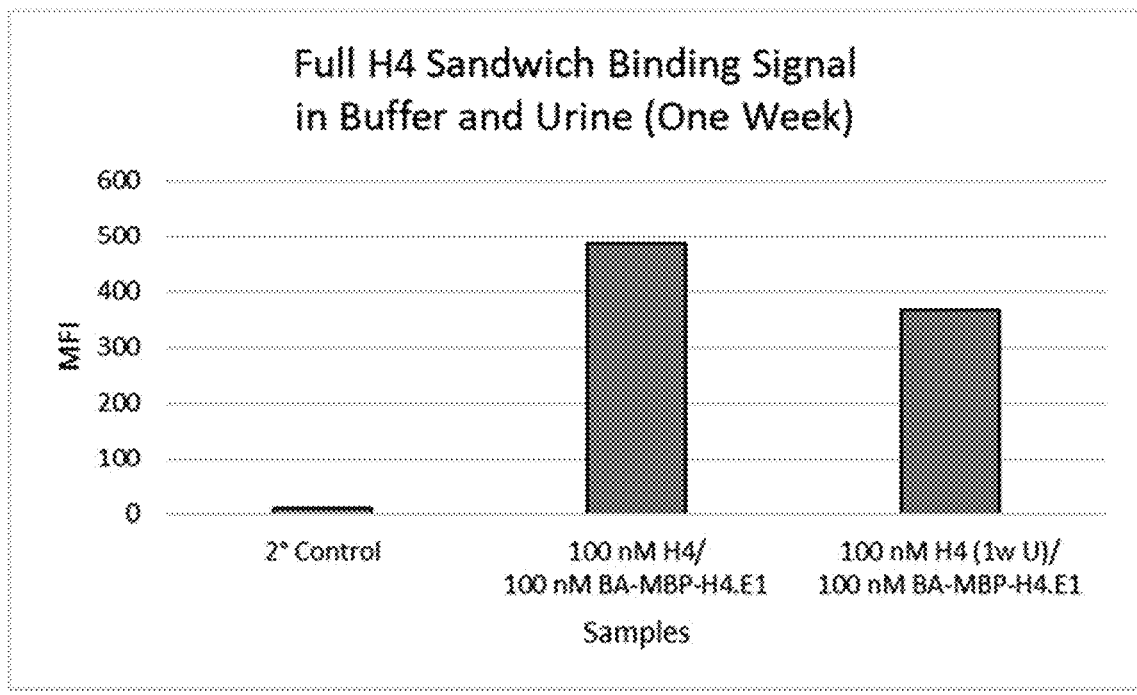

FIGS. 95A-95B show H4 full sandwich performance, overnight urine (FIG. 95A), and 1 week urine (FIG. 95B), against urine-treated analytes, quantified using the geometric mean fluorescence intensity, rather than population proportions.

Figure 96:
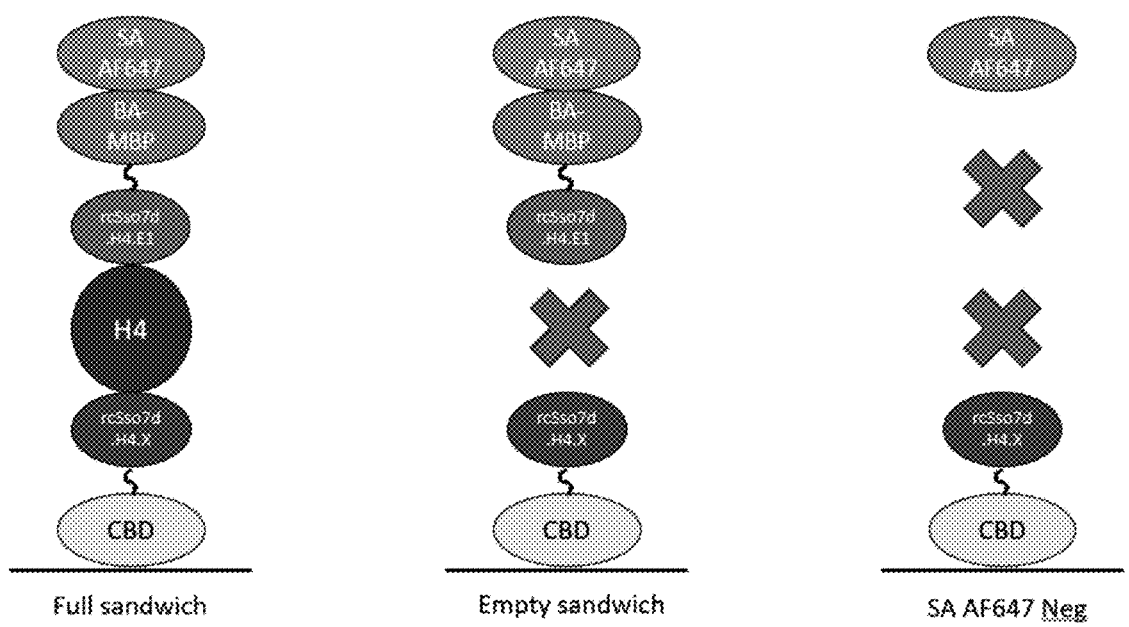

FIG. 96 is a schematic of H4 sandwich assays.

Figure 97:
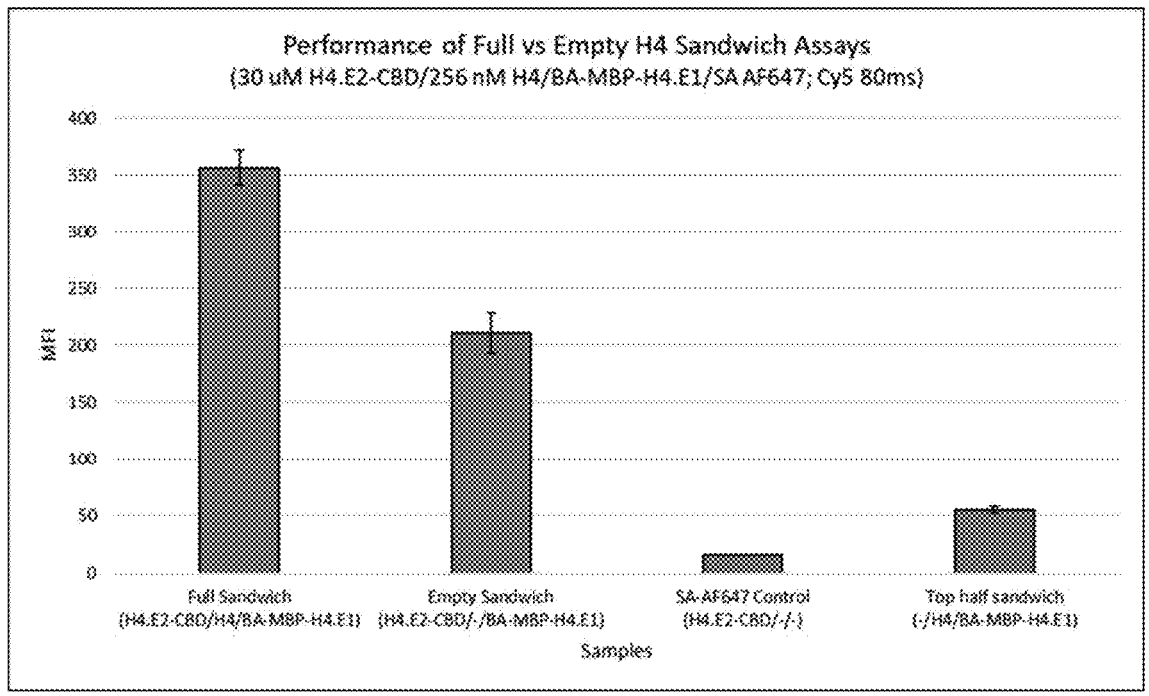

FIG. 97 shows the performance of full vs. empty H4 sandwich assays. BA-MBP-rcSso7d.H4.1 and rcSso7d.H4.2-CBD yield full sandwich.

Figure 98:
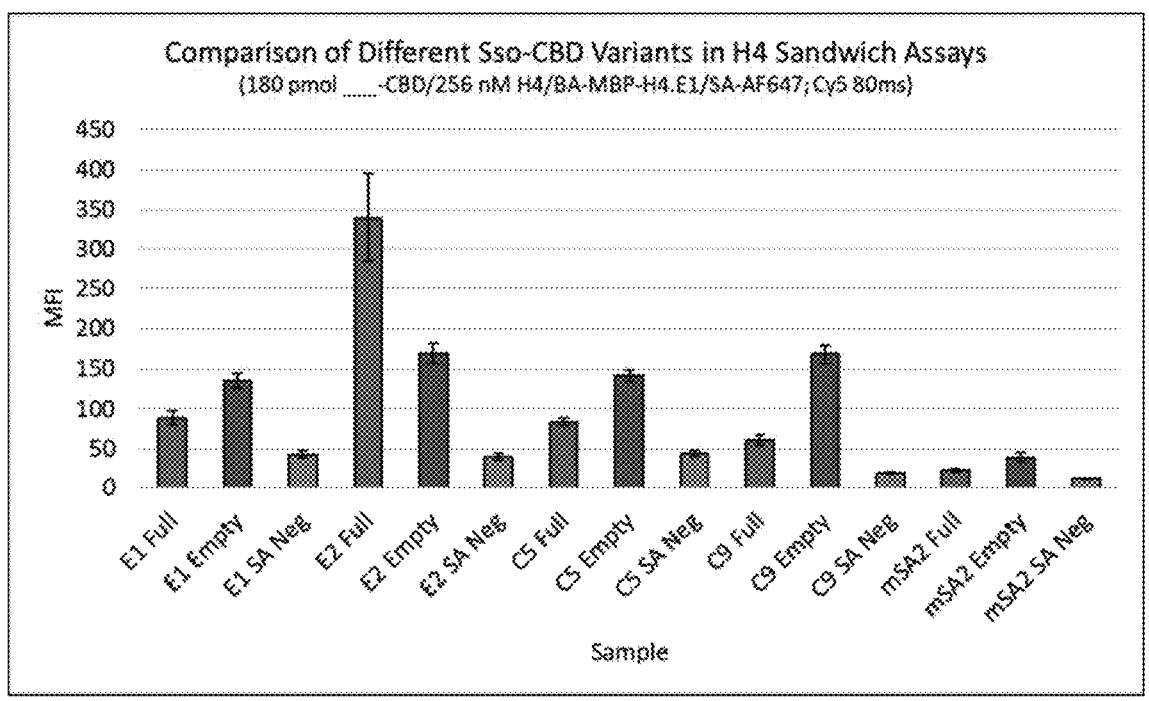

FIG. 98 shows a comparison of different Sso-CBD Variants in H4 sandwich assays. Only rcSso7d.H4.2-CBD yields full sandwich performance.

Figure 99:
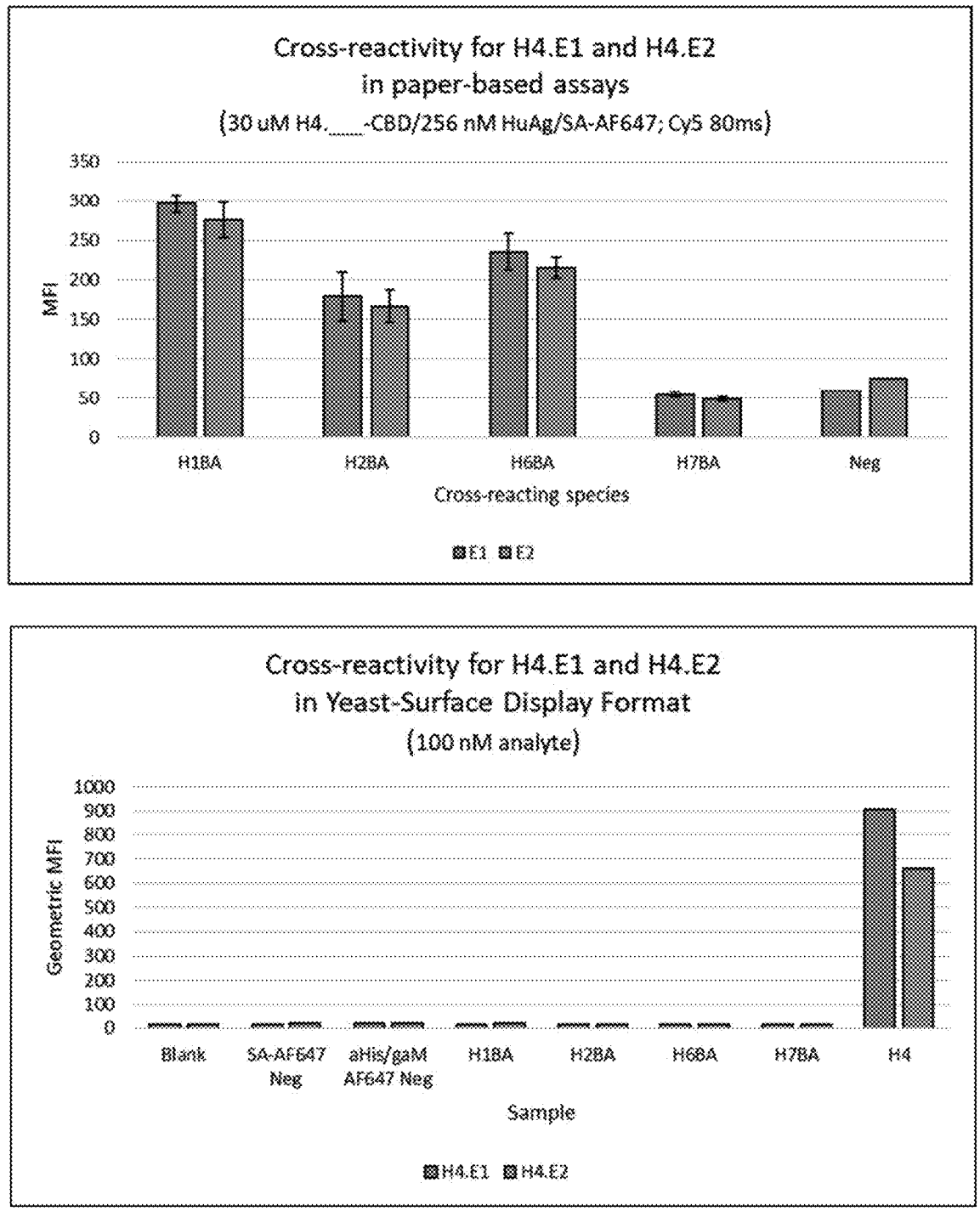

FIG. 99 shows cross-reactivity for H4.E1 and H4.E2 in paper-based assays and in yeast-surface display format.

Figure 100:
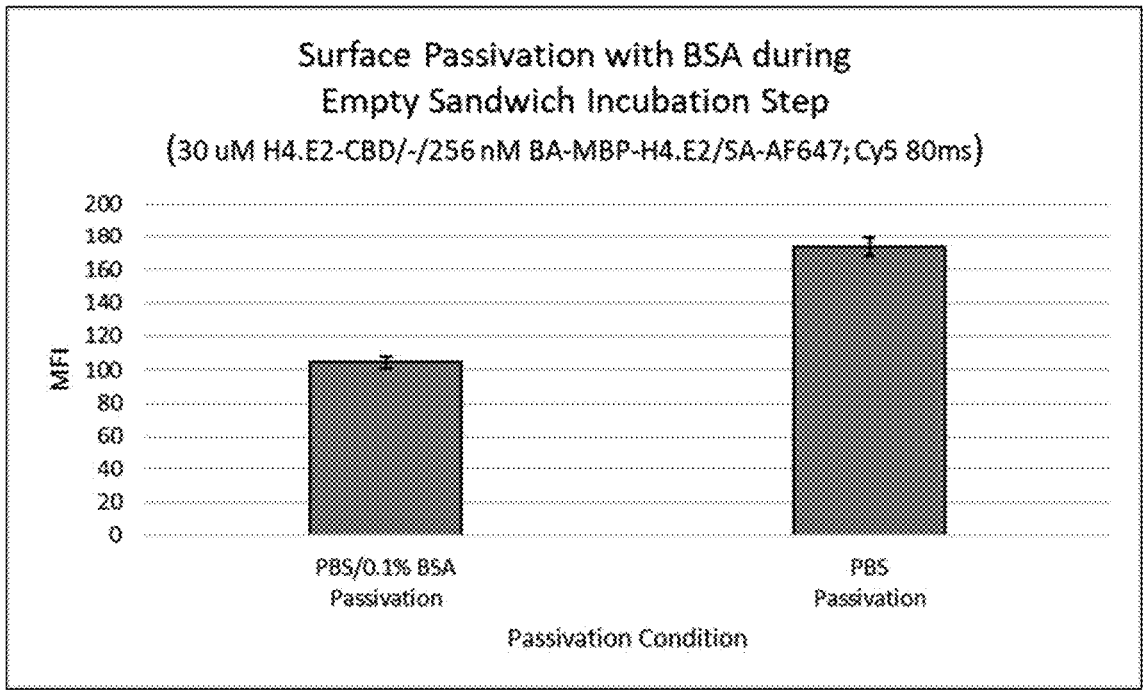

FIG. 100 shows the reduction of nonspecific binding via BSA passivation.

Figure 101:
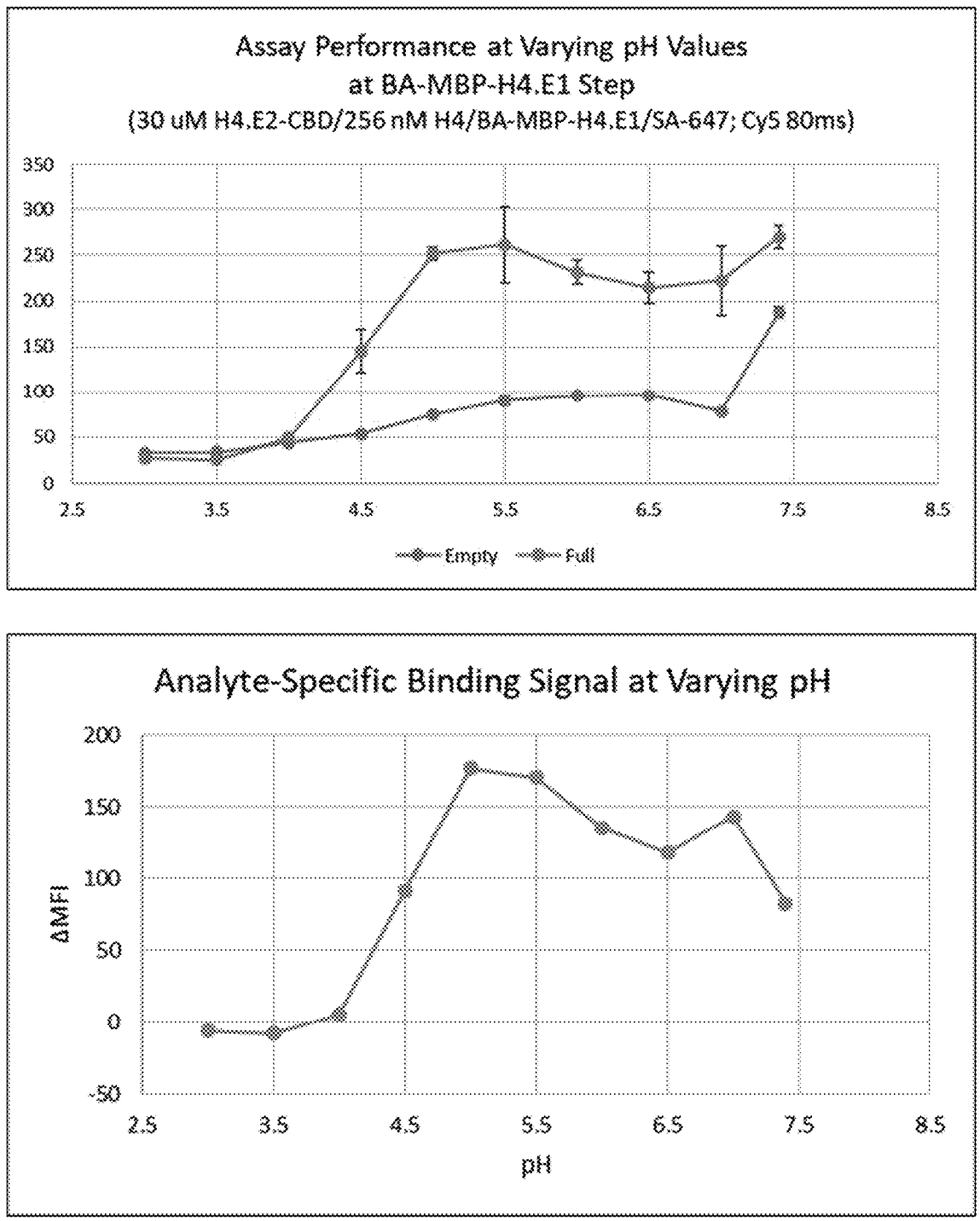

FIG. 101 shows assay performance and analyte-specific binding signal at varying pH values. The results indicate the reduction of non-specific detection reagent binding at pH 5.

Figure 102:
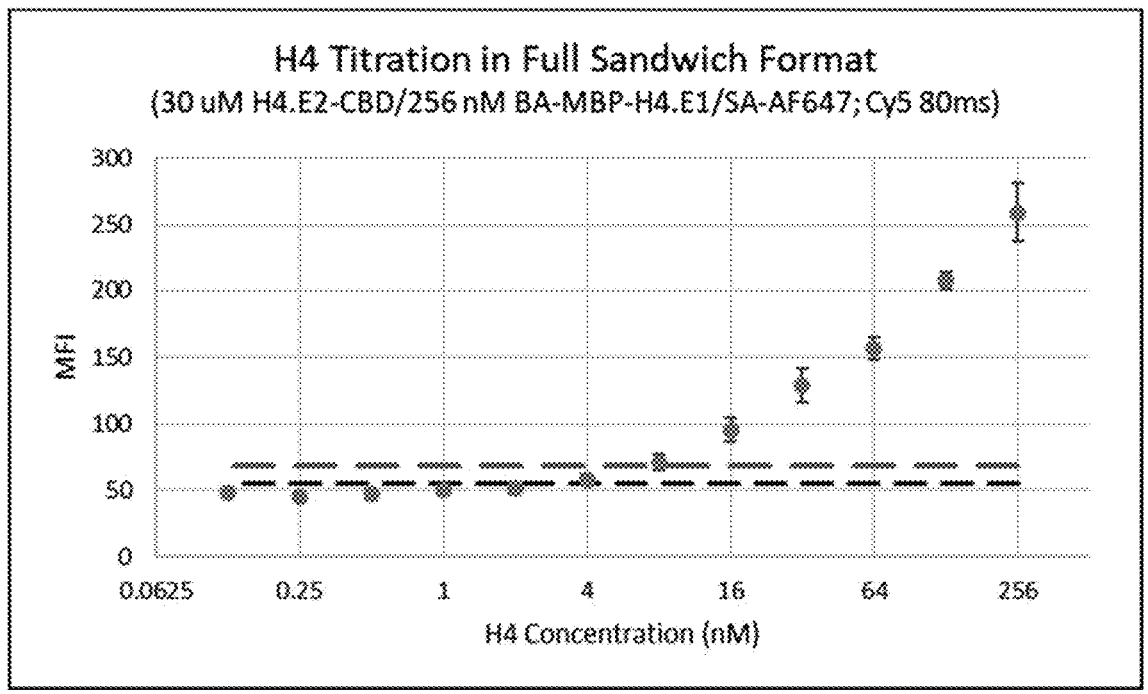

FIG. 102 depicts that H4 titration in full sandwich format with pH 5 wash shows LOD of 8 nM.

Figure 103:
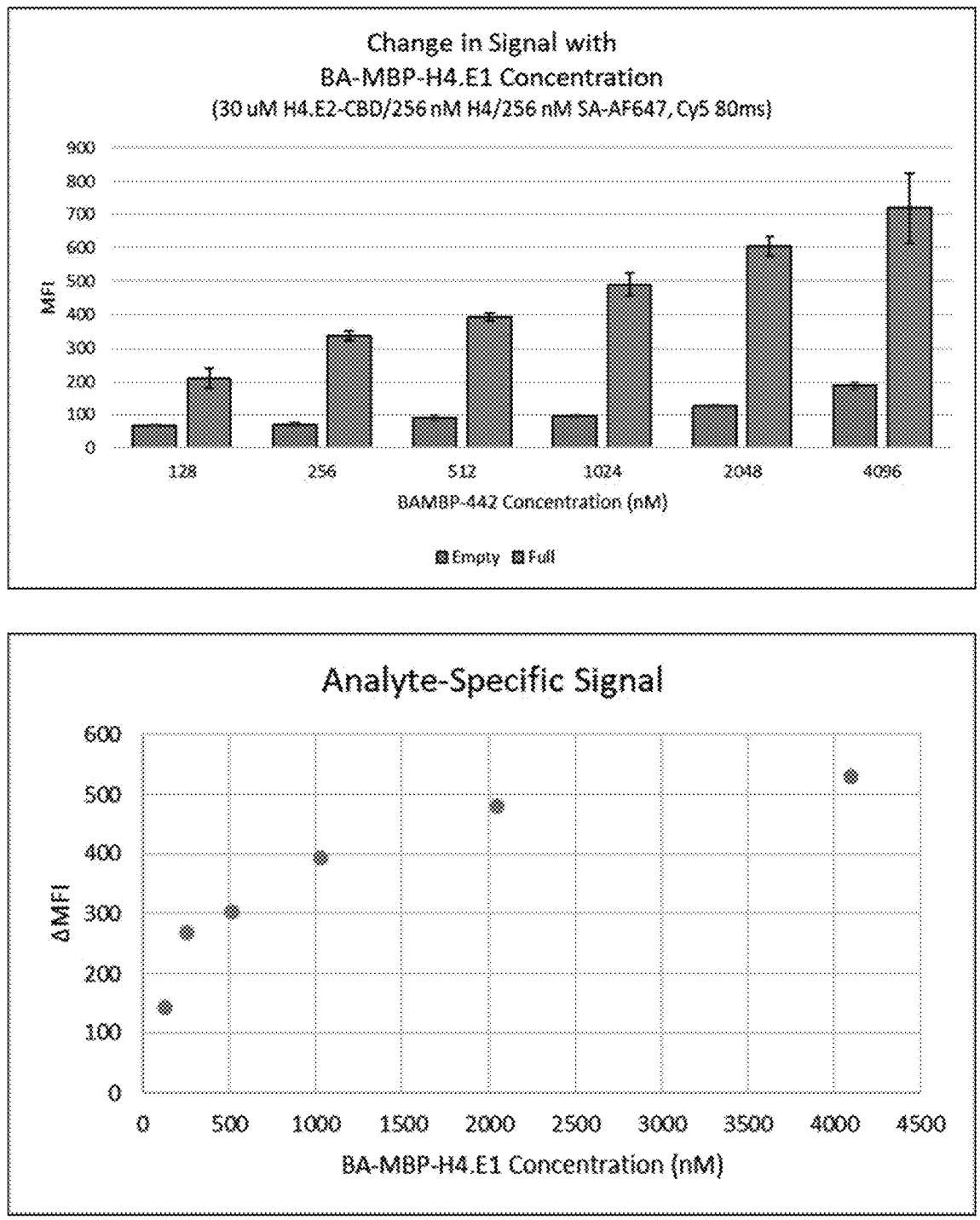

FIG. 103 shows change in signal with BA-MBP-H4.E1 concentration, and analyte-specific signal. The results show that increased signal was observed with increased BA-MBP-H4.1 concentration.

DETAILED DESCRIPTION

According to the law of mass action, the stoichiometry and kinetics of a target-binding interaction can be favorably influenced via three general approaches: i) increasing the molar abundance and concentration of the soluble antigen, ii) increasing the abundance and concentration of its surface-immobilized binding partner, or iii) enhancing the affinity of this binding interaction under relevant assay conditions. (Esteban et al., 2013) These guiding principles have been borne out in numerous experimental studies, which have demonstrated the advantageous impact of antigen pre-concentration (Ahmed et al., 2016; Giri et al., 2016; Tang et al., 2016) and enhanced binding affinity (Kaastrup et al., 2013; Ricci et al., 2016) upon target capture and assay sensitivity.

Previous studies have also explored the impact of the abundance of the surface-immobilized binding species upon the sensitivity of analyte detection. (Esteban et al., 2013; Parsa et al., 2008; Peluso et al., 2003) However, while these studies confirmed improved diagnostic sensitivity for assays conducted at a higher abundance of immobilized binder, only modest densities of surface-bound species (e.g., picomoles/cm$^2$) were achieved, and the target analyte was in molar excess of the immobilized binders. The implications of operating within the true target-depletion regime, wherein the binding protein is present in significant molar excess of the analyte, have not been thoroughly investigated.

In order to explore the consequences of enhanced binder immobilization upon target capture efficiency, a simplified binding model has been developed which employs a pseudo first-order rate constant (PFORC) to describe the antigen-binding interaction. This PFORC assumes a significant molar excess of the immobilized binding species, such that the abundance of available binder is effectively undiminished by the capture of soluble antigen. These modeling results indicate that within this high-abundance adsorption regime, the target antigen is rapidly and efficiently depleted from solution. Furthermore, this model suggests that at a large molar excess, the affinity of the immobilized binder has little effect upon the capture efficiency—so long as the local concentration of surface-bound species is at least ten-fold higher than the dissociation constant ($K_D$), the binding reaction will proceed to near-completion. Thus, if this molar excess can be achieved, protein engineering efforts need not be invested into the affinity maturation of selected binders—depending on the specific immobilized abundance, a modest binding affinity in the high nanomolar or even low micromolar range could be sufficient for efficient target capture.

Figure 1:
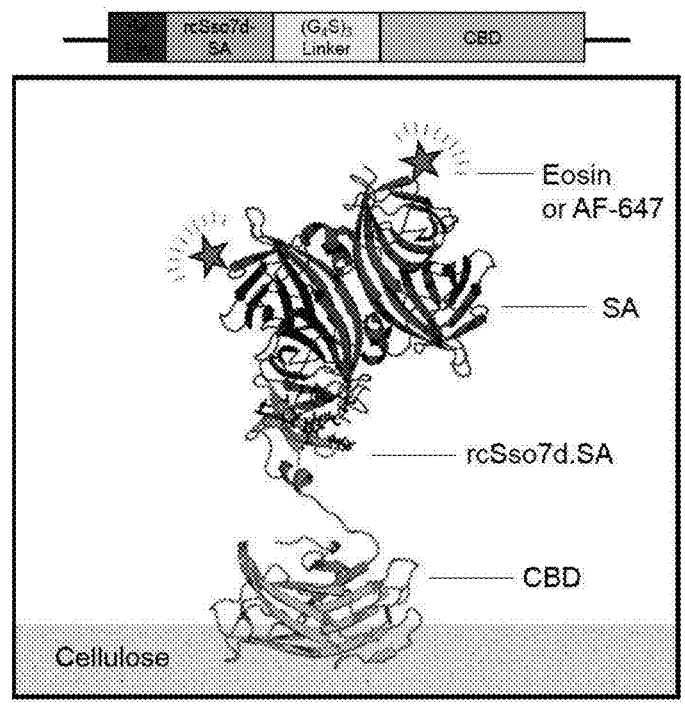
FIG. 1. Schematic representation of the rcSso7d.SA-CBD genetic construct, and the relevant binding complexes for this immunoassay format. CBD: cellulose binding domain; rcSso7d: reduced charge protein Sso7d from *Sulfolobus solfataricus*; SA: streptavidin; AF-647: ALEXA FLUOR® 647. PDB Structures: 4JO5 (CBD); (Yaniv et al., 2013) 1SSO (Sso7d); (Baumann et al., 1994) 1MEP (SA). (Hyre et al., 2006) FIGS. 2A-2B. Comparison of analytical solution and PFORC model results.

The predictions of this PFORC model were validated experimentally using a bifunctional fusion protein construct that combines a Type 3a cellulose-binding domain (CBD) with a modular binding scaffold based on the thermostable rcSso7d protein (Miller et al., 2016; Traxlmayr et al., 2016) (FIG. 1). Previous studies have demonstrated the use of CBD fusion proteins for the bio-functionalization of cellulose substrates, in applications including protein purification, (Sugimoto et al., 2012; Tomme et al., 1998) textile manufacturing, (Levy and Shoseyov, 2002) and immunoassay development. (Dai et al., 2016; Holstein et al., 2016; Hussack et al., 2009; Kim et al., 2013) These studies have indicated that this CBD species adsorbs to cellulose in molar quantities which, in a standard diagnostic context, would yield a significant excess of immobilized protein relative to the soluble target. (Dai et al., 2016; Li et al., 2016) The experimental studies have confirmed that the use of this substrate-anchoring domain in a paper-based assay format permits the rapid and oriented adsorption of the antigen-binding protein (e.g., engineered reduced charge rcSso7d) on un-modified chromatography paper (e.g., WHATMAN® Grade 1 Qualitative Filtration Paper) in sufficient abundance to completely capture all of the antigen from solution and thereby deplete the antigen from the solution. In some embodiments, up to 0.5 nanomoles of antigen from solution were captured, thereby depleting all antigen from 10 µL of a 50 µM solution. For the sample volumes and antigen concentrations observed in typical diagnostic assays (i.e. microliters, and concentrations in the picomolar to low nanomolar range), this antigen-binding protein abundance may represent greater than a 1000-fold molar excess relative to the soluble target. The high local concentration of this immobilized CBD fusion protein within the paper substrate (~760 µM) also increases the rate of target capture, biasing the binding equilibrium toward the rapid depletion of the dilute antigen from solution. At this molar abundance, target antigens are captured from solution with nearly 100% efficiency, maximizing the attainable sensitivity for any given diagnostic system.

This surface-anchoring approach can be adapted to any substrate for which there is a known anchoring moiety, so long as the given bulk material features sufficient accessible surface area for the high-abundance immobilization of the binding construct, and is also structured so as to facilitate efficient transport of the antigen to the surface. For instance, solid-binding peptides have been used to immobilize biomolecules to a variety of substrates, ranging from metals and metal oxides to plastics, minerals, semiconductors, and carbon-based materials. (Care et al., 2017, 2015; Kumada, 2014; Seker and Demir, 2011) This strategy can also be extended to any immobilized target or class of binding domain which can interact with or be expressed as a genetic fusion to this anchoring moiety (e.g. antigens, antibodies and antibody fragments, non-antibody binding scaffolds, DNA oligonucleotides and aptamers, etc.). (Holstein et al., 2016; Hussack et al., 2009; Rosa et al., 2014).

Lastly, this system has also been shown to be generalizable across varying soluble targets—the enhanced capture efficiency of the rcSso7d-CBD fusion protein was confirmed using two different engineered rcSso7d antigen-binding protein variants. One engineered rcSso7d antigen-binding protein variant was raised against the 52.8-kDa model antigen streptavidin and attached to CBD (rcSso7d.SA-CBD). Thus, the rcSso7d.SA-CBD fusion protein contains a motif (e.g., amino acid sequence) that binds to or recognizes streptavidin. Another engineered rcSso7d antigen-binding protein variant was raised against the 33.1-kDa urine-based biomarker of active tuberculosis, Rv1656 (Napolitano et al., 2008) and attached to CBD (rcSso7d.Rv1656-CBD). Thus, the rcSso7d.Rv1656-CBD fusion protein contains a motif (e.g., amino acid sequence) that binds to or recognizes the antigen Rv1656.

Accordingly, aspects of the present disclosure relate to the development of a general strategy to enhance the capture of a target, such as a target molecule or antigen of interest, using a bifunctional fusion protein which includes an antigen-binding protein or antigen-binding domain and a substrate-anchoring domain, such as a cellulose binding domain (CBD) or a carbohydrate binding module (CBM).

Bifunctional Fusion Proteins

In some aspects, provided herein is a bifunctional fusion protein that incorporates a substrate-anchoring domain and a target-binding domain, such as an antigen-binding protein or an antigen-binding domain. In some embodiments, the substrate-anchoring domain is a CBM or CBD. In some embodiments the CBM has carbohydrate-binding activity. In some embodiments, the CBM is CBM1, CBM2, CBM3, CBM4, CBM5, CBM6, CBM9, CBM10, CBM11, CBM12, CBM14, CBM15, CBM17, CBM18, CBM19, CBM20, CBM21, CBM25, CBM27, CBM28, CBM32, CBM33, CBM48, or CBM49. The nucleic acid and amino acid sequences of CBMs contemplated herein have been described, such as those disclosed in www.cazypedia.org/index.php/Carbohydrate-binding_modules, and can be readily identified by one of ordinary skill in the art using a BLAST search.

In some embodiments, the substrate-anchoring domain is a CBD. Orthologs of CBDs have been described in various species, including, but not limited to *Micromonospora mirobrigensis* (GenBank ID: SCF42127.1), *Mycobacterium tuberculosis* (GenBank ID: CNE10097.1), *Micromonospora nigra* (GenBank ID: SCL15442.1), *Micromonospora mirobrigensis* (GenBank ID: SCF04121.1), *Cellulomonas Fimi* (PDB: 1EXH_A), *Mycobacterium kansasii* 732 (GenBank: EUA13076.1), *Ruminococcus albus* 8 (GenBank: EGC02462.1), *Leifsonia aquatic* (NCBI Reference Sequence: WP_021763186.1), *Schizosaccharomyces pombe* (NCBI Reference Sequence: NP_593986.1), *Desulfitobacterium hafniense* (GenBank: CDX04743.1). CBDs expressed in other species that are known to one of ordinary skill in the art, such as CBDs of families I, II, III and IV disclosed, for instance, in Tomme et al., *J Chromatogr B Biomed Sci Appl* (1998) 715(1):283-96, are also contemplated herein.

Different types of CBDs are also contemplated herein. In some embodiments, a type 1 CBD is contemplated herein and serves as the substrate-anchoring domain of a bifunctional fusion protein described herein. In some embodiments, the type 1 CBD is identified by SEQ ID NO: 10.

Amino acid sequence of type 1 CBD (SEQ ID NO: 10)

```
                                                 (SEQ ID NO: 10)
AGPGANPPGTTTTSRPATTTGSSPGPQACSSVWGQCGGQNWSGPTCCASG

STCVYSNDYYSQCLPGANPPGTTTTSRPATTTGSSPGPTQSHYGQCGGIG

YSGPTVCASGTTCQVLNPYYSQCL
```

Orthologs of type 1 CBDs have been described in various species, including, but not limited to *Trichoderma reesei* QM6a (NCBI Reference Sequence: XP_006969224.1); *Rhizopus oryzae* (GenBank: BAC53988.1); *Schizosaccharomyces japonicus* yFS275 (NCBI Reference Sequence: XP_002172247.1); *Trichoderma virens* Gv29-8 (NCBI Reference Sequence: XP_013954979.1); *Trichoderma viride* (GenBank: CAA37878.1) are also contemplated herein. Type 1 CBDs or orthologs thereof in other species known to one of ordinary skill in the art are also contemplated herein.

In some embodiments, a type 3a CBD is contemplated herein and serves as the substrate-anchoring domain of a bifunctional fusion protein described herein. In some embodiments, the type 3a CBD is a domain of the CipA protein from *Clostridium thermocellum* (Genbank: HF912725.1; UniProtKB/TrEMBL: N1JW75)

Amino acid sequence of CipA protein from *Clostridium thermocellum* (SEQ ID NO: 1)

```
                                                  (SEQ ID NO: 1)
MRKVISMLLV VAMLTTIFAA MIPQTVSAAT MTVEIGKVTA

AVGSKVEIPI TLKGVPSKGM ANCDFVLGYD PNVLEVTEVK

PGSIIKDPDP SKSFDSAIYP DRKMIVFLFA EDSGRGTYAI

TQDGVFATIV ATVKSAAAAP ITLLEVGAFA DNDLVEISTT

FVAGGVNLGS SVPTTQPNVP SDGVVVEIGK VTGSVGTTVE

IPVYFRGVPS KGIANCDFVF RYDPNVLEII GIDPGDIIVD

PNPTKSFDTA IYPDRKIIVF LFAEDSGTGA YAITKDGVFA

KIRATVKSSA PGYITFDEVG GFADNDLVEQ KVSFIDGGVN

VGNATPTKGA TPTNTATPTK SATATPTRPS VPTNTPTNTP

ANTPVSGNLK VEFYNSNPSD TTNSINPQFK VTNTGSSAID

LSKLTLRYYY TVDGQKDQTF WCDHAAIIGS NGSYNGVTSN

VKGTFVKMSS STNNADTYLE ISFTGGTLEP GAHVQIQGRF

AKNDWSNYTQ SNDYSFKSAS QFVEWDQVTA YLNGVLVWGK

EPGGSVVPST QPVTTPPATT KPPATTIPPS DDPNAIKIKV

DTVNAKPGDT VNIPVRFSGI PSKGIANCDF VYSYDPNVLE

IIEIKPGELI VDPNPDKSFD TAVYPDRKII VFLFAEDSGT

GAYAITKDGV FATIVAKVKS GAPNGLSVIK FVEVGGFANN

DLVEQKTQFS DGGVNVGGTT VPTTPPASTT PTDDPNAIKI

KVDTVNAKPG DTVNIPVRFS GIPSKGIANC DFVYSYDPNV

LEIIEIKPGE LIVDPNPDKS FDTAVYPDRK IIVFLLTEDS

GTGAYAITKD GVFATIVAKV KSGAPNGLSV IKFVEVGGFA

NNDLVEQKTQ FFDGGVNVGD TTVPTTPTTP VTTPTDDPNA
```

```
VRIKVDTVNA KTGDTVRIPV RFSGIPSKGI ANCDFVYSYD

PNVLEIIEIE PGDIIVDPNP DKSFDTAVYP DRKIIVFLFA

EDSGTGAYAI TKDGVFATIV AKVKSGAPNG LSVIKFVEVG

GFANNDLVEQ KTQFFDGGVN VGDTTEPATP TTPVTTPTTT

DGLDAVRIKV DTVNAKPGDT VRIPVRFSGI PSKGIANCDF

VYSYDPNVLE IIEIEPGDII VDPNPDKSFD TAVYPDRKII

VFLFAEDSGT GAYAITKDGV FATIVAKVKS GAPNGLSVIK

FVEVGGFANN DLVEQRTQFF DGGVNVGDTT VPTTPTTPVT

TPTDDSNAVR IKVDTVNAKP GDTVRIPVRF SGIPSKGIAN

CDFVYSYDPN VLEIIEIEPG DIIVDPNPDK SFDTAVYPDR

KIIVFLFAED SGTGAYAITK DGVFATIVAK VKSGAPNGLS

VIKFVEVGGF ANNDLVEQKT QFFDGGVNVG DTTVPTTSPT

TTPPEPTIAP NKLTLKIGRA EGRPGDTVEI PVNLYGVPQK

GIASGDFVVS YDPNVLEIIE IEPGELIVDP NPTKSFDTAV

YPDRKMIVFL FAEDSGTGAY AITEDGVFAT IVAKVKEGAP

EGFSAIEISE FGAFADNDLV EVETDLINGG VLVTNKTVIE

GYKVSGYILP DFSFDATVAP LVKAGFKVEI VGTELYAVTD

ANGYFEITGV PANASGYTLK ISRATYLDRV IANVVVTGDT

SVSTSQAPIM MWVGDIVKDN SINLLDVAEV IRCFNATKGS

ANYVEELDIN RNGAINMQDI MIVHKHFGAT SSDY
```

In some embodiments, the underlined valine (V) residue of SEQ ID NO: 1 is an isoleucine (I), which corresponds to SEQ ID NO: 15.

Amino acid sequence of CipA protein from *Clostridium thermocellum* with an isoleucine in place of a valine (SEQ ID NO:15)

```
                                                 (SEQ ID NO: 15)
MRKVISMLLV VAMLTTIFAA MIPQTVSAAT MTVEIGKVTA

AVGSKVEIPI TLKGVPSKGM ANCDFVLGYD PNVLEVTEVK

PGSIIKDPDP SKSFDSAIYP DRKMIVFLFA EDSGRGTYAI

TQDGVFATIV ATVKSAAAAP ITLLEVGAFA DNDLVEISTT

FVAGGVNLGS SVPTTQPNVP SDGVVVEIGK VTGSVGTTVE

IPVYFRGVPS KGIANCDFVF RYDPNVLEII GIDPGDIIVD

PNPTKSFDTA IYPDRKIIVF LFAEDSGTGA YAITKDGVFA

KIRATVKSSA PGYITFDEVG GFADNDLVEQ KVSFIDGGVN

VGNATPTKGA TPTNTATPTK SATATPTRPS VPTNTPTNTP

ANTPVSGNLK VEFYNSNPSD TTNSINPQFK VTNTGSSAID

LSKLTLRYYY TVDGQKDQTF WCDHAAIIGS NGSYNGITSN

VKGTFVKMSS STNNADTYLE ISFTGGTLEP GAHVQIQGRF

AKNDWSNYTQ SNDYSFKSAS QFVEWDQVTA YLNGVLVWGK

EPGGSVVPST QPVTTPPATT KPPATTIPPS DDPNAIKIKV

DTVNAKPGDT VNIPVRFSGI PSKGIANCDF VYSYDPNVLE
```

-continued

IIEIKPGELI VDPNPDKSFD TAVYPDRKII VFLFAEDSGT

GAYAITKDGV FATIVAKVKS GAPNGLSVIK FVEVGGFANN

DLVEQKTQFS DGGVNVGGTT VPTTPPASTT PTDDPNAIKI

KVDTVNAKPG DTVNIPVRFS GIPSKGIANC DFVYSYDPNV

LEIIEIKPGE LIVDPNPDKS FDTAVYPDRK IIVFLLTEDS

GTGAYAITKD GVFATIVAKV KSGAPNGLSV IKFVEVGGFA

NNDLVEQKTQ FFDGGVNVGD TTVPTTPTTP VTTPTDDPNA

VRIKVDTVNA KTGDTVRIPV RFSGIPSKGI ANCDFVYSYD

PNVLEIIEIE PGDIIVDPNP DKSFDTAVYP DRKIIVFLFA

EDSGTGAYAI TKDGVFATIV AKVKSGAPNG LSVIKFVEVG

GFANNDLVEQ KTQFFDGGVN VGDTTEPATP TTPVTTPTTT

DGLDAVRIKV DTVNAKPGDT VRIPVRFSGI PSKGIANCDF

VYSYDPNVLE IIEIEPGDII VDPNPDKSFD TAVYPDRKII

VFLFAEDSGT GAYAITKDGV FATIVAKVKS GAPNGLSVIK

FVEVGGFANN DLVEQRTQFF DGGVNVGDTT VPTTPTTPVT

TPTDDSNAVR IKVDTVNAKP GDTVRIPVRF SGIPSKGIAN

CDFVYSYDPN VLEIIEIEPG DIIVDPNPDK SFDTAVYPDR

KIIVFLFAED SGTGAYAITK DGVFATIVAK VKSGAPNGLS

VIKFVEVGGF ANNDLVEQKT QFFDGGVNVG DTTVPTTSPT

TTPPEPTIAP NKLTLKIGRA EGRPGDTVEI PVNLYGVPQK

GIASGDFVVS YDPNVLEIIE IEPGELIVDP NPTKSFDTAV

YPDRKMIVFL FAEDSGTGAY AITEDGVFAT IVAKVKEGAP

EGFSAIEISE FGAFADNDLV EVETDLINGG VLVTNKTVIE

GYKVSGYILP DFSFDATVAP LVKAGFKVEI VGTELYAVTD

ANGYFEITGV PANASGYTLK ISRATYLDRV IANVVVTGDT

SVSTSQAPIM MWVGDIVKDN SINLLDVAEV IRCFNATKGS

ANYVEELDIN RNGAINMQDI MIVHKHFGAT SSDY

The amino acid sequence of the type 3a CBD of CipA protein from *Clostridium thermocellum*, which corresponds to amino acids 364-522 of the CipA protein from *Clostridium thermocellum* corresponds to SEQ ID NO: 2.

(SEQ ID NO: 2)

PVSGNLK VEFYNSNPSD TTNSINPQFK VTNTGSSAID

LSKLTLRYYY TVDGQKDQTF WCDHAAIIGS NGSYNGVTSN

VKGTFVKMSS STNNADTYLE ISFTGGTLEP GAHVQIQGRF

AKNDWSNYTQ SNDYSFKSAS QFVEWDQVTA YLNGVLVWGK EP

In some embodiments, the underlined valine (V) residue of SEQ ID NO: 2 is an isoleucine (I), which corresponds to SEQ ID NO: 16.

(SEQ ID NO: 16)

PVSGNLK VEFYNSNPSD TTNSINPQFK VTNTGSSAID

LSKLTLRYYY TVDGQKDQTF WCDHAAIIGS NGSYNGITSN

-continued

VKGTFVKMSS STNNADTYLE ISFTGGTLEP GAHVQIQGRF

AKNDWSNYTQ SNDYSFKSAS QFVEWDQVTA YLNGVLVWGK EP

Orthologs of type 3a CBDs have been described in various species, including, but not limited to *Ruminiclostridium thermocellum* AD2 (GenBank: ALX08828.1), *Caldicellulosiruptor lactoaceticus* 6A (GenBank: AEM74847.1), *Niastella koreensis* GR20-10 (GenBank: AEV99440.1), *Actinobacteria bacterium* OV450 (GenBank: KPH97519), *Spirosoma linguale* DSM 74 (GenBank: ADB37689.1). Type 3 CBDs, including type 3a CBDs, from other species known to one of ordinary skill in the art are also contemplated herein.

In some embodiments, the CBD includes a variant that is at least or about 50% identical, at least or about 60% identical, at least or about 70% identical, at least or about 80% identical, at least or about 85% identical, at least or about 90% identical, at least or about 95% identical, at least or about 96% identical, at least or about 97% identical, at least or about 98% identical, at least or about 99% identical, at least or about 99.5% identical, at least or about 99.9% identical, or about 100% identical to the amino acid sequence of SEQ ID NO: 1.

In some embodiments, the type 1 CBD includes a variant that is at least or about 50% identical, at least or about 60% identical, at least or about 70% identical, at least or about 80% identical, at least or about 85% identical, at least or about 90% identical, at least or about 95% identical, at least or about 96% identical, at least or about 97% identical, at least or about 98% identical, at least or about 99% identical, at least or about 99.5% identical, at least or about 99.9% identical, or about 100% identical to the amino acid sequence of SEQ ID NO: 10.

In some embodiments, the type 3a CBD includes a variant that is at least or about 50% identical, at least or about 60% identical, at least or about 70% identical, at least or about 80% identical, at least or about 85% identical, at least or about 90% identical, at least or about 95% identical, at least or about 96% identical, at least or about 97% identical, at least or about 98% identical, at least or about 99% identical, at least or about 99.5% identical, at least or about 99.9% identical, or about 100% identical to the amino acid sequence of SEQ IDNO: 2 or SEQ ID NO:16.

In some embodiments, the CBD includes a variant which is shorter or longer than the amino acid sequence of SEQ ID NO: 1 or SEQ ID NO: 15 by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids, by 200 amino acids, by 300 amino acids, by 400 amino acids, by 500 amino acids, 800 amino acids, 1000 amino acids, 1200 amino acids, 1400 amino acids or more.

In some embodiments, the type 1 CBD includes a variant which is shorter or longer than the amino acid sequence of a type 1 CBD of SEQ ID NO: 10 by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids, or more.

In some embodiments, the type 3a CBD includes a variant which is shorter or longer than the amino acid sequence of a CBD of SEQ ID NO: 2 or SEQ ID NO: 16 by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids, or more.

According to some aspects, the bifunctional fusion protein contains a target-binding domain, such as an antigen-binding protein or antigen-binding domain. In some embodiments, the antigen-binding protein is an engineered Sso7d antigen-binding protein. The Sso7d protein from the hyperthermophilic archaeon *Sulfolobus solfataricus* is a small protein (7 kDa) with high thermal stability ($T_m$ of 98° C.), which is highly positively charged since it is a DNA-binding protein. The high positive charges in Sso7d introduce a strong specificity constraint for binding epitopes and leads to nonspecific interaction with mammalian cell membranes. Charge-neutralized variants of Sso7d that maintain high thermal stability have been reported (Traxlmayr et al., *J Biol Chem* (2016) 291(43):22496-508).

In some embodiments, the Sso7d antigen-binding protein comprises the amino acid sequence of SEQ ID NO: 12, corresponding to the amino acid sequence of Sso7d from *Sulfolobus solfataricus* (UniProtKb: P39476; European Nucleotide Archive: AAK42212.1) Amino acid sequence of Sso7d from *Sulfolobus solfataricus* (SEQ ID NO: 12):

```
                                        (SEQ ID NO: 12)
MATVKFKYKGEEKEVDISKIKKVWRVGKMISFTYDEGGGKTGRGAVSEKD

APKELLQMLEKQKK
```

Orthologs of Sso7d have been described in various species, including *Sulfolobus islandicus* (NCBI Reference Sequence: WP_012713334.1), *Sulfolobus tokodaii* (NCBI Reference Sequence: WP_010978621.1), *Sulfolobus* sp. A20 (Sequence ID: WP_069284107.1), *Acidianus hospitalis* (NCBI Reference Sequence: WP_013777046.1), and *Acidianus manzaensis* (GenBank: ARM76167.1).

In some embodiments, the Sso7d antigen-binding protein is a reduced-charge variant of Sso7d (rcSso7d). In some embodiments, the rcSso7d antigen-binding protein comprises the amino acid sequence of SEQ ID NO: 3.

Amino acid sequence of rcSso7d from *Sulfolobus solfataricus* (SEQ ID NO: 3):

```
                                        (SEQ ID NO: 3)
MATVKFTYQGEEKQVDISKIKKVWRVGQMISFTYDEGGGATGRGAVSEKD

APKELLQMLEKQ
```

In some embodiments, the engineered antigen-binding protein is Sso7a. In some embodiments, the Sso7a antigen-binding protein is from *Sulfolobus solfataricus* (UniProtKB: P61991; European Nucleotide Archive: AAK42090.1).

Amino acid sequence of Sso7a from *Sulfolobus solfataricus* (SEQ ID NO: 11):

```
                                        (SEQ ID NO: 11)
   MATVKFKYKG EEKQVDISKI KKVWRVGKMI SFTYDEGGGK

TGRGAVSEKD APKELLQMLE KQKK
```

In some embodiments, a reduced charge variant of Sso7a is contemplated herein.

In some embodiments, the antigen-binding protein is Sac7d from *Sulfolobus acidocaldarius* (UniProtKB: P13123). In some embodiments, the antigen-binding protein is a reduced-charge variant of Sac7d (rcSac7d).

Amino acid sequence of Sac7d from *Sulfolobus acidocaldarius* (SEQ ID NO: 13):

```
                                        (SEQ ID NO: 13)
   MVKVKFKYKG EEKEVDTSKI KKVWRVGKMV SFTYDDNGKT

GRGAVSEKDA PKELLDMLAR AEREKK
```

In some embodiments, the Sso7 antigen-binding protein is a variant that is at least or about 50% identical, at least or about 60% identical, at least or about 70% identical, at least or about 80% identical, at least or about 85% identical, at least or about 90% identical, at least or about 95% identical, at least or about 96% identical, at least or about 97% identical, at least or about 98% identical, at least or about 99% identical, at least or about 99.5% identical, at least or about 99.9% identical, or about 100% identical to the amino acid sequence of SEQ ID NO: 3, SEQ ID NO: 11, SEQ ID NO: 12, or SEQ ID NO: 13.

In some embodiments, the Sso7 antigen-binding protein includes variants which are shorter or longer than amino acid sequence of SEQ ID NO: 3, SEQ ID NO: 11, SEQ ID NO: 12, or SEQ ID NO: 13 by about 5 amino acids, by about 10 amino acids, by about 15 amino acids, by about 20 amino acids, by about 25 amino acids, by about 30 amino acids, by about 40 amino acids, by about 50 amino acids, or more.

Any orthologs of the sequences described herein may be identified conducting a BLAST search of the sequence of interest.

In some embodiments, the bifunctional fusion protein incorporates a substrate-anchoring domain and a target-binding domain, in which the target-binding domain is expressed as a genetic fusion to the substrate-anchoring domain. In some embodiments, the target-binding domain is not expressed as a genetic fusion to the substrate-anchoring domain. In some embodiments, the target-binding domain interacts with the substrate-anchoring domain. Non-limiting examples of a target-binding domain includes, without limitation, antigens, enzymes, peptides, antibodies, antibody fragments, non-antibody binding scaffolds, DNA oligonucleotides, aptamers, etc. (See e.g., Care et al., Trends Biotechnol (2015) 33(5):259-68). Additional examples of a target-binding domain or a target-binding protein include, protein A, lipocalins, fibronectin domains, Ankyrin concensus repeat domains, scFv, and thioredoxin. (See e.g., Skerra et al., Curr Opin Biotechnol (2007) 18(4):295-304). Additional target-binding domains known to one of ordinary skill in the art are also contemplated herein.

The amino acid sequence of an exemplary rcSso7d.SA-CBD bifunctional fusion protein construct described herein can be represented as follows:

```
                                                                    (SEQ ID NO: 14)
MGSSHHHHHHSSGLVPRGSH MATVKFTYQGEEKQVDISKIKIVARDGQYIDFKYDEGGGAYGYGWVSEK

DAPKELLQMLEKQGGGGSGGGGSGGGGS PVSGNLKVEFYNSNPSDTTNSINPQFKVTNTGSSAIDLSKL
```

-continued

TLRYYYTVDGQKDQTFWCDHAAIIGSNGSYNGITSNVKGTFVKMSSSTNNADTYLEISFTGGTLEPGAH

VQIQGRFAKNDWSNYTQSNDYSFKSASQFVEWDQVTAYLNGVLVWG*

The single underlined amino acids correspond to a histidine tag-thrombin site for purification. The double underlined amino acids correspond to the rcSso7d.SA (i.e., rcSso7d antigen binding protein variant that binds to streptavidin—SA). The dash underlined amino acids correspond to the (G$_4$S)$_3$ linker (SEQ ID NO: 125). The zig-zag underlined amino acids correspond to the CBD. In some embodiments, any of the bifunctional fusion protein constructs described herein have a similar arrangement, consisting of a purification tag and cleavage site, followed by the amino acid sequence of an antigen-binding protein contemplated herein, followed by a linker, and followed by the amino acid sequence of a CBD domain contemplated herein.

rcSso7d antigen-binding protein which recognizes and/or binds to the antigen of interest comprises an amino acid sequence that recognizes and/or binds to streptavidin (e.g., rcSso7d.SA or rcSso7d.SA-CBD), such as the amino acid sequence (SEQ ID NO: 4)
MATVKFTYQGEEKQVDISKIKIVARDGQYIDF

KYDEGGGAYGYGWVSEKDAPKELLQMLEKQ.

Additional non-limiting examples of engineered rcSso7d antigen-binding protein variants that bind to streptavidin or to the goat anti-chicken antibody AF488 are listed in Table 1.

TABLE 1

Engineered rcSso7d antigen-binding protein variants that bind to streptavidin or to the goat anti-chicken antibody

| rcSso7d Variant | SEQ ID NO | Amino Acid Sequence (N-terminus to C-terminus) |
|---|---|---|
| SA-AF647 | 17 | MATVKFTYQGEEKQVDISKIKYVYRWGHYIYFWYDEGGGASGWGWVSEKDAPKELLQ |
|  | 18 | MATVKFTYQGEEKQVDISKIKHVRRWGQWIYFIYDEGGGARGNGYVSEKDAPKELLQ |
|  | 19 | MATVKFTYQGEEKQVDISKIKRVRRYGQWIAFHYDEGGGAAGWGYVSEKDAPKELLQ |
|  | 20 | MATVKFTYQGEEKQVDISKIKWVWRGGQGIIFWYDEGGGARGYGRVSEKDAPKELLQ |
|  | 21 | MATVKFTYQGEEKQVDISKIKRVIRIGQYIYFWYDEGGGARGWGYVSEKDAPKELLQ |
|  | 22 | MATVKFTYQGEEKQVDISKIKWVHRWGQRIRFWYDEGGGAAGNGKVSEKDAPKELLQ |
|  | 23 | MATVKFTYQGEEKQVDISKIKWVIRWGQWIWFKYDEGGGASGWGYVSEKDAPKELLQ |
|  | 24 | MATVKFTYQGEEKQVDISKIKRVRRWGQWIYFRYDEGGGAYGSGYVSEKDAPKELLQ |
|  | 25 | MATVKFTYQGEEKQVDISKIKYVYRWGQWIYFWYDEGGGAWGRGYVSEKDAPKELLQ |
| Goat anti-Chicken antibody AF488 | 26 | MATVKFTYQGEEKQVDISKIKYVRRYGQYIGFIYDEGGGAWGKGYVSEKDAPKELLQ |
|  | 27 | MATVKFTYQGEEKQVDISKIKHVRRYGQWIRFRYDEGGGASGWGIVSEKDAPKELLQ |
|  | 28 | MATVKFTYQGEEKQVDISKIKSVKRSGQGIKFIYDEGGGAYGHGRVSEKDAPKELLQ |

In some embodiments, the target-binding protein is an engineered rcSso7d antigen-binding protein, which binds to an antigen. As described herein, an "antigen" or "antigen of interest" refers to any molecule that can bind to the target-binding domain, such as the engineered rcSso7d antigen-binding protein. In some embodiments, an antigen is a molecule capable of inducing an immune response (to produce an antibody) in a host organism. In some embodiments, an antigen is a molecule which does not induce an immune response. In some embodiments, an antigen is an exogenous antigen, an endogenous antigen, an autoantigen, or a neoantigen (e.g., viral antigen, a tumor antigen, etc.).

In some embodiments, the antigen or antigen of interest is a tuberculosis antigen or tuberculosis molecule. A tuberculosis antigen or tuberculosis molecule is an antigen or molecule that is produced by *Mycobacterium tuberculosis* in either its active or latent form, or it may represent a biochemical response to the presence of the *M. tuberculosis* (in either its active or latent form) from the infected subject (e.g. disease-specific immunoglobulins, signaling cytokines, compound biomarkers representing a signature response across several biochemical entities, etc.). In some embodiments, the engineered rcSso7d antigen-binding protein includes a motif which recognizes and/or binds to a specific antigen of interest. In some embodiments, the engineered In some embodiments, the engineered Sso7d antigen-binding protein (e.g., rcSso7d) which recognizes and/or binds to the antigen of interest comprises an amino acid sequence that recognizes and/or binds to a marker for tuberculosis, such as an antigen produced by active tuberculosis. In some embodiments, the engineered rcSso7d antigen-binding protein which recognizes and/or binds to the antigen of interest includes a sequence that recognizes and/or binds to the marker for tuberculosis Rv-1656 (e.g., rcSso7d.Rv-1656 or rcSso7d.Rv-1656-CBD), such as the amino acid sequence (SEQ ID NO: 5)
MATVKFTYQGEEKQVDISKIKWVRRYGQYIGF

SYDEGGGAWGKGYVSEKDAPKELLQMLEKQ.

In some embodiments, the engineered Sso7d antigen-binding protein (e.g., rcSso7d) which recognizes and/or binds to the antigen of interest comprises an amino acid sequence that recognizes and/or binds to a marker for tuberculosis, such as an antigen produced by active tuberculosis. In some embodiments, the marker for tuberculosis is Rv1656, Rv1681, Rv2392, Rv1729c or TBCG_03312.

Additional non-limiting examples of an antigen or antigen of interest produced in tuberculosis which can be recognized by or can bind to any of the bifunctional fusion proteins described herein include detection of the bacterium that causes tuberculosis (i.e., *Mycobacterium tuberculosis*), described herein to detect and diagnose tuberculosis are listed in Table 2 (See e.g., Tucci et al., Front Microbiol (2014) 5(549):1-6).

TABLE 2

Exemplary antigens associated with *Mycobacterium tuberculosis*.

| Gene | Rv Number | Protein | Diagnosis |
|---|---|---|---|
| apa | Rv1860 | Alanine proline rich secreted protein APA | Tested in sputum and serum of active smear-positive tuberculosis patients (Chanteau et al., *Int J Tuberc Lung Dis* (2000) 4: 377-83). |
| esxA | Rv3875 | 6 kDa Early secretory antigen target ESXA. | Detected in cerebrospinal fluid (CSF) of tuberculous meningitis patients (Kashyap et al. *Infection* (2009) 37: 508-13). |
| fbpA | Rv3804c | Secreted antigen 85-A FBPA | Antigen 85 complex proteins have been detected in sputum (Wallis et al., *J Infect Dis* (1998) 178: 1115-21 and serum (Kashyap et al., *BMC Infect Dis* (2007) 7: 74) specimens of tuberculosis patients. |
| fbpB | Rv1886c | Secreted antigen 85-B FBPB | |
| fbpD | Rv3803c | Secreted MPT51/MPB51 antigen protein FBPD | |
| glcB | Rv1837c | Malate synthase G (GlcB) | Promising in cerebral spinal fluid in tuberculous meningitis (Haidar et al., *PLoS ONE* (2012) 7: e44630). |
| groEL2 | Rv0440 | 60 kDa chaperonin 2 GROEL2 | Promising in ELISA of serum samples of tuberculosis patients (Rajan et al., *Int J Tuberc Lung Dis* (2007) 11: 792-7). |
| hspX | Rv2031c | Heat shock protein HSPX | Assayed with promising results in CSF in tuberculous meningitis (Haidar et al., *PLoS ONE* (2012) 7: e44630). |
| moeX | Rv1681 | Possible molybdopterin biosynthesis protein MoeX | Identified by mass spectrometry in urine from active tuberculosis patients (Pollock et al., *J Clin Microbiol* (2013) 51: 1367-73). |
| mpt64 | Rv1980c | 24 kDa immunogenic protein MPT64 | A lateral flow assay was developed for the identification of *M. tuberculosis* complex in liquid culture media by using anti-MPB64 monoclonal antibodies (Akyar et al., *Indian J Med Microbiol* (2010) 28: 308-12). |
| pstS1 | Rv0934 | Periplasmic phosphate-binding lipoprotein PSTS1 | Assayed in cerebral spinal fluid in tuberculous meningitis (Haidar et al., *PLoS ONE* (2012) 7: e44630). |
| TB31.7 | Rv2623 | Universal stress protein family protein TB31.7 | Potential biomarker for the diagnosis of latent as well as active tuberculous meningitis infection. Assayed in CSF (Jain et al., *Dis Markers* (2013) 35: 311-6). | detection of specific regions of the genome of *M. tuberculosis*, such as regions detected by the GeneXpert MTB/RIF nucleic acid amplification test, antigens that are shed from *M. tuberculosis* into body fluids surrounding the one or more infected tissues, which can reach the blood circulation and be eliminated from the body of the subject, such as in urine. The antigen could be detected from both pulmonary tuberculosis or extrapulmonary tuberculosis (See e.g., Tucci et al., *Front Microbiol* (2014) 5(549):1-6). Lipoarabinomannan (LAM) is another antigen contemplated herein. LAM is a component of the outer cell wall of all Mycobacteria shed from metabolically active or degrading cells, which is cleared by the kidney and detectable in urine, which can be detected by the bifunctional fusion protein and methods described herein. (See e.g., Hunter et al. *J Biol Chem* (1986) 261(26):12345-51; Chan et al. *Infect Immun* (1991) 59(5): 1755-61). The bifunctional fusion protein that can detect LAM includes a target-binding protein, such as an engineered rcSso7d antigen-binding protein, that is selected for binding to the antigen of interest, LAM.

Additional non-limiting examples of antigens that can be detected using the bifunctional fusion protein and methods The bifunctional fusion protein described herein can be exemplified by the use of the rcSso7d.Rv1656-CBD bifunctional fusion protein bound to a cellulose-containing substrate, such as a chromatography paper (e.g., WHATMAN® Grade 1 Qualitative Filtration Paper).

The bifunctional fusion protein bound to the cellulose-containing substrate can be contacted with a sample, such as a biological sample (e.g., urine), obtained from a subject, that contains an antigen of interest. The antigen of interest can be a urine-based biomarker of active tuberculosis obtained from a subject that has or is suspected of having tuberculosis, which, in some instances, may be used to determine whether the subject has tuberculosis. In some embodiments, the biomarker for tuberculosis is Rv1656, LAM, any of the biomarkers listed in Table 2 or any biomarkers for tuberculosis known to one of ordinary skill in the art.

Additional non-limiting examples of antigens or antigens of interest include antibodies, peptides, etc. In some embodiments, the antigen or antigen of interest is a biomarker for prostate cancer[e.g., prostate specific antigen (PSA)], a biomarker for cardiac arrest (e.g., troponin), neuro-filament light or a biomarker for traumatic brain injury, tau protein or a biomarker for Alzheimer's Disease, NS1 or a biomarker for Dengue Fever or a biomarker for Zika virus, pLDH, HRP2, aldolase, HSP70, or a biomarker for malaria, interferon-γ-inducible protein-10 (IP-10) or a biomarker for human immunodeficiency virus (HIV), Schistosome GST or a biomarker for Schistosomiasis, cancer antigen 125 (CA-125) or a biomarker for ovarian cancer, or outer surface protein A (ospA) or a biomarker for Lyme Disease.

In some embodiments, the antigen or antigen of interest is a non-tuberculosis antigen.

In some embodiments, the antigen or antigen of interest is one or more cytokines. In some embodiments, a cytokine is a hemokine, an interferon, an interleukin, a lymphokine, a tumor necrosis factor, a chemokine, a pro-inflammatory cytokine, or an anti-inflammatory cytokine. Non-limiting examples of cytokines include interleukins, such as interleukin (IL)-1α, interleukin (IL)-β, interleukin (IL)-2, interleukin (IL)-3, interleukin (IL)-4, interleukin (IL)-5, interleukin (IL)-6, interleukin (IL)-7, interleukin (IL)-8, interleukin (IL)-9, interleukin (IL)-10, interleukin (IL)-11, interleukin (IL)-12, interleukin (IL)-13, interleukin (IL)-18; interferons, such as interferon (IFN)-α, interferon (IFN)-β, interferon (IFN)-γ; macrophage inflammatory proteins, such as macrophage inflammatory protein (MIP)-1α, macrophage inflammatory protein (MIP)-1β; tumor necrosis factor (TNF)-β, stem cell factor (SCF), granulocyte-macrophage colony-stimulating factor (GM-CSF), granulocyte-colony stimulating factor (G-CSF), MIP-ly, leukemia inhibitory factor (LIF), c-kit ligand, thrombopoietin (TPO), CD40 ligand (CD40L), tumor necrosis factor-related activation-induced cytokine (TRANCE) or ft3 ligand (flt-3L). Other cytokines known to one of ordinary skill in the art (see e.g., Zhang et al. *Int Anesthesiology Clin* (2007) 45(2):27-7) are also contemplated herein.

In some embodiments, the antigen or antigen of interest is released or secreted by a member of the genus Flavivirus. In some embodiments, the member of the genus Flavivirus is West Nile virus (WNV), St. Louis encephalitis virus (SLEV), Japanese encephalitis virus (JEV), yellow fever virus (YFV), dengue virus (DENV) or Zika virus (ZIKV). (See e.g., Guzman et al. *Lancet* (2015) 385:453-65). Other members of the genus Flavivirus known to one of ordinary skill in the art are also contemplated herein. In some embodiments, the antigen or antigen of interest is Flavivirus non-structural 1 (NS1). In some embodiments, the NS1 antigen or antigen of interest is released by a member of the genus Flavivirus, such as WNV, SLEV, JEV, SLEV, JEV, YFV, DEVN or ZIKV. The nucleic acid and/or amino acid sequences of NS1 antigen or antigen of interest released by WNV, SLEV, JEV, SLEV, JEV, YFV, DEVN or ZIKV are known and/or can be readily identified by one of ordinary skill in the art. In some embodiments, the antigen or antigen of interest is released or secreted by the member of a genus that is not Flavivirus. In some embodiments, the antigen or antigen of interest is released or secreted by an organism that causes malaria, such as an organism that is known to one of ordinary skill in the art. In some embodiments, the antigen or antigen of interest is released or secreted by a member of the genus *Plasmodium*. In some embodiments, the antigen or antigen of interest is released or secreted by *Plasmodium falciparum, Plasmodium vivax, Plasmodium malariae, Plasmodium ovale*. In some embodiments, the antigen or antigen of interest is *plasmodium* lactate dehydrogenase (pLDH), histidine-rich protein 2 (HRP2), or *plasmodium* aldolase. The nucleic acid and/or amino acid sequences of an pLDH, HRP2 or *plasmodium* aldolase are known to one of ordinary skill in the art and could be readily identified using tools, such as a BLAST search.

In some embodiments, the antigen or antigen of interest is a detection reagent. In some embodiments, the detection reagent is a fluorophore. In some embodiments, the antigen or antigen of interest is a fluorophore, such as ALEXA FLUOR® 647 (AF647). In some embodiments, the fluorophore is hydroxycoumarin, methoxycoumarin, aminocoumarin, CY2®, FAM, ALEXA FLUOR® 405 (AF405), ALEXA FLUOR® 488 (AF488), Fluorescein FITC, ALEXA FLUOR® 430 (AF430), ALEXA FLUOR® 532 (AF532), HEX, CY3®, TRITC, ALEXA FLUOR® 546 (AF546), ALEXA FLUOR® 555 (AF555), R-phycoerythrin (PE), RHODAMINE RED™-X, Tamara, CY3.5® 581, Rox, ALEXA FLUOR@ 568 (AF568), RED 613™, TEXAS RED®, ALEXA FLUOR® 594 (AF594), ALEXA FLUOR® 633 (AF633), Allophycocyanin, CY5®, ALEXA FLUOR® 660 (AF660), CY5.5®, TruRed, ALEXA FLUOR® 680 (AF680), CY7®, CY7.5® or any other fluorophores known to one of ordinary skill in the art (see e.g., www.biosyn.com/Images/ArticleImages/Comprehensive %20fluorophore %20list.pdf). In some embodiments, the fluorophore is a fluorescent protein or a chromophore, such as green fluorescent protein (GFP), chromoprotein from the coral *Acropora millepora* (amilCP), a chromoprotein from the coral *Acropora* millepora (amilGFP), a fluorescent protein from *Acropora millepora* (amilRFP), etc., or other species chemically linked to a detection reagent known to one of ordinary skill in the art. In some embodiments, one or more fluorophores could be used for the purification of chemically-labeled molecules to ensure 100% or near 100% labeling efficiency. In some embodiments, the antigen or antigen of interest is a molecule that emit a detectable signal. In some embodiments, the molecule is phycoerythrin. In some embodiments, the molecule that emits a detectable signal is a color-producing enzyme (e.g., beta-galactosidase), APEX2 for metal sequestration and high contrast electron microscopy (EM), or a chemiluminescent species. In some embodiments, any of the antigen-binding proteins disclosed herein, such as a multimeric rcSso7d binding protein associated or not associated with a substrate-anchoring domain includes a binding face that binds an analyte, antigen or antigen of interest and a second binding face that binds one or more of the detection reagents disclosed herein. Other detection reagents, fluorophores or molecules that emit a detectable signal known to one of ordinary skill in the art are also contemplated herein. In some embodiments, the detection reagent, fluorophore or molecule that emits a detectable signal is directly or indirectly linked to one or more of streptavidin, to IgG antibody (polyclonal or monoclonal), any of the biomarkers disclosed herein, any of the antigen-binding proteins disclosed herein [e.g., rcSso7d, rcSso7d-based detection reagents (e.g., BA-MBP-rcSso7d)], a nucleic acid (e.g., DNA, RNA, etc.), or an organic or inorganic nanoparticle (e.g., a nanoparticle comprising gold, carbon, latex, cellulose, etc.)

In some embodiments, the substrate-anchoring domain, such as a CBD, and the target-binding domain, such as an antigen-binding protein or an antigen-binding domain (e.g., an engineered rcSso7d antigen-binding protein) are directly attached. The substrate-anchoring domain, such as a CBD, can be directly attached to the target-binding protein or an antigen-binding domain (e.g., an engineered rcSso7d antigen-binding protein) through a peptide bond between the substrate-anchoring domain and the target-binding protein or antigen-binding domain. In some embodiments, the substrate-anchoring domain, such as a CBD, and the target-binding domain, such as an antigen-binding protein or an antigen-binding domain (e.g., engineered rcSso7d antigen-binding protein) are indirectly attached. In some embodiments, the engineered Sso7d antigen-binding protein (e.g., rcSso7d) is indirectly attached to the CBD through a linker (i.e., is linked). Non-limiting examples of linkers contemplated herein include a protein linker; a peptide linker, such as a Gly-Ser linker (e.g., a linker that includes the amino acid sequence GGGGSGGGGSGGGGS (SEQ ID NO: 125), known as $(G_4S)_3$). The Gly-Ser linker can be replicated n number of times, wherein n=1, 2, 3, 4, 5, 6, 7, 8, 9, 10, 15, 20, 25, or 30, for example. Additional non-limiting examples of linkers known to one of ordinary skill in the art, such as chemical linkers (e.g., crosslinkers, bifunctional linkers, trifunctional trilinkers), such as Bis[2-(N-succinimidyl-oxycarbonyloxy)ethyl] sulfone, O,O'-Bis[2-(N-Succinimidyl-succinylamino)ethyl]polyethylene glycol 2,000, O,O'-Bis[2-(N-Succinimidyl-succinylamino)ethyl]polyethylene glycol 3,000, O,O'-Bis[2-(N-Succinimidyl-succinylamino)ethyl] polyethylene glycol 10,000, BS(PEG)$_5$ (PEGylated bis (sulfosuccinimidyl)suberate), 4,4'-Diisothiocyanatostilbene-2,2'-disulfonic acid disodium salt hydrate, rromoacetic acid N-hydroxysuccinimide ester, maleimide-PEG2-succinimidyl ester, SBAP (succinimidyl 3-(bromoacetamido)propionate), 5-Azido-2-nitrobenzoic acid N-hydroxysuccinimide ester, etc.; flexible linkers (e.g., $(Gly)_6$ (SEQ ID NO: 126), $(Gly)_8$ (SEQ ID NO: 127), etc.), rigid linkers (e.g., $(EAAAK)_3$ (SEQ ID NO: 128), A(EAAAK)$_4$ALEA (EAAAK)$_4$A (SEQ ID NO: 129), PAPAP (SEQ ID NO: 130), etc.) and cleavable linkers (e.g., disulfide, VSQTSK-LTR↓JAETVFPDV (SEQ ID NO: 131), RVLL↓AEA (SEQ ID NO: 132); EDVVCC↓SMSY (SEQ ID NO: 133); GGIEGR↓GS (SEQ ID NO: 134); GFLG↓(SEQ ID NO: 135), etc.) naturally-occurring or synthetic, such as those disclosed in Chen et al., *Adv Drug Deliv Rev* (2013) 65(10): 1357-69, are also contemplated herein.

In some embodiments, the C-terminus of the engineered rcSso7d antigen-binding protein is either directly or indirectly attached to the N-terminus of the CBD. In some embodiments, the C-terminus of the engineered rcSso7d antigen-binding protein is directly attached to the N-terminus of the CBD. In some embodiments, the C-terminus of the engineered rcSso7d antigen-binding protein is indirectly attached to the N-terminus of the CBD through a linker. In some embodiments, the N-terminus of the engineered rcSso7d antigen-binding protein is either directly or indirectly attached to the C-terminus of the CBD. In some embodiments, the N-terminus of the engineered rcSso7d antigen-binding protein is directly attached to the C-terminus of the CBD. In some embodiments, the N-terminus of the engineered rcSso7d antigen-binding protein is indirectly attached to the C-terminus of the CBD through a linker.

Expression of Bifunctional Fusion Protein

Also disclosed herein are nucleic acids that encode for any of the bifunctional fusion proteins described herein, libraries that contain any of the nucleic acids and/or bifunctional fusion proteins described herein, and compositions that contain any of the nucleic acids and/or bifunctional fusion proteins described herein. It should be appreciated that libraries containing nucleic acids or proteins can be generated using methods known in the art. A library containing nucleic acids can contain fragments of genes and/or full-length genes and can contain wild-type sequences and mutated sequences. A library containing proteins can contain fragments of proteins and/or full length proteins and can contain wild-type sequences and mutated sequences.

The development and selection of an antigen-binding protein described herein, such as the rcSso7d.SA or the rcSso7d.Rv1656 can be produced by methods disclosed in Miller et al., 2016. Briefly, an antigen-binding protein, such as rcSso7d.SA or the rcSso7d.Rv1656 is selected from a yeast surface display library based on the reduced-charge Sso7d scaffold (rcSso7d). The yeast library can be generated using trinucleotide oligo synthesis and in vivo homologous recombination with a linearized plasmid, such as the pCT-con2 plasmid. (Traxlmayr et al., 2016). Methods of isolation, such as the highly-avid magnetic bead sorting (Ackerman et al., 2009) (MBS) and fluorescence-activated cell sorting (FACS) (Chao et al., 2006) can be employed to select binders against an antigen of interest, such as Rv1656, and stringency increased over rounds of FACS-based library screening, after which a sub-library can be sequenced and the antigen-binding protein that binds the antigen of interest (e.g., rcSso7d.Rv1656) can be selected for further characterization, such as robust expression in a system, such as a bacterial system, for downstream applications. Additional methods for creating a yeast surface display library include methods known to one of ordinary skill in the art.

In some embodiments, one or more of the target-binding proteins, antigens, etc. disclosed herein are expressed in a recombinant expression vector. As used herein, a "vector" may be any of a number of nucleic acids into which a desired sequence or sequences may be inserted by restriction and ligation for transport between different genetic environments or for expression in a host cell. Vectors are typically composed of DNA, although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host cell such as a host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Expression vectors containing all the necessary elements for expression are commercially available and known to those skilled in the art. See, e.g., Sambrook et al., Molecular Cloning: A Laboratory Manual, Second Edition, Cold Spring Harbor Laboratory Press, 1989. Cells are genetically engineered by the introduction into the cells of heterologous DNA (RNA).

A nucleic acid molecule that encodes a bifunctional fusion protein or antigen or any other molecule disclosed herein can be introduced into a cell or cells using methods and techniques that are standard in the art. For example, nucleic acid molecules can be introduced by standard protocols such as transformation including chemical transformation and electroporation, transduction, particle bombardment, etc.

Any type of cell that can be engineered to recombinantly express genes can be used in the methods described herein, including prokaryotic and eukaryotic cells. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., Comamonas spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., Chromobacterium spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus*. In other embodiments, the cell is a fungal cell such as a yeast cell, e.g., *Saccharomyces* spp. (e.g., *S. cerevisiae*), *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp. and industrial polyploid yeast strains. Other examples of fungi include *Aspergillus* spp., *Penicillium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments, the cell is an algal cell, or a plant cell.

Antigen Detection

In some aspects, methods for detecting an antigen of interest are also provided herein. In some embodiments, the method includes contacting any of the bifunctional fusion proteins described herein with a cellulose-containing substrate for a time sufficient for the bifunctional fusion protein to bind to the cellulose-containing substrate; contacting the bifunctional fusion protein bound to the cellulose-containing substrate with a sample comprising an antigen of interest; and detecting the antigen of interest bound by the engineered reduced charge Sso7d antigen-binding protein (e.g., rcSso7d).

In some embodiments, the method includes contacting any of the bifunctional fusion proteins described herein with a sample comprising an antigen of interest, wherein the antigen of interest binds to the bifunctional fusion protein and forms a complex; contacting the complex with a cellulose-containing substrate for a time sufficient for the complex to bind to the cellulose-containing substrate; and detecting the antigen of interest bound by the engineered Sso7d antigen-binding protein.

In some embodiments, the method includes contacting any of the bifunctional fusion proteins described herein, such as rcSso7d-CBD, with a cellulose-containing substrate for a time sufficient for bifunctional fusion protein to bind to the cellulose-containing substrate; contacting a sample, such as a biological sample, comprising an antigen or an antigen of interest for a time sufficient to allow the antigen or antigen of interest to bind to the bifunctional fusion protein and form a complex; contacting the complex with an antibody that recognizes the antigen or antigen of interest; and detecting the antibody. In some embodiments, the antibody is directly or indirectly linked to a fluorophore or a molecule that emits a detectable signal to detect the antigen or antigen of interest. In some embodiments, the antibody is biotinylated. In some embodiments, the biotinylated antibody is contacted with a streptavidin molecule that is directly or indirectly linked to a fluorophore or a molecule that emits a detectable signal to detect the antigen or antigen of interest.

In some embodiments, the bifunctional fusion protein comprises more than one rcSso7d antigen-binding protein. In some embodiments, the bifunctional fusion protein comprises at least or 2, at least or 3, at least or 4, at least or 5, at least or 6, at least or 7, at least or 8, at least or 9, at least or 10, at least or 12, at least or 14, at least or 16, at least or 18, at least or 20, at least or 25, at least or 30, at least or 35, at least or 40, at least or 45, at least or 50, at least or 55, at least or 60, at least or 65, at least or 70, at least or 75, at least or 80, at least or 85, at least or 90, at least or 95, or at least or 100 antigen-binding proteins or domains, such as any of the rcSso7d or its variants disclosed herein.

In some embodiments, the more than one antigen-binding proteins or domains, such as any of the rcSso7d or its variants disclosed herein are genetically fused together. The more than one antigen-binding proteins or domains, such as any of the rcSso7d or its variants disclosed herein are genetically fused together by using an expression vector that includes more than one copy of a nucleic acid sequence that encodes the antigen-binding protein or domain. In some embodiments, the nucleic acid sequences that encodes one antigen-binding protein or domain is separated from another nucleic acid sequence that encodes one antigen-binding protein or domain by a nucleic acid encoding a linker. Non-limiting examples of linkers encoded by a nucleic acid contemplated herein include a protein linker or a peptide linker, such as a Gly-Ser linker (e.g., a linker that includes the amino acid sequence GGGGSGGGGSGGGGS (SEQ ID NO: 125), known as $(G_4S)_3$). The Gly-Ser linker can be replicated n number of times, wherein n=1, 2, 3, 4, 5, 6, 7, 8, 9, 10, 15, 20, 25, or 30, for example. Additional non-limiting examples of linkers disclosed herein and/or known to one of ordinary skill in the art are also contemplated herein. In some embodiments, the more than one antigen-binding proteins or domains, such as any of the rcSso7d or its variants disclosed herein are not genetically fused together. In some embodiments, the more than one antigen-binding proteins or domains, such as any of the rcSso7d or its variants disclosed herein are chemically fused. In some embodiments, the more than one antigen-binding proteins or domains, such as any of the rcSso7d or its variants disclosed herein are chemically fused together. The more than one antigen-binding proteins or domains, such as any of the rcSso7d or its variants disclosed herein are chemically fused by a chemical reagent after the proteins have been expressed from a nucleic acid sequence. In some embodiments, the more than one antigen-binding proteins or domains, such as any of the rcSso7d or its variants disclosed herein are chemically fused after antigen-binding proteins or domains, such as any of the rcSso7d or its variants disclosed herein is expressed, for instance, from an expression vector. In some embodiments, the more than one rcSso7d antigen-binding proteins are chemically fused by a linker, such as a bifunctional linker, or using other methods known to one of ordinary skill in the art. In some embodiments, the more than one antigen-binding proteins or domains, such as any of the rcSso7d or its variants disclosed herein, are chemically fused by a fusion via disulfide linkages between cysteine residues at the N- and C-termini, or via dual-maleimide chemical reagents. In some embodiments, in vivo ligation tags such as HALO or SPY tags to attach orthogonal reactive moieties to the antigen-binding proteins or domains, such as any of the rcSso7d or its variants disclosed herein, allowing separate molecules to react together, are also contemplated herein. In some embodiments, residues of antigen-binding proteins or domains, such as any of the rcSso7d or its variants disclosed herein, could be chemically altered to feature aldehyde moieties, which can be reacted with primary amines to form covalent imine linkages. (See e.g., Tuley et al., *Chemical communications* (2014) 50(56):7424-7426. doi:10.1039/c4cc02000f). In some embodiments, a sortase-based method could be used for in vitro fusion of an antigen-binding protein or domain, such as any of the rcSso7d or its variants disclosed herein.

In some embodiments, the bifunctional fusion protein or the complex is in solution. In some embodiments, the solution includes a buffer, such as a buffer known to one of ordinary skill in the art. The bifunctional protein may be in solution at a desired concentration. In some embodiments, the bifunctional fusion protein is at a desired concentration of or about 5 µM, of or about 10 µM, of or about 15 µM, of or about 20 µM, of or about 25 µM, of or about 30 µM, of or about 35 µM, of or about 40 µM, of or about 45 µM, of or about 50 µM, of or about 60 µM, of or about 70 µM, of or about 80 µM, of or about 90 µM, of or about 100 µM, of or about 200 µM, of or about 300 µM, or of or about 400 µM.

In some embodiments, the bifunctional fusion protein described herein is contacted with the cellulose-containing substrate for about 5 seconds, about 15 seconds, about 20 seconds, about 30 seconds, about 35 seconds, about 40 seconds, about 45 seconds, about 1 minute, about 1.5 minutes, about 2 minutes, about 2.5 minutes, about 3 minutes, about 4 minutes, about 5 minutes, about 7 minutes, about 10 minutes, about 15 minutes, about 20 minutes, about 30 minutes, or about 1 hour.

In some embodiments, the bifunctional fusion protein bound to the cellulose-containing substrate is contacted with a sample that contains an antigen of interest. In some embodiments, the bifunctional fusion protein described herein is contacted with a sample comprising an antigen of interest, wherein the antigen of interest binds to the bifunctional fusion protein and forms a complex; the complex is then contacted with a cellulose-containing substrate for a time sufficient for the complex to bind to the cellulose-containing substrate.

In some embodiments, the sample is a biological sample. The biological sample may be obtained from a subject. As described herein, the term "biological sample" is used to generally refer to any biological material obtained from a subject. The biological sample typically is a fluid sample. Solid tissues may be made into fluid samples using routine methods in the art. In some embodiments, the biological sample is tissue, feces, or a cell obtained from a subject. In some embodiments, the biological sample comprises a bodily fluid from a subject. The bodily fluids can be fluids isolated from anywhere in the body of the subject, preferably a peripheral location, including but not limited to, for example, blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, intra-organ system fluid, ascitic fluid, tumor cyst fluid, amniotic fluid or combinations thereof.

In some embodiments, the cellulose-containing substrate is paper (e.g., chromatography paper) or nitrocellulose. In certain embodiments, the cellulose-containing substrate is modified in an oxidizing chemical bath to yield covalent chemical linkage of the protein to the substrate, passivated with a blocking agent (See e.g., Y. Zhu, et al., *Anal Chem.* (2014) 86:2871-5; M. Vuoriluoto, et al., *ACS Appl. Mater. Interfaces* (2016) 8, 5668-78) to reduce non-specific protein adsorption to the substrate, or pre-incubated with a stabilizing species such as trehalose in order to improve assay functionality and stability. In certain embodiments, the cellulose-containing substrate is not modified (unmodified). In some embodiments, the cellulose-containing substrate is an unmodified chromatography paper, such as unmodified WHATMAN® Grade 1 Qualitative Filtration Paper. Additional non-limiting examples of cellulose-containing substrates also contemplated herein include cellulose powder, cellulose microbeads, cellulosic fabrics/yarns, etc.

In some embodiments, the cellulose-containing substrate is oxidized. In some embodiments, the cellulose-containing substrate is oxidized with sodium metaperiodate to functionalize the cellulose surfaces with aldehyde groups or other methods to oxidize cellulose known to one of ordinary skill in the art. (See e.g., Badu-Tawiah, et al., *Lab Chip*, (2015) 15:655-9).

For instance, a non-limiting example is the use of rcSso7d.Rv1656-CBD bifunctional fusion protein bound to a cellulose-containing substrate, such as a chromatography paper (e.g., WHATMAN® Grade 1 Qualitative Filtration Paper), which is contacted with a sample that contains an antigen of interest, such as an urine-based biomarker of active tuberculosis obtained from a subject that has or is suspected of having tuberculosis, which, in some instances, may be used to determine whether the subject has tuberculosis. In some embodiments, the biomarker for tuberculosis is Rv1656.

Additional non-limiting examples of biomarkers for tuberculosis which could be detected by any of the bifunctional fusion proteins described herein, through any of the methods described herein, include detection of the bacterium that causes tuberculosis (i.e., *Mycobacterium tuberculosis*), detection of specific regions of the genome of *M. tuberculosis*, such as regions detected by the GeneXpert MTB/RIF nucleic acid amplification test. Additional examples of antigens of interest for tuberculosis include antigens that are shed from *M. tuberculosis* into body fluids surrounding the one or more infected tissues, which can reach the blood circulation and be eliminated from the body of the subject, such as in urine. The antigen could be detected from both pulmonary tuberculosis or extrapulmonary tuberculosis. The antigen or antigen of interest could be detected from latent tuberculosis, if they are identified/validated (See e.g., Tucci et al., *Front Microbiol* (2014) 5(549):1-6). For instance, lipoarabinomannan (LAM) is a component of the outer cell wall of all Mycobacteria shed from metabolically active or degrading cells, which is cleared by the kidney and detectable in urine, which can be detected by the bifunctional fusion protein and methods described herein. (See e.g., Hunter et al. *J Biol Chem* (1986) 261(26):12345-51; Chan et al. *Infect Immun* (1991) 59(5): 1755-61).

Additional non-limiting examples of antigens that can be detected using the bifunctional fusion protein and methods described herein to detect and diagnose tuberculosis are listed in Table 2 (See e.g., Tucci et al., Front Microbiol (2014) 5(549):1-6).

Other antigens present in a subject with tuberculosis, which can be detected using the bifunctional fusion protein, methods compositions and kits described herein, known to one of ordinary skill in the art are also contemplated herein.

In some embodiments, the antigen of interest is streptavidin.

In some embodiments, at least or about 0.1 micromole, at least or about 0.2 micromoles, at least or about 0.3 micromoles, at least or about 0.4 micromoles, at least or about 0.5 micromoles, at least or about 0.6 micromoles, at least or about 0.7 micromoles, at least or about 0.8 micromoles, at least or about 0.9 micromoles, at least or about 1 micromole, at least or about 1.1 micromoles, at least or about 1.2 micromoles, at least or about 1.3 micromoles, at least or about 1.4 micromoles, at least or about 1.5 micromoles, at least or about 1.6 micromoles, at least or about 1.7 micromoles, at least or about 1.8 micromoles, at least or about 1.9 micromoles, at least or about 2 micromoles, at least or about 2.1 micromoles, at least or about 2.2 micromoles, at least or about 2.3 micromoles, at least or about 2.4 micromoles, at least or about 2.5 micromoles, at least or about 2.6 micromoles, at least or about 2.7 micromoles, at least or about 2.8 micromoles, at least or about 2.9 micromoles, at least or about 3 micromoles, at least or about 3.5, at least or about 4 micromoles, at least or about 4.5 micromoles, or at least or about 5 micromoles of any of the bifunctional fusion proteins described herein are attached to a cellulose-containing substrate per gram of cellulose of the cellulose-containing substrate.

In some embodiments, at least or about 1 µM, at least or about 25 µM, at least or about 50 µM, at least or about 60 µM, at least or about 70 µM, at least or about 80 µM, at least or about 90 µM, at least or about 100 µM, at least or about 150 µM, at least or about 200 µM, at least or about 250 µM, at least or about 300 µM, at least or about 350 µM, at least or about 400 µM, at least or about 500 µM, at least or about 550 µM, at least or about 600 µM, at least or about 650 µM, at least or about 700 µM, at least or about 750 µM, at least or about 800 µM, at least or about 850 µM, at least or about 900 µM, at least or about 950 µM, at least or about 1 mM, at least or about 1.5 mM, at least or about 2 mM, at least or about 2.5 mM, at least or about 3 mM, at least or about 3.5 mM, at least or about 4 mM, at least or about 4.5 mM, at least or about 5 mM of volume-average concentrations any of the bifunctional fusion proteins described herein are attached to a cellulose-containing substrate.

In some aspects, the molar abundance or molar excess of the antigen-binding protein in the bifunctional fusion protein, such as a rcSso7d linked to a CBD, relative to the antigen of interest allows the rapid capture and, in some embodiments, efficient and complete depletion of the antigen of interest from a sample.

In some embodiments, at least or about a 10-fold molar excess of bifunctional fusion protein or antigen-binding protein completely depletes an antigen of interest from a sample or solution. In some embodiments, at least or about a 10-fold volume-average concentration excess leads to rapid capture and/or immobilization of a bifunctional fusion protein or antigen-binding protein.

In some embodiments, the bifunctional fusion protein is in molar excess of the antigen of interest. In some embodiments, the bifunctional fusion protein is in at least or about 2-fold molar excess, at least or about 3-fold molar excess, at least or about 4-molar excess, at least or about 5-fold molar excess, at least or about 6-fold molar excess, at least or about 7-fold molar excess, at least or about 8-fold molar excess, at least or about 9-fold molar excess, at least or about 10-fold molar excess, at least or about 15-fold molar excess, at least or about 20-fold molar excess, at least or about 25-fold molar excess, at least or about 30-fold molar excess, at least or about 35-fold molar excess, at least or about 40-fold molar excess, at least or about 45-fold molar excess, at least or about 50-fold molar excess, at least or about 60-fold molar excess, at least or about 65-fold molar excess, at least or about 70-fold molar excess, at least or about 80-fold molar excess, at least or about 90-fold molar excess, at least or about 100-fold molar excess, at least or about 200-fold molar excess, at least or about 300-fold molar excess, at least or about 400-fold molar excess, at least or about 500-fold molar excess, at least or about 600-fold molar excess, at least or about 700-fold molar excess, at least or about 800-fold molar excess, at least or about 900-fold molar excess, at least or about 1000-fold molar excess, at least or about 1500-fold molar excess, or at least or about 2000-fold molar excess relative to the antigen of interest in the sample.

In some embodiments, the bifunctional fusion protein is in such excess that the antigen of interest is depleted from the sample. In some embodiments, about or at least 10%, about or at least 20%, about or at least 30%, about or at least 40%, about or at least 50%, about or at least 55%, about or at least 60%, about or at least 65%, about or at least 70%, about or at least 75%, about or at least 80%, about or at least 81%, about or at least 82%, about or at least 83%, about or at least 84%, about or at least 85%, about or at least 86%, about or at least 87%, about or at least 88%, about or at least 89%, about or at least 90%, about or at least 91%, about or at least 92%, about or at least 93%, about or at least 94%, about or at least 95%, about or at least 95.5%, about or at least 96%, about or at least 96.5%, about or at least 97%, about or at least 97.5%, about or at least 98%, about or at least 98.5%, about or at least 99%, about or at least 99.5%, or about 100% of the antigen of interest is depleted from the sample, such as a biological sample.

In some aspects, standard curves can be prepared given the advantageous properties of the disclosure in which complete or near-complete depletion of an antigen of interest can be achieved from a sample or solution. The abundance of the captured antigen can be detected and measured or determined using a readout, such as a fluorescent readout or a colorimetric readout.

In some embodiments, the surface-immobilized concentration of the antigen-binding protein (e.g., rcSso7d.SA-CBD) is quantified using a protein assay, such as a micro bicinchoninic acid (BCA) assay. A standard curve can be prepared by evaporating known quantities of protein onto cellulose test zones, depositing these test zones into the wells of a micro BCA assay, and quantifying the signal development in this format. The same procedure is followed for the experimental samples (following the substrate washing step), and the associated signal for each sample is then mapped to this standard curve in order to determine the mass of immobilized rcSso7d.SA-CBD.

In some embodiments, the sample is a biological sample from a subject. A subject includes, but is not limited to, any mammal, such as a human, a primate, a mouse, a rat, a dog, a cat, a horse, or agricultural stocks (e.g., fish, pigs, cows, sheep, and birds—particularly chickens). In certain embodiments, the subject is a human. In some embodiments, the sample is a solution, such as a buffer solution.

In some embodiments, the cellulose-containing substrate is rinsed with a buffer solution before detecting the antigen of interest bound to the engineered reduced charge Sso7d antigen-binding protein (e.g., rcSso7d). In some embodiments, the buffer is phosphate buffered saline (PBS) or another buffer known to one of ordinary skill in the art that provides a stable environment for a macromolecule, such as a protein, protein complex, antigen, etc.

In some embodiments, the method further includes detecting the antigen of interest bound by the engineered reduced charge Sso7d antigen-binding protein (e.g., rcSso7d) in the bifunctional fusion protein. In some embodiments, the antigen of interest bound to the bifunctional fusion protein is contacted with a cellulose-containing substrate in which the CBD of the bifunctional fusion protein binds the cellulose-containing substrate (e.g., chromatography paper such as WHATMAN® Grade 1 Qualitative Filtration Paper). The method allows for the separation or isolation of the antigen of interest from any other molecules that may be present in a sample, such as a biological sample (e.g., urine). In some embodiments, the presence or amount of the antigen of interest is determined or measured using a signal-generating reagent that specifically recognizes the antigen of interest and generates a signal.

In some embodiments, the bifunctional fusion protein (e.g., rcSso7d-CBD) would be immobilized on a cellulose substrate (e.g., chromatography paper, cellulose powder, etc.), and would then be brought into contact with the solution/biological sample bearing the antigen of interest (either forced convection to draw the fluid across or through the test zone, or soluble co-incubation of the CBD/substrate and antigen). This immobilized complex would then be contacted with a second, epitope-specific variant of rcSso7d (not fused to CBD, but fused instead to a biotin acceptor sequence, or modified with a fluorophore). The second species (e.g., rcSso7d) would bind to a second epitope of the captured antigen. This second species would be conjugated to a means of transducing this binding reaction; several examples are outlined below. All of these steps could be done directly on the cellulose-containing substrate.

Non-limiting examples of signal-generating that can be fused to the antigen-binding protein (e.g., rcSso7d) include, without limitation, gold nanoparticles, enzymes (expressed as fusion partners or indirectly bound to rcSso7d) which yield a colorimetric response, enzymes which yield an amperometric or impedometric signal (e.g., glucose oxidase), a macrophotoinitiator which can initiate a polymerization reaction, cellulose nanobeads, other metallic nanoparticles, dye-filled liposomes, DNA which can be amplified enzymatically, RNA which can be expressed for the production of a color-producing enzyme, etc. The presence or amount of the signal-generating reagent can be detected using an imaging device, such as a digital imager. Additional non-limiting examples of detecting the signal-generating reagent include gold nanoparticles, which can be used in a point-of-care setting, and are the reagents used in traditional pregnancy tests. The spatial localization of gold nanoparticles, mediated by the antigen-binding interaction, concentrates the optical signal (which is also amplified by the occurrence of surface plasmon resonance). This can be detected by the naked eye. Polymerization-based amplification would use the localization of a macrophotoinitiator in order to yield a rapid, durable polymerization response following incubation with a monomer solution and irradiation with the appropriate wavelength of light. Entrained phenolphthalein yields a high-contrast colorimetric readout following the application of a basic solution, which can be detected with the naked eye. An amperometric method, such as fusing glucose oxidase to the second rcSso7d species and contacting the tests with gold probes and a glucose solution, would allow for smart phone based detection. Enzymatic methods can also be used, and rely upon a fusion of the second species (e.g., rcSso7d) to an enzyme and contacting the tests with a labile substrate which becomes colored following enzymatic cleavage. Impedometric means of detecting the signal generating reagent are also possible, and can be achieved using smartphone-compatible adaptors.

In some aspects, provided herein are also methods for enhancing the sensitivity of an assay. The method includes binding of a target to a target-binding species, which includes fusing a target-binding species that binds to a target of interest to a cellulose binding domain (CBD). Any antigen-binding protein that can be attached to a cellulose-binding domain can benefit from its favorable properties; the high immobilized abundance of bifunctional fusion protein with a CBD results in high molar abundance of the binding species, thereby allowing, in some instances, depletion of an antigen of interest and a high local concentration of this species, thereby allowing, in some instances, rapid capture of an antigen of interest. In some embodiments, the antigen of interest is in solution. In contrast to traditional immunoassays in which the immobilized binding partner is the limiting reagent and the antigen of interest is captured slowly and incompletely, the present disclosure allows for the antigen capture/detection to rapidly proceed to completion. Additionally, because the bifunctional fusion protein, and thus the antigen-binding domain, is at a high local abundance, this allows the use of higher sample volumes containing higher amounts of antigen, which would be captured and depleted, in some instances, to provide high signal over a method previously available in the art in which the antigen-binding species is actually the limiting reagent, reducing the amount of antigen that can be captured and detected at a given point. This could be applied to any binding scaffold by expressing the binding scaffold as a fusion partner to the CBD.

Target-Binding Domain

In some embodiments, any of the target-binding domains or any of its variants described herein are not part of a bifunctional fusion protein described herein. In some embodiments, any of the target-binding domains described herein, such as rcSso7d or any of its variants that is not part of a bifunctional fusion protein (e.g., rcSso7d-CBD), is directly or indirectly linked to or expressed with a molecule or protein that increases the solubility of the target-binding domain. In some embodiments, the molecule or protein that increases solubility is a maltose binding protein (MBP; e.g., Gene ID: 1097664) or an MBP comprising the amino acid sequence:

(SEQ ID NO: 124)
MKIEEGKLVIWINGDKGYNGLAEVGKKFEKDTGIKVTVEHPDKLEEKFPQ

VAATGDGPDIIFWAHDRFGGYAQSGLLAEITPDKAFQDKLYPFTWDAVRY

NGKLIAYPIAVEALSLIYNKDLLPNPPKTWEEIPALDKELKAKGKSALMF

NLQEPYFTWPLIAADGGYAFKYENGKYDIKDVGVDNSGAKAGLTFLVDLI

KNKHMNADTDYSIAEAAFNKGETAMTINGPWAWSNIDTSKVNYGVTVLPT

FKGQPSKPFVGVLSAGINAASPNKELAKEFLENYLLTDEGLEAVNKDKPL

GAVALKSYEEELAKDPRIAATMENAQKGEIMPNIPQMSAFWYAVRTAVIN

AASGRQTVDEALKDAQT

In some embodiments, the molecule or protein that increases solubility is small ubiquitin-like modifier (SUMO; e.g., e.g., Gene ID: 7341), glutathione S-transferase (GST; e.g., Gene ID: 101890455), enhanced green fluorescent protein (eGFP; e.g., Gene ID: 20473140), or Thioredoxin (TRX; e.g., Gene ID: 22166). Other molecules or proteins that increase solubility of a protein or protein construct known to one of ordinary skill in the art are also contemplated herein.

In some embodiments, any of the target-binding domains disclosed herein include a biotin acceptor sequence. In some embodiments, any of the target-binding domains disclosed herein are chemically biotinylated. A target-binding domain disclosed herein can be chemically biotinylated by methods known to one of ordinary skill in the art. Non-limiting examples of methods to chemically biotinylate a protein, include the use of sulfo-NHS-LC-biotin. In some embodiments, the method to chemically biotinylate a protein is a variation of NHS conjugation with biotin with different linker arms (e.g., Sulfo-NHS-Biotin, Sulfo-NHS-LC-Biotin, Sulfo-NHS-LC-LC-Biotin). Additional non-limiting examples of methods to chemically biotinylate a protein include sulfhydryl conjugation [e.g., BMCC-Biotin (1-biotinamido-4-[4'-(maleimidomethyl)cyclohexane-carboxamido]butane)), Iodoacetyl-Biotin, and pyridyldithiol-biotin].

In some embodiments, the cellulose-containing substrate is oxidized. In some embodiments, the target-binding domain, such as rcSso7d, includes one or more biotin acceptors. In some embodiments, the target binding domain includes at least 1 or 1, at least 2 or 2, at least 3 or 3, at least 4 or 4, at least 5 or 5, at least 6 or 6, at least 7 or 7, at least 8 or 8, at least 9 or 9, at least 10 or 10, at least 15 or 15, at least 20 or 20, at least 25 or 25, at least 30 or 30, at least 35 or 35, at least 40 or 40, at least 45 or 45, at least 50 or 50, or at least 100 or 100 biotin acceptors. In some embodiments, the biotin acceptor is an amino acid sequence. In some embodiments, the biotin acceptor is a biotin molecule. In some embodiments, the biotin molecule is chemically added to any of the target-binding domains described herein, such as rcSso7d or any of its variants.

In some embodiments, the antigen or antigen of interest described herein binds to the oxidized cellulose substrate. In some embodiments, the antigen or antigen of interest is contacted with a target binding domain that includes one or more biotin acceptors and forms a complex. In some embodiments, the target-binding domain that includes one or more biotin acceptors is contacted with a streptavidin molecule. In some embodiments, the streptavidin is labeled or linked to a fluorophore or a molecule that emits a detectable signal.

Diseases and Conditions

The bifunctional fusion proteins, compositions, methods and kits described herein can be used to detect the presence of molecules, such as antigens, that are generated in response to various diseases or conditions. Non-limiting examples of diseases or conditions that generate molecules, such as antigens, which can be detected include a disease or condition that releases an antigen of interest, such as cancer, cardiovascular diseases, infectious diseases, liver diseases, such as liver failure, Alzheimer's disease, Parkinson's disease, or autoimmune diseases. Any condition which has an associated biochemical signature can theoretically be detected.

The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g., small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In some embodiments, the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma.

Infectious diseases can be caused by bacteria, viruses, fungi, or parasites. Bacteria are responsible for illnesses such as strep throat, urinary tract infections and tuberculosis. Viruses cause a multitude of diseases, ranging from the common cold to AIDS. Fungi cause several skin diseases, such as ringworm and athlete's foot, or can also affect the lungs and/or nervous system. Parasites can cause diseases such as malaria.

Autoimmune disease is a class of diseases in which an subject's own antibodies react with host tissue or in which immune effector T cells are autoreactive to endogenous self-peptides and cause destruction of tissue. Thus, an immune response is mounted against a subject's own antigens, referred to as self-antigens. Autoimmune diseases include but are not limited to rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjögren's syndrome, insulin resistance, and autoimmune diabetes mellitus.

In some embodiments, the disease or condition is prostate cancer and the antigen that can be detected is PSA. In some embodiments, the disease or condition is cardiac arrest and the antigen of interest that can be detected is troponin. In some embodiments, the disease or condition is Alzheimer's disease and the antigen of interest that can be detected is tau protein. In some embodiments, the disease or condition is HIV and the antigen of interest that can be detected is IP-10. In some embodiments, the disease or condition is Schistomiasis and the antigen of interest that can be detected is Schistosome GST. In some embodiments, the disease or condition is ovarian cancer and the antigen of interest that can be detected is CA-125. In some embodiments, the disease or condition is lyme disease and the antigen of interest that can be detected is ospA.

In some embodiments, antigens or antigens of interest produced by vector-borne diseases (e.g., chikungunya, Chagas, Ebola, bubonic plague, Lyme disease, brucellosis, encephalitis, etc.) are also contemplated herein; by food/water-borne illness (e.g., diarrhea, cholera, schistomiasis, bovine spongiform encephalopathy (prion), etc.) are also contemplated herein; by patient-to-patient transmitted infectious disease (e.g., tuberculosis (ESAT-6/CFP-10/Rv1656/LAM), HIV (CD32a), influenza (HA), rhinitis, pneumonia, bronchitis, syphilis, gonnorhea, hepatitis A/B/C, HPV, etc.) are also contemplated herein; by chronic diseases (diabetes/pre-diabetes (glycated hemogloblin), anemia (hemoglobin), liver cirrhosis, cardiac arrest (troponin), Alzheimer's disease, autoimmune disease, etc.) are also contemplated herein. General health assays (protein urine analysis, etc), livestock assays, companion diagnostics for cancer therapeutics are also contemplated herein.

Compositions

In some aspects, compositions of the bifunctional fusion proteins described herein are also provided. In some embodiments, the composition includes any of the bifunctional fusion proteins described herein bound to a cellulose-containing substrate. In some embodiments, the cellulose-containing substrate is paper (e.g., chromatography paper) or nitrocellulose. In certain embodiments, the cellulose-containing substrate is modified in an oxidizing chemical bath to yield covalent chemical linkage of the protein to the substrate, passivated with a blocking agent to reduce non-specific protein adsorption to the substrate, or pre-incubated with a stabilizing species such as trehalose in order to improve assay functionality and stability. In certain embodiments, the cellulose-containing substrate is not modified (unmodified). In some embodiments, the cellulose-containing substrate is an unmodified chromatography paper, such as unmodified WHATMAN® Grade 1 Qualitative Filtration Paper. Additional non-limiting examples of cellulose-containing substrates also contemplated herein include cellulose powder, cellulose microbeads, or cellulosic fabrics/yarns.

In some embodiments, at least or about 0.1 micromole, at least or about 0.2 micromoles, at least or about 0.3 micromoles, at least or about 0.4 micromoles, at least or about 0.5 micromoles, at least or about 0.6 micromoles, at least or about 0.7 micromoles, at least or about 0.8 micromoles, at least or about 0.9 micromoles, at least or about 1 micromole, at least or about 1.1 micromoles, at least or about 1.2 micromoles, at least or about 1.3 micromoles, at least or about 1.4 micromoles, at least or about 1.5 micromoles, at least or about 1.6 micromoles, at least or about 1.7 micromoles, at least or about 1.8 micromoles, at least or about 1.9 micromoles, at least or about 2 micromoles, at least or about 2.1 micromoles, at least or about 2.2 micromoles, at least or about 2.3 micromoles, at least or about 2.4 micromoles, at least or about 2.5 micromoles, at least or about 2.6 micromoles, at least or about 2.7 micromoles, at least or about 2.8 micromoles, at least or about 2.9 micromoles, at least or about 3 micromoles, at least or about 3.5 micromoles, at least or about 4 micromoles, at least or about 4.5 micromoles, or at least or about 5 micromoles of any of the bifunctional fusion proteins described herein are attached to a cellulose-containing substrate per gram of cellulose of the cellulose-containing substrate.

In some embodiments, at least or about 1 $\mu M$, at least or about 25 $\mu M$, at least or about 50 $\mu M$, at least or about 60 $\mu M$, at least or about 70 $\mu M$, at least or about 80 $\mu M$, at least or about 90 $\mu M$, at least or about 100 $\mu M$, at least or about 150 $\mu M$, at least or about 200 $\mu M$, at least or about 250 $\mu M$, at least or about 300 $\mu M$, at least or about 350 $\mu M$, at least or about 400 $\mu M$, at least or about 500 $\mu M$, at least or about 550 $\mu M$, at least or about 600 $\mu M$, at least or about 650 $\mu M$, at least or about 700 $\mu M$, at least or about 750 $\mu M$, at least or about 800 $\mu M$, at least or about 850 $\mu M$, at least or about 900 $\mu M$, at least or about 950 $\mu M$, at least or about 1 mM, at least or about 1.5 mM, at least or about 2 mM, at least or about 2.5 mM, at least or about 3 mM, at least or about 3.5 mM, at least or about 4 mM, at least or about 4.5 mM, at least or about 5 mM of volume-average concentration of any of the bifunctional fusion proteins described herein are attached to a cellulose-containing substrate.

Kits

In some aspects, the bifunctional fusion protein and compositions described herein are provided in a kit. In some embodiments, the kit is used to assess the presence or amount of a molecule, such as an antigen or an antigen of interest and includes a container containing any of the bifunctional fusion proteins described herein.

In some embodiments, the kit further comprises a cellulose-containing substrate. In some embodiments, the bifunctional fusion protein is bound to the cellulose-containing substrate. In some embodiments, at least or about 0.1 micromole, at least or about 0.2 micromoles, at least or about 0.3 micromoles, at least or about 0.4 micromoles, at least or about 0.5 micromoles, at least or about 0.6 micromoles, at least or about 0.7 micromoles, at least or about 0.8 micromoles, at least or about 0.9 micromoles, at least or about 1 micromole, at least or about 1.1 micromoles, at least or about 1.2 micromoles, at least or about 1.3 micromoles, at least or about 1.4 micromoles, at least or about 1.5 micromoles, at least or about 1.6 micromoles, at least or about 1.7 micromoles, at least or about 1.8 micromoles, at least or about 1.9 micromoles, at least or about 2 micromoles, at least or about 2.1 micromoles, at least or about 2.2 micromoles, at least or about 2.3 micromoles, at least or about 2.4 micromoles, at least or about 2.5 micromoles, at least or about 2.6 micromoles, at least or about 2.7 micromoles, at least or about 2.8 micromoles, at least or about 2.9 micromoles, at least or about 3 micromoles, at least or about 3.5, at least or about 4 micromoles, at least or about 4.5 micromoles, or at least or about 5 micromoles of any of the bifunctional fusion proteins described herein are attached to the cellulose-containing substrate per gram of cellulose of the cellulose-containing substrate.

In some embodiments, at least or about 1 $\mu M$, at least or about 25 $\mu M$, at least or about 50 $\mu M$, at least or about 60 $\mu M$, at least or about 70 $\mu M$, at least or about 80 $\mu M$, at least or about 90 $\mu M$, at least or about 100 $\mu M$, at least or about 150 $\mu M$, at least or about 200 $\mu M$, at least or about 250 $\mu M$, at least or about 300 $\mu M$, at least or about 350 $\mu M$, at least or about 400 $\mu M$, at least or about 500 $\mu M$, at least or about 550 $\mu M$, at least or about 600 $\mu M$, at least or about 650 $\mu M$, at least or about 700 $\mu M$, at least or about 750 $\mu M$, at least or about 800 $\mu M$, at least or about 850 $\mu M$, at least or about 900 $\mu M$, at least or about 950 $\mu M$, at least or about 1 mM, at least or about 1.5 mM, at least or about 2 mM, at least or about 2.5 mM, at least or about 3 mM, at least or about 3.5 mM, at least or about 4 mM, at least or about 4.5 mM, at least or about 5 mM of volume-concentration of any of the bifunctional fusion proteins described herein are attached to the cellulose-containing.

In some embodiments, the bifunctional fusion protein is bound to the cellulose-containing substrate. In some embodiments, the cellulose-containing substrate is paper (e.g., chromatography paper), nitrocellulose or cellulose powder. In certain embodiments, the cellulose-containing substrate is modified in an oxidizing chemical bath to yield covalent chemical linkage of the protein to the substrate, passivated with a blocking agent to reduce non-specific protein adsorption to the substrate, or pre-incubated with a stabilizing species such as trehalose in order to improve assay functionality and stability. In certain embodiments, the cellulose-containing substrate is not modified (unmodified). In some embodiments, the cellulose-containing substrate is an unmodified chromatography paper, such as unmodified WHATMAN® Grade 1 Qualitative Filtration Paper. Additional non-limiting examples of cellulose-containing substrates also contemplated herein include cellulose powder, or cellulose microbeads, cellulosic fabrics/yarns.

Examples

Example 1. Paper-Based Diagnostics in the Antigen-Depletion Reime: High-Density Immobilization of Rcsso7d-Cellulose-Binding Domain Fusion Proteins for Efficient Target Capture Materials and Methods
Materials
Unless otherwise stated, all chemical reagents, biological materials, and consumables were procured from the same source as outlined in the supplementary information of Reference 1. All DNA cloning enzymes were purchased from New England Biolabs (Ipswich, Mass., USA). Streptavidin-eosin conjugate was prepared as previously described (Miller et al., 2016, SI).

Yeast Surface Display Selection and Characterization of rcSso7d-Based Binding Variants The development and selection of rcSso7d.SA was described in previous work. (Miller et al., 2016) The Rv1656-binding variant of rcSso7d was selected in similar fashion, from a yeast surface display library based on the reduced-charge Sso7d scaffold (rcSso7d). This yeast library was generated using trinucleotide oligo synthesis and in vivo homologous recombination with the linearized pCTcon2 plasmid. (Traxlmayr et al., 2016).

Figure 8:
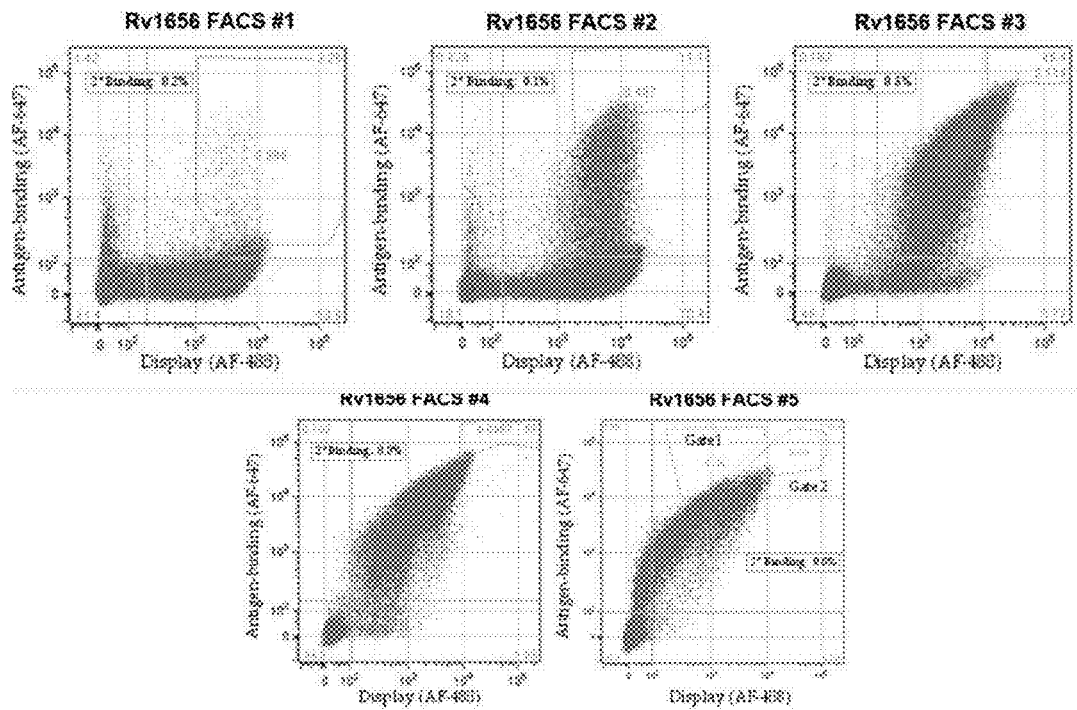
FIG. 8. FACS plots for yeast-surface display selection of Rv1656-binding variants of rcSso7d. Data points represent the measured fluorescence for 20,000 individual yeast cells. Full-length surface display of the rcSso7d scaffold, quantified via the surface localization of the ALEXA FLUOR® 488 fluorophore, is presented on the x-axis. Rv1656 binding activity, quantified via the ALEXA FLUOR® 64 7 fluorophore, is presented on the y-axis. The corner of each quadrant is labeled with the proportion of the library population falling within those bounds, and the sorting gate used to capture the subsequent sub-library is labeled with the captured percentage of the library population. The secondary binding, corresponding to the population proportion which binds to the secondary reagent (SA-AF647), is also noted. The soluble concentration of Rv1656 was 100 nM for the first three rounds of sorting, 50 nM for the fourth round, and 25 nM for the fifth round.

Both highly-avid magnetic bead sorting (Ackerman et al., 2009) (MBS) and fluorescence-activated cell sorting (FACS) (Chao et al., 2006) were used to select binders against a biotinylated Rv1656 target (FIG. 8). The sorting stringency was increased over five rounds of FACS-based library screening, after which a sub-library was sequenced and rcSso7d.Rv1656 was selected for further characterization. The affinity of this species was assessed in a yeast surface display format, via a soluble titration of biotinylated Rv1656 against the displayed rcSso7d variant.

Recombinant Protein Expression, Purification, and Characterization

The genes for rcSso7d.SA and rcSso7d.Rv1656 were both cloned from the pCTcon2 yeast display plasmid into the pET28b(+) bacterial expression plasmid as previously described. (Miller et al., 2016) The rcSso7d.SA-CBD gene product was generated by Integrated DNA Technologies (IDT; Coralville, Iowa, USA) via gene synthesis, and traditional PCR cloning was used to integrate the rcSso7d.Rv1656 module into this rcSso7d-CBD fusion construct. All gene products were modified with an N-terminal hexahistidine tag for purification via immobilized metal affinity chromatography (IMAC). The pET14b-Rv1656 plasmid was provided by the lab of Dr. Antonio Campos-Neto at the Forsyth Institute. (Napolitano et al., 2008)

The heterologous expression of all protein species was conducted in a BL21(DE3) strain of E. coli, and induced via the addition of 0.5 mM isopropyl β-D-1-thiogalactopyranoside (IPTG). Induced cells were lysed by ultrasonification, and the recombinant product was purified from the clarified lysate via IMAC. A 3-kDa Amicon Ultracentrifuge Filter cassette was used to buffer exchange the 9.24-kDa rcSso7d monomer 1,000-fold into the resuspension buffer (40 mM sodium acetate, pH 5.5). Products featuring a CBD fusion partner were buffer-exchanged using a 3.5 kDa MWCO Slide-A-Lyzer Dialysis Cassette (Thermo Fisher Scientific, Waltham, Mass., USA), in order to prevent the adsorption of the CBD fusion products to the cellulose acetate membrane of the spin filters.

Rv1656 was expressed in similar fashion using BL21 (DE3) E. coli, and was resuspended in 50 mM HEPES buffer (pH 8.0) using a 10kDa MWCO Slide-A-Lyzer Dialysis Cassette. Purified Rv1656 was biotinylated using the EZ-Link Sulfo-NHS-LC-Biotin No-Weigh Format labeling kit from Thermo Fisher Scientific, and desalted using Micro G-25 Spin Columns from Santa Cruz Biotech (Dallas, Tex., USA).

The concentrations of all purified proteins were assessed using a bicinchoninic acid (BCA) assay, and all standards and purified samples were tested in triplicate for greater accuracy. Protein purity was assessed using a freshly cast 15% sodium dodecyl sulfate polyacrylamide gel electrophoresis (SDS-PAGE) gel, stained using COOMASSIE® Brilliant Blue G-250.

Fabrication and Testing of Biofunctional Cellulose Test Zones

Unmodified WHATMAN® No. 1 chromatography paper was used as shipped for the immobilization of rcSso7d-CBD fusion proteins. In order to enable the covalent immobilization of rcSso7d variants lacking a CBD fusion partner, WHATMAN® No. 1 chromatography paper was functionalized in 30 mM sodium metaperiodate solution as previously described. (Miller et al., 2016) This oxidized, aldehyde-functionalized cellulose was stored under vacuum in a desiccator until use, whereas non-functionalized paper was stored under ambient conditions. As previously described, a solid ink printer was used to produce test zone arrays, and this printed wax was melted through the paper thickness (0.18 mm) to yield test zones with an average area of 2.5±0.1 mm$^2$ (unless otherwise noted).

Stock solutions of purified rcSso7d and rcSso7d-CBD variants were diluted to the desired concentrations in resuspension buffer. For bare rcSso7d species, glycerol was also added to the solution at a final volumetric concentration of 10% in order to prevent evaporation during the extended initial incubation. Unless otherwise stated, all binding protein solutions were prepared at a final concentration of 30 µM. Negative controls for functionalized paper samples consisted of test zones contacted with 1 mg/mL bovine serum albumin (BSA). Bare paper test zones were used as the negative control for unmodified paper samples.

Functionalized test zones were modified with the bare rcSso7d variants, washed, and neutralized in Tris-buffered saline as described in previous work. Both rcSso7d-CBD variants were contacted with unmodified paper in 6 µL aliquots for at least thirty seconds, and then washed twice in 20 µL of 1× phosphate-buffered saline (PBS; pH 7.4).

Protein-coated test zones were then contacted with 10 µL of the relevant antigen, diluted to the desired concentration in sterile-filtered 1×PBS/1% w/v BSA. rcSso7d.SA and rcSso7d.SA-CBD species were contacted with either streptavidin eosin (SA-E), prepared as previously described, (Miller et al., 2016) or streptavidin ALEXA FLUOR® 647 (SA-AF647) sourced from Invitrogen (Carlsbad, Calif., USA). rcSso7d.Rv1656-CBD was contacted with biotinylated recombinant Rv1656. All test zones were incubated with antigen solution for 30 minutes at room temperature, after which they were washed twice with PBS. Negative controls were incubated in PBS in the absence of soluble antigen during this period.

Figure 14:
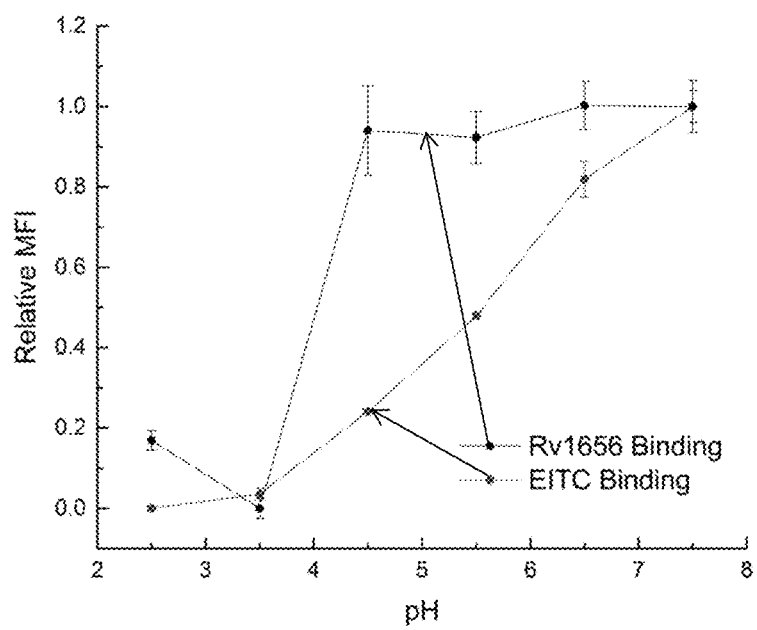
FIG. 14. Comparison of non-specific binding to streptavidin eosin (SA-E) and specific binding to Rv1656 under wash conditions of varying pH. SA-E and Rv1656b solutions were prepared in a series of citric acid/disodium phosphate buffers of varying pH and ionic strengths (with 1% BSA w/v), at a soluble concentration of 256 nM. These solutions were applied to paper samples treated with 30 µM of rcSso7d: Rv1656-CBD for a 30-minute incubation period, and were subsequently washed in buffer of the san1e composition. Samples treated with Rv1656b were subsequently treated with 256 nM SA-AF647 (which does not display non-specific binding) to assess target-specific binding under these incubation conditions. Samples treated with SA-E and Rv1656b were imaged in the TEXAS RED@ channel for 1000 ms and the CY5® channel for 100 ms, respectively, and the observed binding activity was quantified relative to the signal at pH 7.5. Error bars represent the standard deviation of four independent replicates.

Assays incorporating rcSso7d.Rv1656 and rcSso7d.Rv1656-CBD were then subjected to an additional 30-minute incubation with SA-E/SA-AF647 at a concentration of 256 nM. SA-E samples were prepared in a citric acid-sodium phosphate buffer system (50 mM citric acid, 90 mM Na2HPO4, pH 4.5) containing 1% BSA, and washed in the same acidic buffer lacking BSA, in order to reduce non-specific binding of rcSso7d.Rv1656-CBD to the eosin reagent (FIG. 14). Developed samples were blotted dry and stored in the dark in a freezer box until needed for fluorescence microscopy imaging.

Fluorescence Microscopy

All samples were imaged as previously described (Miller et al., 2016), using an Olympus 1X81 Microscope. Unless otherwise noted, all samples developed with SA-E were exposed for 1000 ms using a Semrock TxRed-4040C filter set. Samples developed with SA-AF647 were exposed for either 80 ms or 100 ms (as noted) using a Semrock CY5®-

4040C filter set. The ImageJ Auto Threshold function (Default algorithm) was used to identify the bounds of each sample zone, and the mean fluorescence intensity (MFI) of each sample was calculated by averaging the brightness of all pixels within the thresholded area. Four technical replicates were prepared for all experimental conditions, and the resultant MFI values were averaged for all replicates. Error bars represent one standard deviation from this mean intensity value.

Quantification of Surface-Immobilized CBD Fusion Proteins

A micro BCA assay (Thermo Fisher Scientific) was used to determine the immobilized surface density of the engineered rcSso7d.SA-CBD fusion protein on non-functionalized WHATMAN® No. 1 chromatography paper. A series of standards was prepared by contacting test zones with known masses of rcSso7d.SA-CBD and allowing these solutions to evaporate in a vacuum chamber at room temperature for 30 minutes, yielding complete protein adsorption to the cellulosic substrate. Experimental samples were generated by applying a series of known soluble rcSso7d.SA-CBD concentrations to the test zones, followed by a PBS wash step.

All samples were excised from the test strips and deposited into the wells of a 96-well plate pre-filled with 150 μL of 40 mM sodium acetate (pH 5.5). These test zones were vigorously stirred with clean pipette tips, and 150 μL of Working Reagent was then added to each sample well. The plate was incubated at 37° C. for two hours, and after removing the paper test zones (wringing any entrained fluid back into the sample well), the absorbance at 562 nm was quantified for all samples.

The response curve for the evaporated standards was fit to a second-order polynomial, and this standard curve was used to determine the effective quantity of rcSso7d.SA-CBD immobilized on the washed samples. Proportional rcSso7d.SA-CBD retention was calculated by comparing these experimentally determined quantities to the known protein masses applied to the surface. In order to quantify the binding capacity of the cellulose substrate under these processing conditions, the density of WHATMAN® No. 1 chromatography paper was measured in triplicate, and was found to be $0.088 \pm 0.00016$ mg/mm$^2$. The area of the test zones was measured by determining the pixel density at 40× magnification (0.287 megapixels/mm$^2$), and measuring the thresholded test zone area in ImageJ. For this micro BCA experiment, the average area of the test zones was found to be $3.65 \pm 0.25$ mm$^2$, corresponding to a cellulose mass of $0.32 \pm 0.021$ mg.

Combinatorial Library Screening

The pCTcon2-encoded library of rcSso7d variants is expressed and exported to the exterior of the yeast membrane as a C-terminal fusion to the yeast Aga2p mating protein. This permits the selection of yeast carrier cells based on the binding activity of the displayed protein, allowing the population genetics to be biased towards plasmids encoding for functional rcSso7d variants. In order to select binding variants against the recombinant Rv1656b antigen, two rounds of target positive MBS were used to reduce the library diversity from 1.4 billion to approximately 1 million, and one round of target-negative MBS was used to deplete the library of streptavidin-binding variants. This sub-library was then screened via five rounds of FACS, sequentially increasing the sorting stringency by decreasing the concentration of available antigen and the captured proportion of the library population.

A sub-population of yeast was sequenced following the final FACS round, and rcSso7d.Rv1656 was selected based on its superior binding properties. The binding affinity of the rcSso7d.Rv1656 species was assessed in a yeast-surface display format, via a titration of the soluble, biotinylated Rv1656 antigen against the displayed rcSso7d binding species. The antigen concentration was varied from 256 nM to 0.25 nM, and at every concentration of Rv1656 the yeast cells were resuspended in sufficient volume such that the antigen was present in ten-fold molar excess of the displayed binding species (assuming 50,000 displayed copies per cell, and efficient display in 60% of the population). Samples were incubated with continuous mixing for sufficient time to achieve greater than 99% of theoretical equilibrium binding. Following fluorescent labeling with streptavidin ALEXA FLUOR® 647, the cell surface fluorescence was analyzed using a BD FACS LSR Fortessa II flow cytometer and the FACSDiva software package. All samples were analyzed using the 488 nm and 640 nm lasers, set to a voltage of 300V. The total geometric mean fluorescence intensity of all rcSso7d-displaying cells was quantified, and a sigmoidal function was fit to these data points to determine the affinity of the rcSso7d.Rv1656 binding species.

Production of Gene Constructs rcSso7d-Rv1656 was cloned from the pCTcon2 yeast display plasmid into the pET28b(+) bacterial expression plasmid as previously described. (Miller et al., 2016) Briefly, polymerase chain reaction (PCR) amplification of the desired gene was conducted using the primers rcSso7d-for and rcSso7d-rev (Table 3), at an annealing temperature of 58.3° C. This PCR amplicon was subjected to an NdeI/XhoI double digest at 37° C. for three hours (adding the NdeI enzyme after two hours to prevent aberrant cleavage), and this cleaved product was subsequently ligated into the digested pET-28b(+) plasmid backbone at room temperature in order to generate the stable rcSso7d.Rv1656 construct. All ligation mixtures were purified using the DNA Clean and Concentrator-5 Kit from Zyrno Research (Irvine, Calif., USA), and eluted in 12 μL of PCR-grade water. 4 μL of this ligation product was transformed into DH5a E. coli (F- 9φ80lacZΔM15Δ(lacZYA-argF) U169 recA1 end A1 hsdR17 (rk−, mk+) gal-phoA supEλ44-thi-1 gyrA96 relA1) via electroporation. The entirety of this transformation mixture was plated on LB-kan plates and incubated overnight at 37° C. Positive clones were verified via both N- and C-terminal sequencing, using the T7 promoter and T7 terminator sequencing primers.

This general workflow was used for all cloning projects, and all relevant primers can be found in Table 3. Additional cloning projects involved 1) the amplification and integration of the rcSso7d.SA-CBD GeneBlock into the pET28b(+) plasmid (primers: rcSso7d-for/CBD-rev; $T_m$: 58.3° C.), and integration of the rcSso7d.Rv1656 gene into the CBD construct (primers: rcSso7dfor/rcSso7d-BamHI-rev; $T_m$: 58.3° C.). In this latter project, the PCR amplicon and pET28b(+) plasmid were both subjected to an NdeI/BamHI double digest at 37° C. for one hour in order to excise the rcSso7d.SA gene and prepare complementary sticky ends. All sequence-verified plasmids were transformed into BL21 (DE3) (F- ompT gal dcm lon hsdS$_B$ (r$_B$-m$_B$-)λ(DE3)) E. coli by electroporation for expression and purification.

TABLE 3

Oligonucleotide sequences of primers used in sequencing reactions
and plasmid cloning of selected binders rcSso7d.SA and rcSso7d.Rv1656.

| # | Oligo Name | SEQ ID NO | DNA Sequence (NdeI, XhoI, and BamHI sites) |
|---|---|---|---|
| 1 | rcSso7d-for | 6 | 5'-AGGCAGTCTCATATGGCAACCGTGAAAT-3' |
| 2 | rcSso7d-rev | 7 | 5'-ACCCCTCTCGAGTTATTGCTTTTCCAGCATCTG-3' |
| 3 | rcSso7d-BamHI-rev | 8 | 5'-ACCCCTCTCGAGTTATTAGGATCCTTGCTTTTCCAGCATCTG-3' |
| 4 | CBD-rev | 9 | 5'-AAGTTACGCTCGAGTTAGGGTTCTTTACCCCATACAAGAACACCG-3' |

Derivation of the Exact Analytical Solution for a Monovalent Binding System

For a monovalent binding system, wherein [L] and [R] represent the volumetric molar concentrations of free ligand and free receptor, respectively, and [LR] represents the concentration of the bound complex, the ligand-capture reaction can be described using the following first-order differential equation:

$$\frac{d[LR]}{dt} = k_{on}[L][R] - k_{off}[LR]$$

It is also noted that:

$$[L]=[L]_0-[LR]$$

and $$[R]=[R]_0-(LR)$$

Thus:

$$\frac{d[LR]}{dt} = k_{on}([L]_0 - [LR])([R]_0 - [LR]) - k_{off}[LR]$$

Multiplying out and rearranging:

$$\frac{d[LR]}{dt} = k_{on}([L]_0[R]_0 - [LR][L]_0 - [LR][R]_0 + [LR]^2) - k_{on}K_D[LR]$$

-continued $$\frac{d[LR]}{dt} = k_{on}([L]_0[R]_0 - [LR]([L]_0 + [R]_0 + K_D) + [LR]^2)$$

For simplicity, these terms shall be referred to as:

$$a=[L]_0[R]_0$$

$$b=-([L]_0+[R]_0+K_D)$$

$$c=1$$

Thus:

$$\frac{d[LR]}{dt} = k_{on}(a + b[LR] + c[LR]^2)$$

Performing separation of variables, an equation of the below form is arrived at:

$$\frac{d[LR]}{(a + b[LR] + c[LR]^2)} = k_{on}dt$$

This is of the Ricatti equation class, and can be solved implicitly. This integral is also tabulated in the CRC Handbook of Chemistry and Physics (Formula 108), in the form:

$$\int \frac{dx}{X} = \frac{1}{\sqrt{-q}} \ln\left(\frac{2cx + b - \sqrt{-q}}{2cx + b + \sqrt{-q}}\right)$$

where $$X=a+bx+cx^2$$

and $$q=4ac-b^2$$

This solution form holds for all q<0, which is true for all real solutions of this quadratic equation.

Plugging these values in, the below solution is found:

$$\frac{1}{\sqrt{(-([L]_0 + [R]_0 + K_D))^2 - 4[L]_0[R]_0}} \ln\left(\frac{2[LR](t) - ([L]_0 + [R]_0 + K_D) - \sqrt{(-([L]_0 + [R]_0 + K_D))^2 - 4[L]_0[R]_0}}{2[LR](t) - ([L]_0 + [R]_0 + K_D) + \sqrt{(-([L]_0 + [R]_0 + K_D))^2 - 4[L]_0[R]_0}}\right) = k_m t + \phi$$

This expression can be simplified via the following definitions (Schafer, 1983):

$$D = [L]_0 - [R]_0$$

$$S = [L]_0 + [R]_0$$

$$F = \sqrt{-q} = \sqrt{D^2 + 2SK_D + K_D^2}$$

$$P = \frac{-b - \sqrt{-q}}{2} = \frac{(S + K_D - F)}{2}$$

$$Q = \frac{-b + \sqrt{-q}}{2} = \frac{(S + K_D + F)}{2}$$

Plugging these expressions in:

$$\frac{1}{F}\ln\left(\frac{[LR] - Q}{[LR] - P}\right) = k_{on}t + \phi$$

Rearranging:

$$\ln\left(\frac{[LR] - P}{[LR] - Q}\right) = -Fk_{on}t + \phi$$

$$\frac{[LR] - P}{[LR] - Q} = w_0 e^{-Fk_{on}t}$$

For simplicity, this exponential term is defined to be $w = w_0 e^{-Fk_{on}t}$, and thus:

$$\frac{[LR] - P}{[LR] - Q} = w$$

$$[LR] - P = w([LR] - Q)$$

$$[LR] - w[LR] = P - wQ$$

$$[LR](t) = \frac{P - wQ}{1 - w}$$

Recognizing that at $t=0$, $[LR]=0$, the constant $w_0$ can be solved for:

$$0 = \frac{P - w_0 Q}{1 - w_0}$$

$$w_0 = \frac{P}{Q}$$

$[LR]_{eq}$ can also be solved for by taking the limit as $t \to \infty$:

$$[LR]_{eq} = \frac{P - 0}{1 - 0} = P$$

Thus, the proportion of equilibrium binding at any given time is equal to:

$$\frac{[LR](t)}{[LR]_{eq}} = \frac{P - wQ}{P - wP} = \frac{P - wQ}{P - wP}$$

The time $t_{99}$ at which 99% of equilibrium binding has been achieved is:

$$0.99 = \frac{P - wQ}{P - wP}$$

$$0.99P - 0.99wP = P - wQ$$

$$w(Q - 0.99P) = P - 0.99P$$

$$\frac{P}{Q} e^{-Fk_{on}t_{99}} = \frac{0.01P}{Q - 0.99P}$$

$$t_{99} = -\frac{1}{Fk_{on}}\ln\left(\frac{0.01Q}{Q - 0.99P}\right)$$

These findings can also be non-dimensionalized, substituting either:

$$u = \frac{[LR]}{[R]_0}$$

or $$v = \frac{[LR]}{[L]_0}$$

and $$\tau = k_{off} t$$

Doing so, the below relative equations are arrived at:

$$u = \frac{P\left(1 - e^{-\frac{F}{K_D}\tau}\right)}{[R]_0\left(1 - \frac{P}{Q}e^{-\frac{F}{K_D}\tau}\right)}$$

$$\frac{u}{u_{eq}} = \frac{v}{v_{eq}} = \frac{\left(1 - e^{-\frac{F}{K_D}\tau}\right)}{\left(1 - \frac{P}{Q}e^{-\frac{F}{K_D}\tau}\right)}$$

$$v = \frac{P\left(1 - e^{-\frac{F}{K_D}\tau}\right)}{[L]_0\left(1 - \frac{P}{Q}e^{-\frac{F}{K_D}\tau}\right)}$$

$$\tau_{99} = -\frac{K_D}{F}\ln\left(\frac{0.01Q}{Q - 0.99P}\right)$$

Derivation of Pseudo First-Order Rate Constant Model $$\frac{d[LR]}{dt} = k_{on}[L][R] - k_{off}[LR]$$

Assume that R>>L, so a pseudo first-order rate constant can be established, with $k^* = k_{on}[R]$.

$$\frac{d[LR]}{dt} = k^*[L] - k_{off}[LR]$$

Note that $[L]_{tot} = [L] + [LR]$.

$$\frac{d[LR]}{dt} = k^*([L]_{tot} - [LR]) - k_{off}[LR]$$

-continued $$\frac{d[LR]}{dt} = k^*[L]_{tot} - (k^* + k_{off})[LR]$$

At equilibrium, $$\frac{d[LR]}{dt} = 0.$$

$$0 = k^*[L]_{tot} - (k^* + k_{off})[LR]_{eq}$$

$$k_{off} = \frac{k^*[L]_{tot} - k^*[LR]_{eq}}{[LR]_{eq}}$$

This relation can be used to solve for the theoretical equilibrium binding in this PFORC model:

$$[LR]_{eq} = \frac{k^*[L]_{tot}}{(k^* + k_{off})}$$

Plugging the expression for $k_{off}$ back into the differential equation form:

$$\frac{d[LR]}{dt} = k^*[L]_{tot} - \left(k^* + \frac{k^*[L]_{tot} - k^*[LR]_{eq}}{[LR]_{eq}}\right)[LR]$$

$$\frac{d[LR]}{dt} = k^*[L]_{tot} - \left(\frac{k^*[L]_{tot}}{[LR]_{eq}}\right)[LR]$$

$$\frac{d[LR]}{dt} = k^*[L]_{tot}\left(\frac{[LR]_{eq} - [LR]}{[LR]_{eq}}\right)$$

Integrating:

$$\int_0^{[LR]_t} \frac{d[LR]}{[LR]_{eq} - [LR]} =$$

$$\int_0^t \left(\frac{k^*[L]_{tot}}{[LR]_{eq}}\right) dt - \ln([LR]_{eq} - [LR]_t) + \ln([LR]_{eq}) = \frac{k^*[L]_{tot}}{[LR]_{eq}} t$$

$$\ln\left(\frac{[LR]_{eq} - [LR]_t}{[LR]_{eq}}\right) = -\frac{k^*[L]_{tot}}{[LR]_{eq}} t$$

$$1 - \frac{[LR]_t}{[LR]_{eq}} = e^{-\frac{k^*[L]_{tot}}{[LR]_{eq}} t}$$

$$1 - \frac{[LR]_t}{[LR]_{eq}} = e^{-(k_{off} + k^*)t}$$

$$1 - \frac{[LR]_t}{[LR]_{eq}} = e^{-(k_{off} + k_{on}[R])t}$$

The $t_{99}$, the time at which 99% of equilibrium binding has occurred, was also calculated for each concentration pairing, via the relation:

$$1 - \frac{[LR]_t}{[LR]_{eq}} = e^{-(k_{off} + k_{on}[R])t}$$

$$t_{99} = \frac{-\ln(0.01)}{(k_{off} + k_{on}[R])} \approx \frac{-4.6}{(k_{off} + k_{on}[R])}$$

Cost Calculations

Costs per production run were estimated in similar fashion as in the supplementary information of Reference 1, though the cost of the HisTrap FF Crude column was distributed across five runs, since these columns are reusable. The per-batch cost, then, at a 1000 mL scale, was determined to be $18.02. Given a conservative estimate of 100,000 g rcSso7d-CBD/L, and a per-test usage of 5 µg (6 µL of 30 µM solution per test, with a MW of 27.88 kDa), a 1-L production run yields enough material for 20,000 tests. This results in a per-test cost of $0.0009/test.

In order to assess thermal stability of the rcSso7d.SA-CBD fusion species relative to the bare rcSso7d.SA monomer and to a representative SA-binding polyclonal antibody (pAb.SA), all three species were immobilized on the appropriate substrate (aldehyde-functionalized cellulose in the case of the rcSso7d.SA monomer and pAb.SA, unmodified cellulose in the case of rcSso7d.SA-CBD) at a concentration of 20 µM. Following a 16-hour primary incubation and subsequent inactivation in TBS, the samples were incubated in a humid chamber for 10 minutes in 4 µL of 5 w/v % trehalose solution in 1×PBS. Excess solution was blotted from these samples, and following the application of an additional 2 µL of 5 w/v % trehalose solution, all samples were placed in a vacuum oven at 45° C. until dry (5-7 minutes). These samples were then placed in a Binder oven at 40° C. for varying periods of time, after which they were exposed to a 1 OµL aliquot of 330 nM SA-AF647, and imaged via fluorescence microscopy.

Figure 11A:
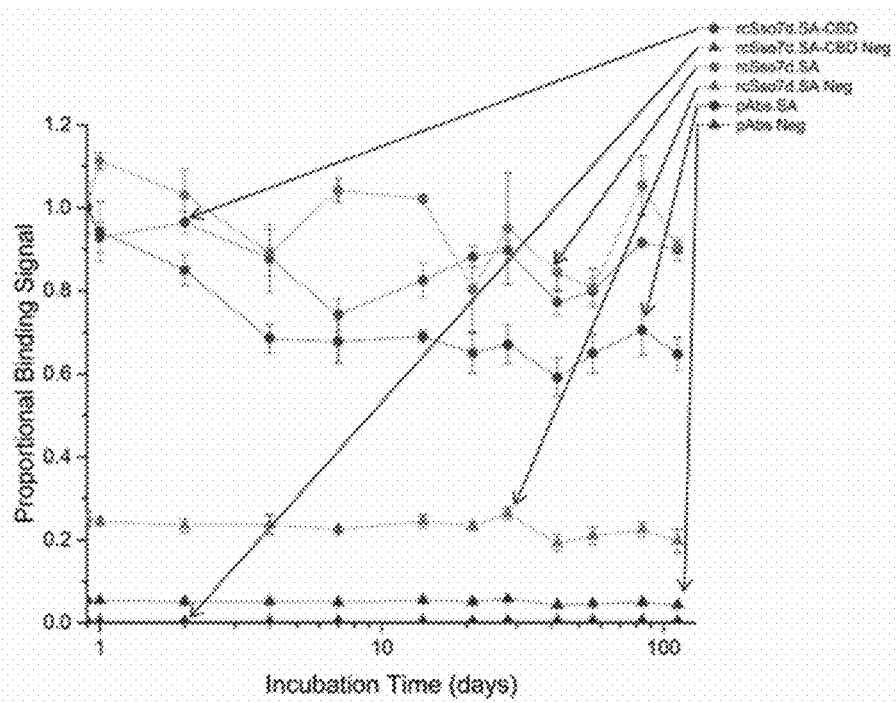
FIGS. 11A-11B. Activity retention for rcSso7d.SA, rcSso7d.SA-CBD, and a commercially available streptavidin-binding polyclonal antibody incubated at 40° C. in the dry, paper-immobilized format. Samples were dried in the presence of 5 w/v % trehalose. Developed samples were contacted with 256 nM SA-AF647 and imaged in the CY5® channel at 80 ms (rcSso7d.SA-CBD), 400 ms (pAbs-SA), and 1000 ms (rcSso7d.SA). All data points are relative to the initial binding activity, and error bars represent the standard deviation of four independent replicates.
Figure 11B:
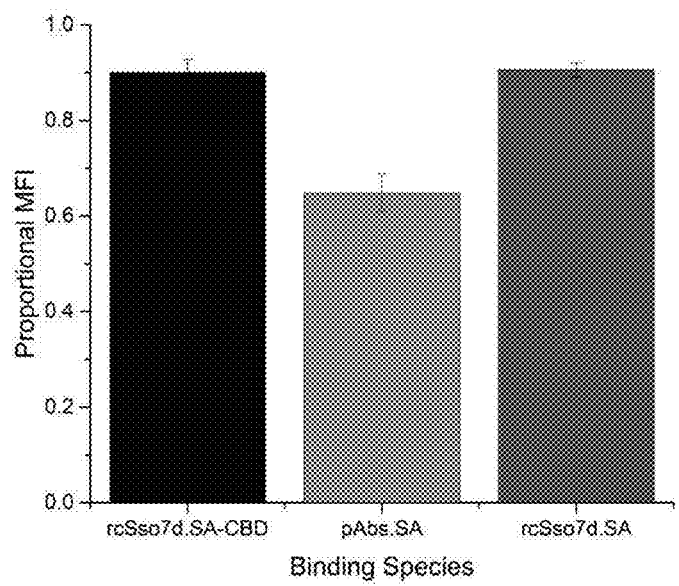

It should be noted that the gain in functionality observed with the rcSso7d-CBD construct does not come at the expense of the thermal stability of this binding species —following four months' dry incubation at 40° C., rcSso7d-CBD was observed to retain activity to the same degree as bare rcSso7d (−90%, compared to −60% for a representative polyclonal antibody; FIGS. 11A-11B).

Maximal binding signal is observed at 30 µM rcSso7d.SA-CBD, and at higher concentrations, mean fluorescence signal is observed to diminish. This is likely due to fluorophore quenching while the molar quantity of binder immobilized from a 30 µM solution of rcSso7d.SA-CBD is sufficient to capture all antigen in a 10 µL antigen solution at a concentration of 100 nM, the higher surface density of immobilized binder places a subpopulation of the captured target in sufficient proximity that the fluorophores can interact and self-quench. In order to avoid this occurrence, an optimal concentration of 30 µM CBD will be employed. This allows the depletion of antigen from solution, without yielding sufficient surface coverage for quenching to occur.

Example 2. Pseudo First-Order Rate Constant Model

In order to explore the effects of operating within the antigen-limited binding regime, a monovalent binding model based on the principles of mass-action kinetics was developed. This binding system can be described mathematically by a simple first-order differential equation:

$$\frac{d[LR]}{dt} = k_{on}[L][R] - k_{off}[LR]$$

Here, [L] and [R] represent the volumetric molar concentrations of free ligand and free receptor, respectively, and [LR] represents the concentration of the bound complex. By employing the law of molar conservation (e.g. $[L]=[L]_0-$

[LR]; [R]$_0$=[R]$_0$−[LR]), this monovalent binding system can be solved analytically to yield the expression:

$$\frac{[LR]_t}{[LR]_{eq}} = \frac{1 - e^{-\left(\sqrt{([L]_0-[R]_0)^2+2([L]_0+[R]_0)K_D+K_D^2}\,k_{on}t\right)}}{1 - \frac{\sqrt{([L]_0 - [R]_0)^2 + 2([L]_0 + [R]_0)K_D + K_D^2}}{\left([L]_0 + [R]_0 + K_D + \sqrt{([L]_0 - [R]_0)^2 + 2([L]_0 + [R]_0)K_D + K_D^2}\right)} e^{-\left(\sqrt{([L]_0-[R]_0)^2+2([L]_0+[R]_0)K_D+K_D^2}\,k_{on}t\right)}}$$

However, when operating in the antigen-depletion regime, this relation can be simplified by noting that antigen capture does not significantly diminish the pool of free receptor, such that a constant concentration of available binding species can be assumed. This permits the use of a pseudo first-order rate constant (PFORC; units: s$^{-1}$) which incorporates the initial receptor concentration:

$$k^* = k_{on}[R]_0$$

By applying this PFORC in the first-order differential equation describing this binding system (derivation also in SI), the following, more compact expression for the proportion of bound antigen (relative to the equilibrium value) is found. Notably, this relation no longer depends upon the initial concentration of the soluble ligand, given that the receptor concentration alone determines the profile of the approach to binding equilibrium.

$$\frac{[LR]_t}{[LR]_{eq}} = 1 - e^{-(k_{off}+k_{on}[R]_0)t}$$

The binding regime affects not only the thermodynamics and stoichiometry of antigen capture, but also the binding kinetics. These basic models also enable the calculation of the time required for the system to reach 99% of equilibrium binding. The exact analytical expression for this value is:

immobilized receptor is in molar excess to the soluble ligand.

Figure 7A:
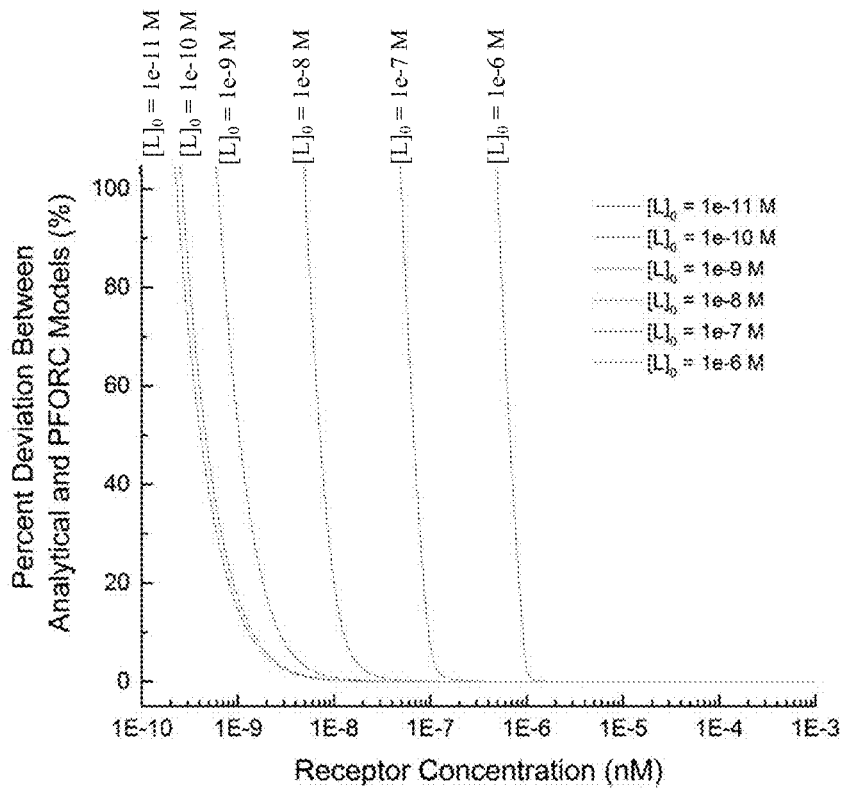
FIGS. 7A-7B. Deviation between the exact analytical solution and PFORC model in the (FIG. 7A) predicted proportional ligand capture at equilibrium and (FIG. 7B) the predicted time required to achieve 99% of equilibrium binding. All plots were generated using $Kv=5.5\times10^{-10}$, the measured affinity of the rcSso7d.SA species. Triangles denote the points at which the receptor concentration is equal to the ligand concentration for the curve of the corresponding color.
Figure 7B:
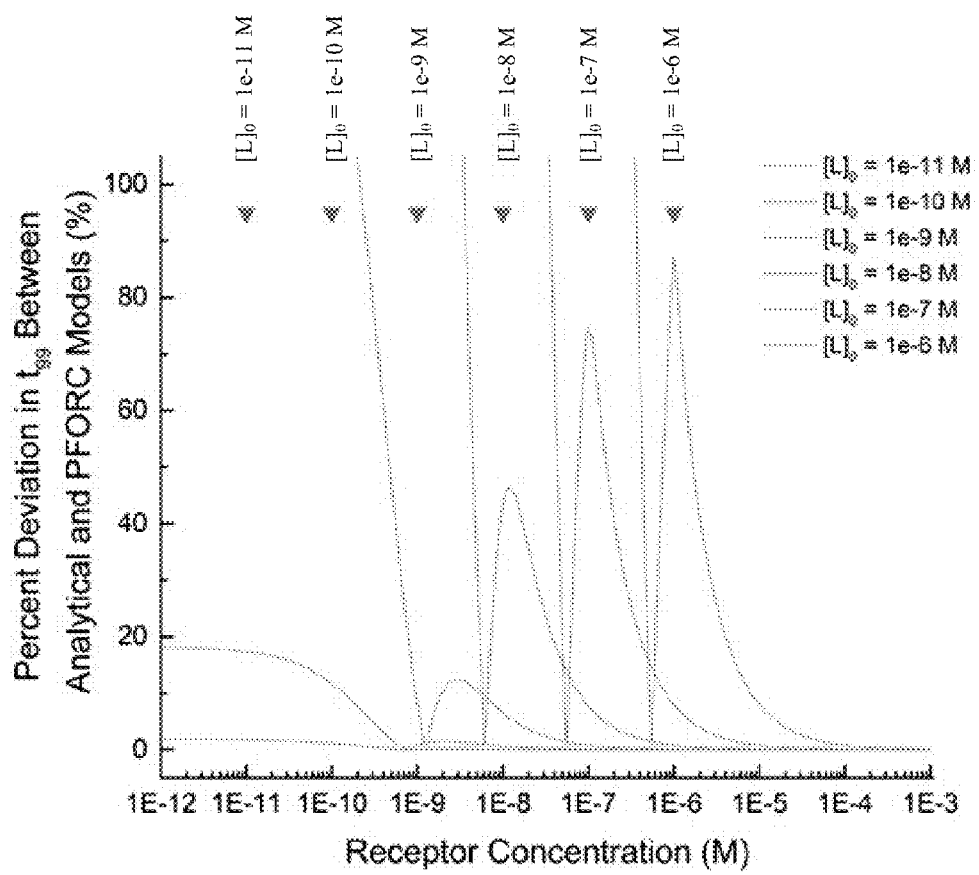

In fact, the PFORC model only appreciably deviates from the analytical solution as the initial receptor concentration either i) approaches the initial concentration of the free ligand, or ii) nears the dissociation constant of the binding pair, whichever value is greater (FIGS. 7A-7B). Generally, the proportional deviation between the analytical solution and the PFORC model only becomes significant for a ligand concentration or a $K_D$ within one order of magnitude of the local concentration of the immobilized receptor. Note that this treatment assumes that all species are present in soluble form in the same volume, thereby establishing a direct link between molar concentration and molar abundance. In the context of a heterogeneous assay, the average local concentration of the immobilized binder within the test zone volume does not directly reflect its molar abundance relative to the soluble target. Thus the molar abundance of the immobilized species must be considered instead of its local concentration, and this quantity must be an order of magnitude greater than the abundance of the soluble target in order to yield antigen depletion as described by the PFORC model.

$$t_{99} = -\frac{1}{k_{on}\sqrt{([L]_0 - [R]_0)^2 + 2([L]_0 + [R]_0)K_D + K_D^2}} \ln\left(\frac{0.01\left([L]_0 + [R]_0 + K_D + \sqrt{([L]_0 - [R]_0)^2 + 2([L]_0 + [R]_0)K_D + K_D^2}\right)}{0.01([L]_0 + [R]_0 + K_D) + 1.99\sqrt{([L]_0 - [R]_0)^2 + 2([L]_0 + [R]_0)K_D + K_D^2}}\right)$$

In contrast, the PFORC model permits the calculation of a simplified, effective rate of reaction ($k_{obs}=k_{off}+k_{on}[R]$), which can be incorporated into the following relation to evaluate $t_{99}$:

$$t_{99} = \frac{-\ln(0.01)}{k_{obs}}$$

Figure 2A:
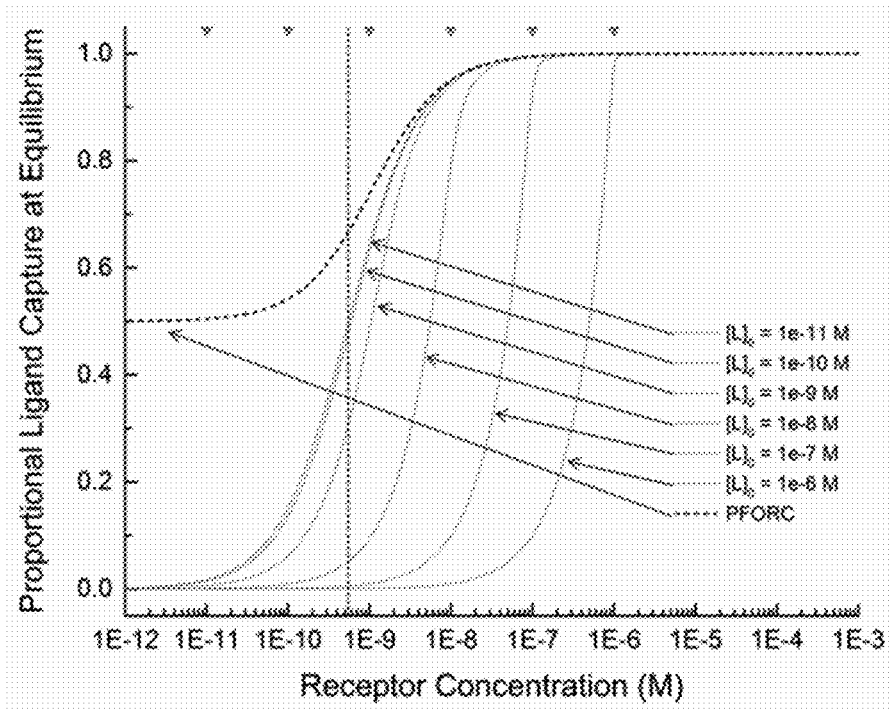
(FIG. 2A) Ligand capture efficiency at equilibrium for the analytical and PFORC models. Curves represent the proportion of free ligand that is bound at equilibrium for varying initial concentrations of ligand and receptor.
Figure 2B:
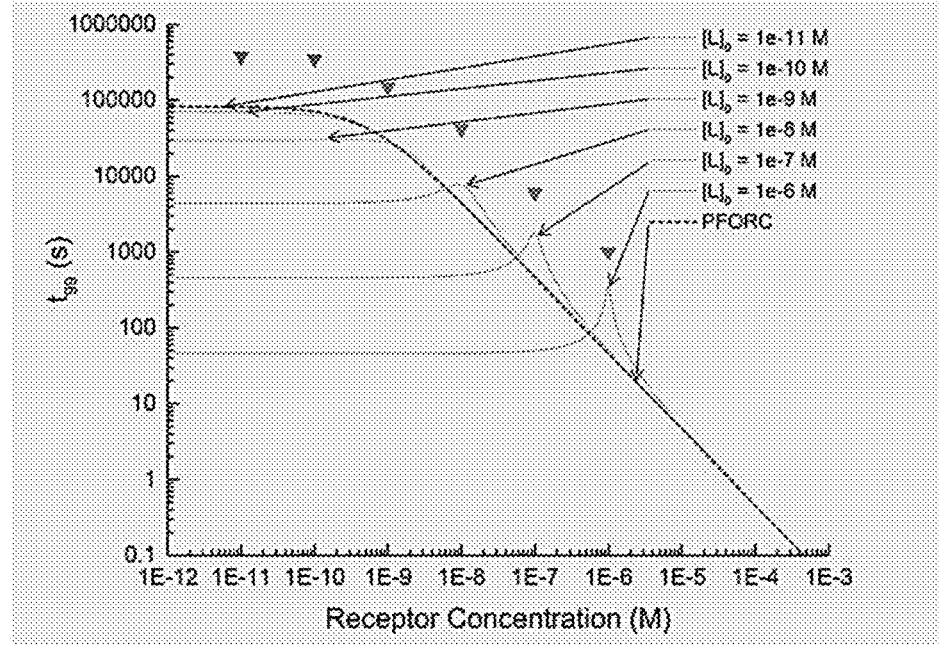
(FIG. 2B) Calculated time required to achieve 99% of equilibrium binding in the analytical and PFORC models. All plots were generated using a KD of $5.5\times10^{-10}$ M. Colored triangles denote the points where the receptor concentration is equivalent to the associated ligand concentration, to highlight the local changes near these values.

By varying the initial receptor and ligand concentrations, proportional ligand capture at equilibrium and $t_{99}$ values can be plotted for both the analytical solution and PFORC approximation (FIGS. 2A-2B), permitting direct comparison of the models and establishing bounds for the validity of the

Example 3. Selection And Characterization of rcSso7d Binding Variants

In order to test the predictions of this basic binding model, two distinct binding variants were developed based on the thermostable rcSso7d scaffold. Both rcSso7d.SA and rcSso7d.Rv1656 were selected from a yeast surface display library of high initial diversity (~1.4 billion library members) via magnetic bead sorting and flow cytometry. The amino acid sequence of these selected binding variants can be seen below (Table 4). As reported by Traxlmayr et al (2016), strong enrichment of the aromatic residues tyrosine and tryptophan was observed. This may serve to impart greater topological diversity and electron density upon the planar rcSso7d binding face, facilitating strong, conformal binding to the target antigen.

TABLE 4

Primary protein structure of selected rcSso7d binders.

| Protein Species | SEQ ID NO | Primary Structure (N → C) (Variable AA residues) | Shorthand Tag |
|---|---|---|---|
| rcSso7d.SA | 4 | MATVKFTYQGEEKQVDISKIKIVARDGQYIDFKYDEGGGAYGYGWVSEKDAPKELLQMLEKQ | IADYDKYYW (SEQ ID NO: 29) |
| rcSso7d.Rv1656 | 5 | MATVKFTYQGEEKQVDISKIKWVRRYGQYIGFSYDEGGGAWGKGYVSEKDAPKELLQMLEKQ | WRYYGSWKY (SEQ ID NO: 30) |

Figure 9:
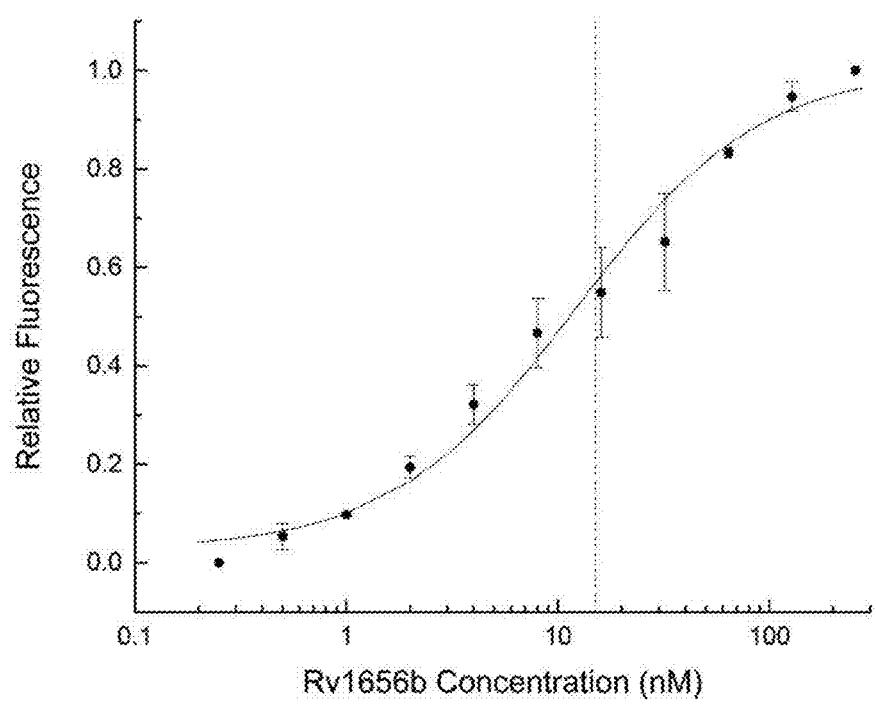
FIG. 9. Affinity determination for rcSso7d.Rv1656 via yeast-surface display titration. For each sample, 500,000 yeast cells were incubated with soluble Rv1656b at a concentration ranging from 256 nM to 0.25 nM, and labeled with SA-AF647. The geometric mean fluorescent intensity was captured for each sample. Each data point represents the average of three technical replicates performed on separate days. Error bars represent the standard deviation of three independent replicates.

The dissociation constants of the rcSso7d.SA and rcSso7d.Rv1656 modules were both measured in the yeast surface display format by titrating soluble, biotinylated antigen against monoclonal yeast populations expressing these binding species as surface-bound fusion proteins. The affinity of rcSso7d.SA was previously reported to be 556±136 µM, (Miller et al., 2016) and the affinity of rcSso7d.Rv1656 was found to be 15.1±7.0 nM (FIG. 9).

In order to incorporate these binding proteins into the rcSso7d-CBD format, the gene encoding the type 3 cellulose binding domain of the CipA protein from *Clostridium thermocellum* (GenBank: HF912725.1, residues 364-522) was synthesized by IDT as a C-terminal fusion partner to the rcSso7d.SA species. This particular cellulose-binding domain was chosen for its high immobilization density and demonstrated activity in an immunoassay format, (Dai et al., 2016; Holstein et al., 2016; Hussack et al., 2009) as well for its thermal (McBee, 1954) and chemical stability. (Berdichevsky et al., 1999) The two fusion partners are joined by a flexible $(G_4S)_3$-linker sequence (SEQ ID NO: 125), and an internal BamHI site is included at the C-terminal end of the rcSso7d gene.

Figure 10:
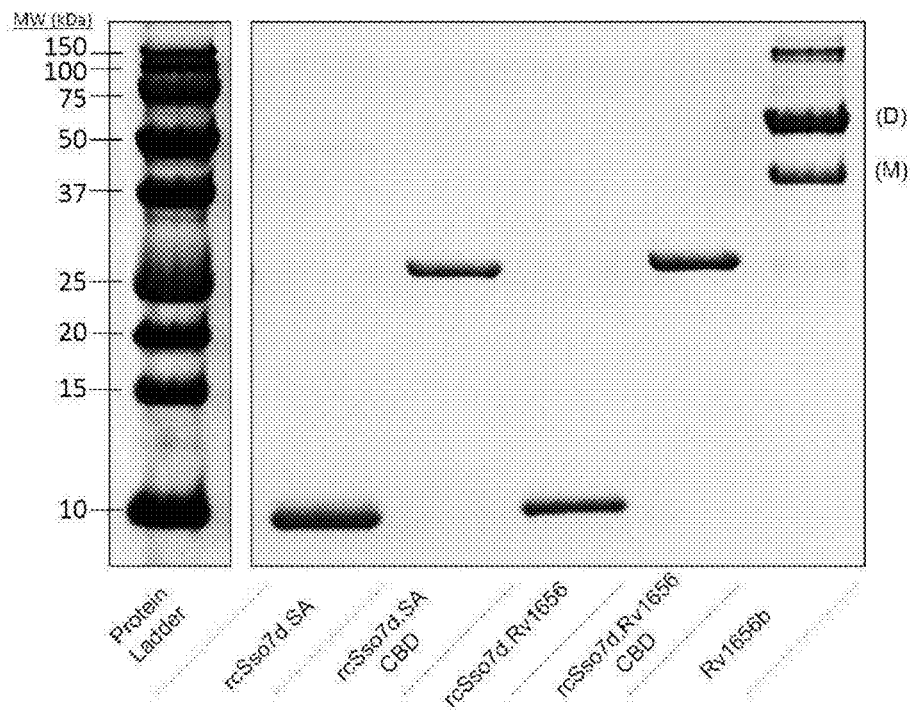
FIG. 10. 15% SDS-PAGE gel of all purified recombinant products. rcSso7d.SA and rcSso7d.Rv1656 are seen to run at their theoretical MW (9.26 k.Da and 9.33 k.Da, respectively), as are rcSso7d.SA-CBD and rcSso7d.Rv1656-CBD (27.88 k.Da and 27.99 kDa, respectively). Biotinylated Rv1656 is observed to run near its theoretical MW of 35.32 k.Da, and a protein dimer is observed at approximately 70 k.Da. A Precision Plus Protein Dual Color Standard was used for the protein ladder. The discrepancy between the expected Rv1656 molecular weight and the observed position of the monomer and dimer bands may be due to the covalent addition of multiple biotin moieties, or the presence of glycerol in the applied protein sample.

These rcSso7d-CBD constructs were expressed in BL21 (DE3) *E. coli* and purified via a reusable IMAC column, yielding a product of electrophoretic purity within a single purification step (FIG. 10). Protein concentration was quantified via a BCA assay, and the protein yield was determined to range from 131.4 mg/$L_{culture}$ (14.28 mg/g wet cell mass (WCM)) for rcSso7d.SA-CBD to 105.5 mg/$L_{culture}$ (8.55 mg/g WCM) for rcSso7d.Rv1656-CBD. Given a calculated cost basis for a single bacterial production run of $18.02, and a conservative per-test usage of 5 micrograms, a single 36-hour production run at a 1000-mL scale can produce enough material for approximately 20,000 assays, at a cost of $0.0009/device. These favorable bio-manufacturing economics enable the high-throughput production of these paper-based assays, at a price point that is well-suited for low-cost biomedical applications in resource-limited settings.

Example 4. Characterization of rcSso7d.SA-CBD Cellulose-Binding Activity

In order to assess the capture efficiency of bioactive cellulose functionalized with the rcSso7d.SA-CBD fusion species, these binding proteins were immobilized in hydrophilic test zones and subsequently contacted with the soluble antigen, forming an immunocomplex. By using these half-sandwich assay formats, it is possible to decouple the typical immunoassay binding steps, allowing each molecular interaction to be evaluated in isolation and engineered for optimal performance prior to re-integration into a full diagnostic format.

Fluorescence microscopy imaging of developed test zones indicates that the cellulose-binding domain strongly binds to unmodified WHATMAN® No. 1 chromatography paper in high abundance (FIG. 3), removing the need for substrate pre-processing steps. This represents a significant process improvement in the production of these paper-based assays, given that typical procedures require functionalization steps for the activation of inert cellulosic substrates, in order to immobilize diagnostic binding proteins in greater abundance. (Credou and Berthelot, 2014; Nery and Kubota, 2016; Shen et al., 2016; Yu et al., 2012; Zhao et al., 2016) These chemical pre-processing methods limit production throughput, and require efficient surface passivation steps following binder immobilization in order to prevent the non-specific adsorption of patient proteins and free detection reagents. (Vuoriluoto et al., 2016; Zhu et al., 2014) Additionally, stochastic chemical conjugation methods result in the non-oriented immobilization of the binding species, which can reduce the solvent accessibility of the target-binding paratope and result in an inactive sub-population of immobilized binder. (Song et al., 2012)

Figure 3:
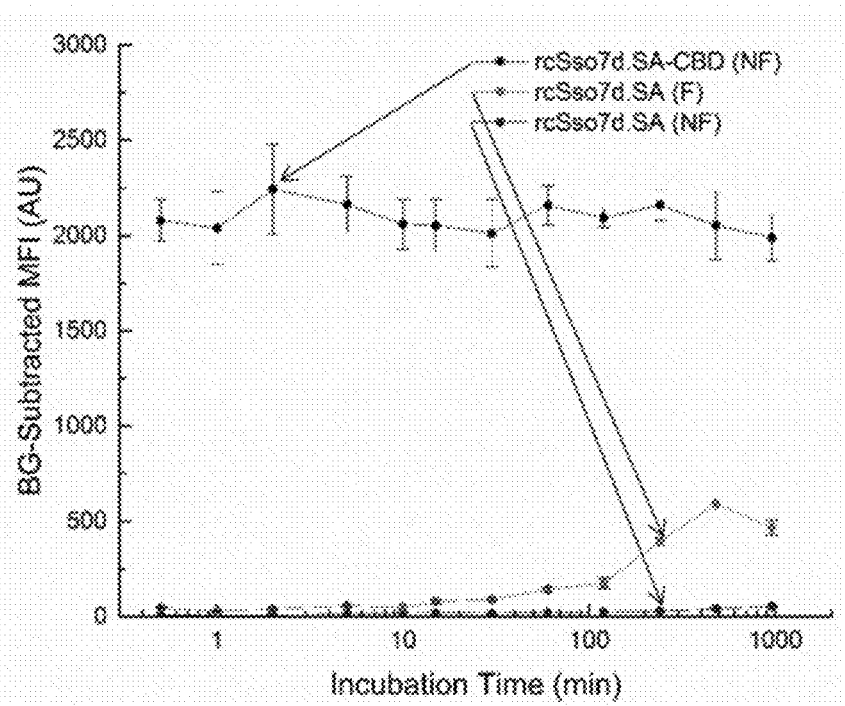
FIG. 3. Time course of primary incubation. rcSso7d.SA-CBD was contacted with non-functionalized paper (NF) and rcSso7d.SA was contacted with both functionalized (F) and non-functionalized (NF) paper for periods of time ranging from 30 seconds to 16 hours, at soluble concentrations of 30 µM (180 picomoles of applied binder). Following washing and substrate neutralization, these samples were subsequently treated with 10 µL of SA-AF647 at a soluble concentration of 256 nM (2.56 picomoles of target). All samples were imaged in the CY5® channel using an exposure time of 80 ms, and background-subtracted using the relevant negative control. Error bars represent the standard deviation of four independent replicates.

Furthermore, given the rate-dependent formation of the imine bond, an extended primary incubation is typically required in order for this covalent immobilization reaction to proceed to completion. Even following this incubation period in the functionalized paper format, this time-dependent process yielded sub-optimal antigen capture for the bare rcSso7d species (FIG. 3).

In contrast, unmodified chromatography paper requires no special pre-treatment, can be stored under ambient conditions, and yields minimal nonspecific protein adsorption both prior to and during immunoassay development. The rcSso7d-CBD fusion also yields oriented display of the antigen-binding rcSso7d module, ensuring maximal paratope accessibility and surface activity. Finally, the CBD fusion rapidly binds to the cellulose substrate in high abundance. Regardless of whether the CBD fusion was contacted with the surface for a primary incubation period of 16 hours or 30 seconds, the binding signal was observed to be roughly equivalent, and significantly greater than that of the bare rcSso7d species (FIG. 3). This drastically reduces the amount of time required to proceed from raw cellulose substrate to fully functional assays, from two days of processing time down to roughly ten minutes.

Example 5. Characterization of Assay Sensitivity Using Cellulose-Immobilized rcSso7d.SA-CBD The greater surface density of the rcSso7d.SA-CBD species also results in the onset of discernible binding signal at lower concentrations of soluble antigen relative to the bare rcSso7d.SA species. Standard definitions of assay sensitivity establish a reliable detection threshold at three standard deviations above the average signal of the negative controls.

Figure 4A:
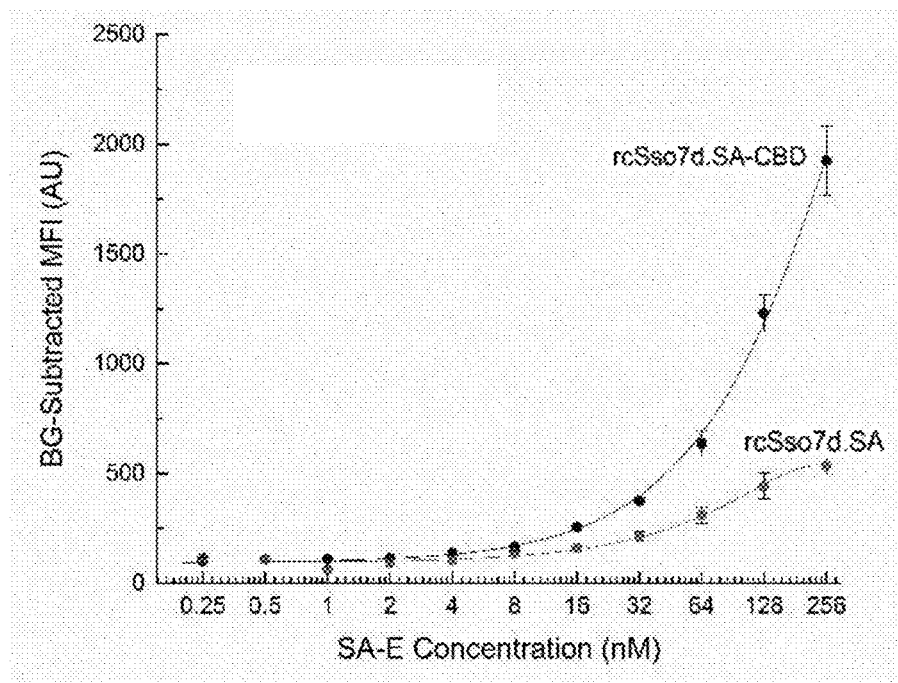
FIGS. 4A-4B. Comparison of antigen titration curves for (FIG. 4A) rcSso7d.SA/rcSso7d.SA-CBD and (FIG. 4B) rcSso7d.Rv1656/rcSso7d.Rv1656-CBD. rcSso7d and rcSso7d-CBD species were contacted with their associated substrates (functionalized and non-functionalized cellulose, respectively) for standard incubation times at a soluble concentration of 20 µM. Sample sets were treated with a serial dilution of (FIG. 4A) SA-E or (FIG. 4B) Rv1656b, at concentrations ranging from 256 nM to 0.25 nM. Samples contacted with Rv1656b were subsequently contacted with SA-E at a concentration of 256 nM. Samples were imaged in the TEXAS RED@ channel using an exposure time of 1000 ms. Datasets were fit with a second-order polynomial (rcSso7d.SA: $-0.008362x^2+3.851x+100.0$, $r^2=0.9904$; rcSso7d.SA-CBD: $-0.01059x^2+9.899x+100.0$, $r^2=0.9986$; rcSso7d.Rv1656: $-0.002774x^2+1.229x+100.0$, $r^2=0.8271$; rcSso7d.Rv1656-CBD: $-0.02791x^2+14.16x+100.0$, $r^2=0.9961$). The baseline for these datasets was adjusted to an arbitrary value of 100AU in order to enable the comparison of signal onset. Error bars represent the standard deviation of four independent replicates.

By comparing the binding curves obtained by treating these species with a serial dilution of SA-E (FIG. 4A), a conservative limit of detection (LOD) of 8.2 nM (IBG=324.3 AU; σ=41.7 AU) is found for the bare rcSso7d species, and 2.56 nM (IBG=150.1 AU; σ=5.9 AU) for rcSso7d.SA-CBD. The background signal due to non-specific SA-E binding was also lower for unmodified cellulose, yielding better discrimination of genuine binding signal from random fluctuations near the noise threshold. The binding curve for rcSso7d.SA-CBD is also seen to continue to rise at high nanomolar concentrations of the soluble antigen, whereas the binding signal appears to saturate for the rcSso7d.SA species. This suggests a significantly higher degree of rcSso7d.SA-CBD surface immobilization, which has implications for the more rapid and efficient capture of the target from solution.

Figure 4B:
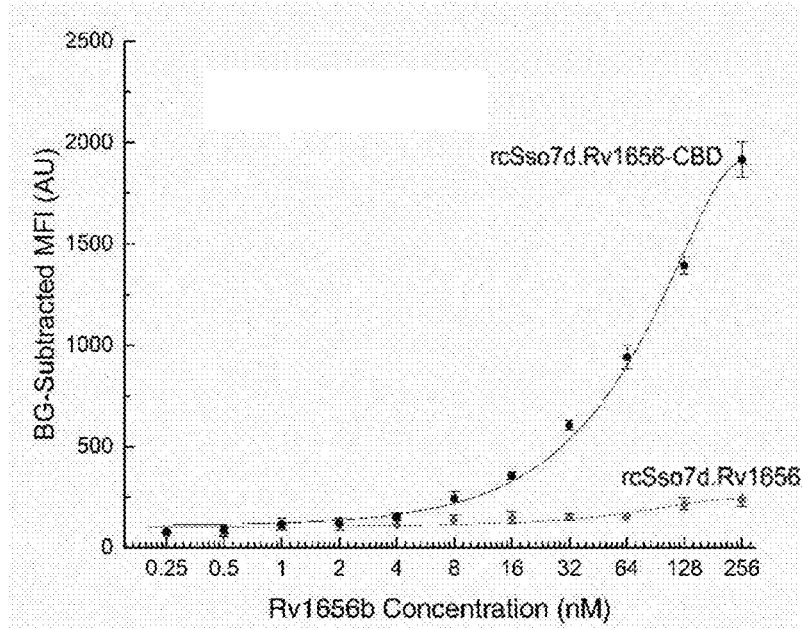

These findings were also validated in a second, orthogonal binding system, using the rcSso7d.Rv1656 binding module (FIG. 4B). In this system, too, a drastically improved binding response was observed with the rcSso7d-CBD fusion species, both in terms of its capture efficiency at high antigen concentrations, and its limit of detection (rcSso7d.Rv1656-CBD: LOD=3.1 nM; IBG=468.8 AU; σ=17.3 AU; rcSso7d.Rv1656: LOD: 48.3 nM; IBG=350.1 AU; σ=32.2 AU). The background signal for the rcSso7d.Rv1656 species is significantly higher on unmodified cellulose, due to a limited degree of nonspecific binding to the aromatic eosin species (see FIG. 14).

It should be noted that the effect of the 30-fold difference in affinity between these two binders can be observed qualitatively in the bare rcSso7d format. However, upon integration of these distinct binding species into the rcSso7d-CBD format, the binding curves are much more similar, suggesting that at higher immobilization densities, the binding affinity has little impact upon the ultimate capture efficiency.

Example 6. Identification of the Antigen-Binding Reime

Figure 12:
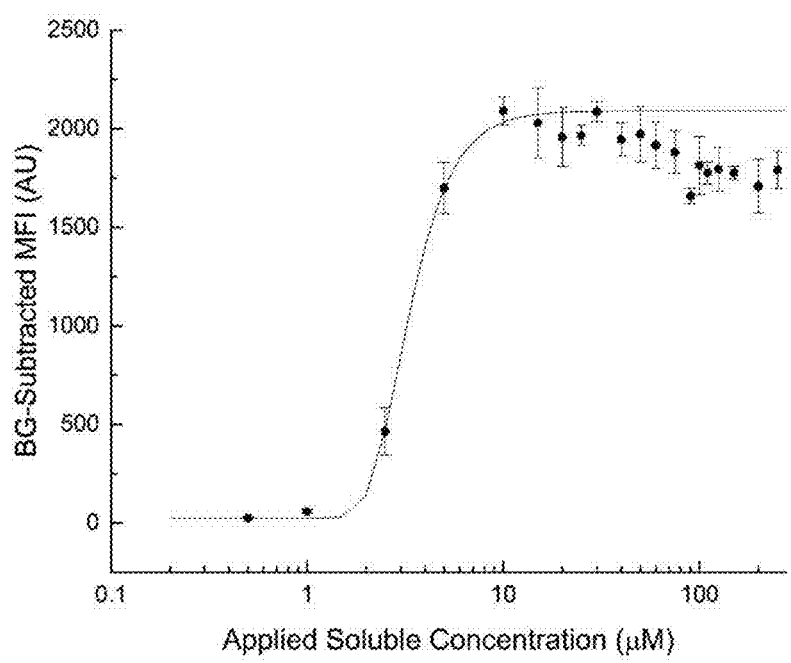
FIG. 12. Demonstration of signal saturation at high CBD concentrations. Various soluble concentrations of rcSso7d.SA-CBD (ranging from 0.5 to 250 µM) were applied to cellulose test zones for 30 minutes. Samples were contacted with SA-AF647 at 100 nM and imaged in the CY5® channel at an exposure time of 150 ms. Though antigen depletion seems to occur at approximately 10 µM, fluorophore quenching is observed at higher applied concentrations. This is likely due to the greater proximity ofrcSso7d.SA-CBD species on the substrate at higher surface coverage, which allows subpopulations of the captured SA-AF647 to bind in sufficient proximity for fluorophore quenching to occur. Error bars represent the standard deviation of four independent replicates.

While these observations demonstrate the benefits of incorporating the CBD fusion partner, it is necessary to characterize the binding regime directly in order to confidently validate the predictions of the PFORC model. Given the clear improvement in capture efficiency observed with the rcSso7d.SA-CBD species, it was sought to determine whether this antigen binding could be further enhanced by contacting the cellulose substrate with greater molar quantities of rcSso7d.SA-CBD (FIG. 12). A series of soluble rcSso7d.SA-CBD concentrations, ranging from 0.5 mg/mL to 7 mg/mL (18.3 µM to 256 µM), was applied to the paper test zones. These sample sets were incubated with a serial dilution of SA-E, ranging from 256 nM to 0.25 nM (FIG. 11A).

Figure 5A:
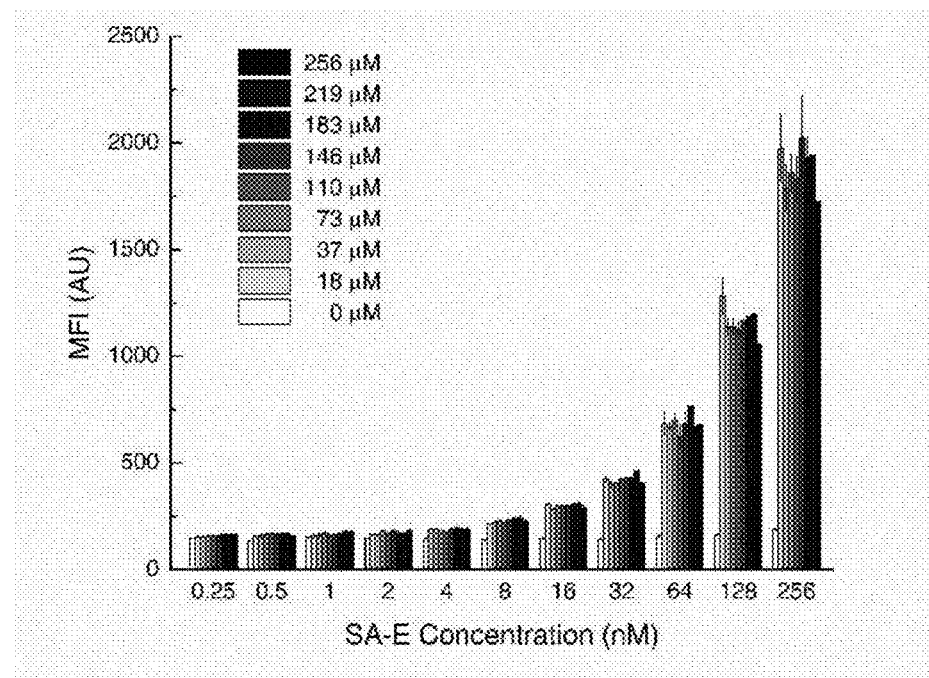
FIGS. 5A-5B.
Figure 5B:
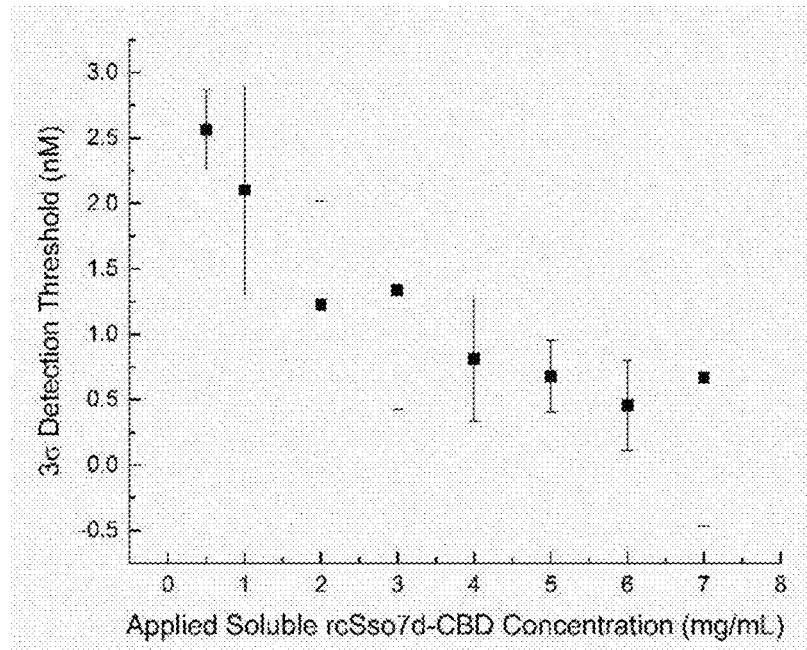

The resulting binding curves for each antigen titration are exceptionally regular, yielding an average $r^2$ value of 0.9994 when fit with a second-order polynomial. These curves generally overlap, but while no large-scale trends are immediately apparent in these clustered data sets, it was found that higher soluble concentrations of applied binder do yield greater capture efficiency at antigen concentrations in the low nanomolar range. Using the negative control dataset from all SA-E concentrations applied to bare cellulose ($I_{BG}$=150.1 AU; σ=5.9 AU), a conservative three-sigma threshold MFI of $I_{th}$=167.8 AU was calculated. Applying the second-order polynomial fit equations for each sample set, it was found that as the applied concentration of rcSso7d.SA-CBD increases, the minimum detectable antigen concentration decreases (FIG. 5B). This finding suggests that additional rcSso7d.SA-CBD binds to the cellulose substrate at higher applied concentrations, and indicates that this greater surface coverage yields improved capture efficiency at dilute antigen concentrations. Given that significantly higher MFI values are observed for more concentrated antigen solutions, this improvement in capture efficiency at low antigen concentrations is likely due to enhanced binding kinetics, rather than due to insufficient molar quantities of the immobilized binder at lower applied concentrations of rcSso7d.SA-CBD.

The general overlap of the rcSso7d.SA-CBD binding curves indicates that this binding system is operating in one of two regimes: either a) the assay is in fact within the antigen-depletion regime, such that there is no additional target to capture at a given soluble antigen concentration, or b) the cellulose substrate is saturated with immobilized rcSso7d.SA-CBD, preventing the adsorption of any additional binder. While these preliminary results suggest that the substrate is not saturated (namely the enhanced capture efficiency observed at dilute antigen concentrations with increased quantities of applied rcSso7d.SA-CBD), this finding was sought to be confirmed experimentally by directly quantifying the abundance of the immobilized rcSso7d.SA-CBD species on the cellulose substrate.

Example 7. Direct Quantification of rcSso7d-CBD Surface Abundance

Figure 6:
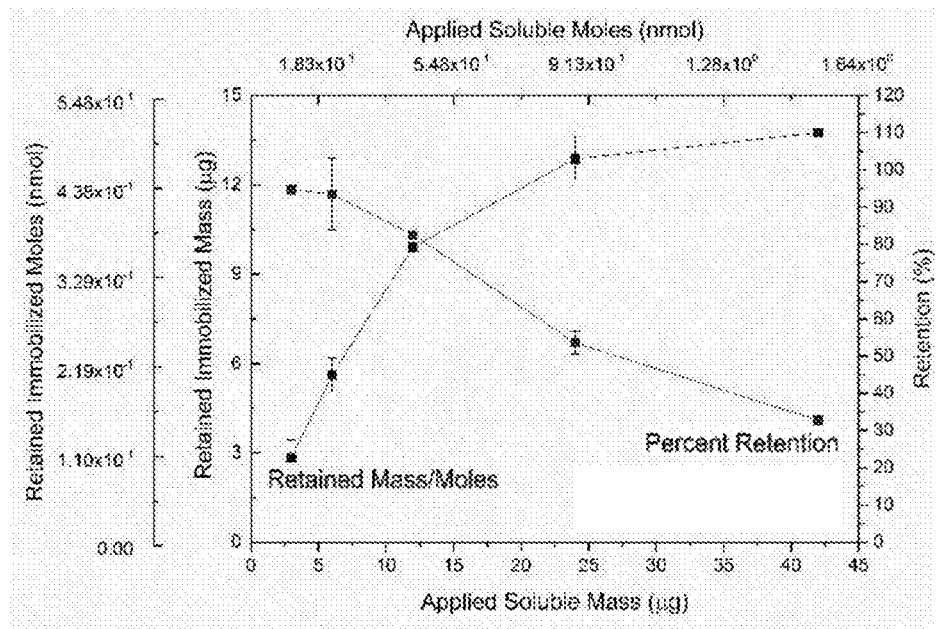
FIG. 6. Micro BCA assay data indicating the adsorption efficiency of rcSso7d.SA-CBD on non-functionalized cellulose. A standard curve of known masses of adsorbed rcSso7d.SA-CBD was used to quantify the immobilization density of rcSso7d.SA-CBD on washed samples. Experimentally determined immobilized masses, assessed via this standard curve, are plotted against the known quantity of applied rcSso7d.SA-CBD, as is the percent retention. Error bars represent the standard deviation of four independent replicates.
Figure 13:
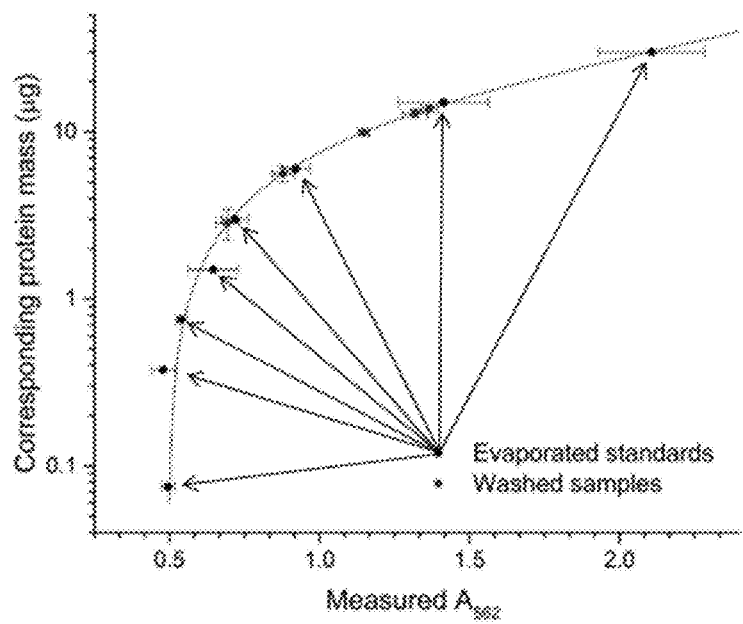
FIG. 13. BCA assay data for the quantification of surface-immobilized rcSso7d.SA-CBD. Absorbance at 562 nm was quantified for all samples, and these values (in black) were correlated with the known mass of rcSso7d.SA-CBD evaporated on the cellulose surface. Absorbance values from washed, experimental samples (in light gray), were fit to this standard curve. Standards were fit with a second-order polynomial ($r^2$=0.9978). Error bars represent the standard deviation of four independent replicates.

In order to further verify the relevant binding regime for this binding system, a micro BCA assay was used to quantify the immobilized surface concentration of the rcSso7d.SA-CBD species. Known masses of rcSso7d.SA-CBD were evaporated onto test zones in order to generate a standard curve that was directly comparable to the washed experimental samples. A highly regular response curve was observed for all standard samples ($r^2$=0.9978), and all washed samples fell within the bounds of this standard curve (FIG. 13). A clear monotonic increase is observed for these experimental samples, indicating that the substrate is far from saturation under the binding conditions used at the standard concentration of 30 µM (FIG. 6).

This serves to confirm that antigen depletion is responsible for the similar response curves observed at varying soluble rcSso7d-CBD concentrations. The signal development observed for the washed samples indicates a molar abundance of rcSso7d-CBD that ranges from 0.1-0.5 nmol/test zone. Given an average test zone mass of 0.32±0.021 mg, this equates to a surface density that varies from 0.32-1.56 µmol of rcSso7d-CBD/g cellulose, which agrees with previously reported values. (Dai et al., 2016; Li et al., 2016)

It should be noted that the efficiency of rcSso7d.SA-CBD immobilization decreases as higher soluble concentrations of protein are applied, indicating that substrate saturation can in fact occur at high immobilized surface density. Whereas the application of 0.1-0.2 nmol of rcSso7d-CBD to the surface results in an immobilized yield of ~90%, this efficiency drops to ~30% at an application of 1.5 nmol. Though higher densities of immobilized binder do allow enhanced capture efficiency at low antigen concentrations, these diminishing returns will necessarily impose practical and economic constraints on how near to saturation the surface coverage can be driven.

Figure 15:
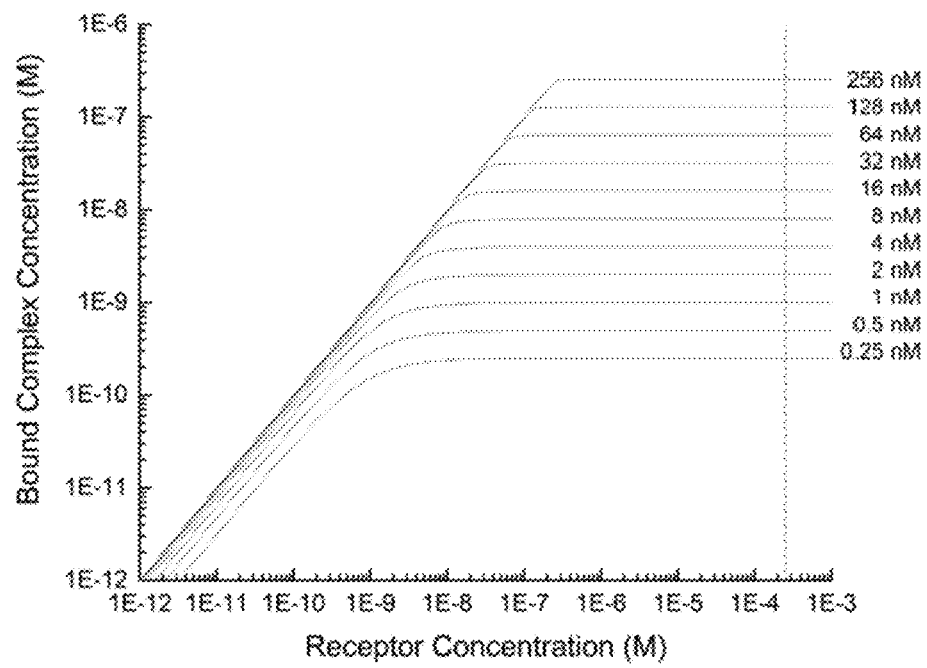
FIG. 15. Theoretical binding profiles generated using the exact analytical solution, for the antigen concentrations used in all titration experiments. The dotted line represents the approximate local concentration ofrcSso7d.SA-CBD in the test zone volume, and demonstrates operation within the antigen depletion regime for all ligand concentrations.

At a standard molar application of 180 picomoles (corresponding to a soluble concentration of 30 µM), the observed immobilization efficiency of 90% yields approximately 162 picomoles immobilized on the test substrate (corresponding to an average local concentration of ~360 µM). At this molar abundance, immobilized rcSso7d.SA-CBD is present in 63.3-fold molar excess relative to the soluble antigen when contacted with a 10-µL sample at the highest titration concentration (256 nM). Under these conditions, the PFORC model predicts that rapid, complete depletion of the soluble ligand will occur (FIG. 15). This approximation will remain valid for all dissociation constants and soluble target concentrations below 1.62 µM (for a 10 µL sample volume).

Figure 16:
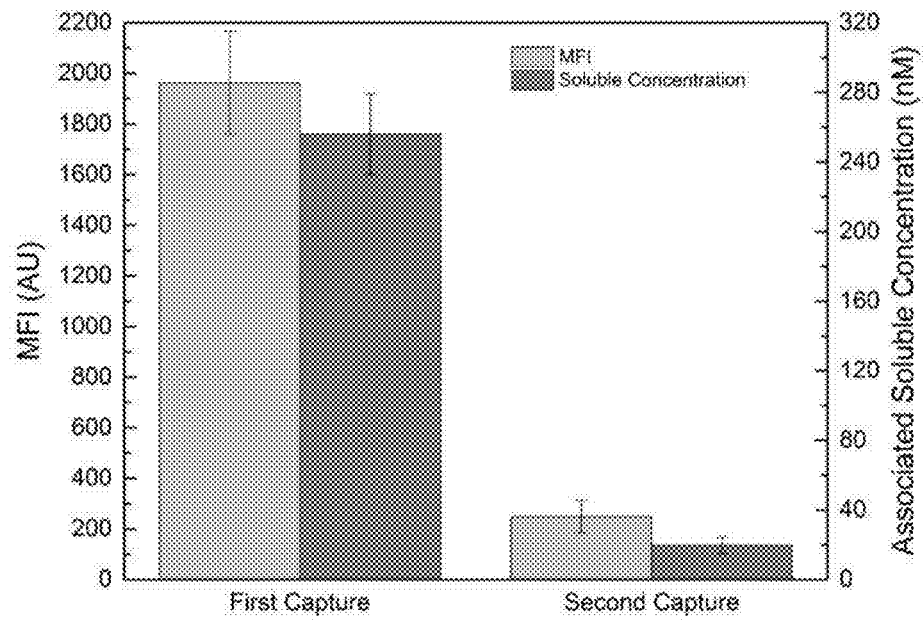
FIG. 16. Depletion of antigen from 10-L samples of SA-AF647 at 256 nM. Nonfunctionalized paper samples were treated with 6 µL of rcSso7d.SA-CBD at 30 µM for at least thirty seconds. A serial dilution of SA-AF647 (0.25-256 nM; 10 µL; 30 minutes) was used to generate a standard binding curve. SA-AF647 was chosen for its low background signal ($I_{BG}$=8.9 AU), so as to deplete the antigen only via specific binding interactions. Test zones coated with rcSso7d.SA-CBD were incubated with 256 nM SA-AF647 for 30 minutes. The flow-through from this first sample set (noted as "first capture") was then withdrawn and applied directly to a second set (noted as "second capture"). Developed test zones were imaged in the CY5® channel using an exposure time of 80 ms. Error bars represent the standard deviation of four independent replicates.
Figure 17:
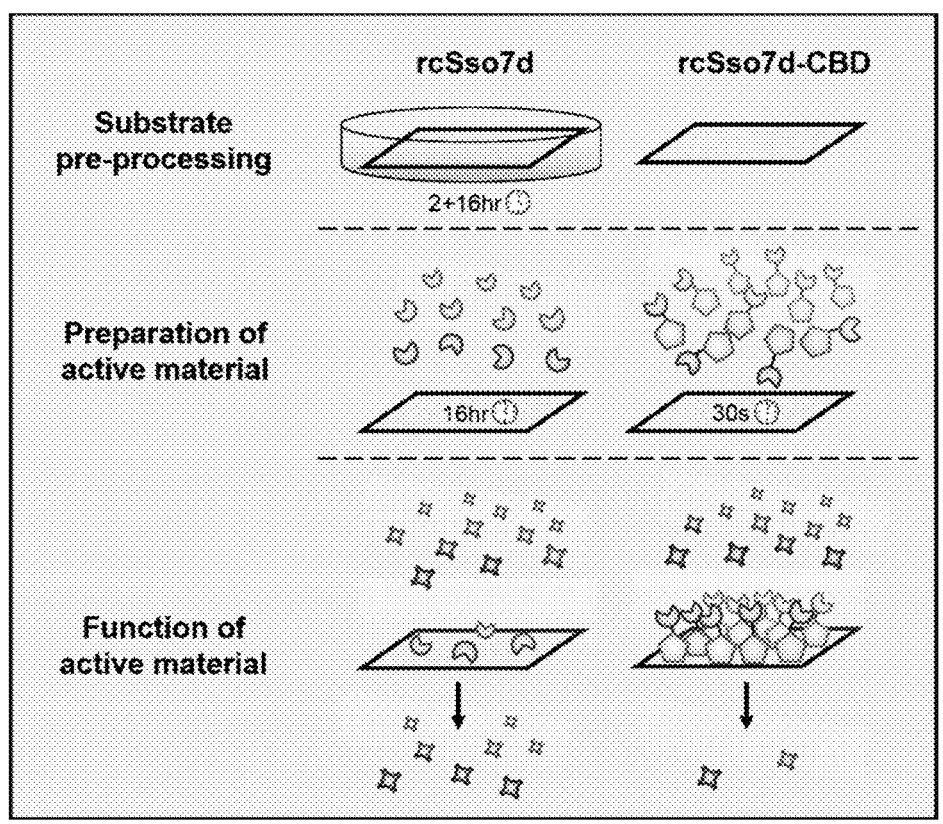
FIG. 17. Substrate pre-processing, preparation of active material, and function of active material for rcSso7d and rcSso7d-CBD.
Figure 18:
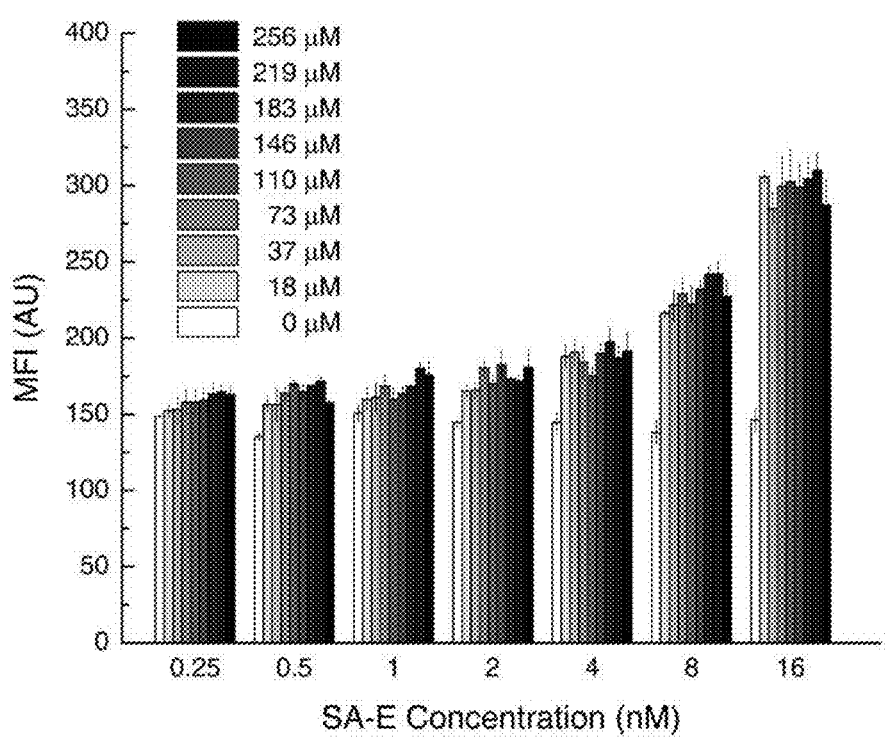
FIG. 18. MFI (AU) versus SA-E concentration (nM).
Figure 19:
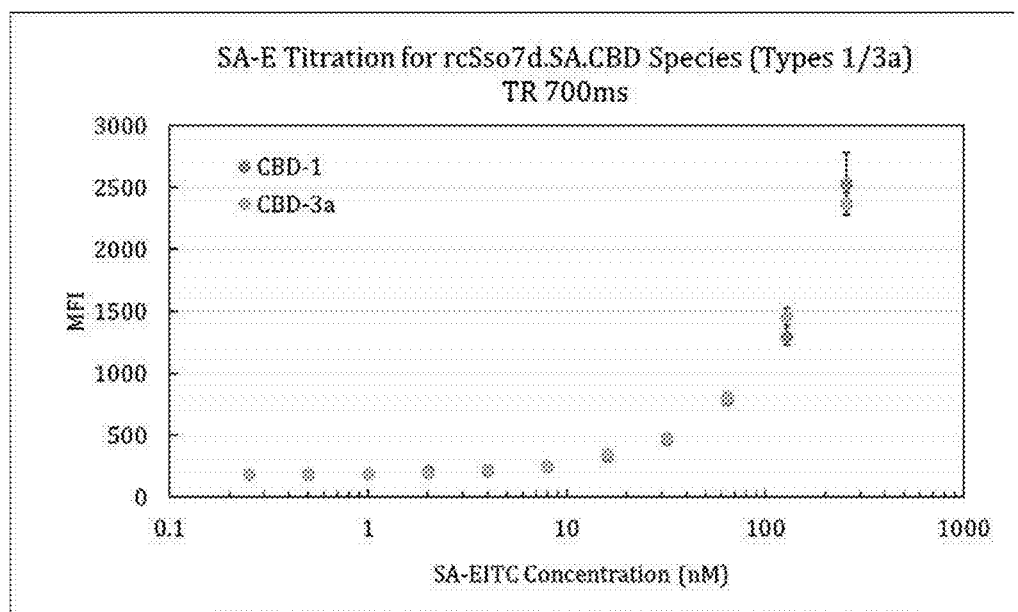
Figure 26:
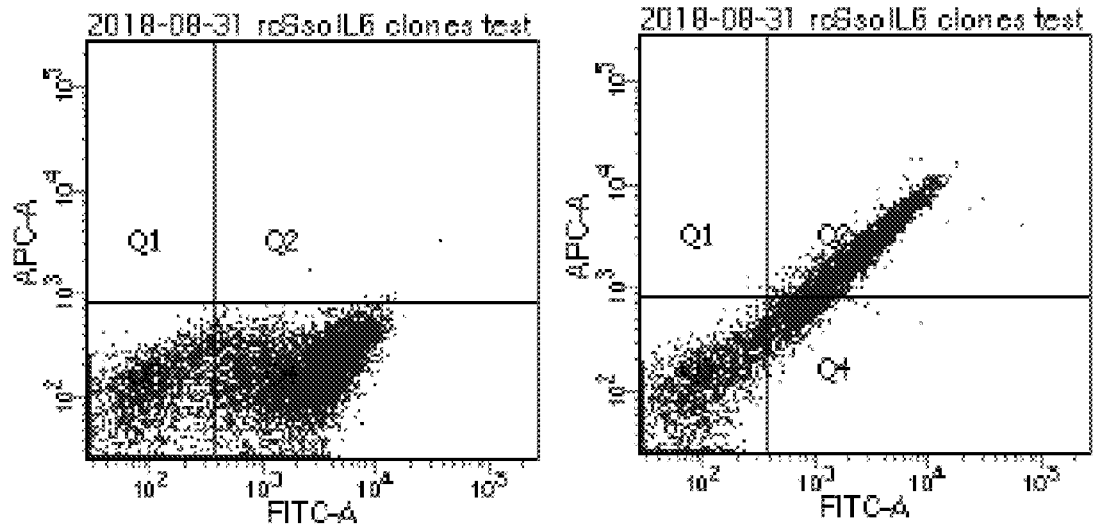
FIG. 26 shows flow cytometry data indicating the specific binding activity of Human IL-6 protein binder rcSso7d.IL6.1.
Figure 28:
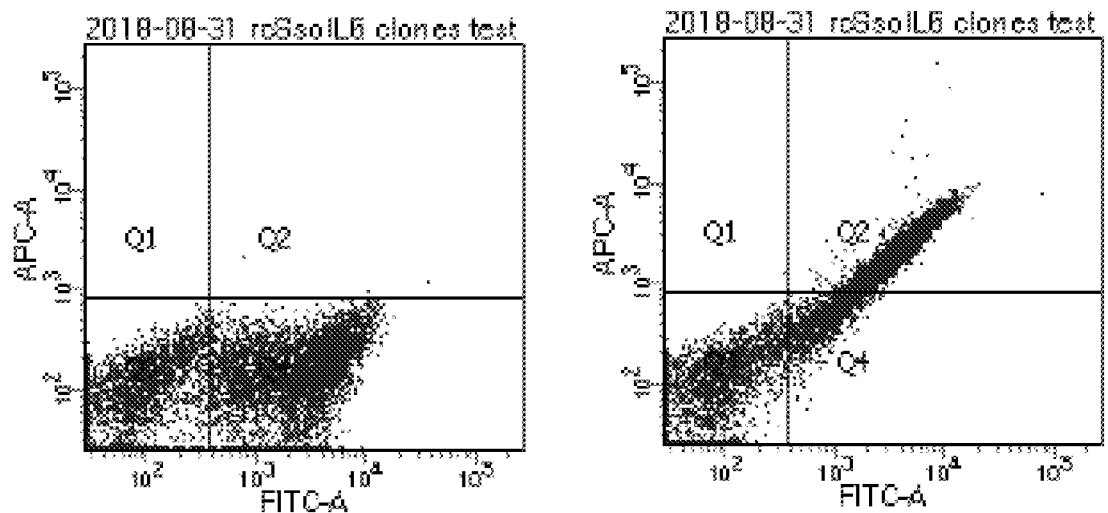
FIG. 28 shows flow cytometry data indicating the specific binding activity of Human IL-6 protein binder rcSso7d.IL6.3.
Figure 29:
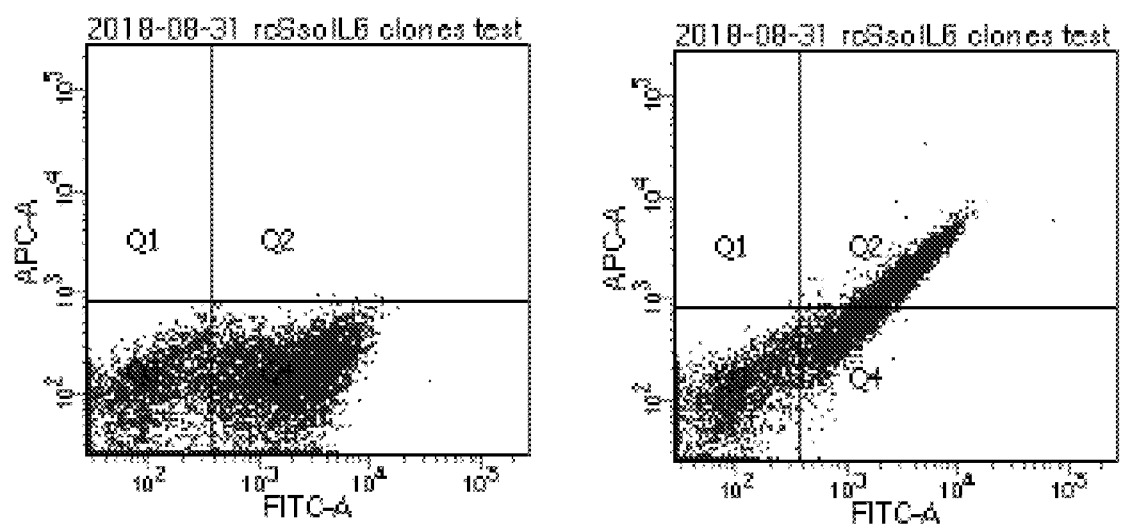
FIG. 29 shows flow cytometry data indicating the specific binding activity of Human IL-6 protein binder rcSso7d.IL6.4.
Figure 30:
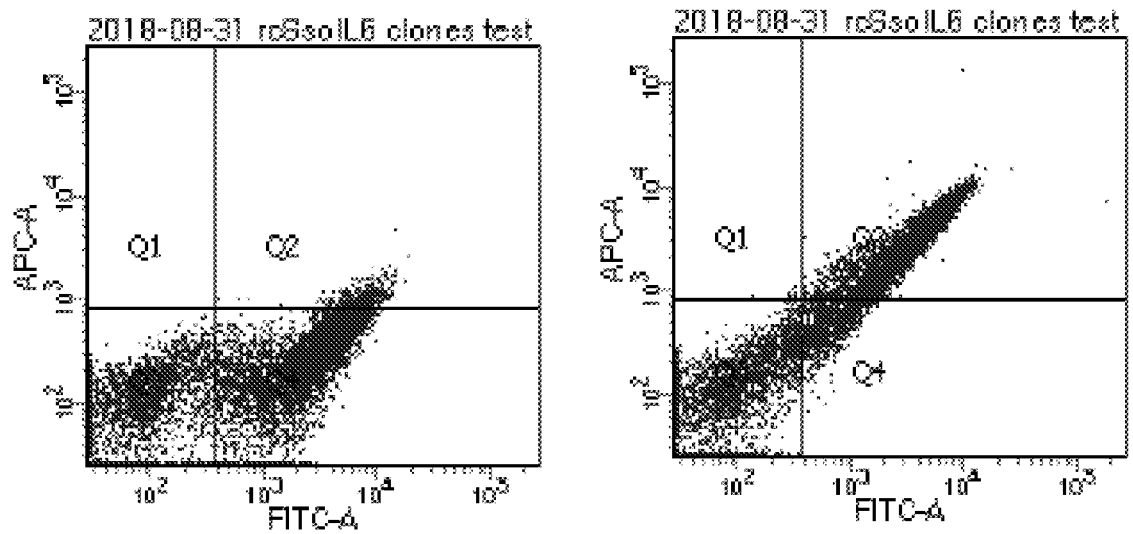
FIG. 30 shows flow cytometry data indicating the specific binding activity of Human IL-6 protein binder rcSso7d.IL6.5.
Figure 32:
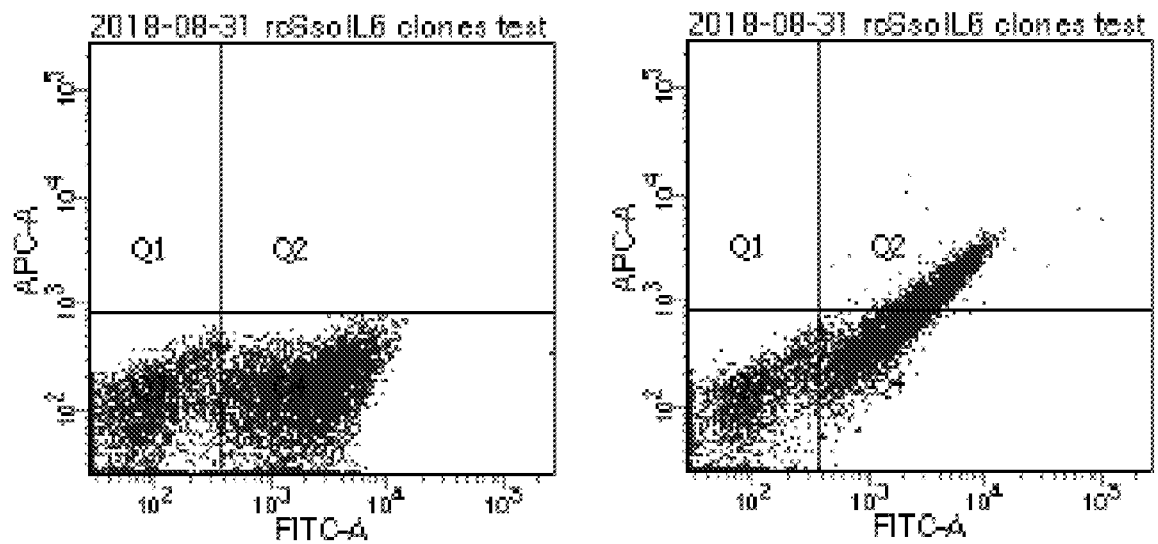
FIG. 32 shows flow cytometry data indicating the specific binding activity of Human IL-6 protein binder rcSso7d.IL6.7.

Finally, in order to directly test this prediction experimentally, the flow-through was collected following a 30-minute incubation of a 256 nM solution of SA-AF647 (10 µL) on rcSso7d.SA-CBD-coated test zones. This flow-through was applied directly to a second set of test zones coated with rcSso7d.SA-CBD, and following an additional 30-minute incubation, these sample sets were washed and imaged in the CY5® channel. By using a standard curve of known concentrations of SA-AF647 applied to rcSso7d.SA-CBD-based assays (data not shown), the resultant fluorescence measurements can be correlated with their associated antigen concentration (FIG. 16). These results indicate that following the initial depletion of SA-AF647 from a 256 nM solution, the concentration of the subsequent solution is 20.7 nM. This represents a capture efficiency of 92.2% during the initial incubation, confirming that rcSso7d.SA-CBD captures the available antigen with high efficiency.

In this study, the effects of operating within the antigen-depletion regime, using a simplified pseudo first-order rate constant model to predict the capture efficiency of immunoassays incorporating a molar excess of an immobilized binder, have been considered. In order to test these predictions, an rcSso7d-CBD fusion protein has been developed which can be readily expressed in bacteria and facilely purified in high molar yields. It has been demonstrated that this species rapidly adsorbs to unmodified cellulose, resulting in a molar abundance of the binding species which is sufficient for the near-complete depletion of a soluble antigen from solution. These findings were validated with two distinct binding systems, and serve to validate the predictions of this simple PFORC model.

By operating within this antigen-depletion regime, it was possible to maximize the analyte capture efficiency of the bioactive cellulose substrate. Given that this captured target is the biological signal which a diagnostic amplification method must render visually discernible, this enhanced capture efficiency guarantees that the maximum possible signal floor for a given biomarker can be achieved for every sample collected from a heterogeneous patient population. This general strategy, which uses a substrate-anchoring moiety for high-abundance surface adsorption of the target-binding species, is expected to be an applicable method of boosting diagnostic sensitivity in a broad array of assay formats.

Example 8. SA-E Titration for rcSso7d-CBD Types 1 and 3a

For both sample sets the bifunctional rcSso7d.SA-CBD fusion protein was contacted with the cellulose test zone at a soluble concentration of 20 µM. These rcSso7d.SA-CBD modified cellulose substrates were then contacted with streptavidin-eosin (SA-E) at a range of different concentrations, from 0.5 nM to 256 nM. Following a thirty-minute incubation, these samples were washed twice in 20 µL of 1×PBS buffer, and the samples were imaged on a fluorescence microscope in the TEXAS RED@ channel at an exposure time of 700 ms. Each data point represents the mean fluorescence of the sample, and the error bars indicate the standard deviation about the average of four experimental replicates. The similar binding curves indicate that both the rcSso7d.SA-CBD1 and rcSso7d.SA-CBD3a perform similarly, binding to the cellulose substrate in high abundance and depleting the soluble antigen from solution.

Example 9. Selection and Characterization of rcSso7d Binding Variants that Bind to Flavivirus NS1 Proteins Moderate binding proteins were developed that bind to flavivirus non-structural 1 (NS1) proteins, including Zika virus NS1 and Dengue 2 virus NS1. Zika virus NS1 (Zika.NS1) was recombinantly expressed and purified with an N-terminal hexahistidine tag. A biotinylated version of Zika virus NS1 (Zika.NS1-BA) was cloned, expressed, and purified with an additional biotin acceptor sequence tag on the C-terminus. Dengue 2 virus NS1 (Dengue2.NS1) was recombinantly expressed and purified with an N-terminal hexahistidine tag. A biotinylated version of Zika virus NS1 (Dengue2.NS1-BA) was cloned, expressed, and purified with an additional biotin acceptor sequence tag on the C-terminus.

The amino acid sequence of the selected binding variants can be seen below (Table 5). Flow cytometry data indicating the specific binding activity of each particular rcSso7d clone for the selected rcSso7d binding variants that bind to flavivirus non-structural 1 (NS1) proteins is shown in the FACS plots in FIGS. 20A-20C, 21A-21C, 22A-22C, 23A-23C, 24A-24C, and 25A-25C.

Flow cytometry data was collected using the yeast-surface display platform, in which the particular rcSso7d variant is displayed on the surface of a clonal population of yeast. The target-specific binding activity of each particular rcSso7d variant was assessed using fluorescent reagents specific to epitope fusion tags associated with the target biomarker (either the biotin acceptor tag or the hexahistidine tag).

Datasets include both secondary controls and experimental samples demonstrating baseline binding in an idealized 0.1% BSA/PBS buffer. Secondary controls indicate the extent of off-target binding to the fluorescent reagents used to detect binding activity, and are thus a proximate measure of the binding specificity of the rcSso7d variant. The experimental samples indicate the activity of the surface-displayed rcSso7d variant against the purified Zika.NS1 and Dengue2.NS 1 biomarkers, at a concentration denoted in the corresponding figure. The x-axis signifies rcSso7d expression level on the surface of the yeast (using the cMyc or HA tags on the yeast-surface displayed rcSso7d with a biotinylated antibody). The y-axis signifies binding to the antigen of interest (in this case, NS 1). Specific binding variants are observed to exhibit an increase in fluorescence signal on the y-axis of the flow cytometry plots.

TABLE 5

Primary protein structure of selected rcSso7d binding variants that bind to Flavivirus NS1 proteins.

| Protein Species | SEQ ID NO | Primary Structure (N → C) (Variable AA residues) | Shorthand Tag | Binding targets | Validated conditions |
|---|---|---|---|---|---|
| rcSso7d.NS1.1 (rcSso7d.NS1.D3) | 31 | MATVKFTYQGEEKQVDISKIKNVHRHGQKIYFIYDEGGGAKGHGKVSEKDAPKELLQMLEKQ | NHHKYIKHK (SEQ ID NO: 37) | ZIKV NS1, DENV2 NS1 | 0.1% BSA/PBS |
| rcSso7d.NS1.2 (rcSso7d.NS1.A4) | 32 | MATVKFTYQGEEKQVDISKIKHVKRHGQWIKFAYDEGGGAKGKGKVSEKDAPKELLQMLEKQ | HKHWKAKK (SEQ ID NO: 38) | ZIKV NS1, DENV2 NS1 | 0.1% BSA/PBS |
| rcSso7d.NS1.3 (rcSso7d.NS1.A6) | 33 | MATVKFTYQGEEKQVDISKIKKVHRKGQIIRFRYDEGGGAWGHGYVSEKDAPKELLQMLEKQ | KHKIRRWHY (SEQ ID NO: 39) | ZIKV NS1, DENV2 NS1 | 0.1% BSA/PBS |
| rcSso7d.NS1.4 (rcSso7d.NS1.B2) | 34 | MATVKFTYQGEEKQVDISKIKHVKRHGQKIYFRYDEGGGAGGRGRVSEKDAPKELLQMLEKQ | HKHKYRGRR (SEQ ID NO: 40) | ZIKV NS1, DENV2 NS1 | 0.1% BSA/PBS |
| rcSso7d.NS1.5 (rcSso7d.NS1.E10) | 35 | MATVKFTYQGEEKQVDISKIKRVYRHGQWIHFRYDEGGGARGHGHVSEKDAPKELLQMLEKQ | RYHWHRRHH (SEQ ID NO: 41) | ZIKV NS1, DENV2 NS1 | 0.1% BSA/PBS |
| rcSso7d.NS1.6 (rcSso7d.NS1.H7) | 36 | MATVKFTYQGEEKQVDISKIKRVSRKGQRIYFRYDEGGGAHGKGKVSEKDAPKELLQMLEKQ | RSKRYRHKK (SEQ ID NO: 42) | ZIKV NS1, DENV2 NS1 | 0.1% BSA/PBS |

Example 10. Selection and Characterization of rcSso7d Binding Variants that Bind to Human Interleukin-6 (IL-6) Protein Binding proteins were developed that bind to human interleukin-6 (IL-6). The amino acid sequence of selected rcSso7d binding variants that bind to human interleukin-6 (IL-6) protein can be seen below (Table 6). Flow cytometry data indicating the specific binding activity of each particular rcSso7d clone for the selected rcSso7d binding variants that bind to human interleukin-6 (IL-6) protein is shown in the FACS plots in FIGS. 26A-26B, 27A-27B, 28A-28B, 29A-29B, 30A-30B, 31A-31B, and 32A-32B.

Flow cytometry data was collected using the yeast-surface display platform, in which the particular rcSso7d variant is displayed on the surface of a clonal population of yeast. The target-specific binding activity of each particular rcSso7d variant was assessed using fluorescent reagents specific to epitope fusion tags associated with the target biomarker (either the biotin acceptor tag or the hexahistidine tag).

Datasets include both three-component negative controls and experimental samples demonstrating baseline binding in an idealized 0.1% BSA/PBS buffer. Three-component negative controls undergo the same conditions as the experimental samples but do not include the target biomarker; thus, they indicate the extent of off-target binding to the fluorescent reagents used to detect binding activity, and are thus a proximate measure of the binding specificity of the rcSso7d variant. The experimental samples indicate the activity of the surface-displayed rcSso7d variant against human IL-6, at a concentration denoted in the corresponding figure. The x-axis signifies rcSso7d expression level on the surface of the yeast (using the cMyc or HA tags on the yeast-surface displayed rcSso7d with a biotinylated antibody). The y-axis signifies binding to the antigen of interest (in this case, IL-6). Specific binding variants are observed to exhibit an increase in fluorescence signal on the y-axis of the flow cytometry plots.

TABLE 6

Primary protein structure of selected rcSso7d binding variants that bind to human interleukin-6 (IL-6) protein.

| Protein Species | SEQ ID NO | Primary Structure (N → C) (Variable AA residues) | Shorthand Tag | Binding targets | Validated conditions |
|---|---|---|---|---|---|
| rcSso7d.IL6.1 | 43 | MATVKFTYQGEEKQVDISKIKIVGRHGQWIYFWYDEGGGANGNGWVSEKDAPKELLQMLEKQ | IGHWYWNNW (SEQ ID NO: 50) | Human IL-6 | 0.1% BSA/PBS |
| rcSso7d.IL6.2 | 44 | MATVKFTYQGEEKQVDISKIKIVGRHGQWIYFWYDEGGGADGNGWVSEKDAPKELLQMLEKQ | IGHWYWDNW (SEQ ID NO: 51) | Human IL-6 | 0.1% BSA/PBS |
| rcSso7d.IL6.3 | 45 | MATVKFTYQGEEKQVDISKIKIVGRHGQWIYFWYDEGGGAYGNGWVSEKDAPKELLQMLEKQ | IGHWYWYNW (SEQ ID NO: 52) | Human IL-6 | 0.1% BSA/PBS |

TABLE 6-continued

Primary protein structure of selected rcSso7d binding variants
that bind to human interleukin-6 (IL-6) protein.

| Protein Species | SEQ ID NO | Primary Structure (N → C) (Variable AA residues) | Shorthand Tag | Binding targets | Validated conditions |
|---|---|---|---|---|---|
| rcSso7d.IL6.4 | 46 | MATVKFTYQGEEKQVDISKIKIVG RSGQWIYFWYDEGGGAWGNGW VSEKDAPKELLQMLEKQ | IGSWYWWNW (SEQ ID NO: 53) | Human IL-6 | 0.1% BSA/PBS |
| rcSso7d.IL6.5 | 47 | MATVKFTYQGEEKQVDISKIKIVG RWGQWIYFWYDEGGGASGNGW VSEKDAPKELLQMLEKQ | IGWWYWSNW (SEQ ID NO: 54) | Human IL-6 | 0.1% BSA/PBS |
| rcSso7d.IL6.6 | 48 | MATVKFTYQGEEKQVDISKIKWV RRDGQIIYFNYDEGGGAWGWGD VSEKDAPKELLQMLEKQ | WRDIYNWWD (SEQ ID NO: 55) | Human IL-6 | 0.1% BSA/PBS |
| rcSso7d.IL6.7 | 49 | MATVKFTYQGEEKQVDISKIKWV RRWGQWIYFNYDEGGGAWGWG DVSEKDAPKELLQMLEKQ | WRWWYNWWD (SEQ ID NO: 56) | Human IL-6 | 0.1% BSA/PBS |

Example 11. rcSso7d Protein Fusions rcSso7d.NS1.1-CBD
rcSso7d.NS1.1 (SEQ ID NO: 31) was cloned into a CBD construct, rcSso7d.NS1.1-CBD.

rcSso7d.NS1.1-CBD
(SEQ ID NO: 57)
*MGSSHHHHHHSSGLVPRGSH*MATVKFTYQGEEKQVDISKIKNVRHGQKI

YFIYDEGGGAKGHGKVSEKDAPKELLQMLEKQGSGGGGSGGGGSGGGGSP

VSGNLKVEFYNSNPSDTTNSINPQFKVTNTGSSAIDLSKLTLRYYYTVDG

QKDQTFWCDHAAIIGSNGSYNGITSNVKGTFVKMSSSTNNADTYLEISFT

GGTLEPGAHVQIQGRFAKNDWSNYTQSNDYSFKSASQFVEWDQVTAYLNG

VLVWGKEP*

The italicized amino acids in the above sequence refer to a Hexahistidine tag, the underlined amino acids refer to the rcSso7d.NS1.1 sequence, and the bolded amino acids refer to the CBD sequence.

Figures 33A, 33B:
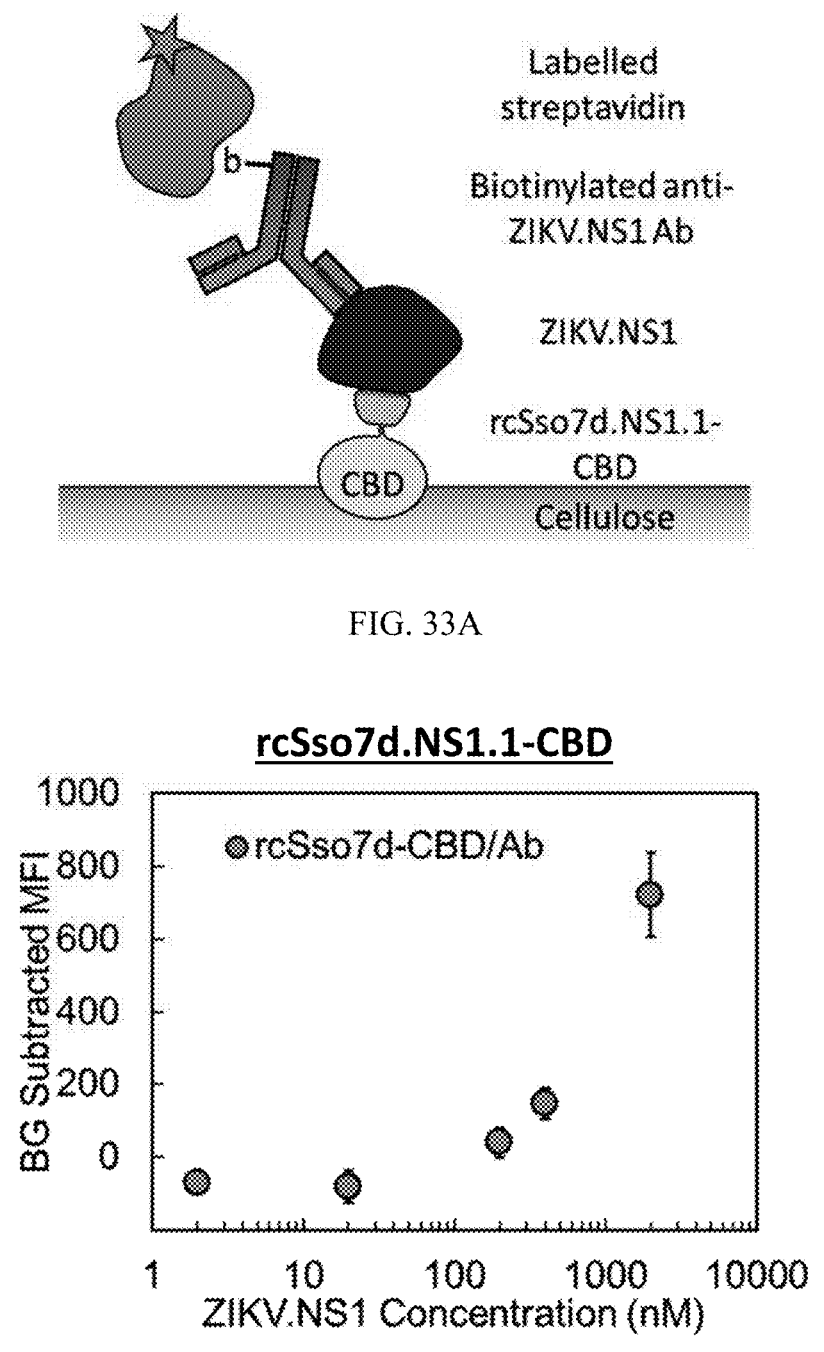

The construct was tested on cellulose paper by first immobilizing rcSso7d.NS1.1-CBD to cellulose and following with incubations of Zika virus NS1 (at various concentrations), biotinylated anti-Zika virus NS1 antibody, and streptavidin-AF 647 (see FIGS. 33A-33B). Negative controls were conducted using the same conditions as the experimental samples but with bovine serum albumin (BSA) instead of NS1 protein. The test zones were then imaged using fluorescent microscopy and analyzed to determine the mean fluorescence intensity of each test zone. The background (fluorescence without presence of antigen) was subtracted from the sample to obtain background subtracted MFI. It was demonstrated that rcSso7d.NS1.1-CBD protein fusion has function detecting Zika virus NS1 protein from solution.

BA-MBP-rcSso7d.H4 and MBP-rcSso7d.H4-bx
rcSso7d.H4 was cloned into MBP (maltose binding protein) fusion protein construct with BA (biotin acceptor sequence). rcSso7d.H4 was also cloned into MBP without BA to chemically biotinylate that protein fusion (MBP-rcSso7d.H4-bx). In the following amino acid sequences, the italicized amino acids refer to a Hexahistidine tag, the bolded amino acids refer to the biotin acceptor sequence, the bolded and underlined amino acids refer to the MBP sequence, and the underlined amino acids refer to rcSso7d.H4.

BA-MBP-rcSso7d.H4
(SEQ ID NO: 58)
*MGSSHHHHHHSSGLVPRGSH*MMAGGLNDIFEAQKIEWHELKGGGGSGGGG

SEFPKIEEGKLVIWINGDKGYNGLAEVGKKFEKDTGIKVTVEHPDKLEEKE

PQVAATGDGPDIIFWAHDREGGYAQSGLLAEITPDKAFQDKLYPFTWDAV

RYNGKLIAYPIAVEALSLIYNKDLLPNPPKTWEEIPALDKELKAKGKSAL

MFNLQEPYFTWPLIAADGGYAFKYENGKYDIKDVGVDNSGAKAGLTFLVD

LIKNKHMNADTDYSIAEAAFNKGETAMTINGPWAWSNIDTSKVNYGVTVL

PTFKGQPSKPFVGVLSAGINAASPNKELAKEFLENYLLTDEGLEAVNKDK

PLGAVALKSYEEELAKDPRIAATMENAQKGEIMPNIPQMSAFWYAVRTAV

INAASGRQTVDEALKDAQTGSGGGGSGGGGST_ATVKFTYQGEEKQVDIS_

_KIKSVWRRGQRIWFRYDEGGGAWGAGKVSEKDAPKELLQMLEKQ_

MBP-rcSso7d.H4
(SEQ ID NO: 59)
*MGSSHHHHHHSSGLVPRGSH*KIEEGKLVIWINGDKGYNGLAEVGKKFEK

DTGIKVTVEHPDKLEEKEPQVAATGDGPDIIFWAHDRFGGYAQSGLLAEI

TPDKAFQDKLYPFTWDAVRYNGKLIAYPIAVEALSLIYNKDLLPNPPKTW

EEIPALDKELKAKGKSALMENLQEPYFTWPLIAADGGYAFKYENGKYDIK

DVGVDNSGAKAGLTFLVDLIKNKHMNADTDYSIAEAAFNKGETAMTINGP

WAWSNIDTSKVNYGVTVLPTFKGQPSKPFVGVLSAGINAASPNKELAKEF

LENYLLTDEGLEAVNKDKPLGAVALKSYEEELAKDPRIAATMENAQKGEI

MPNIPQMSAFWYAVRTAVINAASGRQTVDEALKDAQTGSGGGGSGGGGSM

_ATVKFTYQGEEKQVDISKIKSVWRRGQRIWFRYDEGGGAWGAGKVSEKDA_

_PKELLQMLEKQ_

The MBP fusion proteins were compared to BA-rcSso7d.H4 and rcSso7d.H4-bx, which are the protein sequences that do not contain the MBP fusion proteins, in order to demonstrate the effects of the MBP fusion partner.

```
BA-rcSso7d.H4
                                             (SEQ ID NO: 60)
MGSSHHHHHHSSGLVPRGSHMTSMAGGLNDIFEAQKIEWHEHMATVKFTY

QGEEKQVDISKIKSVWRRGQRIWFRYDEGGGAWGAGKVSEKDAPKELLQM

LEKQGG rcSso7d.H4
                                             (SEQ ID NO: 61)
MGSSHHHHHHSSGLVPRGSHMATVKFTYQGEEKQVDISKIKSVWRRGQRI

WFRYDEGGGAWGAGKVSEKDAPKELLQMLEKQ
```

Figure 34:
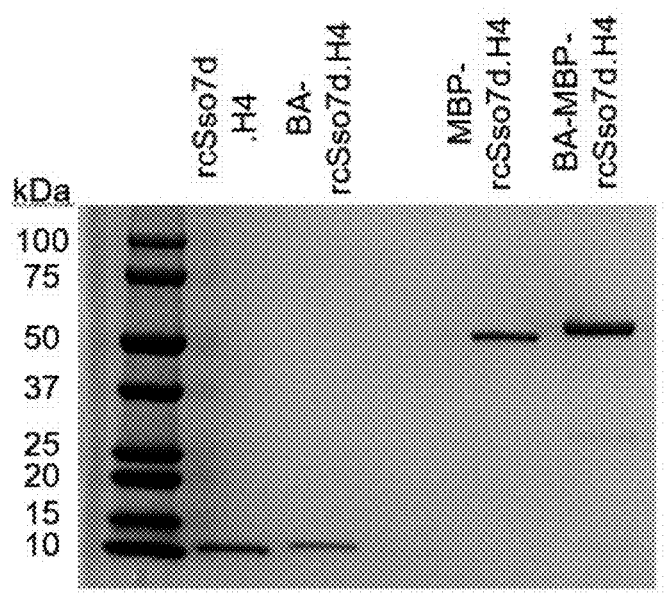
FIG. 34 shows a 12% SDS-PAGE gel image demonstrating the purity of four proteins (rcSso7d.H4, BA-rcSso7d.H4, MBP-rcSso7d.H4, and BA-MBP-rcSso7d.H4) after expression and purification.

All four proteins (rcSso7d.H4, BA-rcSso7d.H4, MBP-rcSso7d.H4, and BA-MBP-rcSso7d.H4) were expressed and purified. rcSso7d.H4 and MBP-rcSso7d.H4 were chemically biotinylated. A portion of the BA-rcSso7d.H4 and BA-MBP-rcSso7d.H4 proteins were purified on a monomeric avidin column to separate out the subpopulations that had biotins on the protein (see FIG. 34).

Biotin efficiency was quantified for both the biotin acceptor sequence (BA), which added biotin to the BA sequence during expression in *E. coli*, and chemical biotinylation using Sulfo-NHS-LC-Biotin to conjugate biotins to free amines on the protein (see Table 7). The purification yield after monomeric avidin column purification indicates issues with biotin accessibility when the BA sequence is directly fused to the protein; however, having the MBP structured protein between the BA and rcSso7d sequences reduce effects of biotin accessibility. Product yield of the proteins after chemical conjugation also indicates that rcSso7d.H4 lost structural integrity as indicated by the majority of the protein precipitating out of solution. The addition of the MBP fusion improved protein solubility and stability, as indicated by the much higher product yields.

TABLE 7

| Protein | Approx. Biotins per Protein | Approx. Avidin Column Purification Yield | Approx. Chemical Conjugation Product Yield |
|---|---|---|---|
| rcSso7d.H4-b$_x$ | —† | —‡ | <1% |
| BA-rcSso7d.H4 | 0.35 | 5% | —§ |
| BA-MBP-rcSso7d.H4 | 0.60 | 50% | —§ |
| MBP-rcSso7d.H4-b$_x$ | 11 | —‡ | 50% |

Figure 35:
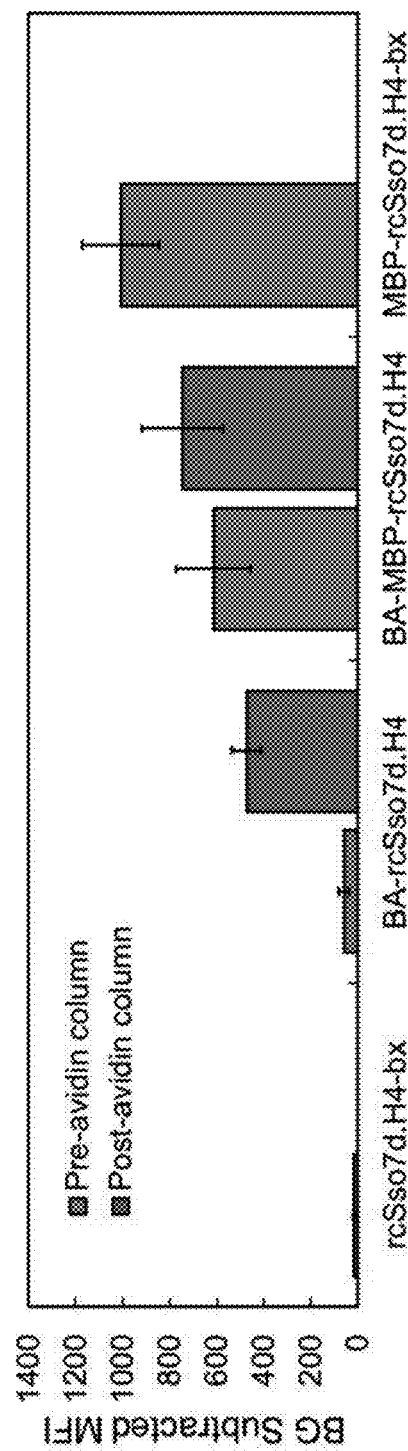
FIG. 35 shows binder performance of four protein constructs, including both pre-avidin purified and post-avidin purified subpopulations for BA-rcSso7d.H4 and BA-MBP-rcSso7d.H4.

All protein constructs (and both pre-avidin purified and post-avidin purified subpopulations for BA-rcSso7d.H4 and BA-MBP-rcSso7d.H4) were tested by first immobilizing TB antigen Rv1656 on oxidized cellulose and following with incubations with the rcSso7d.H4 construct and streptavidin-AF 647. Negative controls were conducted using the same conditions as the experimental samples but with immobilized bovine serum albumin (BSA) instead of TB antigen protein. The test zones were then imaged using fluorescent microscopy and analyzed to determine the mean fluorescence intensity of each test zone. The background (fluorescence without presence of antigen) was subtracted from the sample to obtain background subtracted MFI.

rcSso7d.H4-bx resulted in reduced signal (in addition to the low product yield after conjugation). The addition of MBP for MBP-rcSso7d.H4-bx demonstrated a much higher signal, part of which can be attributed to the increased biotin valency (multiple biotins per protein). For BA-rcSso7d.H4, the performance after avidin column purification was much higher than the theoretical increase from 35% to 100% biotinylation. This significant increase-about an order of magnitude increase in background-subtracted MFI-may be attributed to the inaccessibility of biotins on BA-rcSso7d.H4. Through avidin column purification, only the proteins with biotins that were accessible to avidin were collected; therefore, the post-avidin column purified populations reflected the proteins with accessible biotins while the pre-avidin column purified population contained mainly proteins with inaccessible biotins (see FIG. 35). For BA-MBP-Sso.TB, the post-avidin column fraction demonstrated an increase in signal intensity as compared to the pre-avidin column population; this can be attributed to the increase in proportional biotinylation since this variant did not appear to have biotin accessibility issues. Compared to BA-rcSso7d.H4, BA-MBP-rcSso7d.H4 demonstrated an increase in signal, which may be a result of the intrinsic improved accessibility of biotins on BA-MBP-rcSso7d.H4 and also potentially diminished steric hindrance effects, which may have caused the smaller rcSso7d.H4 to dissociate from the TB antigen as a result of streptavidin binding.

Protein fusions of rcSso7d.H4 and MBP (maltose binding protein) were developed as a structure protein mass with improved solubility characteristics to demonstrate improved signal detection when used as the detection reagent.

Multimerized BA-(rcSso7d.H4)$_n$ rcSso7d.H4 multimers (1×, 2×, 3×) were cloned into BA (biotin acceptor sequence) constructs BA-rcSso7d.H4(1×), BA-rcSso7d.H4(2×), and BA-rcSso7d.H4(3×). In the following amino acid sequences, the italicized amino acids refer to a Hexahistidine tag, the bolded amino acids refer to the biotin acceptor sequence, and the underlined amino acids refer to rcSso7d.H4.

```
BA-rcSso7d.H4(1x)
                                             (SEQ ID NO: 62)
MGSSHHHHHHSSGLVPRGSHMTSMAGGLNDIFEAQKIEWHEHMATVKFTY

QGEEKQVDISKIKSVWRRGQRIWFRYDEGGGAWGAGKVSEKDAPKELLQM

LEKQGG

BA-rcSso7d.H4(2x)
                                             (SEQ ID NO: 63)
MGSSHHHHHHSSGLVPRGSHMTSMAGGLNDIFEAQKIEWHEHMATVKFTY

QGEEKQVDISKIKSVWRRGQRIWFRYDEGGGAWGAGKVSEKDAPKELLQM

LEKQGGGSGGGSMATVKFTYQGEEKQVDISKIKSVWRRGQRIWFRYDE

GGGAWGAGKVSEKDAPKELLQMLEKQGG

BA-rcSso7d.H4(3x)
                                             (SEQ ID NO: 64)
MGSSHHHHHHSSGLVPRGSHMTSMAGGLNDIFEAQKIEWHEHMATVKFTY

QGEEKQVDISKIKSVWRRGQRIWFRYDEGGGAWGAGKVSEKDAPKELLQM

LEKQGGGSGGGSMATVKFTYQGEEKQVDISKIKSVWRRGQRIWFRYDE

GGGAWGAGKVSEKDAPKELLQMLEKQGGGSGGGSMATVKFTYQGEEKQ

VDISKIKSVWRRGQRIWFRYDEGGGAWGAGKVSEKDAPKELLQMLEKQGG
```

Figure 36A:
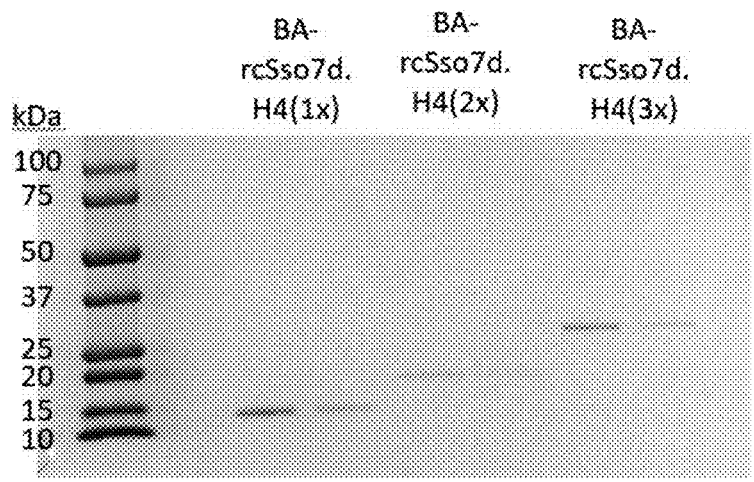
FIG. 36A shows a 12% SDS-PAGE image demonstrating the purity of three multimerized proteins (BA-(rcSso7d.H4)$_1$, BA-(rcSso7d.H4)$_2$, and BA-(rcSso7d.H4)$_3$) after expression and purification.
Figure 36B:
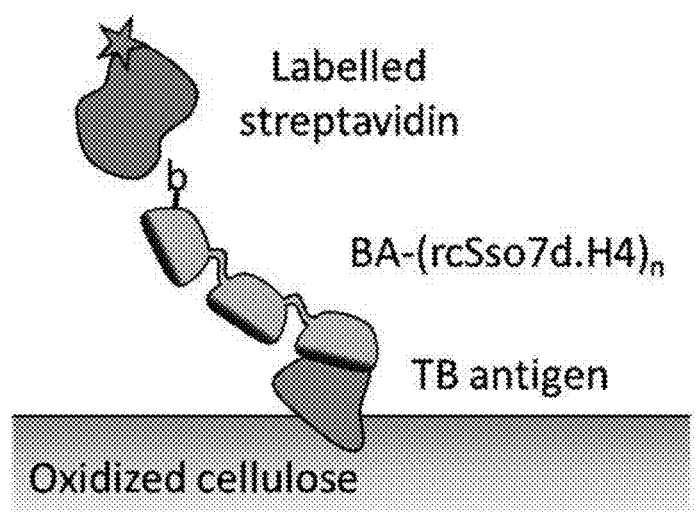
FIG. 36B shows a schematic representation of TB antigen Rv1656 immobilized to cellulose followed by incubations of the BA-(rcSso7d.H4)$_n$ and streptavidin-AF 647.
Figure 36C:
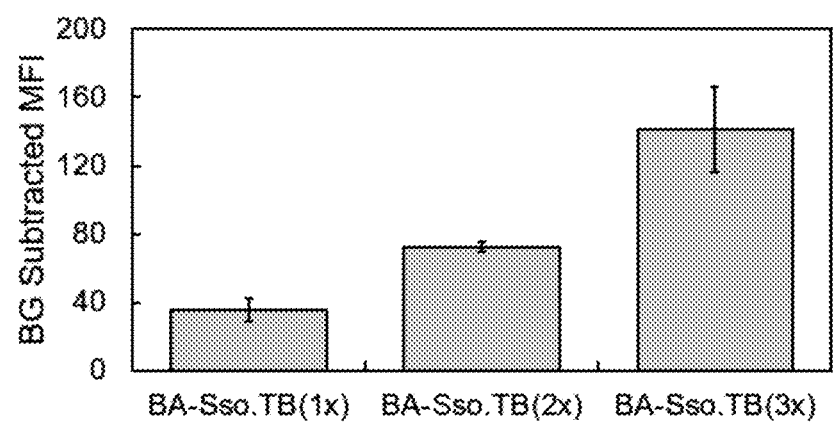
FIG. 36C shows binder performance of BA-(rcSso7d.H4)$_n$ constructs in cellulose paper-based assay.

Preliminary tests were conducted using BA-(rcSso7d.H4)$_1$, BA-(rcSso7d.H4)$_2$, and BA-(rcSso7d.H4)$_3$ after expression and purification. SDS-PAGE shows purity of each protein (each protein run at two different dilutions) (see FIG. 36A). Each multimerized protein was then tested by first immobilizing TB antigen Rv1656 to oxidized cellulose paper and following with incubations of the BA-(rcSso7d.H4)$_n$ and streptavidin-AF 647 (see FIGS. 36B-36C). Negative controls were conducted using the same conditions as the experimental samples but with immobilized bovine serum albumin (BSA) instead of TB antigen protein.

The test zones were then imaged using fluorescent microscopy and analyzed to determine the mean fluorescence intensity of each test zone. The background (fluorescence without presence of antigen) was subtracted from the sample to obtain background subtracted MFI.

The multimers of rcSso7d.H4 with biotin acceptor sequence (BA) were developed to be used as detection reagent.

Example 12. Selection and Characterization of rcSso7d Binding Variants that Bind to Urine-Based TB Biomarkers Biotinylation In some cases, the biomarker has been expressed with an in vivo biotinylation tag (termed BA), which provides a chemical handle by which the capture of the biomarker can be detected, using a fluorescent streptavidin reagent. This biotinylated species can be further purified using a monomeric avidin column, in order to yield a preparation with 100% biotinylation efficiency.

Magnetic-Bead Sorting and Fluorescence-Activated Cell Sorting (FACS)

Binding variants of rcSso7d were developed using the yeast-surface display platform, in which a combinatorial library of rcSso7d variants is displayed on the surface of a population of yeast cells. This library was screened using magnetic-bead sorting and fluorescence activated cell sorting in order to enrich the population for rcSso7d variants binding to the target of interest. Briefly, the biotinylated target was incubated with streptavidin-coated magnetic Dynabeads in order to coat these beads with the target. Target-covered beads were incubated with the combinatorial yeast library for a sufficient period of time for analyte-specific rcSso7d-variants to bind to the beads. These clones were then drawn from solution using a magnetic rack. In instances where urine-based biomarkers were the target of interest, the biomarker could be incubated in a urine sample for 4-16 hours at 25-37° C., in order to bias selection toward binding variants which interact with the urine-treated form of the analyte.

The library was also screened using fluorescence-activated cell sorting. Soluble biotinylated analyte was incubated with the yeast library after it was screened with magnetic beads. A fluorophore was associated with analyte-bound rcSso7d variants, either using fluorophore-conjugated streptavidin, or by using an epitope-specific antibody (e.g. mouse anti-hexahistidine/goat anti-mouse ALEXA FLUOR® 647). In order to prevent the selection of binders against fluorescent reagents, orthogonal sets were used in alternating rounds (e.g. streptavidin phycoerythrin, and mouse anti-hexahistidine/goat anti-mouse ALEXA FLUOR® 647). Yeast cells bearing binding variants of the rcSso7d molecule (as evidenced by fluorescent signal) were sorted into culture media for expansion and further sorting.

Flow Cytometry Analysis

Flow cytometry data was collected using the yeast-surface display platform, in which the particular rcSso7d variant is displayed on the surface of a clonal population of yeast. The target-specific binding activity of each particular rcSso7d variant was assessed using fluorescent reagents specific to epitope fusion tags associated with the target biomarker (either the BA tag or the hexahistidine tag).

Figure 38:
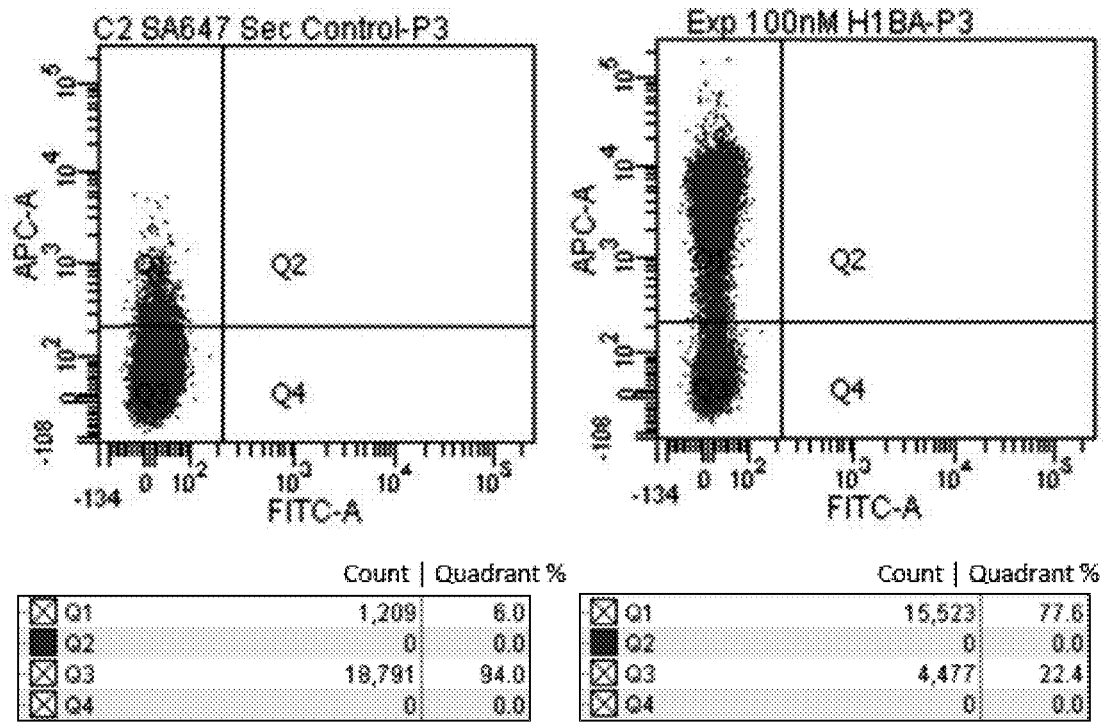
FIG. 38 shows flow cytometry data indicating the specific binding activity of H1 binder rcSso7d.H1BA.1.

Datasets discussed below include both secondary controls and experimental samples demonstrating baseline binding in an idealized 0.1% BSA/PBS buffer. Secondary controls indicate the extent of off-target binding to the fluorescent reagents used to detect binding activity, and are thus a proximate measure of the binding specificity of the rcSso7d variant. The experimental samples indicate the activity of the surface-displayed rcSso7d variant against the purified TB biomarker, at a concentration denoted in the corresponding figure. Specific binding variants are observed to exhibit a large difference in proportional binding between the secondary control and the experimental sample (observed in the tables below the FACS plots). Generally, high binding signal correlates with a significant population of labeled yeast in the positive quadrants (Q1 and Q2)—differences in the orientation/layout of these plots are due to the use of different fluorophores (ALEXA FLUOR® 647 and streptavidin-phycoerythrin, e.g. FIGS. 38 and 39), or the orthogonal labeling of yeast cells to quantify rcSso7d display (e.g. FIGS. 40A-40C).

H1 Binders

Antigen name: H1

Protein ID: Rv1681

Gene ID: MT1721

(See e.g., Kashino et al. Clin Exp Immunol (2008) 153:56-62; Pollock et al., *J Clin Microbiol* (2013) 51:1367-73)

Figure 37:
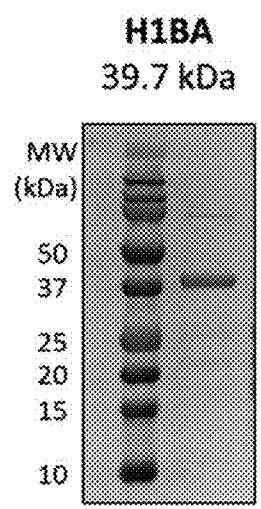
FIG. 37 shows a 12% SDS-PAGE gel showing purified protein preparation of H1BA.

H1BA (see FIG. 37)

(SEQ ID NO: 65)

*MGSSHHHHHHSSGLVPRGSH*MVIIELMRRVVGLAQGATAEVAVYGDRDRD

LAERWCANTGNTLVRADVDQTGVTLVVRRGHPPDPASVLGPDRLPGVRL

WLYTNFHCNLCCDYCCVSSSPSTPHRELGAERIGRIVGEAARWGVRELFL

TGGEPFLLPDIDTIIATCVKQLPTTVLTNGMVFKGRGRRALESLPRGLAL

QISLDSATPELHDAHRGAGTWVKAVAGIRLALSLGFRVRVAATVASPAPG

ELTAFHDFLDGLGIAPGDQLVRPIALEGAASQGVALTRESLVPEVTVTAD

GVYWHPVAATDERALVTRTVEPLTPALDMVSRLFAEQWTRAAEEAALFPC

A<u>(GSMAGGLNDIFEAQKIEWHE)</u>*

The italicized amino acids in the above sequence refer to a Hexahistidine tag and the underlined amino acids in parentheseses refer to a (Biotin acceptor sequence).

The amino acid sequence of selected rcSso7d binding variants that bind to H1 can be seen below (Table 8). Flow cytometry data indicating the specific binding activity of each particular rcSso7d clone for the selected rcSso7d binding variants that bind to H1 is shown in the FACS plots in FIGS. 38-43. For example, flow cytometry data indicating the specific binding activity of rcSso7d.H1BA.1 is shown in the FACS plots in FIG. 38. Flow cytometry data indicating the specific binding activity of rcSso7d.H1BA.2 is shown in the FACS plots in FIG. 39. Flow cytometry data indicating the specific binding activity of rcSso7d.H1BA.3 is shown in the FACS plots in FIGS. 40A-40C. Flow cytometry data indicating the specific binding activity of rcSso7d.H1BA.4 is shown in the FACS plots in FIG. 41. Flow cytometry data indicating the specific binding activity of rcSso7d.H1BA.5 is shown in the FACS plots in FIG. 42. Flow cytometry data indicating the specific binding activity of rcSso7d.H1BA.6 is shown in the FACS plots in FIG. 43.

TABLE 8

Primary protein structure of selected rcSso7d binding variants that bind to H1.

| Protein Species | SEQ ID NO | Primary Structure (N → C) (Variable AA residues) | Shorthand Tag | Binding targets | Validated conditions |
|---|---|---|---|---|---|
| reSso7d.H1BA.1 (1.4.1) | 66 | MATVKFTYQGEEKQVDIS KIKHVRRWGQYIIFAYDE GGGAYGGGWVSEKDAP KELLQMLEKQ | HRWYIAYGW (SEQ ID NO: 72) | H1BA | 0.1% BSA/PBS |
| reSso7d.H1BA.2 (1.E2.1) | 67 | MATVKFTYQGEEKQVDIS KIKHVIRNGQYIIFAYDEG GGAYGGGWVSEKDAPKE LLQMLEKQ | RAYYIAYAW (SEQ ID NO: 73) | H1BA | 0.1% BSA/PBS, heat, urine |
| reSso7d.H1BA.3 (1.E2.2) | 68 | MATVKFTYQGEEKQVDIS KIKHVIRNGQYIIFAYDEG GGAYGGGWVSEKDAPKE LLQMLEKQ | HINYIAYGW (SEQ ID NO: 74) | H1-bx | 0.1% BSA/PBS |
| reSso7d.H1BA.4 (1.E2.3) | 69 | MATVKFTYQGEEKQVDIS KIKNVYRWGQYIIFSYDE GGGAYGWGWVSEKDAP KELLQMLEKQ | NYWYISYWW (SEQ ID NO: 75) | H1-bx | 0.1% BSA/PBS |
| reSso7d.H1BA.5 (1.E2.4) | 70 | MATVKFTYQGEEKQVDIS KIKYVRRYGQYIGFIYDE GGGAWGKGYVSEKDAP KELLQMLEKQ | YRYYGIWKY (SEQ ID NO: 76) | H1BA | 0.1% BSA/PBS |
| reSso7d.H1BA.6 (H1BA.PF5.1) | 71 | MATVKFTYQGEEKQVDIS KIKDVWRWGQWIDFIYD EGGGADGWGRVSEKDAP KELLQMLEKQ | DWWWDIDWR (SEQ ID NO: 77) | H1BA | 0.1% BSA/PBS |

Figure 40B:
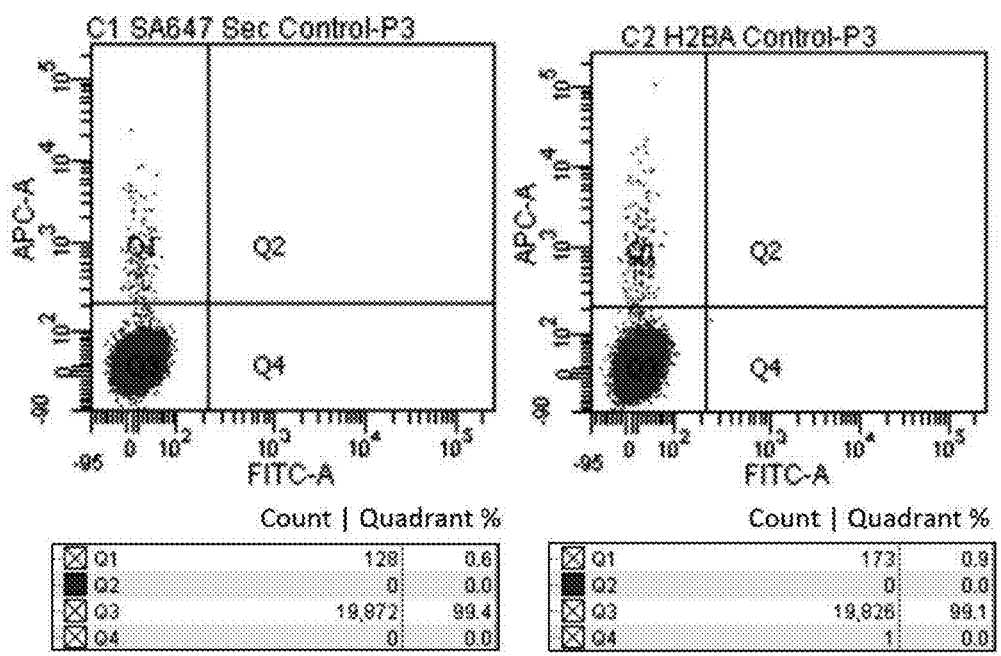

FIGS. 40B and 40C show the binding specificity of clone H1BA.3 to the H1BA antigen, demonstrating the marked difference between its binding activity against H1BA (71.5% positive) and its binding activity against the antigens H2BA, H6BA, and H7BA (0.9%, 0.9%, and 1.3%, respectively).

H2 Binders
Antigen name: H2
Protein ID: Rv2392
Gene ID: MT2462

Figure 44:
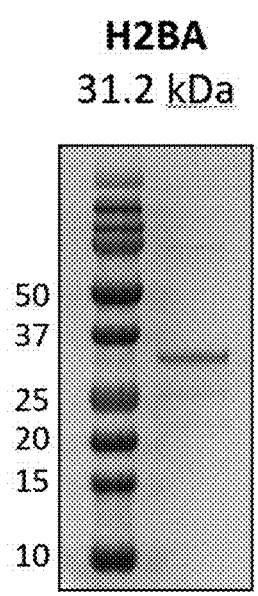
FIG. 44 shows a 12% SDS-PAGE gel image showing purified protein preparation of of H2BA.

H2BA (see FIG. 44)
(SEQ ID NO: 78)
*MGSSHHHHHHSSGLVPRGSH*MSGETTRLTEPQLRELAARGAAELDGATAT

DMLRWTDETFGDIGGAGGGVSGHRGWTTCNYVVASNMADAVLVDLAAKVR

PGVPVIFLDTGYHFVETIGTRDAIESVYDVRVLNVTPEHTVAEQDELLGK

DLFARNPHECCRLRKVVPLGKTLRGYSAWVTGLRRVDAPTRANAPLVSFD

ETFKLVKVNPLAAWTDQDVQEYIADNDVLVNPLVREGYPSIGCAPCTAKP

AEGADPRSGRWQGLAKTECGLHAS<u>(GSMAGGLNDIFEAQKIEWHE)</u>*

The italicized amino acids in the above sequence refer to a Hexahistidine tag and the underlined amino acids in parentheseses refer to a (Biotin acceptor sequence).

The amino acid sequence of selected rcSso7d binding variants that bind to H2 can be seen below (Table 9). Flow cytometry data indicating the specific binding activity of rcSso7d.H2BA.1 is shown in the FACS plots in FIG. 45.

TABLE 9

Primary protein structure of selected rcSso7d binding variants that bind to H2.

| Protein Species | SEQ ID NO | Primary Structure (N → C) (Variable AA residues) | Shorthand Tag | Binding targets | Validated conditions |
|---|---|---|---|---|---|
| reSso7d.H2BA.1 (H2BA.PF5.1) | 79 | MATVKFTYQGEEKQV DISKIKRVIRYGQAIAF AYDEGGGARGYGWVS EKDAPKELLQMLEKQ | RIYAAARYW (SEQ ID NO: 81) | H2BA | 0.1% BSA/PBS, heat, urine (limited) |
| re5so7d.H2BA.2 (H2BA.PUF5.2) | 80 | MATVKFTYQGEEKQV DISKIKYVGRWGQNIG FAYDEGGGAYGYGGV SEKDAPKELLQMLEKQ | YGWNGAYYG (SEQ ID NO: 82) | H2BA | |

TABLE 9-continued

Primary protein structure of selected rcSso7d binding variants that bind to H2.

| Protein Species | SEQ ID NO | Primary Structure (N → C) (Variable AA residues) | Shorthand Tag | Binding targets | Validated conditions |
|---|---|---|---|---|---|

H4 Binders
Antigen name: H4
Protein ID: Rv1656
Gene ID: MT1694
(See e.g., Napolitano et al., 2008)

Figure 46:
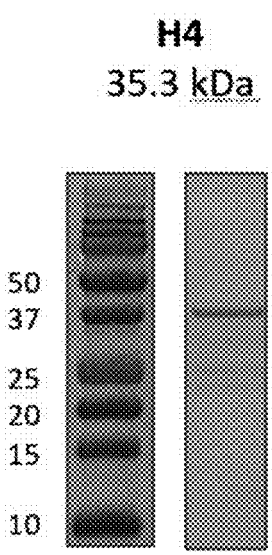
FIG. 46 shows a 12% SDS-PAGE gel showing purified protein preparation of H4.

H4 (see FIG. 46)
(SEQ ID NO: 83)
*MGSSHHHHHHSSGLVPRGSH*MVIRHFLRDDDLSPAEQAEVLELAAELKKD
PVSRRPLQGPRGVAVIFDKNSTRTRFSFELGIAQLGGHAVVVDSGSTQLG
RDETLQDTAKVLSRYVDAIVWRTFGQERLDAMASVATVPVINALSDEFHP
CQVLADLQTIAERKGALRGLRLSYFGDGANNMAHSLLLGGVTAGIHVTVA
APEGFLPDPSVRAAAERRAQDTGASVTVTADAHAAAAGADVLVTDTWTSM
GQENDGLDRVKPFRPFQLNSRLLALADSDAIVLHCLPAHRGDEITDAVMD
GPASAVWDEAENRLHAQKALLVWLLERS*

The italicized amino acids in the above sequence refer to a Hexahistidine tag.

The amino acid sequence of selected rcSso7d binding variants that bind to H4 can be seen below (Table 10). Flow cytometry data indicating the specific binding activity of each particular rcSso7d clone for the selected rcSso7d binding variants that bind to H4 is shown in the FACS plots in FIGS. 47-55. For example, flow cytometry data indicating the specific binding activity of rcSso7d.H4.1 is shown in the FACS plots in FIG. 47. Flow cytometry data indicating the specific binding activity of rcSso7d.H4.2 is shown in the FACS plots in FIG. 48. Flow cytometry data indicating the specific binding activity of rcSso7d.H4.3 is shown in the FACS plots in FIG. 49. Flow cytometry data indicating the specific binding activity of rcSso7d.H4.4 is shown in the FACS plots in FIG. 50. Flow cytometry data indicating the specific binding activity of rcSso7d.H4.5 is shown in the FACS plots in FIG. 51. Flow cytometry data indicating the specific binding activity of rcSso7d.H4.6 is shown in the FACS plots in FIG. 52. Flow cytometry data indicating the specific binding activity of rcSso7d.H4.7 is shown in the FACS plots in FIG. 53. Flow cytometry data indicating the specific binding activity of rcSso7d.H4.8 is shown in the FACS plots in FIG. 54. Flow cytometry data indicating the specific binding activity of rcSso7d.H4.9 is shown in the FACS plots in FIG. 55. Flow cytometry data indicating the specific binding activity of rcSso7d.H4.2/H4/BA-MBP-rcSso7d.H4.1 is shown in the FACS plots in FIGS. 56A-56B.

FIGS. 56A-56B indicate the performance of binders H4.1 and H4.2 in a full sandwich assay format, wherein H4.1 has been solubly expressed in the BA-MBP-rcSso7d fusion construct, and biotinylated variants have been purified via a monomeric avidin column. In these samples, the yeast-surface displayed rcSso7d.H4.2 variant has been sequentially incubated with the H4 antigen at 100 nM (except for in the case of the secondary control), the purified BA-MBP-rcSso7d.H4.1 protein, and streptavidin ALEXA FLUOR® 647. FIG. 56A shows baseline binding signal for the full immunocomplex (with H4 incubated in buffer) is compared to the full immunocomplex binding signal with H4 incubated in urine overnight at 37° C. FIG. 56B compares similar samples, except the H4 antigen has been incubated in urine for one week at 37° C.

TABLE 10

Primary protein structure of selected rcSso7d binding variants that bind to H4.

| Protein Species | SEQ ID NO | Primary Structure (N → C) (Variable AA residues) | Shorthand Tag | Binding targets | Validated conditions |
|---|---|---|---|---|---|
| rcSso7d.H4.1 (H4.1, 4.4.2) | 84 | MATVKFTYQGEEKQVDIS KIKSVWRRGQRIWFRYD EGGGAWGAGKVSEKDAP KELLQMLEKQ | SWRRWRWAK (SEQ ID NO: 93) (close variant: SWRRWRWAR (SEQ ID NO: 94) | H4 | 0.1% BSA/PBS, heat, urine |
| rcSso7d.H4.2 (H4.2, 4.5) | 85 | MATVKFTYQGEEKQVDIS KIKWVRRYGQYIGFSYDE GGGAWGKGYVSEKDAP KELLQMLEKQ | WRYYGSWKY (SEQ ID NO: 95) | H4 | 0.1% BSA/PBS, heat, urine |

TABLE 10-continued

Primary protein structure of selected rcSso7d
binding variants that bind to H4.

| Protein Species | SEQ ID NO | Primary Structure (N → C) (Variable AA residues)  Shorthand Tag | Binding targets | Validated conditions |
|---|---|---|---|---|
| rcSso7d.H4.3 (P4-10, C2) | 86 | MATVKFTYQGEEKQVDIS HWRNYRWAA KIKHVWRRGQNIYFRYD (SEQ ID NO: 96) EGGGAWGAGAVSEKDAP KELLQMLEKQ | H4 | 0.1% BSA/PBS |
| rcSso7d.H4.4 (P4-12, C3) | 87 | MATVKFTYQGEEKQVDIS SKNSDDAEK KIKSVKRNGQSIDFDYDE (SEQ ID NO: 97) GGGAAGEGKVSEKDAPK ELLQMLEKQ | H4 | 0.1% BSA/PBS |
| rcSso7d.H4.5 (P4-17, C5) | 88 | MATVKFTYQGEEKQVDIS GYHSWRWWI KIKGVYRHGQSIWFRYD (SEQ ID NO: 98) EGGGAWGWGIVSEKDAP KELLQMLEKQ | H4 | 0.1% BSA/PBS |
| rcSso7d.H4.6 (P5-4, C6) | 89 | MATVKFTYQGEEKQVDIS SHYKYDIKH KIKSVHRYGQKIYFDYDE (SEQ ID NO: 99) GGGAIGKGHVSEKDAPK ELLQMLEKQ | H4 | 0.1% BSA/PBS |
| rcSso7d.H4.7 (P5-5, C7) | 90 | MATVKFTYQGEEKQVDIS YWHHARHWS KIKYVWRHGQHIAFRYD (SEQ ID NO: EGGGAHGWGSVSEKDAP 100) KELLQMLEKQ | H4 | 0.1% BSA/PBS |
| rcSso7d.H4.8 (P5-8, C8) | 91 | MATVKFTYQGEEKQVDIS DWHHISYAH KIKDVWRHGQHIIFSYDE (SEQ ID NO: GGGAYGAGHVSEKDAPK 101) ELLQMLEKQ | H4 | 0.1% BSA/PBS |
| rcSso7d.H4.9 (P5-10, C9) | 92 | MATVKFTYQGEEKQVDIS YKIYSNHHI KIKYVKRIGQYISFNYDE (SEQ ID NO: GGGAHGHGIVSEKDAPK 102) ELLQMLEKQ | H4 | 0.1% BSA/PBS |
| rcSso7d.H4.2/H4/ BA-MBP- rcSso7d.H4.1 | | | H4 | 0.1% BSA/PBS, heat, urine (1 week) |

H6 Binders

Antigen name: H6

Protein ID: Rv 1729c

Gene ID: MT1770

Figure 57:
FIG. 57 shows a 12% SDS-PAGE gel showing purified protein preparation of H6BA.

H6BA (see FIG. 57)

(SEQ ID NO: 103)

*MGSSHHHHHHSSGLVRGSH*MVARTDDDNWDLTSSVGVTATIVAVGRALAT

KDPRGLINDPFAEPLVRAVGLDLFTKMMDGELDMSTIADVSPAVAQAMVY

GNAVRTKYFDDYLLNATAGGIRQVAILASGLDSRAYRLPWPTRTVVYEID

QPKVMEFKTTTLADLGAEPSAIRRAVPIDLRADWPTALQAAGFDSAAPTA

WLAEGLLIYLKPQTQDRLFDNITALSAPGSMVATEFVTGIADFSAERART

ISNPFRCHGVDVDLASLVYTGPRNHVLDYLAAKGWQPEGVSLAELFRRSG

LDVRAADDDTIFISGCLTDHSSISPPTAAGWREF<u>(GSMAGGLNDIFEAQK

IEWHE)</u>*

The italicized amino acids in the above sequence refer to a Hexahistidine tag and the underlined amino acids in parentheseses refer to a (Biotin acceptor sequence).

Figure 58A:
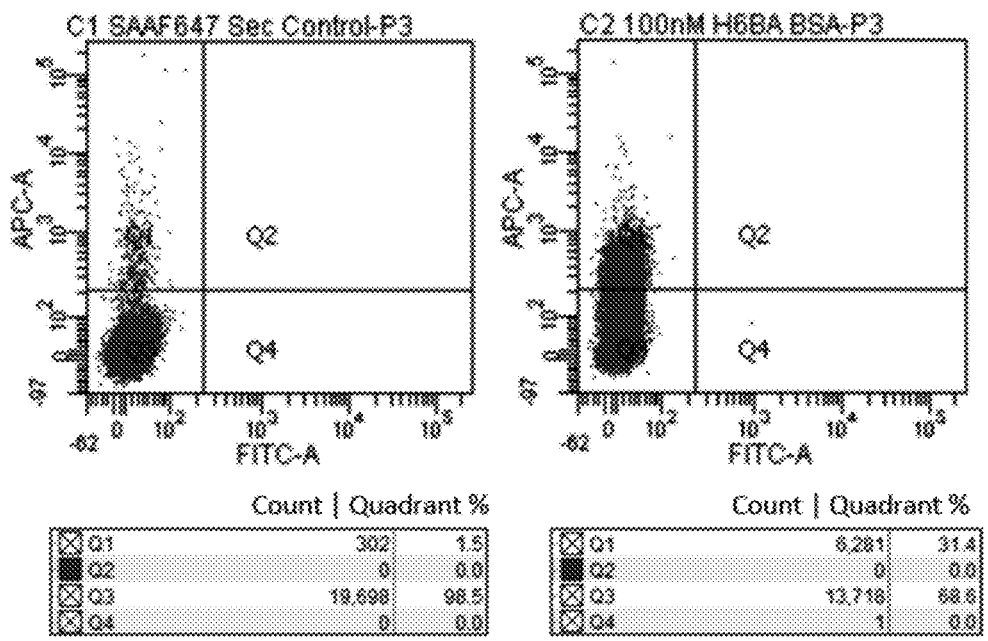
Figure 59A:
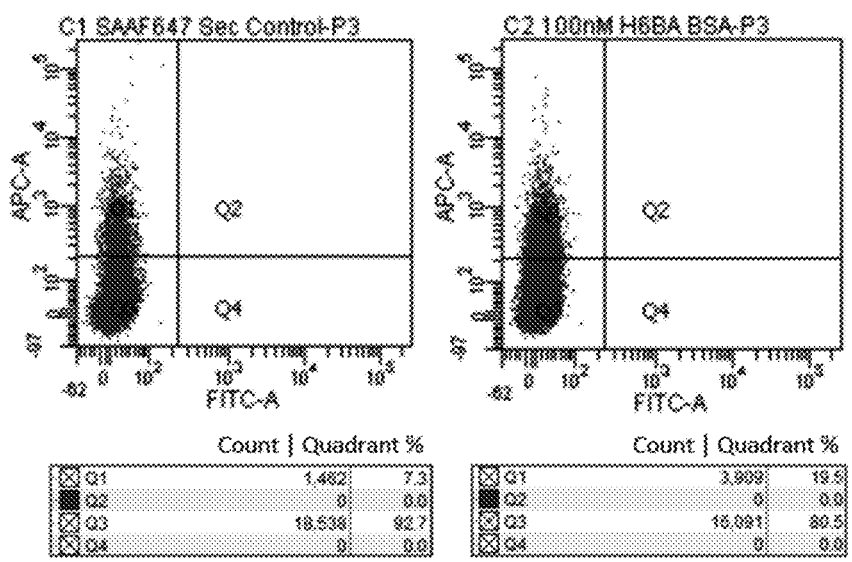

The amino acid sequence of selected rcSso7d binding variants that bind to H6 can be seen below (Table 11). Flow cytometry data indicating the specific binding activity of each particular rcSso7d clone for the selected rcSso7d binding variants that bind to H6 is shown in the FACS plots in FIGS. 58-60. For example, flow cytometry data indicating the specific binding activity of rcSso7d.H6BA.1 is shown in the FACS plots in FIGS. 58A-58B. Flow cytometry data indicating the specific binding activity of rcSso7d.H6BA.2 is shown in the FACS plots in FIGS. 59A-59B. Flow cytometry data indicating the specific binding activity of rcSso7d.H6BA.3 is shown in the FACS plots in FIGS. 60A-60B.

TABLE 11

Primary protein structure of selected rcSso7d binding variants that bind to H6.

| Protein Species | SEQ ID NO | Primary Structure (N → C) (Variable AA residues) | Shorthand Tag | Binding targets | Validated conditions |
|---|---|---|---|---|---|
| rcSso7d.H6BA.1 (6.PF2.2) | 104 | MATVKFTYQGEEKQVDISKIKWVYRYGQYIIFGYDEGGGAKGNGYVSEKDAPKELLQMLEKQ | WYYYIGKNY (SEQ ID NO: 107) | H6BA | 0.1% BSA/PBS, heat, urine |
| rcSso7d.H6BA.2 (6.PF2.4) | 105 | MATVKFTYQGEEKQVDISKIKWVYRWGQYIIFAYDEGGGAAGKGSVSEKDAPKELLQMLEKQ | WYWYIAAKS (SEQ ID NO: 108) | H6BA | 0.1% BSA/PBS |
| rcSso7d.H6BA.3 (6.PF2.5) | 106 | MATVKFTYQGEEKQVDISKIKRVIRAGQSIIFSYDEGGGAIGHGWVSEKDAPKELLQMLEKQ | RIASISIHW (SEQ ID NO: 109) | H6BA | 0.1% BSA/PBS, heat, urine |

H7 Binders
Antigen name: H7
Protein ID: TBCG_03312
Gene ID: ZP_04927296.1

Figure 61:
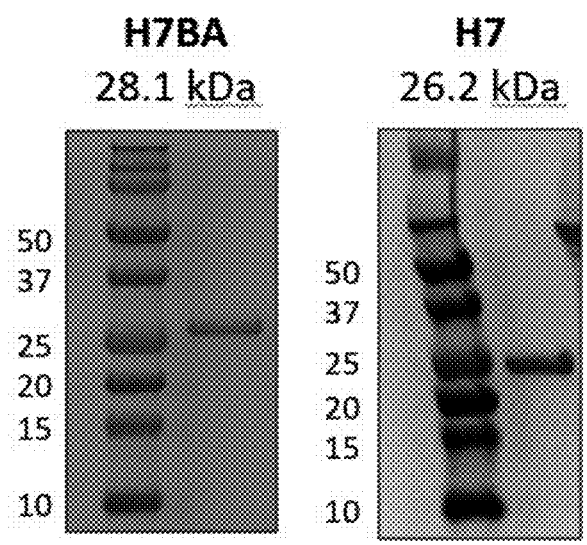
FIG. 61 shows a 12% SDS-PAGE gel showing purified protein preparation of H7BA and H7.

H7BA (see FIG. 61)

(SEQ ID NO: 110)
*MGSSHHHHHHSSGLVPRGS*HMTLNLSVDEVLTTTRSVRKRLDFDKPVPRD
VLMECLELALQAPTGSNSQGWQWVFVEDAAKKKAIADVYLANARGYLSGP
APEYPDGDTRGERMGRVRDSATYLAEHMHRAPVLLIPCLKGREDESAVGG
VSFWASLFPAVWSFCLALRSRGLGSCWTTLHLLDNGEHKVADVLGIPYDE
YSQGGLLPIAYTQGIDFRPAKRLPAESVTHWNGW(GSMAGGLNDIFEAQK
IEWHE)*

The italicized amino acids in the above sequence refer to a Hexahistidine tag and the underlined amino acids in parentheseses refer to a (Biotin acceptor sequence).

The amino acid sequence of selected rcSso7d binding variants that bind to H7 can be seen below (Table 12). Flow cytometry data indicating the specific binding activity of rcSso7d.H7.1 is shown in the FACS plots in FIG. 62.

TABLE 12

Primary protein structure of selected rcSso7d binding variants that bind to H7.

| Protein Species | SEQ ID NO | Primary Structure (N → C) (Variable AA residues) | Shorthand Tag | Binding targets | Validated conditions |
|---|---|---|---|---|---|
| rcSso7d.H7.1 (7.B10) | 111 | MATVKFTYQGEEKQVDISKIKYVYRWGQRIWFRYDEGGGAIGRGRVSEKDAPKELLQMLEKQ | YYWRWRIRR (SEQ ID NO: 112) (close variant: YYWRWRSYR (SEQ ID NO: 113) | H7, H7BA | 0.1% BSA/PBS, heat, urine |

Figure 63:
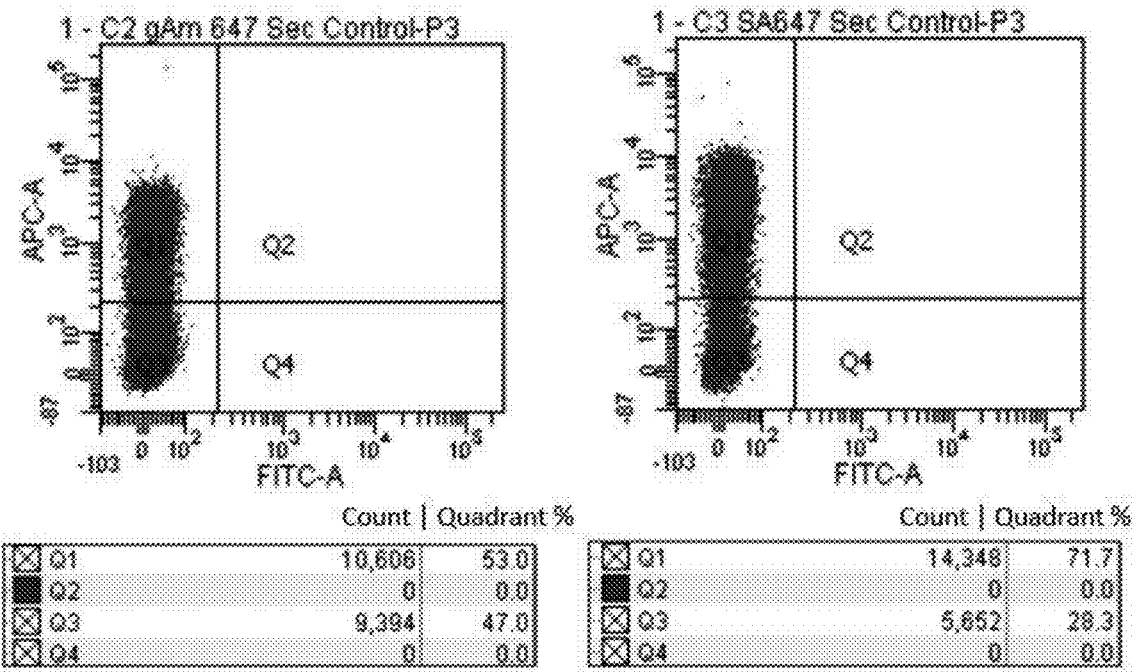
FIG. 63 shows flow cytometry data indicating the specific binding activity of AF647 binder rcSso7d.AF647.1.
Figure 64:
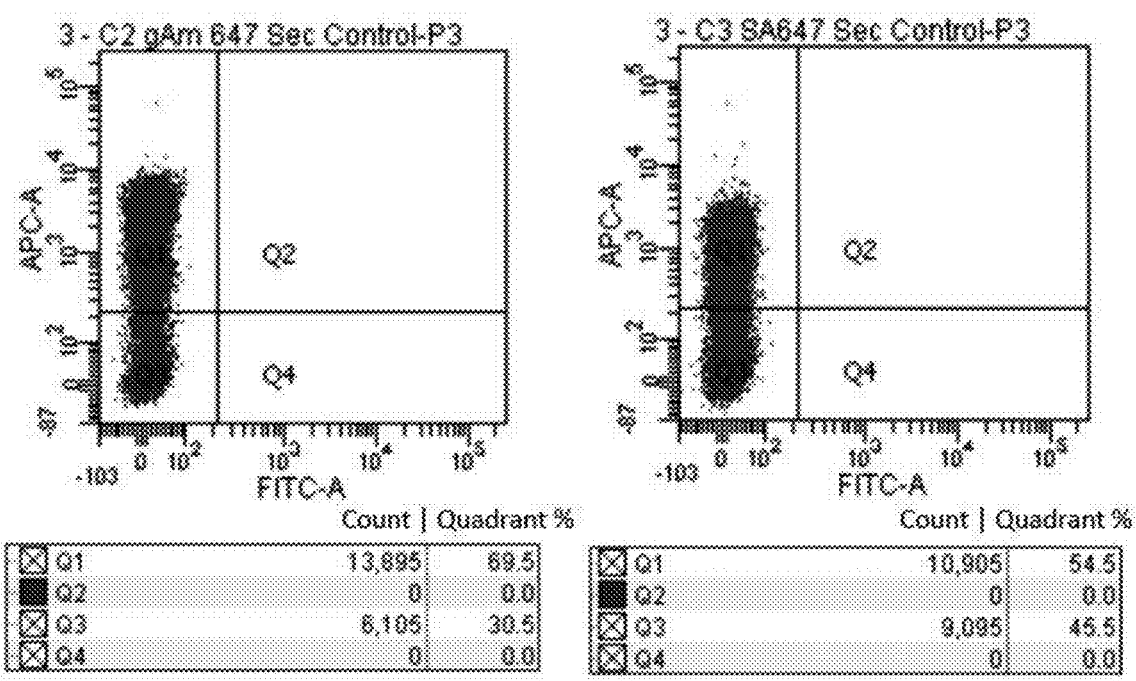
FIG. 64 shows flow cytometry data indicating the specific binding activity of AF647 binder rcSso7d.AF647.2.

ALEXA FLUOR® 647 (AF647) Binders
Antigen name: ALEXA FLUOR® 647
Classification: Small molecule The amino acid sequence of selected rcSso7d binding variants that bind to ALEXA FLUOR@ 647 (AF647) can be seen below (Table 13). FIGS. 63 and 64 detail binding variants that have been found to bind to two distinct reagents which have been labeled with the ALEXA FLUOR® 647 fluorophore (a goat anti-mouse antibody and streptavidin). Flow cytometry data indicating the specific binding activity of rcSso7d.AF647.1 is shown in the FACS plots in FIG. 63. Flow cytometry data indicating the specific binding activity of rcSso7d.AF647.2 is shown in the FACS plots in FIG. 64.

TABLE 13

Primary protein structure of selected rcSso7d binding variants that bind to Alexa Fluor 647 (AF647).

| Protein Species | SEQ ID NO | Primary Structure (N → C) (Variable AA residues) | Shorthand Tag | Binding targets | Validated conditions |
|---|---|---|---|---|---|
| rcSso7d.AF647.1 (6.PF2.1) | 114 | MATVKFTYQGEEKQVDISKIKWVIR YGQKIAFGYDEGGGAKGAGAVSEK DAPKELLQMLEKQ | WIYKAGKAA (SEQ ID NO: 116) | Alexa Fluor 647 | 0.1% BSA/PBS |
| rcSso7d.AF647.2 (6.PF2.3) | 115 | MATVKFTYQGEEKQVDISKIKKVW RYGQWIYFIYDEGGGAKGRGWVS EKDAPKELLQMLEKQ | KWYWYIKRW (SEQ ID NO: 117) | Alexa Fluor 647 | 0.1% BSA/PBS |

The binder performance of selected rcSso7d binding variants is summarized below in Table 14.

TABLE 14

TB Antigen Binder Performance

| Clone | Secondary control signal | Baseline binding | Geometric MFI | Antigen concentration (nM) | Urine-based binding (overnight) | Geometric MFI | Antigen concentration (nM) |
|---|---|---|---|---|---|---|---|
| H1BA.1 | 6% | 77.60% | | 100 | N/A | | N/A |
| H1BA.2 | N/A | 62.60% | 267 | 100 | 0.10% | 3.95 | 100 |
| H1BA.3 | 0.40% | 74.10% | 1396 | 100 | 8.10% | 48.1 | 100 |
| H1BA.4 | 0% | 31.40% | | 100 | N/A | | N/A |
| H1BA.5 | 0.90% | 32.50% | | 100 | N/A | | N/A |
| H1BA.6 | 0.50% | 70.40% | 1920 | 100 | 1.30% | 40.1 | 100 |
| H2BA.1 | 3.20% | 55.10% | 474 | 100 | 8.20% | 73.2 | 100 |
| H4.1 | 0% | 69.30% | | 100 | 68.20% | | 100 |
| H4.2 | 0% | 60.40% | | 100 | 63.60% | | 100 |
| H4.3 | 0% | 25.80% | | 100 | N/A | | N/A |
| H4.4 | 0% | 7.80% | | 100 | N/A | | N/A |
| H4.5 | 0.60% | 30.80% | | 100 | N/A | | N/A |
| H4.6 | 0% | 15.30% | | 100 | N/A | | N/A |
| H4.7 | 0% | 13.40% | | 100 | N/A | | N/A |
| H4.8 | 0% | 3.50% | | 100 | N/A | | N/A |
| H4.9 | 0% | 19.60% | | 100 | N/A | | N/A |
| H4.1/H4.2 Full Sandwich | 0.60% | 70.90% | 1108 | 100 | 69% | 828 | 100 |
| H4.1/H4.2 Full Sandwich (1 w) | 2.30% | 62.20% | 486 | 100 | 57.40% | 366 | 100 |
| H6BA.1 | 1.50% | 31.40% | | 100 | 2% | | 100 |
| H6BA.2 | 7.30% | 19.50% | | 100 | 6.60% | | 100 |
| H6BA.3 | 1.70% | 58.50% | | 100 | 13.50% | | 100 |
| H7.1 | 1.80% | 70% | | 100 | 68.40% | | 100 |

Cloning and Purification of rcSso7d.H4.5-CBD and rcSso7d.H4.9-CBD

Several of the H4-binding rcSso7d variants have been cloned into the rcSso7d-CBD construct. These include the H4.2 clone, discussed herein above, as well as, H4.5, and H4.9. rcSso7d.H4.5 and rcSso7d.H4.9 were cloned into CBD constructs rcSso7d.H4.5-CBD and rcSso7d.H4.9-CBD, respectively, and purified. FIGS. 65A-65B illustrate the plasmid maps for rcSso7d.H4.5-CBD and rcSso7d.H4.9-CBD, as well as the purification chromatograms associated with these binding species.

Immunoassay Performance of rcSso7d.H4.5-CBD and rcSso7d.H4.9-CBD

Figure 66A:
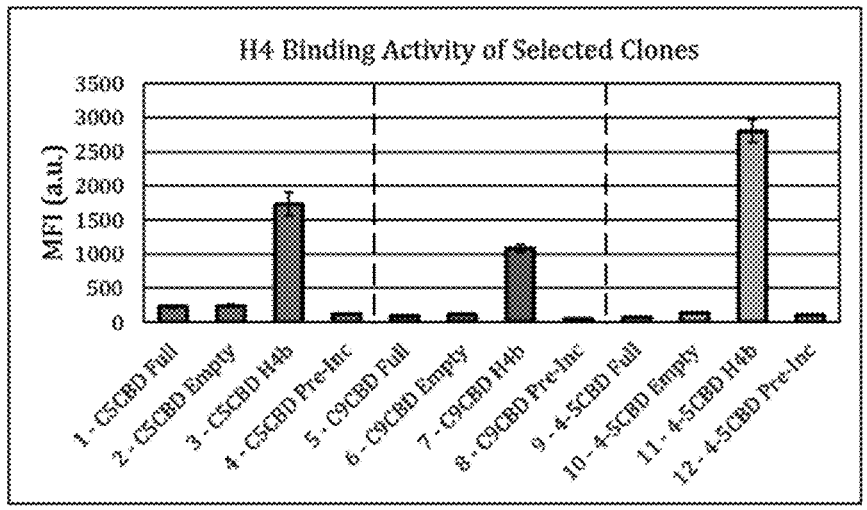
FIGS. 66A-66D show immunoassay performance of rcSso7d.H4.5-CBD, rcSso7d.H4.9-CBD, and rcSso7d.H4.2-CBD.
Figure 66B:
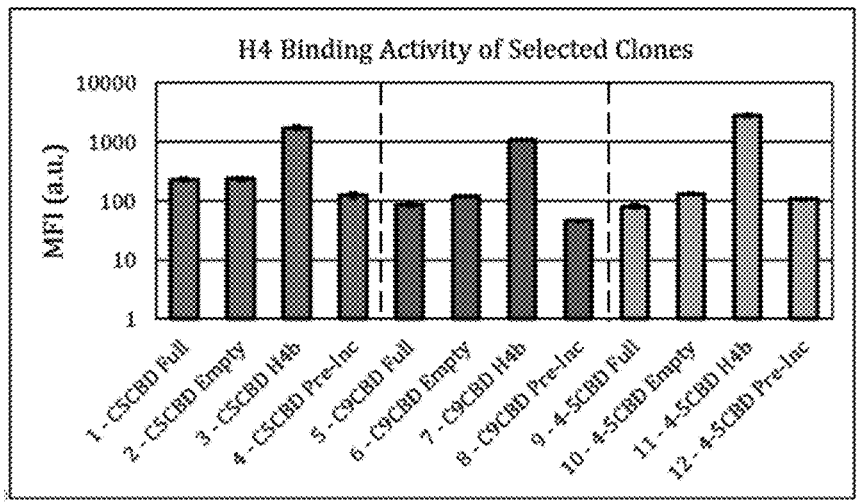
Figure 66C:
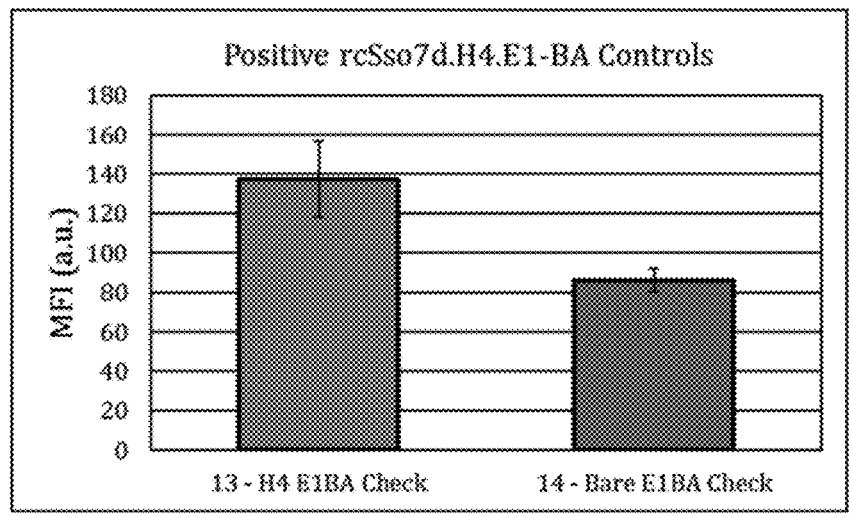
Figure 66D:
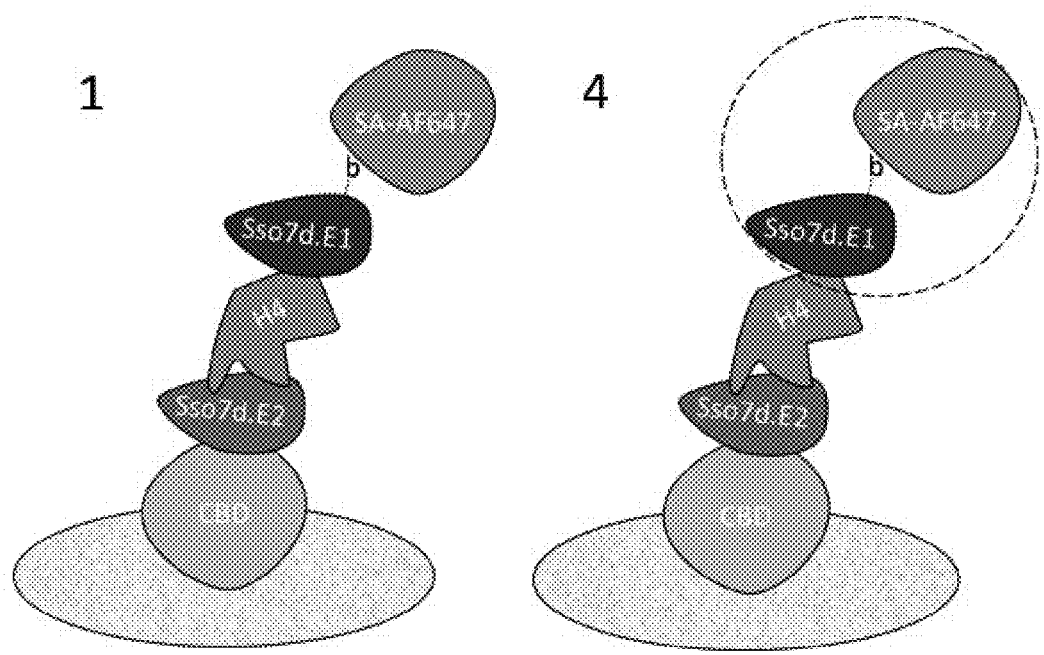

Binding activity of purified variants rcSso7d.H4.5-CBD, rcSso7d.H4.9-CBD, and rcSso7d.H4.2-CBD, is shown in FIGS. 66A-66D and are denoted as C5-CBD, C9-CBD, and 4-5CBD, respectively. FIG. 66A indicates the performance of each of these species in a full sandwich (with the H4.1-BA construct), an empty sandwich, a half sandwich with a biotinylated H4 variant, and with the H4.1-BA and H4 pre-incubated prior to being brought into contact with the rcSso7d.H4-CBD variant. In the full sandwich format, 180 picomoles of the rcSso7d-CBD fusion is immobilized on a cellulose test spot. Following two 20 µL wash steps in phosphate-buffered saline, 10 µL of soluble H4 at 256 nM is contacted with the spot. Following another wash step, the surface is contacted with 10 µL of soluble H4.E1-BA at 256 nM, and after an additional wash step the surface is contacted with 10 µL of streptavidin ALEXA FLUOR® 647 at 256 nM. In the case of the empty sandwich, all steps are identical except instead of contacting the surface with H4, the surface is incubated in PBS for an equivalent period of time. The half-sandwich experiment uses a chemically biotinylated form of H4, which is brought into contact with the rcSso7d-CBD-coated surface. Following a wash step, the surface is contacted with streptavidin ALEXA FLUOR® 647. The pre-incubation samples are identical to the full sandwich, except the H4.E1-BA and streptavidin ALEXA FLUOR@ 647 are pre-incubated together in the bulk solution, at a 1:1 molar ratio.

The half-sandwich data (the large bars in FIGS. 66A and 66B) indicates that the selected variants retain their function in the CBD format. The full sandwiches yield no signal, due to the limited accessibility of the directly attached biotin species, demonstrated in FIG. 66C.

Demonstration of the Principle Using a Different CBD Variant: dCBD Data rcSso7d.SA-dCBD
(SEQ ID NO: 118)
MGSSHHHHHHSSGLVPRGSHMATVKFTYQGEEKQVDISKIKIVARDGQYI

DFKYDEGGGAYGYGWVSEKDAPKELLQMLEKQGSAGPGANPPGTTTTSRP

ATTTGSSPGPQACSSVWGQCGGQNWSGPTCCASGSTCVYSNDYYSQCLPG

ANPPGTTTTSRPATTTGSSPGPTQSHYGQCGGIGYSGPTVCASGTTCQVL

Figure 67:
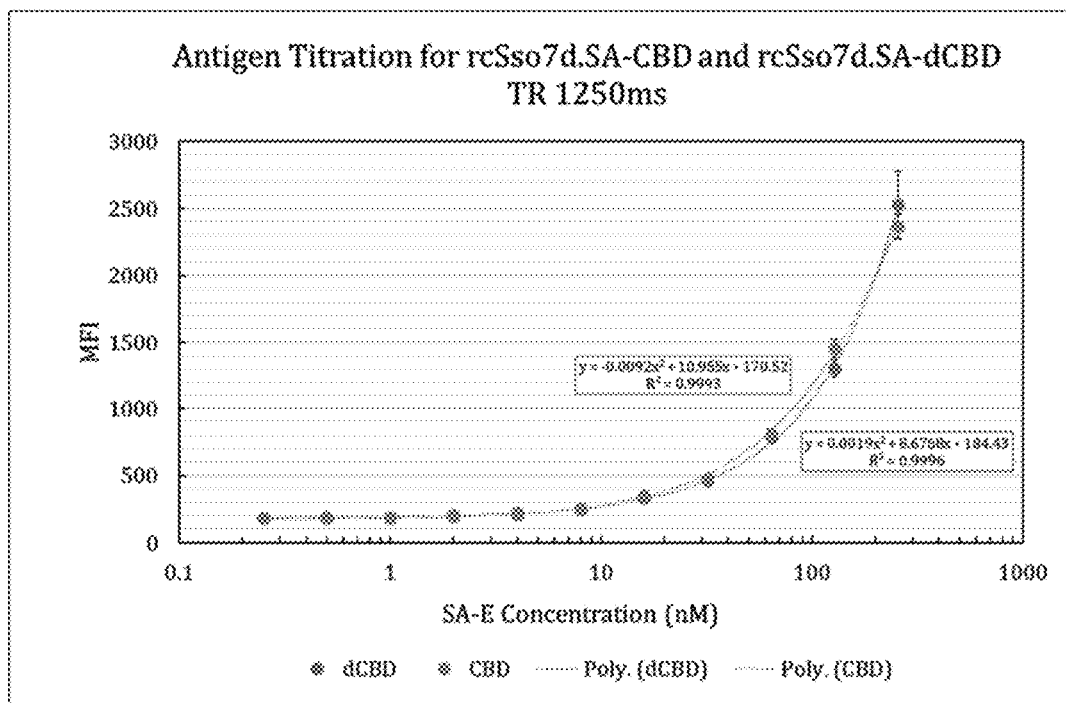
FIG. 67 shows the results of antigen titration for rcSso7d.SA-CBD and rcSso7d.SA-dCBD and demonstrates the principle of using a different CBD variant (dCBD).

NPYYSQCL* dCBD is a member of the Carbohydrate-binding module family 1 (CBM-1). Similar performance is observed with this dCBD variant as with the CBM-3 variant (CBD) previously reported (see FIG. 67). There is a 30 second primary incubation time. 6 µL of 30 pM applied protein and rapid depletion of soluble analyte from solution. FIG. 67 demonstrates proof that the approach of using an rcSso7d-CBD fusion construct is relevant for other members of the carbohydrate-binding module family. Here, the sequence for the rcSso7d.SA-dCBD construct has been included, and a representative titration of a fluorescent streptavidin-eosin reagent has been prepared for two distinct sample sets, produced using rcSso7d.SA-CBD and rcSso7d.SA-dCBD. These data sets indicate similar performance between the Type 3 CBD and the Type 1 dCBD species.

Example 13. Multimerized rcSso7d-CBD Variants

Multimerized (rcSso7d.SA)$_n$-CBD for Further Enhancement of Surface Abundance

Figure 68A:
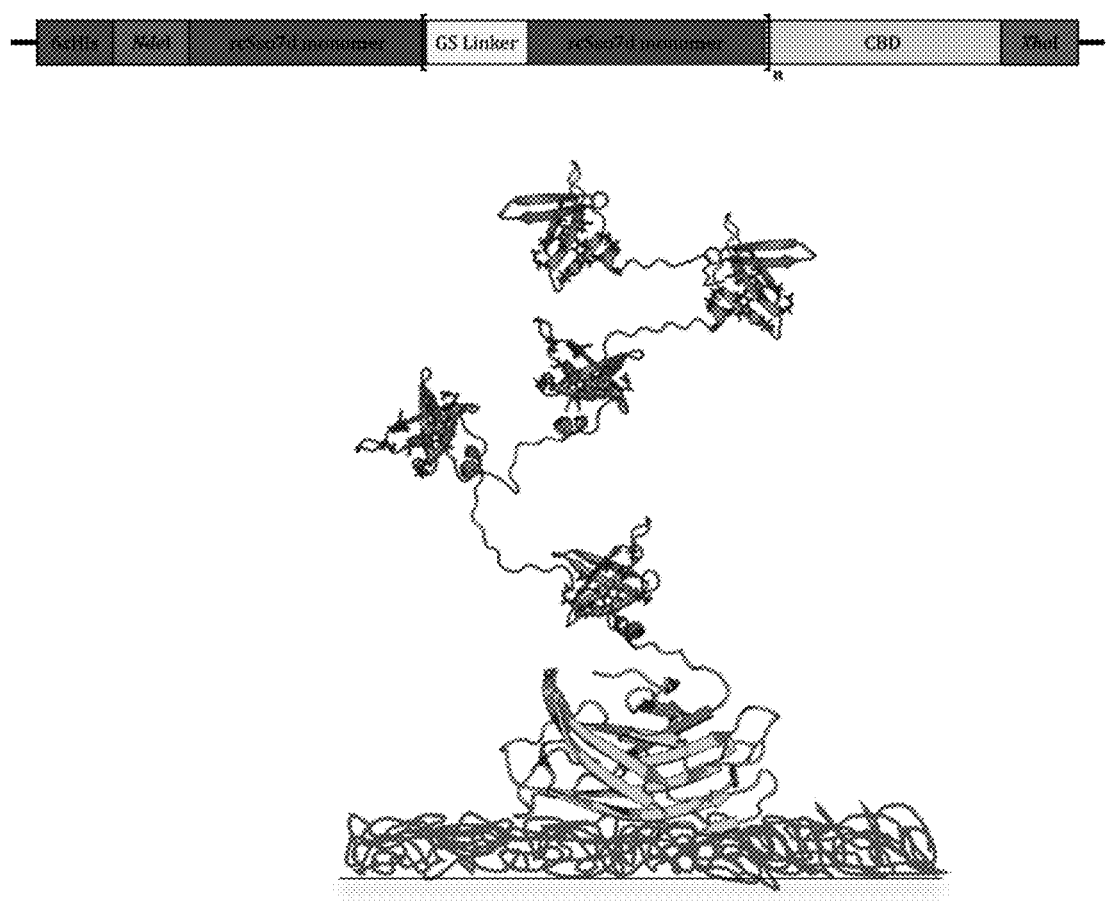
FIGS. 68A-68C show multimerized (rcSso7d.SA)$_n$-CBD for further enhancement of surface abundance.

Multimerized rcSso7d-CBD variants 1x-rcSso7d.SA-CBD, 2x-rcSso7d.SA-CBD, and 3x-rcSso7d.SA-CBD, were created, with one, two, or three independent rcSso7d.SA binding modules genetically fused together and integrated into the CBD binding construct (see FIG. 68A). An approach for producing multimerized species has been documented, for instance, in Paloni, et al. *Biomacromolecules* (2018) 19(9):3814-24). The sequences for these variants are shown below. A general schematic for this fusion construct is illustrated in FIG. 68A, indicating that a (G$_4$S)$_3$ linker sequence (SEQ ID NO: 125) is included between each rcSso7d binding variant, as well as between the final rcSso7d module and the CBD fusion partner.

1x-rcSso7d.SA-CBD
(SEQ ID NO: 119)
MGSSHHHHHHSSGLVPRGSHMATVKFTYQGEEKQVDISKIKIVARDGQYI

DFKYDEGGGAYGYGWVSEKDAPKELLQMLEKQGSGGGSGGGSGGGGSP

VSGNLKVEFYNSNPSDTTNSINPQFKVTNTGSSAIDLSKLTLRYYYTVDG

QKDQTFWCDHAAIIGSNGSYNGITSNVKGTFVKMSSSTNNADTYLEISFT

GGTLEPGAHVQIQGRFAKNDWSNYTQSNDYSFKSASQFVEWDQVTAYLNG

VLVWGKEP*

2x-rcSso7d.SA-CBD
(SEQ ID NO: 120)
MGSSHHHHHHSSGLVPRGSHMATVKFTYQGEEKQVDISKIKIVARDGQYI

DFKYDEGGGAYGYGWVSEKDAPKELLQMLEKQGGGGSGGGGSMATVKFTY

QGEEKQVDISKIKIVARDGQYIDFKYDEGGGAYGYGWVSEKDAPKELLQM

LEKQGSGGGGSGGGGSGGGGSPVSGNLKVEFYNSNPSDTTNSINPQFKVT

NTGSSAIDLSKLTLRYYYTVDGQKDQTFWCDHAAIIGSNGSYNGITSNVK

GTFVKMSSSTNNADTYLEISFTGGTLEPGAHVQIQGRFAKNDWSNYTQSN

DYSFKSASQFVEWDQVTAYLNGVLVWGKEP*

3x-rcSso7d.SA-CBD
(SEQ ID NO: 121)
MGSSHHHHHHSSGLVPRGSHMATVKFTYQGEEKQVDISKIKIVARDGQYI

DFKYDEGGGAYGYGWVSEKDAPKELLQMLEKQGGGGSGGGGSMATVKFTY

QGEEKQVDISKIKIVARDGQYIDFKYDEGGGAYGYGWVSEKDAPKELLQM

LEKQGGGGSGGGGSMATVKFTYQGEEKQVDISKIKIVARDGQYIDFKYDE

GGGAYGYGWVSEKDAPKELLQMLEKQGSGGGGSGGGGSGGGGSPVSGNLK

VEFYNSNPSDTTNSINPQFKVTNTGSSAIDLSKLTLRYYYTVDGQKDQTF

WCDHAAIIGSNGSYNGITSNVKGTFVKMSSSTNNADTYLEISFTGGTLEP

GAHVQIQGRFAKNDWSNYTQSNDYSFKSASQFVEWDQVTAYLNGVLVWGK

EP*

Figure 68B:
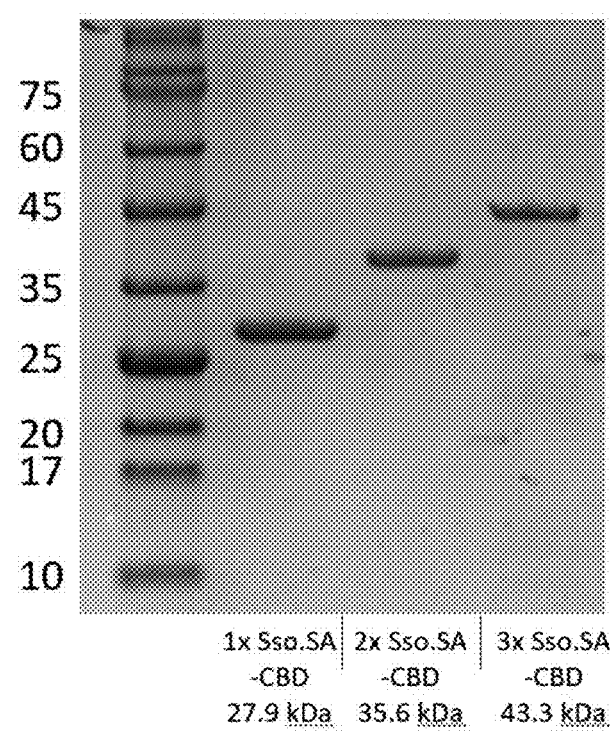
Figure 68C:
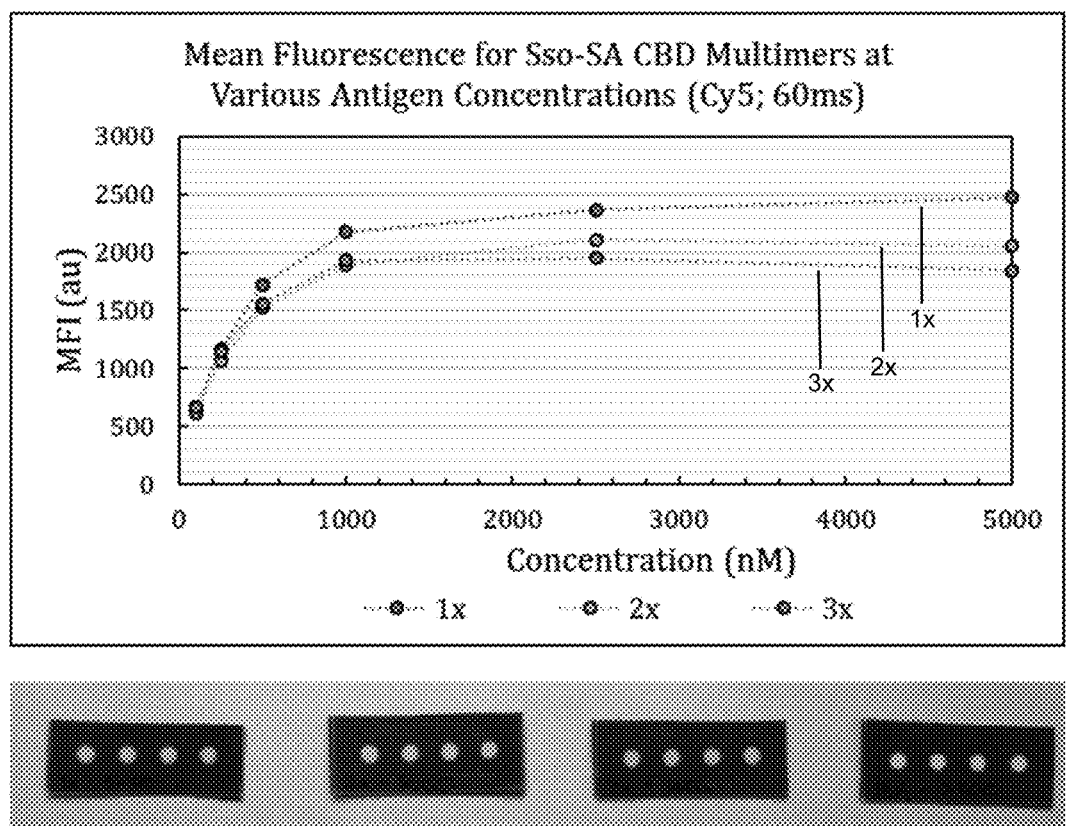

A 12% SDS-PAGE gel shown in FIG. 68B demonstrates the purity of the 1x-, 2x-, and 3x-CBD variants following purification with immobilized metal affinity chromatography. The performance of these immobilized rcSso7d-CBD variants in antigen-capture assays is indicated in FIG. 68C, using streptavidin ALEXA FLUOR® 647 as the analyte. Notably, the signal appears to drop off for the higher rcSso7d-CBD multimers at high analyte concentrations, which runs counter to the expected trend—as the surface-immobilized 1x-rcSso7d-CBD species is saturated, it would be expected that there would be additional free rcSso7d modules for the 2x and 3x variants, and that the binding signal would continue to increase for those constructs. Upon visual inspection of the 5 µM samples (depicted beneath the graph), it appears that the 2x and 3x are both darker than the 1x variant, suggesting that additional analyte is in fact being captured for these samples. This suggests that the decrease in the mean fluorescence signal may actually be due to fluorescent quenching, as the higher-order binding constructs sequester a greater molar quantity of the fluorescent analyte in close proximity. This indicates that the use of multimeric (rcSso7d)x-CBD constructs may indeed serve to more efficiently capture analyte, and may yield significant benefits in the large-volume processing format, where the timescale for analyte capture must match the short timescale during which the analyte is in contact with the test zone.

Immobilization of rcSso7d.SA-CBD on Cellulose Powder for Combing Through Large Volumes It was demonstrated that the rcSso7d.SA-CBD protein can be immobilized on cellulose powder, which can be mixed into a large volume sample for the efficient capture of a soluble analyte. 180 picomoles of rcSso7d.SA-CBD was applied to a circular test zone (see the positive control in FIG. 69) or to an equivalent mass of cellulose powder (represented in the experimental sample). Two 10 mL aliquots of a 2 nM solution of streptavidin ALEXA FLUOR@ 647 were prepared. One was forced across the paper test zone by pressure-driven flow, using a syringe pump, and was circulated back and forth across the test zone for 40 minutes at a volumetric flowrate of 5 mL/min. The rcSso7d.SA-CBD-coated cellulose powder was spiked into the other aliquot, which was incubated with mixing for an equivalent time period. Following the analyte incubation step, this powder was retained by flowing the analyte solution across a paper test zone, concentrating the powder and captured analyte in a relatively small region for detection and quantification. The analyte signal seems more disperse, but the average intensity is roughly equivalent, suggesting that a more robust method for concentrating the powder may allow the sensitive detection of a chemical species captured by the cellulose powder reagent.

Example 14. Large-Volume Processing Data

The high-abundance immobilization enabled by rcSso7d-CBD constructs is uniquely enabling for the enhancement of analytical sensitivity via large-volume processing.

Figure 70:
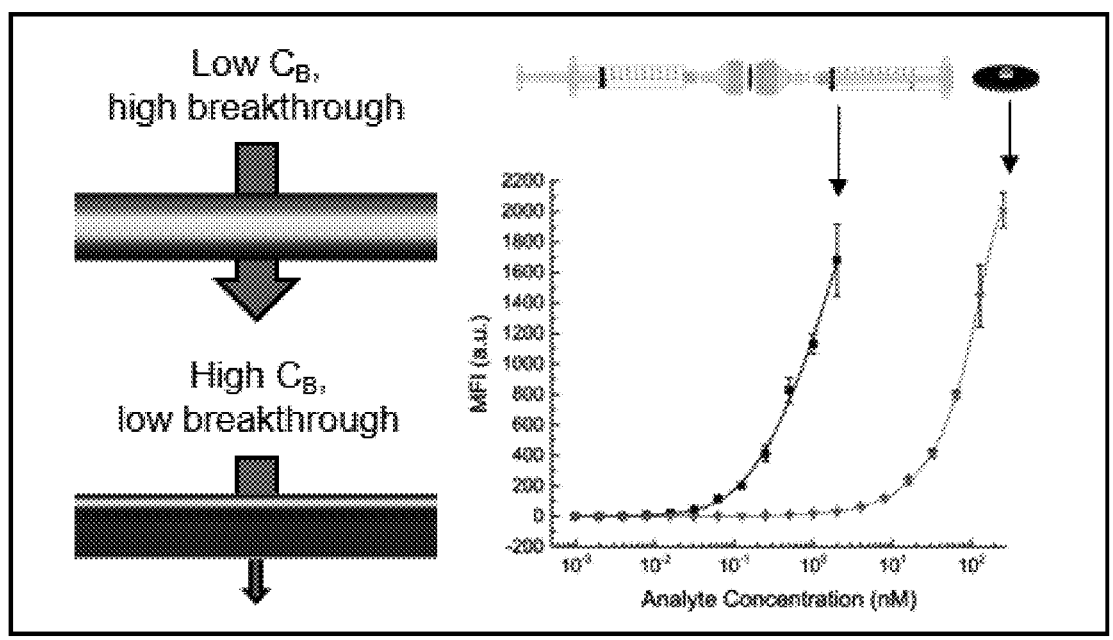
FIG. 70 is a schematic showing large-volume processing.

Large-volume processing data was previously disclosed, (see Miller et al., *Anal Chem* (2018) 90(15):9472-9) and demonstrates the enabling nature of the concentration domain achieved by using the CBD fusion species. The higher immobilized concentration of the binder enables capture of dilute analyte from a flowing system within the brief period that the analyte is in contact with the test zone. This permits the processing of large sample volumes within a clinically relevant timescale, and the capture of greater quantities of analyte even at lower concentrations, increasing analytical sensitivity (see FIG. 70).

Figure 71:
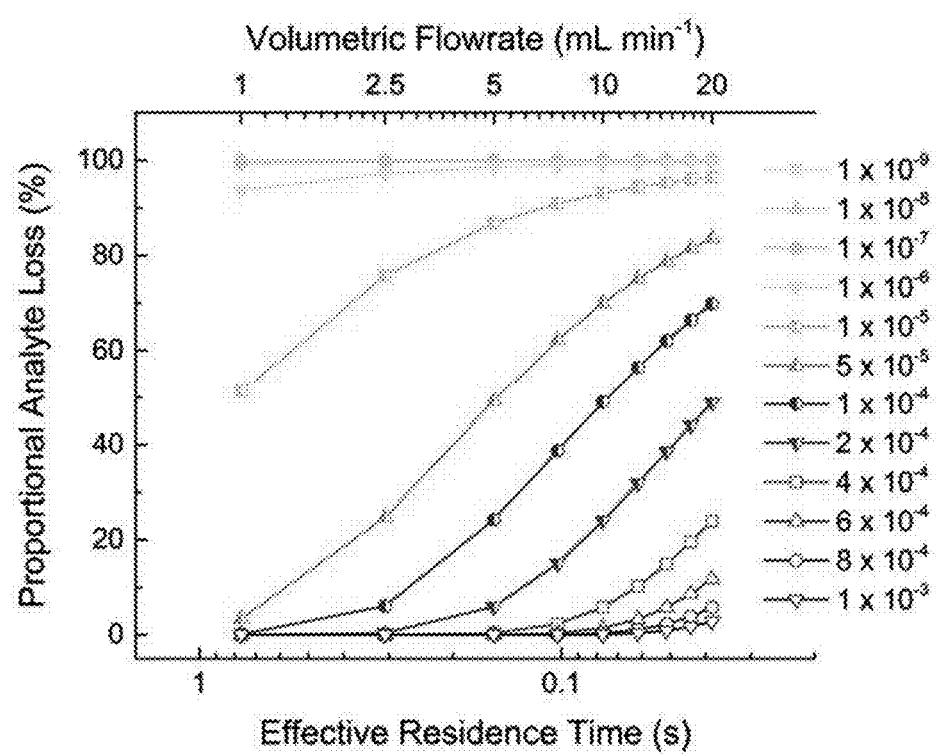
FIG. 71 shows finite-element modeling data demonstrating proportional analyte breakthrough at varying volumetric flow rates and with varying concentrations of binding reagents. These curves depict how analyte capture is influenced by the relationship between the kinetics of the binding reaction and the rates of transport processes within cellulose. Each curve represents a single 10 mL recirculation at a different local binder concentration (mol L-1; denoted in the legend). The inlet analyte concentration is 1 nM.

Finite-element modeling data demonstrating proportional analyte breakthrough at varying volumetric flow rates and with varying concentrations of binding reagents is shown in FIG. 71. These curves depict how analyte capture is influenced by the relationship between the kinetics of the binding reaction and the rates of transport processes within cellulose. Each curve represents a single 10 mL recirculation at a different local binder concentration (mol $L^{-1}$; denoted in the legend). The inlet analyte concentration is 1 nM.

Figure 72:
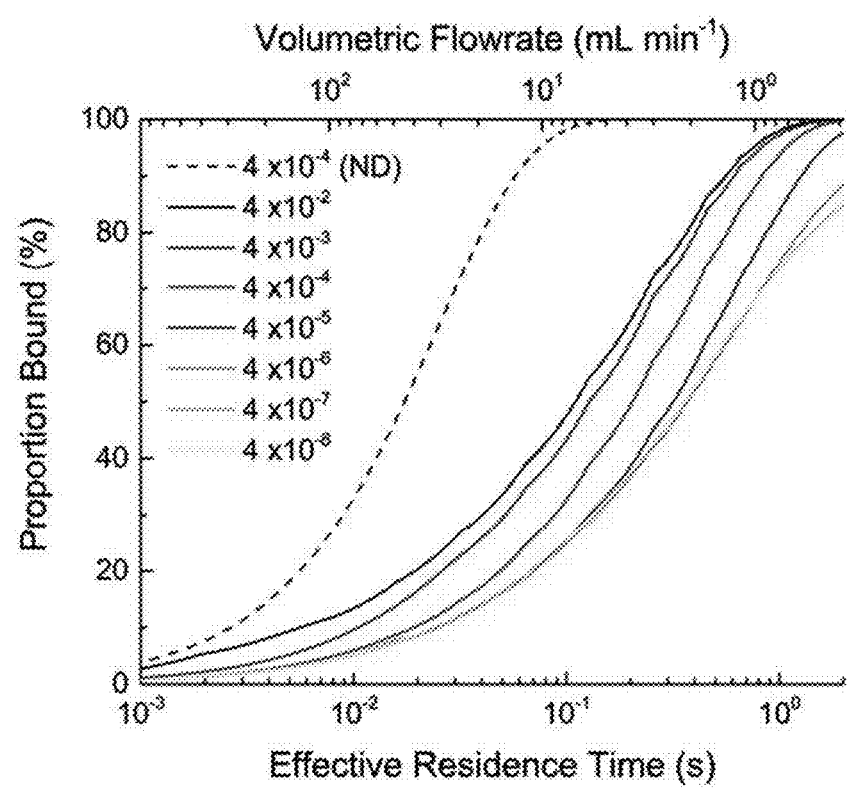
FIG. 72 shows proportional binding curves predicted by the finite-element model in the diffusive limit. In this scenario, the rate of diffusion to the cellulose fibers is the rate-limiting process, as the immobilized binder is localized to the pore walls and the rate of analyte capture is assumed to be rapid relative to diffusion. The dashed curve (ND) represents the binding performance predicted by the non-diffusive, homogeneous distribution model at standard rcSso7d-CBD concentration (400 µM). Solid curves represent binding in the diffusion-limited case at varying local concentrations of the immobilized binder (mol $L^{-1}$). The leftmost diffusive curve (black) corresponding to a local surface concentration of 40 mM was used to simulate instantaneous capture; no appreciable increase in the binding proportion is seen for higher local concentrations.

Proportional binding curves predicted by the finite-element model in the diffusive limit are shown in FIG. 72. In this scenario, the rate of diffusion to the cellulose fibers is the rate-limiting process, as the immobilized binder is localized to the pore walls and the rate of analyte capture is assumed to be rapid relative to diffusion. The dashed curve (ND) represents the binding performance predicted by the non-diffusive, homogeneous distribution model at standard rcSso7d-CBD concentration (400 µM). Solid curves represent binding in the diffusion-limited case at varying local concentrations of the immobilized binder (mol L-1). The leftmost diffusive curve (black) corresponding to a local surface concentration of 40 mM was used to simulate instantaneous capture; no appreciable increase in the binding proportion is seen for higher local concentrations.

Figure 73:
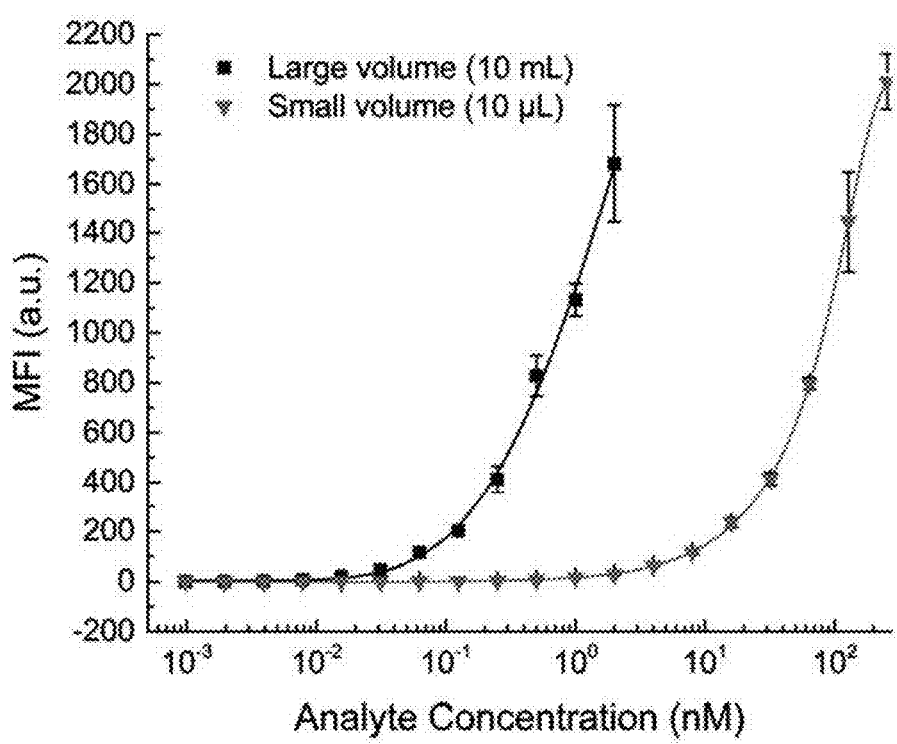
FIG. 73 shows sensitivity enhancement through large-volume processing. Mean fluorescence intensity (MFI) observed at varying analyte concentrations for large- (10 mL; 5 mL min-1; 20 recirculations) and small-volume (10 µL; 40 min) samples. Lines of best fit were generated using a five-point sigmoidal curve (Eq. S10). (Miller et al. *Anal Chem* (2018) 90(15):9472-9). Error bars represent the standard deviation of three (larg (Eq. S10) four (small-volume) independent replicates.

Sensitivity enhancement through large-volume processing is shown in FIG. 73. Mean fluorescence intensity (MFI) observed at varying analyte concentrations for large- (10 mL; 5 mL min-1; 20 recirculations) and small-volume (10 µL; 40 min) samples. Lines of best fit were generated using a five-point sigmoidal curve (eq S10). Error bars represent the standard deviation of three (large-volume) or four (small-volume) independent replicates.

A comparison between analyte titration curves for rcSso7d-CBD at varying local concentrations is shown in FIGS. 74A-74B. Mean fluorescence intensity (MFI) observed at varying analyte concentrations for large- (10 mL) and small-volume (10 µL) samples using test zones with local rcSso7d-CBD concentrations of 400 and 40 µM (see FIG. 74A). Data points corresponding to the 400 µM/10 µL samples directly overlap with those corresponding to the 40 µM/10 µL samples (FIG. 87). Fluorescence ratios comparing the corresponding large- and small-volume samples at local rcSso7d-CBD concentrations of 400 and 40 µM are shown in FIG. 74B. Large-volume samples consist of 10 mL of analyte solution (5 mL $min^{-1}$, 20 recirculations). Small-volume samples consisted of 10 µL incubated on the test zones for an equivalent 40 min period. Error bars represent the standard deviation of three (large-volume) or four (small-volume) independent replicates.

Assay performance for varying flow rates and total processing times is shown in FIGS. 75A-75D. Absolute mean fluorescence intensity (MFI) is shown in FIG. 75A, proportional MFI (relative to samples processed for the same period of time at 1 mL $min^{-1}$) is shown in FIG. 75B, and signal development efficiency (MFI $min^{-1}$) for varying single-pass residence times and total processing times is shown in FIG. 75C. Signal development as a function of the number of recirculations is depicted in FIG. 75D. Linear trend lines indicate the performance of samples produced using a common volumetric flow rate (denoted in the legend). Sample specifications: 10 mL and 1 nM SA-AF647. Error bars represent the standard deviation of three independent replicates.

Syringe-based assay format is depicted in FIG. 76. Paper samples were excised and secured in a 13 mm Swinnex filter holder. A 10-mL syringe was connected upstream and used to pre-fill the filter holder with the analyte solution. A Qosina Female-to-Female Luer-Lok connector was used to join this cassette to a second syringe downstream, and any remaining air is bled from the system. In all cases, the top of the test zone (the surface to which the rcSso7d.SA-CBD solution was applied) was oriented so as to be the first side contacted by the analyte solution.

Set-up of COMSOL proportional analyte capture model is depicted in FIGS. 77A-77D. The test zone was modeled as a two-dimensional reactor volume, throughout which the immobilized binder was homogeneously distributed. Depth=L=180 µm; width=2rtz=1.8 mm. Analyte concentration at the inlet (at left) was 1 nM. The binder concentration and volumetric flow rate for the sample sets were varied across the different subfigures: 1 µM, 1 mL min-1 (FIG. 77A), 1 µM, 20 mL min-1 (FIG. 77B), 400 µM, 1 mL min-1 (FIG. 77C), and 400 µM, 20 mL mini (FIG. 77D). Within each sub-figure, the rows of test snapshots correspond to the soluble analyte, free binder, and the occupied binder (from top to bottom). Test zone snapshots were captured every sixty seconds, at timepoints denoted along the top of each sub-figure. Legends at right denote the concentrations of the relevant species for the corresponding row of cross-sectional snapshots. In order to capture system dynamics, color-bars were scaled relative to the relevant species for each set of operating conditions, rather than representing a universal concentration scale.

Set-up of COMSOL diffusion model is shown in FIG. 78. An idealized circular pore (r=5.5 µm) was initialized with an analyte concentration of 1 nM. The surrounding matrix represents a binder-functionalized fibrous network, at an average binder concentration of 40 mM. Analyte diffusion and capture was allowed to proceed over the course of 2 seconds, to model diffusive capture over a range of different sample residence times. Each snapshot represents a different time-point, denoted above the pore image, and the color-bar represents the concentration of the soluble analyte.

Confirmation of fluid flow across the entire assay cross-sectional area is shown in FIG. 79. Insoluble cellulose powder (50 µm diameter) was added to the sample volume in order to track the fluid flow as the sample was recirculated across the test zone. Rather than focusing solely within the hydrophilic region, the powder distributes across the entire cross-sectional area, indicating that the hydrophobic region permits fluid flow once it becomes sufficiently wetted. Thus, the relevant flow volume is 12.81 µL, rather than that associated strictly with the binder-functionalized region (0.45 µL).

Proportional binder occupancy at varying concentrations and volumetric flow rates is shown in FIG. 80. Each line plot represents operation at a different local binder concentration (denoted in the legend). For all data sets, analyte was introduced at a concentration of 1 nM, and data was collected immediately following a single simulated 10-mL recirculation.

Correlation of flow rate, binder concentration, analyte capture, and Dal is shown in FIGS. 81A-81B. Standard curves correlating volumetric flow rate, binder concentration (mol L-1), and Damköhler number, as well as rates of proportional analyte capture predicted by the pseudo first-order rate model are shown in FIG. 81A. Predicted proportional binding curves for varying local concentrations of immobilized binder are shown in FIG. 81B.

Deviation between finite-element analysis and PFORC model is shown in FIGS. 82A-82B. A comparison of the finite element model of analyte binding in the non-diffusive limit (dashed lines) and the pseudo first-order rate constant model (solid lines) is shown in FIG. 82A. Absolute basis point deviation between the FEA model and PFORC model for all processing conditions is shown in FIG. 82B. The greatest deviation between the predictive models is observed in regions of dynamic signal change.

A Damköhler master curve is shown in FIG. 83. All dimensional binding curves generated via the pseudo first-order rate model collapse onto a single dimensionless binding curve describing system performance. This relation is valid for all cases in which the immobilized binder is in significant molar excess (>10×) of the soluble analyte. Dashed lines highlight the value of the Damköhler number at which 50% of the analyte is captured.

Binding isotherms are shown in FIG. 84. Curves denote the theoretical proportional analyte capture observed for a given volumetric flow rate (or residence time) at varying concentrations of immobilized binder. The dashed line indicates the operating regime of the standard rcSso7d-CBD system (CB=400 µM).

Titration curves near the point of signal onset are shown in FIG. 85. All large-volume samples consisted of 10 mL sample volumes, driven across the test zone at 5 mL min-1 for 20 recirculations. All small-volume samples consisted of 10 µL sample volumes, applied directly to the test zones and allowed to incubate for an equivalent 40-minute period. Dataset is identical to that seen in FIG. 73. Error bars represent the standard deviation of three (large-volume) or four (small-volume) independent replicates.

A calculation of immobilized protein abundance on functionalized paper is shown in FIGS. 86A-86B. Titration data is shown in FIG. 86A for rcSso7d.SA-CBD applied to non-functionalized paper (black) and rcSso7d.SA applied to aldehyde functionalized paper (red), for streptavidin-eosin (SA-E) concentrations ranging from 0.25 nM to 256 nM and 10 µL sample volumes. Proportional analyte capture at varying applied analyte concentrations is shown in FIG. 86B. Analysis is conducted for all applied concentrations wherein there is an appreciable difference between signals observed for the functionalized and non-functionalized samples. All tests were incubated with the analyte solution for thirty minutes. Error bars represent the standard deviation of four independent replicates.

A comparison between small-volume titration curves for rcSso7d-CBD at local concentrations of 400 µM and 40 µM is shown in FIG. 87. Dataset is identical to that seen in FIG. 74A. Small-volume samples consisted of 10 µL incubated on the test zones for a 40-minute period. Error bars represent the standard deviation of four independent replicates.

Linear regression slopes, which correlate the number of recirculations and the degree of signal development, decline with increasing volumetric flow rate (see FIG. 88). In nearly all cases, linear regression curves are observed to correlate well with the experimental data, as indicated by Pearson coefficients near ±1.

A representative manual titration curve using streptavidin-eosin as the soluble analyte is shown in FIG. 89. Samples were processed for 20 recirculations each. Each data point represents a single assay replicate. Manual samples were processed at a flow rate that could be sustained without physical discomfort (~25 mL min-1). Samples were exposed for 1000 ms using a TXRED®-4040C filter set.

Example 15. Binder Activity in Urine Samples

The binding activity of various binders against urine-treated analytes, quantified using the geometric mean fluorescence intensity, rather than population proportions is shown in FIGS. 90, 91, 93, 94 and 95A-95B. The binding specificity of rcSso7d.H1BA.3, quantified with the geometric mean fluorescence intensity is shown in FIG. 92. The performance of the BA-MBP-rcSso7d.H4.1 and rcSso7d.H4.2-CBD species in a paper-based immunoassay format are shown in FIGS. 96-103.

FIG. 96 includes a schematic of the full sandwich immunoassay (as well as the empty versions used to assess binding specificity). FIG. 97 documents the performance of these binding reagents in various formats (the full immunocomplex and empty immunocomplexes), indicating significant analyte-specific activity for the full sandwich. FIG. 98 demonstrates that this analyte-specific activity is specific to the complementary binding species rcSso7d.H4.1 and rcSso7d.H4.2—other H4-binding variants yield no discernible signal in the full sandwich format. FIG. 99 demonstrates the limited cross-reactivity of the H4.1-CBD and H4.2-CBD species against other tuberculosis antigens in the paper-based format. Where high signal is seen, this is likely due to a) inadequate surface passivation, b) the high abundance of the CBD binding species, and c) the near-permanent nature of the streptavidin-based detection method. When the same rcSso7d.H4.1/rcSso7d.H4.2 species are challenged with other TB antigens in the yeast-surface display format, the only appreciable signal is observed with the H4 species. FIGS. 100 and 101 document efforts to reduce non-specific binding of detection reagents to reduce background signal, both by passivating the surface in bovine serum albumin for empty sandwich assays (FIG. 100) and by varying the pH of the solution in which the BA-MBP-rcSso7d.H4.1 species is applied/washed (FIG. 101). These findings were applied to produce the titration curve seen in FIG. 102. The limit of detection, determined as the fluorescence value three standard deviations above the mean negative signal, was observed to be approximately 8 nM. FIG. 103 documents further efforts to enhance assay sensitivity, demonstrating that by boosting the applied concentration of BA-MBP-rcSso7d.H4.1, the analyte-specific signal can be greatly increased for a given applied concentration of H4.

REFERENCES

Ackerman, M., Levary, D., Tobon, G., Hackel, B., Orcutt, K. D., Wittrup, K. D., 2009. Biotechnol. Prog. 25, 774-783.
Ahmed, S., Bui, M.-P. P. N., Abbas, A., 2016. Biosens. Bioelectron. 77, 249-263.
Baumann, H., Knapp, S., Lundback, T., Ladenstein, R., Hard, T., 1994. Nat. Struct.Biol. 1, 808-819.
Berdichevsky, Y., Lamed, R., Frenkel, D., Gophna, U., Bayer, E. A., Yaron, S., Shoham, Y., Benhar, I., 1999. Protein Expr. Purif. 17, 249-259.
Care, A., Bergquist, P. L., Sunna, A., 2015. Trends Biotechnol. 33, 259-268.
Care, A., Petroll, K., Gibson, E. S. Y., Bergquist, P. L., Sunna, A., 2017. Biotechnol. Biofuels 10, 1-16.
Chao, G., Lau, W. L., Hackel, B. J., Sazinsky, S. L., Lippow, S. M., Wittrup, K. D., 2006. Nat. Protoc. 1, 755-68.
Credou, J., Berthelot, T., 2014. J. Mater. Chem. B 2, 4767-4788.
Dai, G., Hu, J., Zhao, X., Wang, P., 2016. Sensors Actuators B Chem. 238, 138-144.
Esteban, B., De, A., Watkins, H. M., Pingarro, J. M., Plaxco, K. W., Palleschi, G., Ricci, F., 2013. Anal. Chem. 1-5.
Giri, B., Pandey, B., Neupane, B., Ligler, F. S., 2016. TrAC-Trends Anal. Chem. 79, 326-334.
Holstein, C. A., Chevalier, A., Bennett, S., Anderson, C. E., Keniston, K., Olsen, C., Li, B., Bales, B., Moore, D. R., Fu, E., Baker, D., Yager, P., 2016. Anal. Bioanal. Chem. 408, 1335-1346.
Hussack, G., Luo, Y., Veldhuis, L., Hall, J. C., Tanha, J., MacKenzie, R., 2009. Sensors 9, 5351-5367.
Hyre, D. E., Le Trong, I., Merritt, E. A., Eccleston, J. F., Green, N. M., Stenkamp, R. E., Stayton, P. S., 2006. Protein Sci. 15, 459-467.
Kaastrup, K., Chan, L., Sikes, H. D., 2013. Anal. Chem. 85, 8055-8060.
Kelley, S. O., Mirkin, C. A., Walt, D. R., Ismagilov, R. F., Toner, M., Sargent, E. H., 2014. Nat. Nanotechnol. 9, 969-980.
Kim, H. D., Choi, S. L., Kim, H., Sohn, J. H., Lee, S. G., 2013. Biotechnol. Bioprocess Eng. 18, 575-580.
Kumada, Y., 2014. Biochim. Biophys. Acta-Proteins Proteomics 1844, 1960-1969.
Levy, I., Shoseyov, O., 2002. Biotechnol. Adv. 20, 191-213.Li, M., Yue, Y., Zhang, Z. J., Wang, Z. Y., Tan, T. W., Fan, L. H., 2016. Bioconjug. Chem. 27, 1579-1583.
McBee, R. H., 1954. J. Bacteriol. 67, 505-6.
Miller, E. A., Traxlmayr, M. W., Shen, J., Sikes, H. D., 2016. Mol. Syst. Des. Eng. 1, 377-381.
Napolitano, D. R., Pollock, N., Kashino, S. S., Rodrigues, V., Campos-Neto, A., 2008. Clin. Vaccine Immunol. 15, 638-43.
Nery, E. W., Kubota, L. T., 2016. J. Pharm. Biomed. Anal. 117, 551-559.
Parsa, H., Chin, C. D., Mongkolwisetwara, P., Lee, B. W., Wang, J. J., Sia, S. K., 2008. Lab Chip 8, 2062.
Peluso, P., Wilson, D. S., Do, D., Tran, H., Venkatasubbaiah, M., Quincy, D., Heidecker, B., Poindexter, K., Tolani, N., Phelan, M., Witte, K., Jung, L. S., Wagner, P., Nock, S., 2003. Anal. Biochem. 312, 113-24.
Ricci, F., Vallde-B6lisle, A., Simon, A. J., Porchetta, A., Plaxco, K. W., 2016. Ace. Chem. Res. 49, 1884-1892.
Rissin, D. M., Wilson, D. H., Duffy, D. C., 2013. Chapter 2.13: Measurement of Single Protein Molecules Using Digital ELISA, in: The Immunoassay Handbook. Elsevier, pp. 223-242.
Rosa, A. M. M., Louro, A. F., Martins, S. A. M., Inicio, J., Azevedo, A. M., Prazeres, D. M. F., 2014. Anal. Chem. 86, 4340-4347.
Seker, U. O. S., Demir, H. V., 2011. Molecules 16, 1426-1451.
Shen, M., Rusling, J., Dixit, C. K., 2016. Methods 116, 95-111.
Song, H. Y., Zhou, X., Hobley, J., Su, X., 2012. Langmuir 28, 997-1004.
Sugimoto, N., Igarashi, K., Samejima, M., 2012. Protein Expr. Purif. 82, 290-296.
Tang, R., Yang, H., Choi, J. R., Gong, Y., Hu, J., Feng, S., Pingguan-Murphy, B., Mei, Q., Xu, F., 2016. Talanta 152, 269-276.
Tomme, P., Boraston, A., McLean, B., Kormos, J., Creagh, A. L., Sturch, K., Gilkes, N. R., Haynes, C. A., Warren, R. A. J., Kilburn, D. G., 1998. J. Chromatogr. B Biomed. Appl. 715, 283-296.
Traxlmayr, M. W., Kiefer, J. D., Srinivas, R. R., Lobner, E., Tisdale, A. W., Mehta, N. K., Yang, N.J., Tidor, B., Wittrup, K. D., 2016. J. Biol. Chem. 291, 22496-22508.
Vuoriluoto, M., Orelma, H., Zhu, B., Johansson, L.-S. S., Rojas, O. J., 2016. ACS Appl. Mater. Interfaces 8, 5668-5678.
Yaniv, O., Morag, E., Borovok, I., Bayer, E. A., Lamed, R., Frolow, F., Shimon, L. J. W., 2013. Acta Cryst 69, 733-737.
Yu, A., Shang, J., Cheng, F., Paik, B. A., Kaplan, J., Andrade, R. B., Ratner, D. M., 2012. Langmuir 28, 11265-11273.
Zhao, M., Li, H., Liu, W., Guo, Y., Chu, W., 2016. Biosens. Bioelectron. 79, 581-588.
Zhu, Y., Xu, X., Brault, N. D., Keefe, A. J., Han, X., Deng, Y., Xu, J., Yu, Q., Jiang, S., 2014. Anal. Chem. 86, 2871-2875.
Miller, E. A., Traxlmayr, M. W., Shen, J., Sikes, H. D., 2016. Mol. Syst. Des. Eng. 1, 377-381.
Schafer, D. E., 1983. Measurement of Receptor-Ligand Binding: Theory and Practice, in: Lambrecht, R. M., Rescigno, A. (Eds.). Springer Berlin Heidelberg, Berlin, Heidelberg, pp. 445-507.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B," when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B," the disclosure also contemplates the alternative embodiments "a composition consisting of A and B" and "a composition consisting essentially of A and B."

What is claimed is:

1. A method for detecting an antigen of interest, the method comprising:
   (a) contacting a bifunctional fusion protein comprising a cellulose binding domain (CBD) and an engineered reduced-charge Sso7d (rcSso7d) antigen-binding protein with a cellulose-containing substrate for a time sufficient for the bifunctional fusion protein to bind the cellulose-containing substrate, wherein the rcSso7d antigen-binding protein comprises an amino acid sequence that is at least 85% identical to SEQ ID NO: 3 and has a reduced charge relative to SEQ ID NO: 12, and wherein the CBD comprises an amino acid sequence that is at least 85% identical to SEQ ID NO: 2, SEQ ID NO: 16, or SEQ ID NO: 10;
   (b) contacting the bifunctional fusion protein bound to the cellulose-containing substrate with a sample comprising an antigen of interest; and
   (c) detecting the antigen of interest bound by the engineered rcSso7d antigen-binding protein.

2. The method of claim 1, wherein the antigen of interest is a tuberculosis antigen.

3. The method of claim 1, wherein the antigen of interest is a polypeptide encoded by the gene locus Rv1656 or streptavidin.

4. The method of claim 1, wherein the bifunctional fusion protein is in molar excess of the antigen of interest.

5. The method of claim 4, wherein the bifunctional fusion protein is in at least 10-fold molar excess of the antigen of interest.

6. The method of claim 1, wherein the cellulose-containing substrate is paper or nitrocellulose.

7. The method of claim 1, wherein the cellulose-containing substrate is chromatography paper.

* * * * *

SEQUENCE LISTING

<160> NUMBER OF SEQ ID NOS: 135

<210> SEQ ID NO 1
<211> LENGTH: 1674
<212> TYPE: PRT

<213> ORGANISM: Clostridium thermocellum

<400> SEQUENCE: 1

| Met | Arg | Lys | Val | Ile | Ser | Met | Leu | Leu | Val | Ala | Met | Leu | Thr | Thr |
|---|---|---|---|---|---|---|---|---|---|---|---|---|---|---|
| 1 | | | | 5 | | | | | 10 | | | | | 15 |

| Ile | Phe | Ala | Ala | Met | Ile | Pro | Gln | Thr | Val | Ser | Ala | Ala | Thr | Met | Thr |
|---|---|---|---|---|---|---|---|---|---|---|---|---|---|---|---|
| | | | 20 | | | | | 25 | | | | | 30 | | |

| Val | Glu | Ile | Gly | Lys | Val | Thr | Ala | Ala | Val | Gly | Ser | Lys | Val | Glu | Ile |
|---|---|---|---|---|---|---|---|---|---|---|---|---|---|---|---|
| | | 35 | | | | | 40 | | | | | 45 | | | |

| Pro | Ile | Thr | Leu | Lys | Gly | Val | Pro | Ser | Lys | Gly | Met | Ala | Asn | Cys | Asp |
|---|---|---|---|---|---|---|---|---|---|---|---|---|---|---|---|
| 50 | | | | | 55 | | | | | 60 | | | | | |

| Phe | Val | Leu | Gly | Tyr | Asp | Pro | Asn | Val | Leu | Glu | Val | Thr | Glu | Val | Lys |
|---|---|---|---|---|---|---|---|---|---|---|---|---|---|---|---|
| 65 | | | | | 70 | | | | | 75 | | | | | 80 |

| Pro | Gly | Ser | Ile | Ile | Lys | Asp | Pro | Asp | Pro | Ser | Lys | Ser | Phe | Asp | Ser |
|---|---|---|---|---|---|---|---|---|---|---|---|---|---|---|---|
| | | | | 85 | | | | | 90 | | | | | 95 | |

| Ala | Ile | Tyr | Pro | Asp | Arg | Lys | Met | Ile | Val | Phe | Leu | Phe | Ala | Glu | Asp |
|---|---|---|---|---|---|---|---|---|---|---|---|---|---|---|---|
| | | | 100 | | | | | 105 | | | | | 110 | | |

| Ser | Gly | Arg | Gly | Thr | Tyr | Ala | Ile | Thr | Gln | Asp | Gly | Val | Phe | Ala | Thr |
|---|---|---|---|---|---|---|---|---|---|---|---|---|---|---|---|
| | | | 115 | | | | | 120 | | | | | 125 | | |

| Ile | Val | Ala | Thr | Val | Lys | Ser | Ala | Ala | Ala | Pro | Ile | Thr | Leu | Leu |
|---|---|---|---|---|---|---|---|---|---|---|---|---|---|---|
| | 130 | | | | | 135 | | | | | 140 | | | |

| Glu | Val | Gly | Ala | Phe | Ala | Asp | Asn | Asp | Leu | Val | Glu | Ile | Ser | Thr | Thr |
|---|---|---|---|---|---|---|---|---|---|---|---|---|---|---|---|
| 145 | | | | | 150 | | | | | 155 | | | | | 160 |

| Phe | Val | Ala | Gly | Gly | Val | Asn | Leu | Gly | Ser | Ser | Val | Pro | Thr | Thr | Gln |
|---|---|---|---|---|---|---|---|---|---|---|---|---|---|---|---|
| | | | | 165 | | | | | 170 | | | | | 175 | |

| Pro | Asn | Val | Pro | Ser | Asp | Gly | Val | Val | Glu | Ile | Gly | Lys | Val | Thr |
|---|---|---|---|---|---|---|---|---|---|---|---|---|---|---|
| | | | 180 | | | | | 185 | | | | | 190 | |

| Gly | Ser | Val | Gly | Thr | Thr | Val | Glu | Ile | Pro | Val | Tyr | Phe | Arg | Gly | Val |
|---|---|---|---|---|---|---|---|---|---|---|---|---|---|---|---|
| | 195 | | | | | 200 | | | | | 205 | | | | |

| Pro | Ser | Lys | Gly | Ile | Ala | Asn | Cys | Asp | Phe | Val | Phe | Arg | Tyr | Asp | Pro |
|---|---|---|---|---|---|---|---|---|---|---|---|---|---|---|---|
| | 210 | | | | | 215 | | | | | 220 | | | | |

| Asn | Val | Leu | Glu | Ile | Ile | Gly | Ile | Asp | Pro | Gly | Asp | Ile | Ile | Val | Asp |
|---|---|---|---|---|---|---|---|---|---|---|---|---|---|---|---|
| 225 | | | | | 230 | | | | | 235 | | | | | 240 |

| Pro | Asn | Pro | Thr | Lys | Ser | Phe | Asp | Thr | Ala | Ile | Tyr | Pro | Asp | Arg | Lys |
|---|---|---|---|---|---|---|---|---|---|---|---|---|---|---|---|
| | | | | 245 | | | | | 250 | | | | | 255 | |

| Ile | Ile | Val | Phe | Leu | Phe | Ala | Glu | Asp | Ser | Gly | Thr | Gly | Ala | Tyr | Ala |
|---|---|---|---|---|---|---|---|---|---|---|---|---|---|---|---|
| | | | 260 | | | | | 265 | | | | | 270 | | |

| Ile | Thr | Lys | Asp | Gly | Val | Phe | Ala | Lys | Ile | Arg | Ala | Thr | Val | Lys | Ser |
|---|---|---|---|---|---|---|---|---|---|---|---|---|---|---|---|
| | | 275 | | | | | 280 | | | | | 285 | | | |

| Ser | Ala | Pro | Gly | Tyr | Ile | Thr | Phe | Asp | Glu | Val | Gly | Gly | Phe | Ala | Asp |
|---|---|---|---|---|---|---|---|---|---|---|---|---|---|---|---|
| | 290 | | | | | 295 | | | | | 300 | | | | |

| Asn | Asp | Leu | Val | Glu | Gln | Lys | Val | Ser | Phe | Ile | Asp | Gly | Gly | Val | Asn |
|---|---|---|---|---|---|---|---|---|---|---|---|---|---|---|---|
| 305 | | | | | 310 | | | | | 315 | | | | | 320 |

| Val | Gly | Asn | Ala | Thr | Pro | Thr | Lys | Gly | Ala | Thr | Pro | Thr | Asn | Thr | Ala |
|---|---|---|---|---|---|---|---|---|---|---|---|---|---|---|---|
| | | | | 325 | | | | | 330 | | | | | 335 | |

| Thr | Pro | Thr | Lys | Ser | Ala | Thr | Ala | Thr | Pro | Thr | Arg | Pro | Ser | Val | Pro |
|---|---|---|---|---|---|---|---|---|---|---|---|---|---|---|---|
| | | | 340 | | | | | 345 | | | | | 350 | | |

| Thr | Asn | Thr | Pro | Thr | Asn | Thr | Pro | Ala | Asn | Thr | Pro | Val | Ser | Gly | Asn |
|---|---|---|---|---|---|---|---|---|---|---|---|---|---|---|---|
| | | | 355 | | | | | 360 | | | | | 365 | | |

| Leu | Lys | Val | Glu | Phe | Tyr | Asn | Ser | Asn | Pro | Ser | Asp | Thr | Thr | Asn | Ser |
|---|---|---|---|---|---|---|---|---|---|---|---|---|---|---|---|
| | 370 | | | | | 375 | | | | | 380 | | | | |

| Ile | Asn | Pro | Gln | Phe | Lys | Val | Thr | Asn | Thr | Gly | Ser | Ser | Ala | Ile | Asp |
|---|---|---|---|---|---|---|---|---|---|---|---|---|---|---|---|
| 385 | | | | | 390 | | | | | 395 | | | | | 400 |

```
Leu Ser Lys Leu Thr Leu Arg Tyr Tyr Tyr Thr Val Asp Gly Gln Lys
                405                 410                 415

Asp Gln Thr Phe Trp Cys Asp His Ala Ala Ile Ile Gly Ser Asn Gly
            420                 425                 430

Ser Tyr Asn Gly Val Thr Ser Asn Val Lys Gly Thr Phe Val Lys Met
        435                 440                 445

Ser Ser Ser Thr Asn Asn Ala Asp Thr Tyr Leu Glu Ile Ser Phe Thr
    450                 455                 460

Gly Gly Thr Leu Glu Pro Gly Ala His Val Gln Ile Gln Gly Arg Phe
465                 470                 475                 480

Ala Lys Asn Asp Trp Ser Asn Tyr Thr Gln Ser Asn Asp Tyr Ser Phe
                485                 490                 495

Lys Ser Ala Ser Gln Phe Val Glu Trp Asp Gln Val Thr Ala Tyr Leu
            500                 505                 510

Asn Gly Val Leu Val Trp Gly Lys Glu Pro Gly Gly Ser Val Val Pro
        515                 520                 525

Ser Thr Gln Pro Val Thr Pro Pro Ala Thr Thr Lys Pro Pro Ala
    530                 535                 540

Thr Thr Ile Pro Pro Ser Asp Asp Pro Asn Ala Ile Lys Ile Lys Val
545                 550                 555                 560

Asp Thr Val Asn Ala Lys Pro Gly Asp Thr Val Asn Ile Pro Val Arg
                565                 570                 575

Phe Ser Gly Ile Pro Ser Lys Gly Ile Ala Asn Cys Asp Phe Val Tyr
            580                 585                 590

Ser Tyr Asp Pro Asn Val Leu Glu Ile Glu Ile Lys Pro Gly Glu
        595                 600                 605

Leu Ile Val Asp Pro Asn Pro Asp Lys Ser Phe Asp Thr Ala Val Tyr
    610                 615                 620

Pro Asp Arg Lys Ile Ile Val Phe Leu Phe Ala Glu Asp Ser Gly Thr
625                 630                 635                 640

Gly Ala Tyr Ala Ile Thr Lys Asp Gly Val Phe Ala Thr Ile Val Ala
                645                 650                 655

Lys Val Lys Ser Gly Ala Pro Asn Gly Leu Ser Val Ile Lys Phe Val
            660                 665                 670

Glu Val Gly Gly Phe Ala Asn Asn Asp Leu Val Glu Gln Lys Thr Gln
        675                 680                 685

Phe Ser Asp Gly Gly Val Asn Val Gly Gly Thr Thr Val Pro Thr Thr
    690                 695                 700

Pro Pro Ala Ser Thr Thr Pro Thr Asp Asp Pro Asn Ala Ile Lys Ile
705                 710                 715                 720

Lys Val Asp Thr Val Asn Ala Lys Pro Gly Asp Thr Val Asn Ile Pro
                725                 730                 735

Val Arg Phe Ser Gly Ile Pro Ser Lys Gly Ile Ala Asn Cys Asp Phe
            740                 745                 750

Val Tyr Ser Tyr Asp Pro Asn Val Leu Glu Ile Glu Ile Lys Pro
        755                 760                 765

Gly Glu Leu Ile Val Asp Pro Asn Pro Asp Lys Ser Phe Asp Thr Ala
    770                 775                 780

Val Tyr Pro Asp Arg Lys Ile Ile Val Phe Leu Phe Leu Thr Glu Asp Ser
785                 790                 795                 800

Gly Thr Gly Ala Tyr Ala Ile Thr Lys Asp Gly Val Phe Ala Thr Ile
                805                 810                 815

Val Ala Lys Val Lys Ser Gly Ala Pro Asn Gly Leu Ser Val Ile Lys
```

-continued

```
              820                 825                 830
Phe Val Glu Val Gly Gly Phe Ala Asn Asn Asp Leu Val Glu Gln Lys
              835                 840                 845
Thr Gln Phe Phe Asp Gly Gly Val Asn Val Gly Asp Thr Thr Val Pro
              850                 855                 860
Thr Thr Pro Thr Thr Pro Val Thr Thr Pro Thr Asp Pro Asn Ala
865                 870                 875                 880
Val Arg Ile Lys Val Asp Thr Val Asn Ala Lys Thr Gly Asp Thr Val
                    885                 890                 895
Arg Ile Pro Val Arg Phe Ser Gly Ile Pro Ser Lys Gly Ile Ala Asn
              900                 905                 910
Cys Asp Phe Val Tyr Ser Tyr Asp Pro Asn Val Leu Glu Ile Ile Glu
              915                 920                 925
Ile Glu Pro Gly Asp Ile Val Asp Pro Asn Pro Asp Lys Ser Phe
              930                 935                 940
Asp Thr Ala Val Tyr Pro Asp Arg Lys Ile Ile Val Phe Leu Phe Ala
945                 950                 955                 960
Glu Asp Ser Gly Thr Gly Ala Tyr Ala Ile Thr Lys Asp Gly Val Phe
                    965                 970                 975
Ala Thr Ile Val Ala Lys Val Lys Ser Gly Ala Pro Asn Gly Leu Ser
              980                 985                 990
Val Ile Lys Phe Val Glu Val Gly Gly Phe Ala Asn Asn Asp Leu Val
              995                1000                1005
Glu Gln Lys Thr Gln Phe Phe Asp Gly Gly Val Asn Val Gly Asp
         1010                1015                1020
Thr Thr Glu Pro Ala Thr Pro Thr Thr Pro Val Thr Thr Pro Thr
         1025                1030                1035
Thr Thr Asp Gly Leu Asp Ala Val Arg Ile Lys Val Asp Thr Val
         1040                1045                1050
Asn Ala Lys Pro Gly Asp Thr Val Arg Ile Pro Val Arg Phe Ser
         1055                1060                1065
Gly Ile Pro Ser Lys Gly Ile Ala Asn Cys Asp Phe Val Tyr Ser
         1070                1075                1080
Tyr Asp Pro Asn Val Leu Glu Ile Ile Glu Ile Glu Pro Gly Asp
         1085                1090                1095
Ile Ile Val Asp Pro Asn Pro Asp Lys Ser Phe Asp Thr Ala Val
         1100                1105                1110
Tyr Pro Asp Arg Lys Ile Ile Val Phe Leu Phe Ala Glu Asp Ser
         1115                1120                1125
Gly Thr Gly Ala Tyr Ala Ile Thr Lys Asp Gly Val Phe Ala Thr
         1130                1135                1140
Ile Val Ala Lys Val Lys Ser Gly Ala Pro Asn Gly Leu Ser Val
         1145                1150                1155
Ile Lys Phe Val Glu Val Gly Gly Phe Ala Asn Asn Asp Leu Val
         1160                1165                1170
Glu Gln Arg Thr Gln Phe Phe Asp Gly Gly Val Asn Val Gly Asp
         1175                1180                1185
Thr Thr Val Pro Thr Thr Pro Thr Thr Pro Val Thr Thr Pro Thr
         1190                1195                1200
Asp Asp Ser Asn Ala Val Arg Ile Lys Val Asp Thr Val Asn Ala
         1205                1210                1215
Lys Pro Gly Asp Thr Val Arg Ile Pro Val Arg Phe Ser Gly Ile
         1220                1225                1230
```

```
Pro Ser Lys Gly Ile Ala Asn Cys Asp Phe Val Tyr Ser Tyr Asp
    1235            1240                1245

Pro Asn Val Leu Glu Ile Ile Glu Ile Glu Pro Gly Asp Ile Ile
    1250            1255                1260

Val Asp Pro Asn Pro Asp Lys Ser Phe Asp Thr Ala Val Tyr Pro
    1265            1270                1275

Asp Arg Lys Ile Ile Val Phe Leu Phe Ala Glu Asp Ser Gly Thr
    1280            1285                1290

Gly Ala Tyr Ala Ile Thr Lys Asp Gly Val Phe Ala Thr Ile Val
    1295            1300                1305

Ala Lys Val Lys Ser Gly Ala Pro Asn Gly Leu Ser Val Ile Lys
    1310            1315                1320

Phe Val Glu Val Gly Gly Phe Ala Asn Asn Asp Leu Val Glu Gln
    1325            1330                1335

Lys Thr Gln Phe Phe Asp Gly Gly Val Asn Val Gly Asp Thr Thr
    1340            1345                1350

Val Pro Thr Thr Ser Pro Thr Thr Thr Pro Pro Glu Pro Thr Ile
    1355            1360                1365

Ala Pro Asn Lys Leu Thr Leu Lys Ile Gly Arg Ala Glu Gly Arg
    1370            1375                1380

Pro Gly Asp Thr Val Glu Ile Pro Val Asn Leu Tyr Gly Val Pro
    1385            1390                1395

Gln Lys Gly Ile Ala Ser Gly Asp Phe Val Val Ser Tyr Asp Pro
    1400            1405                1410

Asn Val Leu Glu Ile Ile Glu Ile Glu Pro Gly Glu Leu Ile Val
    1415            1420                1425

Asp Pro Asn Pro Thr Lys Ser Phe Asp Thr Ala Val Tyr Pro Asp
    1430            1435                1440

Arg Lys Met Ile Val Phe Leu Phe Ala Glu Asp Ser Gly Thr Gly
    1445            1450                1455

Ala Tyr Ala Ile Thr Glu Asp Gly Val Phe Ala Thr Ile Val Ala
    1460            1465                1470

Lys Val Lys Glu Gly Ala Pro Glu Gly Phe Ser Ala Ile Glu Ile
    1475            1480                1485

Ser Glu Phe Gly Ala Phe Ala Asp Asn Asp Leu Val Glu Val Glu
    1490            1495                1500

Thr Asp Leu Ile Asn Gly Gly Val Leu Val Thr Asn Lys Thr Val
    1505            1510                1515

Ile Glu Gly Tyr Lys Val Ser Gly Tyr Ile Leu Pro Asp Phe Ser
    1520            1525                1530

Phe Asp Ala Thr Val Ala Pro Leu Val Lys Ala Gly Phe Lys Val
    1535            1540                1545

Glu Ile Val Gly Thr Glu Leu Tyr Ala Val Thr Asp Ala Asn Gly
    1550            1555                1560

Tyr Phe Glu Ile Thr Gly Val Pro Ala Asn Ala Ser Gly Tyr Thr
    1565            1570                1575

Leu Lys Ile Ser Arg Ala Thr Tyr Leu Asp Arg Val Ile Ala Asn
    1580            1585                1590

Val Val Val Thr Gly Asp Thr Ser Val Ser Thr Ser Gln Ala Pro
    1595            1600                1605

Ile Met Met Trp Val Gly Asp Ile Val Lys Asp Asn Ser Ile Asn
    1610            1615                1620
```

-continued

```
Leu Leu Asp Val Ala Glu Val Ile Arg Cys Phe Asn Ala Thr Lys
    1625                1630                1635

Gly Ser Ala Asn Tyr Val Glu Glu Leu Asp Ile Asn Arg Asn Gly
    1640                1645                1650

Ala Ile Asn Met Gln Asp Ile Met Ile Val His Lys His Phe Gly
    1655                1660                1665

Ala Thr Ser Ser Asp Tyr
    1670

<210> SEQ ID NO 2
<211> LENGTH: 159
<212> TYPE: PRT
<213> ORGANISM: Clostridium thermocellum

<400> SEQUENCE: 2

Pro Val Ser Gly Asn Leu Lys Val Glu Phe Tyr Asn Ser Asn Pro Ser
1               5                   10                  15

Asp Thr Thr Asn Ser Ile Asn Pro Gln Phe Lys Val Thr Asn Thr Gly
                20                  25                  30

Ser Ser Ala Ile Asp Leu Ser Lys Leu Thr Leu Arg Tyr Tyr Tyr Thr
            35                  40                  45

Val Asp Gly Gln Lys Asp Gln Thr Phe Trp Cys Asp His Ala Ala Ile
50                  55                  60

Ile Gly Ser Asn Gly Ser Tyr Asn Gly Val Thr Ser Asn Val Lys Gly
65                  70                  75                  80

Thr Phe Val Lys Met Ser Ser Ser Thr Asn Asn Ala Asp Thr Tyr Leu
                85                  90                  95

Glu Ile Ser Phe Thr Gly Gly Thr Leu Glu Pro Gly Ala His Val Gln
            100                 105                 110

Ile Gln Gly Arg Phe Ala Lys Asn Asp Trp Ser Asn Tyr Thr Gln Ser
        115                 120                 125

Asn Asp Tyr Ser Phe Lys Ser Ala Ser Gln Phe Val Glu Trp Asp Gln
    130                 135                 140

Val Thr Ala Tyr Leu Asn Gly Val Leu Val Trp Gly Lys Glu Pro
145                 150                 155

<210> SEQ ID NO 3
<211> LENGTH: 62
<212> TYPE: PRT
<213> ORGANISM: Sulfolobus acidocaldarius

<400> SEQUENCE: 3

Met Ala Thr Val Lys Phe Thr Tyr Gln Gly Glu Glu Lys Gln Val Asp
1               5                   10                  15

Ile Ser Lys Ile Lys Lys Val Trp Arg Val Gly Gln Met Ile Ser Phe
                20                  25                  30

Thr Tyr Asp Glu Gly Gly Gly Ala Thr Gly Arg Gly Ala Val Ser Glu
            35                  40                  45

Lys Asp Ala Pro Lys Glu Leu Leu Gln Met Leu Glu Lys Gln
        50                  55                  60

<210> SEQ ID NO 4
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 4
```

Met Ala Thr Val Lys Phe Thr Tyr Gln Gly Glu Glu Lys Gln Val Asp
1               5                   10                  15

Ile Ser Lys Ile Lys Ile Val Ala Arg Asp Gly Gln Tyr Ile Asp Phe
                20                  25                  30

Lys Tyr Asp Glu Gly Gly Gly Ala Tyr Gly Tyr Gly Trp Val Ser Glu
            35                  40                  45

Lys Asp Ala Pro Lys Glu Leu Leu Gln Met Leu Glu Lys Gln
    50                  55                  60

<210> SEQ ID NO 5
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 5

Met Ala Thr Val Lys Phe Thr Tyr Gln Gly Glu Glu Lys Gln Val Asp
1               5                   10                  15

Ile Ser Lys Ile Lys Trp Val Arg Arg Tyr Gly Gln Tyr Ile Gly Phe
                20                  25                  30

Ser Tyr Asp Glu Gly Gly Gly Ala Trp Gly Lys Gly Tyr Val Ser Glu
            35                  40                  45

Lys Asp Ala Pro Lys Glu Leu Leu Gln Met Leu Glu Lys Gln
    50                  55                  60

<210> SEQ ID NO 6
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 6
aggcagtctc atatggcaac cgtgaaat                                    28

<210> SEQ ID NO 7
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 7 accccctctcg agttattgct tttccagcat ctg                             33

<210> SEQ ID NO 8
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 8 accccctctcg agttattagg atccttgctt ttccagcatc tg                   42

<210> SEQ ID NO 9
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 9
aagttacgct cgagttaggg ttctttaccc catacaagaa caccg            45

<210> SEQ ID NO 10
<211> LENGTH: 124
<212> TYPE: PRT
<213> ORGANISM: Artificial Sequence
<220> FEATURE:
<223> OTHER INFORMATION: Synthetic Polypeptide

<400> SEQUENCE: 10

Ala Gly Pro Gly Ala Asn Pro Pro Gly Thr Thr Thr Ser Arg Pro
1               5                   10                  15

Ala Thr Thr Thr Gly Ser Ser Pro Gly Pro Gln Ala Cys Ser Ser Val
                20                  25                  30

Trp Gly Gln Cys Gly Gly Gln Asn Trp Ser Gly Pro Thr Cys Cys Ala
            35                  40                  45

Ser Gly Ser Thr Cys Val Tyr Ser Asn Asp Tyr Tyr Ser Gln Cys Leu
        50                  55                  60

Pro Gly Ala Asn Pro Pro Gly Thr Thr Thr Ser Arg Pro Ala Thr
65                  70                  75                  80

Thr Thr Gly Ser Ser Pro Gly Pro Thr Gln Ser His Tyr Gly Gln Cys
                85                  90                  95

Gly Gly Ile Gly Tyr Ser Gly Pro Thr Val Cys Ala Ser Gly Thr Thr
            100                 105                 110

Cys Gln Val Leu Asn Pro Tyr Tyr Ser Gln Cys Leu
        115                 120

<210> SEQ ID NO 11
<211> LENGTH: 64
<212> TYPE: PRT
<213> ORGANISM: Sulfolobus acidocaldarius

<400> SEQUENCE: 11

Met Ala Thr Val Lys Phe Lys Tyr Lys Gly Glu Glu Lys Gln Val Asp
1               5                   10                  15

Ile Ser Lys Ile Lys Lys Val Trp Arg Val Gly Lys Met Ile Ser Phe
                20                  25                  30

Thr Tyr Asp Glu Gly Gly Gly Lys Thr Gly Arg Gly Ala Val Ser Glu
            35                  40                  45

Lys Asp Ala Pro Lys Glu Leu Leu Gln Met Leu Glu Lys Gln Lys Lys
        50                  55                  60

<210> SEQ ID NO 12
<211> LENGTH: 64
<212> TYPE: PRT
<213> ORGANISM: Sulfolobus acidocaldarius

<400> SEQUENCE: 12

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Lys Met Ile Ser Phe
                20                  25                  30

Thr Tyr Asp Glu Gly Gly Gly Lys Thr Gly Arg Gly Ala Val Ser Glu
            35                  40                  45

Lys Asp Ala Pro Lys Glu Leu Leu Gln Met Leu Glu Lys Gln Lys Lys
        50                  55                  60

<210> SEQ ID NO 13
<211> LENGTH: 66
<212> TYPE: PRT
<213> ORGANISM: Sulfolobus acidocaldarius

<400> SEQUENCE: 13

Met Val Lys Val Lys Phe Lys Tyr Lys Gly Glu Glu Lys Glu Val Asp
1               5                   10                  15

Thr Ser Lys Ile Lys Lys Val Trp Arg Val Gly Lys Met Val Ser Phe
            20                  25                  30

Thr Tyr Asp Asp Asn Gly Lys Thr Gly Arg Gly Ala Val Ser Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 14
<211> LENGTH: 253
<212> TYPE: PRT
<213> ORGANISM: Artificial Sequence
<220> FEATURE:
<223> OTHER INFORMATION: Synthetic Polypeptide

<400> SEQUENCE: 14

Met Gly Ser Ser His His His His His His Ser Gly Leu Val Pro
1               5                   10                  15

Arg Gly Ser His Met Ala Thr Val Lys Phe Thr Tyr Gln Gly Glu Glu
            20                  25                  30

Lys Gln Val Asp Ile Ser Lys Ile Lys Ile Val Ala Arg Asp Gly Gln
        35                  40                  45

Tyr Ile Asp Phe Lys Tyr Asp Glu Gly Gly Ala Tyr Gly Tyr Gly
    50                  55                  60

Trp Val Ser Glu Lys Asp Ala Pro Lys Glu Leu Leu Gln Met Leu Glu
65                  70                  75                  80

Lys Gln Gly Gly Gly Gly Ser Gly Gly Gly Gly Ser Gly Gly Gly Gly
            85                  90                  95

Ser Pro Val Ser Gly Asn Leu Lys Val Glu Phe Tyr Asn Ser Asn Pro
            100                 105                 110

Ser Asp Thr Thr Asn Ser Ile Asn Pro Gln Phe Lys Val Thr Asn Thr
            115                 120                 125

Gly Ser Ser Ala Ile Asp Leu Ser Lys Leu Thr Leu Arg Tyr Tyr Tyr
        130                 135                 140

Thr Val Asp Gly Gln Lys Asp Gln Thr Phe Trp Cys Asp His Ala Ala
145                 150                 155                 160

Ile Ile Gly Ser Asn Gly Ser Tyr Asn Gly Ile Thr Ser Asn Val Lys
                165                 170                 175

Gly Thr Phe Val Lys Met Ser Ser Thr Asn Asn Ala Asp Thr Tyr
            180                 185                 190

Leu Glu Ile Ser Phe Thr Gly Gly Thr Leu Glu Pro Gly Ala His Val
        195                 200                 205

Gln Ile Gln Gly Arg Phe Ala Lys Asn Asp Trp Ser Asn Tyr Thr Gln
    210                 215                 220

Ser Asn Asp Tyr Ser Phe Lys Ser Ala Ser Gln Phe Val Glu Trp Asp
225                 230                 235                 240

Gln Val Thr Ala Tyr Leu Asn Gly Val Leu Val Trp Gly
                245                 250

<210> SEQ ID NO 15
<211> LENGTH: 1674
<212> TYPE: PRT
<213> ORGANISM: Clostridium thermocellum

<400> SEQUENCE: 15

```
Met Arg Lys Val Ile Ser Met Leu Leu Val Ala Met Leu Thr Thr
1               5                   10                  15

Ile Phe Ala Ala Met Ile Pro Gln Thr Val Ser Ala Ala Thr Met Thr
            20                  25                  30

Val Glu Ile Gly Lys Val Thr Ala Ala Val Gly Ser Lys Val Glu Ile
            35                  40                  45

Pro Ile Thr Leu Lys Gly Val Pro Ser Lys Gly Met Ala Asn Cys Asp
        50                  55                  60

Phe Val Leu Gly Tyr Asp Pro Asn Val Leu Glu Val Thr Glu Val Lys
65                  70                  75                  80

Pro Gly Ser Ile Ile Lys Asp Pro Asp Pro Ser Lys Ser Phe Asp Ser
                85                  90                  95

Ala Ile Tyr Pro Asp Arg Lys Met Ile Val Phe Leu Phe Ala Glu Asp
            100                 105                 110

Ser Gly Arg Gly Thr Tyr Ala Ile Thr Gln Asp Gly Val Phe Ala Thr
        115                 120                 125

Ile Val Ala Thr Val Lys Ser Ala Ala Ala Pro Ile Thr Leu Leu
    130                 135                 140

Glu Val Gly Ala Phe Ala Asp Asn Asp Leu Val Glu Ile Ser Thr Thr
145                 150                 155                 160

Phe Val Ala Gly Gly Val Asn Leu Gly Ser Ser Val Pro Thr Thr Gln
                165                 170                 175

Pro Asn Val Pro Ser Asp Gly Val Val Glu Ile Gly Lys Val Thr
            180                 185                 190

Gly Ser Val Gly Thr Thr Val Glu Ile Pro Val Tyr Phe Arg Gly Val
        195                 200                 205

Pro Ser Lys Gly Ile Ala Asn Cys Asp Phe Val Phe Arg Tyr Asp Pro
    210                 215                 220

Asn Val Leu Glu Ile Ile Gly Ile Asp Pro Gly Asp Ile Ile Val Asp
225                 230                 235                 240

Pro Asn Pro Thr Lys Ser Phe Asp Thr Ala Ile Tyr Pro Asp Arg Lys
                245                 250                 255

Ile Ile Val Phe Leu Phe Ala Glu Asp Ser Gly Thr Gly Ala Tyr Ala
            260                 265                 270

Ile Thr Lys Asp Gly Val Phe Ala Lys Ile Arg Ala Thr Val Lys Ser
        275                 280                 285

Ser Ala Pro Gly Tyr Ile Thr Phe Asp Glu Val Gly Gly Phe Ala Asp
    290                 295                 300

Asn Asp Leu Val Glu Gln Lys Val Ser Phe Ile Asp Gly Gly Val Asn
305                 310                 315                 320

Val Gly Asn Ala Thr Pro Thr Lys Gly Ala Thr Pro Thr Asn Thr Ala
                325                 330                 335

Thr Pro Thr Lys Ser Ala Thr Ala Pro Thr Arg Pro Ser Val Pro
            340                 345                 350

Thr Asn Thr Pro Thr Asn Thr Pro Ala Asn Thr Pro Val Ser Gly Asn
        355                 360                 365

Leu Lys Val Glu Phe Tyr Asn Ser Asn Pro Ser Asp Thr Thr Asn Ser
```

```
                370                 375                 380
Ile Asn Pro Gln Phe Lys Val Thr Asn Thr Gly Ser Ser Ala Ile Asp
385                 390                 395                 400

Leu Ser Lys Leu Thr Leu Arg Tyr Tyr Tyr Thr Val Asp Gly Gln Lys
                405                 410                 415

Asp Gln Thr Phe Trp Cys Asp His Ala Ala Ile Ile Gly Ser Asn Gly
                420                 425                 430

Ser Tyr Asn Gly Ile Thr Ser Asn Val Lys Gly Thr Phe Val Lys Met
                435                 440                 445

Ser Ser Ser Thr Asn Asn Ala Asp Thr Tyr Leu Glu Ile Ser Phe Thr
450                 455                 460

Gly Gly Thr Leu Glu Pro Gly Ala His Val Gln Ile Gln Gly Arg Phe
465                 470                 475                 480

Ala Lys Asn Asp Trp Ser Asn Tyr Thr Gln Ser Asn Asp Tyr Ser Phe
                485                 490                 495

Lys Ser Ala Ser Gln Phe Val Glu Trp Asp Gln Val Thr Ala Tyr Leu
                500                 505                 510

Asn Gly Val Leu Val Trp Gly Lys Glu Pro Gly Gly Ser Val Val Pro
                515                 520                 525

Ser Thr Gln Pro Val Thr Thr Pro Ala Thr Thr Lys Pro Pro Ala
                530                 535                 540

Thr Thr Ile Pro Pro Ser Asp Asp Pro Asn Ala Ile Lys Ile Lys Val
545                 550                 555                 560

Asp Thr Val Asn Ala Lys Pro Gly Asp Thr Val Asn Ile Pro Val Arg
                565                 570                 575

Phe Ser Gly Ile Pro Ser Lys Gly Ile Ala Asn Cys Asp Phe Val Tyr
                580                 585                 590

Ser Tyr Asp Pro Asn Val Leu Glu Ile Ile Glu Ile Lys Pro Gly Glu
                595                 600                 605

Leu Ile Val Asp Pro Asn Pro Asp Lys Ser Phe Asp Thr Ala Val Tyr
                610                 615                 620

Pro Asp Arg Lys Ile Ile Val Phe Leu Phe Ala Glu Asp Ser Gly Thr
625                 630                 635                 640

Gly Ala Tyr Ala Ile Thr Lys Asp Gly Val Phe Ala Thr Ile Val Ala
                645                 650                 655

Lys Val Lys Ser Gly Ala Pro Asn Gly Leu Ser Val Ile Lys Phe Val
                660                 665                 670

Glu Val Gly Gly Phe Ala Asn Asn Asp Leu Val Glu Gln Lys Thr Gln
                675                 680                 685

Phe Ser Asp Gly Gly Val Asn Val Gly Gly Thr Thr Val Pro Thr Thr
690                 695                 700

Pro Pro Ala Ser Thr Pro Thr Asp Pro Asn Ala Ile Lys Ile
705                 710                 715                 720

Lys Val Asp Thr Val Asn Ala Lys Pro Gly Asp Thr Val Asn Ile Pro
                725                 730                 735

Val Arg Phe Ser Gly Ile Pro Ser Lys Gly Ile Ala Asn Cys Asp Phe
                740                 745                 750

Val Tyr Ser Tyr Asp Pro Asn Val Leu Glu Ile Ile Glu Ile Lys Pro
                755                 760                 765

Gly Glu Leu Ile Val Asp Pro Asn Pro Asp Lys Ser Phe Asp Thr Ala
                770                 775                 780

Val Tyr Pro Asp Arg Lys Ile Ile Val Phe Leu Leu Thr Glu Asp Ser
785                 790                 795                 800
```

```
Gly Thr Gly Ala Tyr Ala Ile Thr Lys Asp Gly Val Phe Ala Thr Ile
                805                 810                 815

Val Ala Lys Val Lys Ser Gly Ala Pro Asn Gly Leu Ser Val Ile Lys
            820                 825                 830

Phe Val Glu Val Gly Gly Phe Ala Asn Asn Asp Leu Val Glu Gln Lys
        835                 840                 845

Thr Gln Phe Phe Asp Gly Gly Val Asn Val Gly Asp Thr Thr Val Pro
    850                 855                 860

Thr Thr Pro Thr Thr Pro Val Thr Thr Pro Thr Asp Pro Asn Ala
865                 870                 875                 880

Val Arg Ile Lys Val Asp Thr Val Asn Ala Lys Thr Gly Asp Thr Val
                885                 890                 895

Arg Ile Pro Val Arg Phe Ser Gly Ile Pro Ser Lys Gly Ile Ala Asn
            900                 905                 910

Cys Asp Phe Val Tyr Ser Tyr Asp Pro Asn Val Leu Glu Ile Glu
        915                 920                 925

Ile Glu Pro Gly Asp Ile Ile Val Asp Pro Asn Pro Asp Lys Ser Phe
    930                 935                 940

Asp Thr Ala Val Tyr Pro Asp Arg Lys Ile Ile Val Phe Leu Phe Ala
945                 950                 955                 960

Glu Asp Ser Gly Thr Gly Ala Tyr Ala Ile Thr Lys Asp Gly Val Phe
                965                 970                 975

Ala Thr Ile Val Ala Lys Val Lys Ser Gly Ala Pro Asn Gly Leu Ser
            980                 985                 990

Val Ile Lys Phe Val Glu Val Gly Gly Phe Ala Asn Asn Asp Leu Val
        995                 1000                1005

Glu Gln Lys Thr Gln Phe Phe Asp Gly Gly Val Asn Val Gly Asp
    1010                1015                1020

Thr Thr Glu Pro Ala Thr Pro Thr Thr Pro Val Thr Thr Pro Thr
1025                1030                1035

Thr Thr Asp Gly Leu Asp Ala Val Arg Ile Lys Val Asp Thr Val
    1040                1045                1050

Asn Ala Lys Pro Gly Asp Thr Val Arg Ile Pro Val Arg Phe Ser
    1055                1060                1065

Gly Ile Pro Ser Lys Gly Ile Ala Asn Cys Asp Phe Val Tyr Ser
    1070                1075                1080

Tyr Asp Pro Asn Val Leu Glu Ile Ile Glu Ile Glu Pro Gly Asp
    1085                1090                1095

Ile Ile Val Asp Pro Asn Pro Asp Lys Ser Phe Asp Thr Ala Val
    1100                1105                1110

Tyr Pro Asp Arg Lys Ile Ile Val Phe Leu Phe Ala Glu Asp Ser
    1115                1120                1125

Gly Thr Gly Ala Tyr Ala Ile Thr Lys Asp Gly Val Phe Ala Thr
    1130                1135                1140

Ile Val Ala Lys Val Lys Ser Gly Ala Pro Asn Gly Leu Ser Val
    1145                1150                1155

Ile Lys Phe Val Glu Val Gly Gly Phe Ala Asn Asn Asp Leu Val
    1160                1165                1170

Glu Gln Arg Thr Gln Phe Phe Asp Gly Gly Val Asn Val Gly Asp
    1175                1180                1185

Thr Thr Val Pro Thr Thr Pro Thr Thr Pro Val Thr Thr Pro Thr
    1190                1195                1200
```

```
Asp Asp Ser Asn Ala Val Arg Ile Lys Val Asp Thr Val Asn Ala
    1205                1210                1215
Lys Pro Gly Asp Thr Val Arg Ile Pro Val Arg Phe Ser Gly Ile
    1220                1225                1230
Pro Ser Lys Gly Ile Ala Asn Cys Asp Phe Val Tyr Ser Tyr Asp
    1235                1240                1245
Pro Asn Val Leu Glu Ile Ile Glu Ile Glu Pro Gly Asp Ile Ile
    1250                1255                1260
Val Asp Pro Asn Pro Asp Lys Ser Phe Asp Thr Ala Val Tyr Pro
    1265                1270                1275
Asp Arg Lys Ile Ile Val Phe Leu Phe Ala Glu Asp Ser Gly Thr
    1280                1285                1290
Gly Ala Tyr Ala Ile Thr Lys Asp Gly Val Phe Ala Thr Ile Val
    1295                1300                1305
Ala Lys Val Lys Ser Gly Ala Pro Asn Gly Leu Ser Val Ile Lys
    1310                1315                1320
Phe Val Glu Val Gly Gly Phe Ala Asn Asn Asp Leu Val Glu Gln
    1325                1330                1335
Lys Thr Gln Phe Phe Asp Gly Gly Val Asn Val Gly Asp Thr Thr
    1340                1345                1350
Val Pro Thr Thr Ser Pro Thr Thr Thr Pro Pro Glu Pro Thr Ile
    1355                1360                1365
Ala Pro Asn Lys Leu Thr Leu Lys Ile Gly Arg Ala Glu Gly Arg
    1370                1375                1380
Pro Gly Asp Thr Val Glu Ile Pro Val Asn Leu Tyr Gly Val Pro
    1385                1390                1395
Gln Lys Gly Ile Ala Ser Gly Asp Phe Val Val Ser Tyr Asp Pro
    1400                1405                1410
Asn Val Leu Glu Ile Ile Glu Ile Glu Pro Gly Glu Leu Ile Val
    1415                1420                1425
Asp Pro Asn Pro Thr Lys Ser Phe Asp Thr Ala Val Tyr Pro Asp
    1430                1435                1440
Arg Lys Met Ile Val Phe Leu Phe Ala Glu Asp Ser Gly Thr Gly
    1445                1450                1455
Ala Tyr Ala Ile Thr Glu Asp Gly Val Phe Ala Thr Ile Val Ala
    1460                1465                1470
Lys Val Lys Glu Gly Ala Pro Glu Gly Phe Ser Ala Ile Glu Ile
    1475                1480                1485
Ser Glu Phe Gly Ala Phe Ala Asp Asn Asp Leu Val Glu Val Glu
    1490                1495                1500
Thr Asp Leu Ile Asn Gly Gly Val Leu Val Thr Asn Lys Thr Val
    1505                1510                1515
Ile Glu Gly Tyr Lys Val Ser Gly Tyr Ile Leu Pro Asp Phe Ser
    1520                1525                1530
Phe Asp Ala Thr Val Ala Pro Leu Val Lys Ala Gly Phe Lys Val
    1535                1540                1545
Glu Ile Val Gly Thr Glu Leu Tyr Ala Val Thr Asp Ala Asn Gly
    1550                1555                1560
Tyr Phe Glu Ile Thr Gly Val Pro Ala Asn Ala Ser Gly Tyr Thr
    1565                1570                1575
Leu Lys Ile Ser Arg Ala Thr Tyr Leu Asp Arg Val Ile Ala Asn
    1580                1585                1590
Val Val Val Thr Gly Asp Thr Ser Val Ser Thr Ser Gln Ala Pro
```

```
                1595                1600                1605

Ile Met  Met Trp Val Gly  Asp Ile Val Lys  Asp Asn  Ser Ile Asn
    1610                1615                1620

Leu Leu  Asp Val Ala Glu  Val Ile Arg Cys  Phe Asn  Ala Thr Lys
    1625                1630                1635

Gly Ser  Ala Asn Tyr Val  Glu Leu Asp Ile  Asn Arg  Asn Gly
    1640                1645                1650

Ala Ile  Asn Met Gln Asp  Ile Met Ile Val  His Lys  His Phe Gly
    1655                1660                1665

Ala Thr  Ser Ser Asp Tyr
    1670

<210> SEQ ID NO 16
<211> LENGTH: 159
<212> TYPE: PRT
<213> ORGANISM: Clostridium thermocellum

<400> SEQUENCE: 16

Pro Val Ser Gly Asn Leu Lys Val Glu Phe Tyr Asn Ser Asn Pro Ser
1               5                   10                  15

Asp Thr Thr Asn Ser Ile Asn Pro Gln Phe Lys Val Thr Asn Thr Gly
            20                  25                  30

Ser Ser Ala Ile Asp Leu Ser Lys Leu Thr Leu Arg Tyr Tyr Tyr Thr
        35                  40                  45

Val Asp Gly Gln Lys Asp Gln Thr Phe Trp Cys Asp His Ala Ala Ile
    50                  55                  60

Ile Gly Ser Asn Gly Ser Tyr Asn Gly Ile Thr Ser Asn Val Lys Gly
65                  70                  75                  80

Thr Phe Val Lys Met Ser Ser Ser Thr Asn Asn Ala Asp Thr Tyr Leu
                85                  90                  95

Glu Ile Ser Phe Thr Gly Gly Thr Leu Glu Pro Gly Ala His Val Gln
            100                 105                 110

Ile Gln Gly Arg Phe Ala Lys Asn Asp Trp Ser Asn Tyr Thr Gln Ser
        115                 120                 125

Asn Asp Tyr Ser Phe Lys Ser Ala Ser Gln Phe Val Glu Trp Asp Gln
    130                 135                 140

Val Thr Ala Tyr Leu Asn Gly Val Leu Val Trp Gly Lys Glu Pro
145                 150                 155

<210> SEQ ID NO 17
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 17

Met Ala Thr Val Lys Phe Thr Tyr Gln Gly Glu Glu Lys Gln Val Asp
1               5                   10                  15

Ile Ser Lys Ile Lys Tyr Val Tyr Arg Trp Gly His Tyr Ile Tyr Phe
            20                  25                  30

Trp Tyr Asp Glu Gly Gly Gly Ala Ser Gly Trp Gly Trp Val Ser Glu
        35                  40                  45

Lys Asp Ala Pro Lys Glu Leu Leu Gln
    50                  55

<210> SEQ ID NO 18
```

```
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 18

Met Ala Thr Val Lys Phe Thr Tyr Gln Gly Glu Glu Lys Gln Val Asp
1               5                   10                  15

Ile Ser Lys Ile Lys His Val Arg Arg Trp Gly Gln Trp Ile Tyr Phe
            20                  25                  30

Ile Tyr Asp Glu Gly Gly Gly Ala Arg Gly Asn Gly Tyr Val Ser Glu
        35                  40                  45

Lys Asp Ala Pro Lys Glu Leu Leu Gln
    50                  55

<210> SEQ ID NO 19
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 19

Met Ala Thr Val Lys Phe Thr Tyr Gln Gly Glu Glu Lys Gln Val Asp
1               5                   10                  15

Ile Ser Lys Ile Lys Arg Val Arg Arg Tyr Gly Gln Trp Ile Ala Phe
            20                  25                  30

His Tyr Asp Glu Gly Gly Gly Ala Ala Gly Trp Gly Tyr Val Ser Glu
        35                  40                  45

Lys Asp Ala Pro Lys Glu Leu Leu Gln
    50                  55

<210> SEQ ID NO 20
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 20

Met Ala Thr Val Lys Phe Thr Tyr Gln Gly Glu Glu Lys Gln Val Asp
1               5                   10                  15

Ile Ser Lys Ile Lys Trp Val Trp Arg Gly Gly Gln Gly Ile Ile Phe
            20                  25                  30

Trp Tyr Asp Glu Gly Gly Gly Ala Arg Gly Tyr Gly Arg Val Ser Glu
        35                  40                  45

Lys Asp Ala Pro Lys Glu Leu Leu Gln
    50                  55

<210> SEQ ID NO 21
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 21

Met Ala Thr Val Lys Phe Thr Tyr Gln Gly Glu Glu Lys Gln Val Asp
1               5                   10                  15

Ile Ser Lys Ile Lys Arg Val Ile Arg Ile Gly Gln Tyr Ile Tyr Phe
            20                  25                  30
```

Trp Tyr Asp Glu Gly Gly Gly Ala Arg Gly Trp Gly Tyr Val Ser Glu
            35                  40                  45

Lys Asp Ala Pro Lys Glu Leu Leu Gln
    50                  55

<210> SEQ ID NO 22
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 22

Met Ala Thr Val Lys Phe Thr Tyr Gln Gly Glu Glu Lys Gln Val Asp
1               5                   10                  15

Ile Ser Lys Ile Lys Trp Val His Arg Trp Gly Gln Arg Ile Arg Phe
            20                  25                  30

Trp Tyr Asp Glu Gly Gly Gly Ala Ala Gly Asn Gly Lys Val Ser Glu
            35                  40                  45

Lys Asp Ala Pro Lys Glu Leu Leu Gln
    50                  55

<210> SEQ ID NO 23
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 23

Met Ala Thr Val Lys Phe Thr Tyr Gln Gly Glu Glu Lys Gln Val Asp
1               5                   10                  15

Ile Ser Lys Ile Lys Trp Val Ile Arg Trp Gly Gln Trp Ile Trp Phe
            20                  25                  30

Lys Tyr Asp Glu Gly Gly Gly Ala Ser Gly Trp Gly Tyr Val Ser Glu
            35                  40                  45

Lys Asp Ala Pro Lys Glu Leu Leu Gln
    50                  55

<210> SEQ ID NO 24
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 24

Met Ala Thr Val Lys Phe Thr Tyr Gln Gly Glu Glu Lys Gln Val Asp
1               5                   10                  15

Ile Ser Lys Ile Lys Arg Val Arg Arg Trp Gly Gln Trp Ile Tyr Phe
            20                  25                  30

Arg Tyr Asp Glu Gly Gly Gly Ala Tyr Gly Ser Gly Tyr Val Ser Glu
            35                  40                  45

Lys Asp Ala Pro Lys Glu Leu Leu Gln
    50                  55

<210> SEQ ID NO 25
<211> LENGTH: 57
<212> TYPE: PRT
<213> ORGANISM: Artificial Sequence
<220> FEATURE:

<223> OTHER INFORMATION: Synthetic Polypeptide

<400> SEQUENCE: 25

Met Ala Thr Val Lys Phe Thr Tyr Gln Gly Glu Glu Lys Gln Val Asp
1               5                   10                  15
Ile Ser Lys Ile Lys Tyr Val Tyr Arg Trp Gly Gln Trp Ile Tyr Phe
                20                  25                  30
Trp Tyr Asp Glu Gly Gly Gly Ala Trp Gly Arg Gly Tyr Val Ser Glu
            35                  40                  45
Lys Asp Ala Pro Lys Glu Leu Leu Gln
        50                  55

<210> SEQ ID NO 26
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 26

Met Ala Thr Val Lys Phe Thr Tyr Gln Gly Glu Glu Lys Gln Val Asp
1               5                   10                  15
Ile Ser Lys Ile Lys Tyr Val Arg Arg Tyr Gly Gln Tyr Ile Gly Phe
                20                  25                  30
Ile Tyr Asp Glu Gly Gly Gly Ala Trp Gly Lys Gly Tyr Val Ser Glu
            35                  40                  45
Lys Asp Ala Pro Lys Glu Leu Leu Gln
        50                  55

<210> SEQ ID NO 27
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 27

Met Ala Thr Val Lys Phe Thr Tyr Gln Gly Glu Glu Lys Gln Val Asp
1               5                   10                  15
Ile Ser Lys Ile Lys His Val Arg Arg Tyr Gly Gln Trp Ile Arg Phe
                20                  25                  30
Arg Tyr Asp Glu Gly Gly Gly Ala Ser Gly Trp Gly Ile Val Ser Glu
            35                  40                  45
Lys Asp Ala Pro Lys Glu Leu Leu Gln
        50                  55

<210> SEQ ID NO 28
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 28

Met Ala Thr Val Lys Phe Thr Tyr Gln Gly Glu Glu Lys Gln Val Asp
1               5                   10                  15
Ile Ser Lys Ile Lys Ser Val Lys Arg Ser Gly Gln Gly Ile Lys Phe
                20                  25                  30
Ile Tyr Asp Glu Gly Gly Gly Ala Tyr Gly His Gly Arg Val Ser Glu
            35                  40                  45

-continued

Lys Asp Ala Pro Lys Glu Leu Leu Gln
            50                  55

<210> SEQ ID NO 29
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 29

Ile Ala Asp Tyr Asp Lys Tyr Tyr Trp
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 30

Trp Arg Tyr Tyr Gly Ser Trp Lys Tyr
1               5

<210> SEQ ID NO 31
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 31

Met Ala Thr Val Lys Phe Thr Tyr Gln Gly Glu Glu Lys Gln Val Asp
1               5                   10                  15

Ile Ser Lys Ile Lys Asn Val His Arg His Gly Gln Lys Ile Tyr Phe
            20                  25                  30

Ile Tyr Asp Glu Gly Gly Gly Ala Lys Gly His Gly Lys Val Ser Glu
        35                  40                  45

Lys Asp Ala Pro Lys Glu Leu Leu Gln Met Leu Glu Lys Gln
    50                  55                  60

<210> SEQ ID NO 32
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 32

Met Ala Thr Val Lys Phe Thr Tyr Gln Gly Glu Glu Lys Gln Val Asp
1               5                   10                  15

Ile Ser Lys Ile Lys His Val Lys Arg His Gly Gln Trp Ile Lys Phe
            20                  25                  30

Ala Tyr Asp Glu Gly Gly Gly Ala Lys Gly Lys Gly Lys Val Ser Glu
        35                  40                  45

Lys Asp Ala Pro Lys Glu Leu Leu Gln Met Leu Glu Lys Gln
    50                  55                  60

<210> SEQ ID NO 33
<211> LENGTH: 62
<212> TYPE: PRT
<213> ORGANISM: Artificial Sequence
<220> FEATURE:

<223> OTHER INFORMATION: Synthetic Polypeptide

<400> SEQUENCE: 33

Met Ala Thr Val Lys Phe Thr Tyr Gln Gly Glu Glu Lys Gln Val Asp
1               5                   10                  15

Ile Ser Lys Ile Lys Lys Val His Arg Lys Gly Gln Ile Ile Arg Phe
            20                  25                  30

Arg Tyr Asp Glu Gly Gly Gly Ala Trp Gly His Gly Tyr Val Ser Glu
        35                  40                  45

Lys Asp Ala Pro Lys Glu Leu Leu Gln Met Leu Glu Lys Gln
    50                  55                  60

<210> SEQ ID NO 34
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 34

Met Ala Thr Val Lys Phe Thr Tyr Gln Gly Glu Glu Lys Gln Val Asp
1               5                   10                  15

Ile Ser Lys Ile Lys His Val Lys Arg His Gly Gln Lys Ile Tyr Phe
            20                  25                  30

Arg Tyr Asp Glu Gly Gly Gly Ala Gly Gly Arg Gly Arg Val Ser Glu
        35                  40                  45

Lys Asp Ala Pro Lys Glu Leu Leu Gln Met Leu Glu Lys Gln
    50                  55                  60

<210> SEQ ID NO 35
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 35

Met Ala Thr Val Lys Phe Thr Tyr Gln Gly Glu Glu Lys Gln Val Asp
1               5                   10                  15

Ile Ser Lys Ile Lys Arg Val Tyr Arg His Gly Gln Trp Ile His Phe
            20                  25                  30

Arg Tyr Asp Glu Gly Gly Gly Ala Arg Gly His Gly His Val Ser Glu
        35                  40                  45

Lys Asp Ala Pro Lys Glu Leu Leu Gln Met Leu Glu Lys Gln
    50                  55                  60

<210> SEQ ID NO 36
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 36

Met Ala Thr Val Lys Phe Thr Tyr Gln Gly Glu Glu Lys Gln Val Asp
1               5                   10                  15

Ile Ser Lys Ile Lys Arg Val Ser Arg Lys Gly Gln Arg Ile Tyr Phe
            20                  25                  30

Arg Tyr Asp Glu Gly Gly Gly Ala His Gly Lys Gly Lys Val Ser Glu
        35                  40                  45

```
Lys Asp Ala Pro Lys Glu Leu Leu Gln Met Leu Glu Lys Gln
         50                  55                  60

<210> SEQ ID NO 37
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 37

Asn His His Lys Tyr Ile Lys His Lys
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 38

His Lys His Trp Lys Ala Lys Lys
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 39

Lys His Lys Ile Arg Arg Trp His Tyr
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 40

His Lys His Lys Tyr Arg Gly Arg Arg
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 41

Arg Tyr His Trp His Arg Arg His His
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 42

Arg Ser Lys Arg Tyr Arg His Lys Lys
```

<210> SEQ ID NO 43
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 43

Met Ala Thr Val Lys Phe Thr Tyr Gln Gly Glu Glu Lys Gln Val Asp
1               5                   10                  15

Ile Ser Lys Ile Lys Ile Val Gly Arg His Gly Gln Trp Ile Tyr Phe
            20                  25                  30

Trp Tyr Asp Glu Gly Gly Gly Ala Asn Gly Asn Gly Trp Val Ser Glu
        35                  40                  45

Lys Asp Ala Pro Lys Glu Leu Leu Gln Met Leu Glu Lys Gln
    50                  55                  60

<210> SEQ ID NO 44
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 44

Met Ala Thr Val Lys Phe Thr Tyr Gln Gly Glu Glu Lys Gln Val Asp
1               5                   10                  15

Ile Ser Lys Ile Lys Ile Val Gly Arg His Gly Gln Trp Ile Tyr Phe
            20                  25                  30

Trp Tyr Asp Glu Gly Gly Gly Ala Asp Gly Asn Gly Trp Val Ser Glu
        35                  40                  45

Lys Asp Ala Pro Lys Glu Leu Leu Gln Met Leu Glu Lys Gln
    50                  55                  60

<210> SEQ ID NO 45
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 45

Met Ala Thr Val Lys Phe Thr Tyr Gln Gly Glu Glu Lys Gln Val Asp
1               5                   10                  15

Ile Ser Lys Ile Lys Ile Val Gly Arg His Gly Gln Trp Ile Tyr Phe
            20                  25                  30

Trp Tyr Asp Glu Gly Gly Gly Ala Tyr Gly Asn Gly Trp Val Ser Glu
        35                  40                  45

Lys Asp Ala Pro Lys Glu Leu Leu Gln Met Leu Glu Lys Gln
    50                  55                  60

<210> SEQ ID NO 46
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 46

Met Ala Thr Val Lys Phe Thr Tyr Gln Gly Glu Glu Lys Gln Val Asp

```
                1               5                  10                  15
Ile Ser Lys Ile Lys Ile Val Gly Arg Ser Gly Gln Trp Ile Tyr Phe
                20                  25                  30

Trp Tyr Asp Glu Gly Gly Gly Ala Trp Gly Asn Gly Trp Val Ser Glu
        35                  40                  45

Lys Asp Ala Pro Lys Glu Leu Leu Gln Met Leu Glu Lys Gln
        50                  55                  60

<210> SEQ ID NO 47
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 47

Met Ala Thr Val Lys Phe Thr Tyr Gln Gly Glu Glu Lys Gln Val Asp
1               5                  10                  15

Ile Ser Lys Ile Lys Ile Val Gly Arg Trp Gly Gln Trp Ile Tyr Phe
                20                  25                  30

Trp Tyr Asp Glu Gly Gly Gly Ala Ser Gly Asn Gly Trp Val Ser Glu
        35                  40                  45

Lys Asp Ala Pro Lys Glu Leu Leu Gln Met Leu Glu Lys Gln
        50                  55                  60

<210> SEQ ID NO 48
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 48

Met Ala Thr Val Lys Phe Thr Tyr Gln Gly Glu Glu Lys Gln Val Asp
1               5                  10                  15

Ile Ser Lys Ile Lys Trp Val Arg Arg Asp Gly Gln Ile Ile Tyr Phe
                20                  25                  30

Asn Tyr Asp Glu Gly Gly Gly Ala Trp Gly Trp Gly Asp Val Ser Glu
        35                  40                  45

Lys Asp Ala Pro Lys Glu Leu Leu Gln Met Leu Glu Lys Gln
        50                  55                  60

<210> SEQ ID NO 49
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 49

Met Ala Thr Val Lys Phe Thr Tyr Gln Gly Glu Glu Lys Gln Val Asp
1               5                  10                  15

Ile Ser Lys Ile Lys Trp Val Arg Arg Trp Gly Gln Trp Ile Tyr Phe
                20                  25                  30

Asn Tyr Asp Glu Gly Gly Gly Ala Trp Gly Trp Gly Asp Val Ser Glu
        35                  40                  45

Lys Asp Ala Pro Lys Glu Leu Leu Gln Met Leu Glu Lys Gln
        50                  55                  60

<210> SEQ ID NO 50
```

```
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 50

Ile Gly His Trp Tyr Trp Asn Asn Trp
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 51

Ile Gly His Trp Tyr Trp Asp Asn Trp
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 52

Ile Gly His Trp Tyr Trp Tyr Asn Trp
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 53

Ile Gly Ser Trp Tyr Trp Trp Asn Trp
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 54

Ile Gly Trp Trp Tyr Trp Ser Asn Trp
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 55

Trp Arg Asp Ile Tyr Asn Trp Trp Asp
1               5

<210> SEQ ID NO 56
<211> LENGTH: 9
```

```
<212> TYPE: PRT
<213> ORGANISM: Artificial Sequence
<220> FEATURE:
<223> OTHER INFORMATION: Synthetic Polypeptide

<400> SEQUENCE: 56

Trp Arg Trp Trp Tyr Asn Trp Trp Asp
1               5

<210> SEQ ID NO 57
<211> LENGTH: 258
<212> TYPE: PRT
<213> ORGANISM: Artificial Sequence
<220> FEATURE:
<223> OTHER INFORMATION: Synthetic Polypeptide

<400> SEQUENCE: 57

Met Gly Ser Ser His His His His His His Ser Ser Gly Leu Val Pro
1               5                   10                  15

Arg Gly Ser His Met Ala Thr Val Lys Phe Thr Tyr Gln Gly Glu Glu
            20                  25                  30

Lys Gln Val Asp Ile Ser Lys Ile Lys Asn Val His Arg His Gly Gln
        35                  40                  45

Lys Ile Tyr Phe Ile Tyr Asp Glu Gly Gly Gly Ala Lys Gly His Gly
    50                  55                  60

Lys Val Ser Glu Lys Asp Ala Pro Lys Glu Leu Leu Gln Met Leu Glu
65                  70                  75                  80

Lys Gln Gly Ser Gly Gly Gly Ser Gly Gly Gly Ser Gly Gly
            85                  90                  95

Gly Gly Ser Pro Val Ser Gly Asn Leu Lys Val Glu Phe Tyr Asn Ser
            100                 105                 110

Asn Pro Ser Asp Thr Thr Asn Ser Ile Asn Pro Gln Phe Lys Val Thr
            115                 120                 125

Asn Thr Gly Ser Ser Ala Ile Asp Leu Ser Lys Leu Thr Leu Arg Tyr
            130                 135                 140

Tyr Tyr Thr Val Asp Gly Gln Lys Asp Gln Thr Phe Trp Cys Asp His
145                 150                 155                 160

Ala Ala Ile Ile Gly Ser Asn Gly Ser Tyr Asn Gly Ile Thr Ser Asn
                165                 170                 175

Val Lys Gly Thr Phe Val Lys Met Ser Ser Thr Asn Asn Ala Asp
                180                 185                 190

Thr Tyr Leu Glu Ile Ser Phe Thr Gly Gly Thr Leu Glu Pro Gly Ala
            195                 200                 205

His Val Gln Ile Gln Gly Arg Phe Ala Lys Asn Asp Trp Ser Asn Tyr
        210                 215                 220

Thr Gln Ser Asn Asp Tyr Ser Phe Lys Ser Ala Ser Gln Phe Val Glu
225                 230                 235                 240

Trp Asp Gln Val Thr Ala Tyr Leu Asn Gly Val Leu Val Trp Gly Lys
                245                 250                 255

Glu Pro

<210> SEQ ID NO 58
<211> LENGTH: 494
<212> TYPE: PRT
<213> ORGANISM: Artificial Sequence
<220> FEATURE:
<223> OTHER INFORMATION: Synthetic Polypeptide

<400> SEQUENCE: 58
```

```
Met Gly Ser Ser His His His His His Ser Ser Gly Leu Val Pro
1               5                   10                  15

Arg Gly Ser His Met Met Ala Gly Gly Leu Asn Asp Ile Phe Glu Ala
            20                  25                  30

Gln Lys Ile Glu Trp His Glu Leu Lys Gly Gly Gly Ser Gly Gly
            35              40              45

Gly Gly Ser Glu Phe Lys Ile Glu Glu Gly Lys Leu Val Ile Trp Ile
50              55                  60

Asn Gly Asp Lys Gly Tyr Asn Gly Leu Ala Glu Val Gly Lys Lys Phe
65                  70              75                  80

Glu Lys Asp Thr Gly Ile Lys Val Thr Val Glu His Pro Asp Lys Leu
                85              90                  95

Glu Glu Lys Phe Pro Gln Val Ala Ala Thr Gly Asp Gly Pro Asp Ile
            100             105                 110

Ile Phe Trp Ala His Asp Arg Phe Gly Gly Tyr Ala Gln Ser Gly Leu
            115             120                 125

Leu Ala Glu Ile Thr Pro Asp Lys Ala Phe Gln Asp Lys Leu Tyr Pro
130             135                 140

Phe Thr Trp Asp Ala Val Arg Tyr Asn Gly Lys Leu Ile Ala Tyr Pro
145                 150             155                 160

Ile Ala Val Glu Ala Leu Ser Leu Ile Tyr Asn Lys Asp Leu Leu Pro
                165             170                 175

Asn Pro Pro Lys Thr Trp Glu Glu Ile Pro Ala Leu Asp Lys Glu Leu
            180             185                 190

Lys Ala Lys Gly Lys Ser Ala Leu Met Phe Asn Leu Gln Glu Pro Tyr
            195             200             205

Phe Thr Trp Pro Leu Ile Ala Ala Asp Gly Gly Tyr Ala Phe Lys Tyr
210             215                 220

Glu Asn Gly Lys Tyr Asp Ile Lys Asp Val Gly Val Asp Asn Ser Gly
225             230             235                 240

Ala Lys Ala Gly Leu Thr Phe Leu Val Asp Leu Ile Lys Asn Lys His
            245             250                 255

Met Asn Ala Asp Thr Asp Tyr Ser Ile Ala Glu Ala Ala Phe Asn Lys
            260             265                 270

Gly Glu Thr Ala Met Thr Ile Asn Gly Pro Trp Ala Trp Ser Asn Ile
            275             280             285

Asp Thr Ser Lys Val Asn Tyr Gly Val Thr Val Leu Pro Thr Phe Lys
            290             295             300

Gly Gln Pro Ser Lys Pro Phe Val Gly Val Leu Ser Ala Gly Ile Asn
305             310             315                 320

Ala Ala Ser Pro Asn Lys Glu Leu Ala Lys Glu Phe Leu Glu Asn Tyr
            325             330                 335

Leu Leu Thr Asp Glu Gly Leu Glu Ala Val Asn Lys Asp Lys Pro Leu
            340             345             350

Gly Ala Val Ala Leu Lys Ser Tyr Glu Glu Leu Ala Lys Asp Pro
            355             360             365

Arg Ile Ala Ala Thr Met Glu Asn Ala Gln Lys Gly Glu Ile Met Pro
370             375             380

Asn Ile Pro Gln Met Ser Ala Phe Trp Tyr Ala Val Arg Thr Ala Val
385             390             395                 400

Ile Asn Ala Ala Ser Gly Arg Gln Thr Val Asp Glu Ala Leu Lys Asp
                405             410                 415
```

```
Ala Gln Thr Gly Ser Gly Gly Gly Ser Gly Gly Gly Ser Thr
            420             425             430

Ser Ala Thr Val Lys Phe Thr Tyr Gln Gly Glu Glu Lys Gln Val Asp
        435                 440                 445

Ile Ser Lys Ile Lys Ser Val Trp Arg Arg Gly Gln Arg Ile Trp Phe
450                 455                 460

Arg Tyr Asp Glu Gly Gly Ala Trp Gly Ala Gly Lys Val Ser Glu
465             470             475             480

Lys Asp Ala Pro Lys Glu Leu Leu Gln Met Leu Glu Lys Gln
                485                 490

<210> SEQ ID NO 59
<211> LENGTH: 461
<212> TYPE: PRT
<213> ORGANISM: Artificial Sequence
<220> FEATURE:
<223> OTHER INFORMATION: Synthetic Polypeptide

<400> SEQUENCE: 59

Met Gly Ser Ser His His His His Ser Ser Gly Leu Val Pro
1               5                   10                  15

Arg Gly Ser His Met Lys Ile Glu Glu Gly Lys Leu Val Ile Trp Ile
            20                  25                  30

Asn Gly Asp Lys Gly Tyr Asn Gly Leu Ala Glu Val Gly Lys Lys Phe
        35                  40                  45

Glu Lys Asp Thr Gly Ile Lys Val Thr Val Glu His Pro Asp Lys Leu
    50                  55                  60

Glu Glu Lys Phe Pro Gln Val Ala Ala Thr Gly Asp Gly Pro Asp Ile
65                  70                  75                  80

Ile Phe Trp Ala His Asp Arg Phe Gly Gly Tyr Ala Gln Ser Gly Leu
                85                  90                  95

Leu Ala Glu Ile Thr Pro Asp Lys Ala Phe Gln Asp Lys Leu Tyr Pro
            100                 105                 110

Phe Thr Trp Asp Ala Val Arg Tyr Asn Gly Lys Leu Ile Ala Tyr Pro
        115                 120                 125

Ile Ala Val Glu Ala Leu Ser Leu Ile Tyr Asn Lys Asp Leu Leu Pro
    130                 135                 140

Asn Pro Pro Lys Thr Trp Glu Glu Ile Pro Ala Leu Asp Lys Glu Leu
145                 150                 155                 160

Lys Ala Lys Gly Lys Ser Ala Leu Met Phe Asn Leu Gln Glu Pro Tyr
                165                 170                 175

Phe Thr Trp Pro Leu Ile Ala Ala Asp Gly Gly Tyr Ala Phe Lys Tyr
            180                 185                 190

Glu Asn Gly Lys Tyr Asp Ile Lys Asp Val Gly Val Asp Asn Ser Gly
        195                 200                 205

Ala Lys Ala Gly Leu Thr Phe Leu Val Asp Leu Ile Lys Asn Lys His
    210                 215                 220

Met Asn Ala Asp Thr Asp Tyr Ser Ile Ala Glu Ala Ala Phe Asn Lys
225                 230                 235                 240

Gly Glu Thr Ala Met Thr Ile Asn Gly Pro Trp Ala Trp Ser Asn Ile
                245                 250                 255

Asp Thr Ser Lys Val Asn Tyr Gly Val Thr Val Leu Pro Thr Phe Lys
            260                 265                 270

Gly Gln Pro Ser Lys Pro Phe Val Gly Val Leu Ser Ala Gly Ile Asn
        275                 280                 285
```

```
Ala Ala Ser Pro Asn Lys Glu Leu Ala Lys Glu Phe Leu Glu Asn Tyr
        290                 295                 300

Leu Leu Thr Asp Glu Gly Leu Glu Ala Val Asn Lys Asp Lys Pro Leu
305                 310                 315                 320

Gly Ala Val Ala Leu Lys Ser Tyr Glu Glu Leu Ala Lys Asp Pro
                325                 330                 335

Arg Ile Ala Ala Thr Met Glu Asn Ala Gln Lys Gly Glu Ile Met Pro
            340                 345                 350

Asn Ile Pro Gln Met Ser Ala Phe Trp Tyr Ala Val Arg Thr Ala Val
                355                 360                 365

Ile Asn Ala Ala Ser Gly Arg Gln Thr Val Asp Glu Ala Leu Lys Asp
            370                 375                 380

Ala Gln Thr Gly Ser Gly Gly Gly Ser Gly Gly Gly Ser Met
385                 390                 395                 400

Ala Thr Val Lys Phe Thr Tyr Gln Gly Glu Glu Lys Gln Val Asp Ile
                405                 410                 415

Ser Lys Ile Lys Ser Val Trp Arg Arg Gly Gln Arg Ile Trp Phe Arg
            420                 425                 430

Tyr Asp Glu Gly Gly Gly Ala Trp Gly Ala Gly Lys Val Ser Glu Lys
                435                 440                 445

Asp Ala Pro Lys Glu Leu Leu Gln Met Leu Glu Lys Gln
450                 455                 460

<210> SEQ ID NO 60
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 60

Met Gly Ser Ser His His His His His His Ser Ser Gly Leu Val Pro
1               5                   10                  15

Arg Gly Ser His Met Thr Ser Met Ala Gly Gly Leu Asn Asp Ile Phe
            20                  25                  30

Glu Ala Gln Lys Ile Glu Trp His Glu His Met Ala Thr Val Lys Phe
        35                  40                  45

Thr Tyr Gln Gly Glu Glu Lys Gln Val Asp Ile Ser Lys Ile Lys Ser
    50                  55                  60

Val Trp Arg Arg Gly Gln Arg Ile Trp Phe Arg Tyr Asp Glu Gly Gly
65                  70                  75                  80

Gly Ala Trp Gly Ala Gly Lys Val Ser Glu Lys Asp Ala Pro Lys Glu
                85                  90                  95

Leu Leu Gln Met Leu Glu Lys Gln Gly Gly
            100                 105

<210> SEQ ID NO 61
<211> LENGTH: 82
<212> TYPE: PRT
<213> ORGANISM: Artificial Sequence
<220> FEATURE:
<223> OTHER INFORMATION: Synthetic Polypeptide

<400> SEQUENCE: 61

Met Gly Ser Ser His His His His His His Ser Ser Gly Leu Val Pro
1               5                   10                  15

Arg Gly Ser His Met Ala Thr Val Lys Phe Thr Tyr Gln Gly Glu Glu
            20                  25                  30
```

```
Lys Gln Val Asp Ile Ser Lys Ile Lys Ser Val Trp Arg Arg Gly Gln
            35                  40                  45

Arg Ile Trp Phe Arg Tyr Asp Glu Gly Gly Ala Trp Gly Ala Gly
 50                  55                  60

Lys Val Ser Glu Lys Asp Ala Pro Lys Glu Leu Leu Gln Met Leu Glu
 65                  70                  75                  80

Lys Gln

<210> SEQ ID NO 62
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 62

Met Gly Ser Ser His His His His His His Ser Ser Gly Leu Val Pro
 1               5                  10                  15

Arg Gly Ser His Met Thr Ser Met Ala Gly Gly Leu Asn Asp Ile Phe
            20                  25                  30

Glu Ala Gln Lys Ile Glu Trp His Glu His Met Ala Thr Val Lys Phe
         35                  40                  45

Thr Tyr Gln Gly Glu Glu Lys Gln Val Asp Ile Ser Lys Ile Lys Ser
 50                  55                  60

Val Trp Arg Arg Gly Gln Arg Ile Trp Phe Arg Tyr Asp Glu Gly Gly
 65                  70                  75                  80

Gly Ala Trp Gly Ala Gly Lys Val Ser Glu Lys Asp Ala Pro Lys Glu
             85                  90                  95

Leu Leu Gln Met Leu Glu Lys Gln Gly Gly
            100                 105

<210> SEQ ID NO 63
<211> LENGTH: 178
<212> TYPE: PRT
<213> ORGANISM: Artificial Sequence
<220> FEATURE:
<223> OTHER INFORMATION: Synthetic Polypeptide

<400> SEQUENCE: 63

Met Gly Ser Ser His His His His His His Ser Ser Gly Leu Val Pro
 1               5                  10                  15

Arg Gly Ser His Met Thr Ser Met Ala Gly Gly Leu Asn Asp Ile Phe
            20                  25                  30

Glu Ala Gln Lys Ile Glu Trp His Glu His Met Ala Thr Val Lys Phe
         35                  40                  45

Thr Tyr Gln Gly Glu Glu Lys Gln Val Asp Ile Ser Lys Ile Lys Ser
 50                  55                  60

Val Trp Arg Arg Gly Gln Arg Ile Trp Phe Arg Tyr Asp Glu Gly Gly
 65                  70                  75                  80

Gly Ala Trp Gly Ala Gly Lys Val Ser Glu Lys Asp Ala Pro Lys Glu
             85                  90                  95

Leu Leu Gln Met Leu Glu Lys Gln Gly Gly Gly Gly Ser Gly Gly Gly
            100                 105                 110

Gly Ser Met Ala Thr Val Lys Phe Thr Tyr Gln Gly Glu Glu Lys Gln
         115                 120                 125

Val Asp Ile Ser Lys Ile Lys Ser Val Trp Arg Arg Gly Gln Arg Ile
            130                 135                 140
```

```
Trp Phe Arg Tyr Asp Glu Gly Gly Ala Trp Ala Gly Lys Val
145                 150                 155                 160

Ser Glu Lys Asp Ala Pro Lys Glu Leu Leu Gln Met Leu Glu Lys Gln
                165                 170                 175

Gly Gly
```

```
<210> SEQ ID NO 64
<211> LENGTH: 250
<212> TYPE: PRT
<213> ORGANISM: Artificial Sequence
<220> FEATURE:
<223> OTHER INFORMATION: Synthetic Polypeptide

<400> SEQUENCE: 64

Met Gly Ser Ser His His His His His His Ser Ser Gly Leu Val Pro
1               5                   10                  15

Arg Gly Ser His Met Thr Ser Met Ala Gly Gly Leu Asn Asp Ile Phe
                20                  25                  30

Glu Ala Gln Lys Ile Glu Trp His Glu His Met Ala Thr Val Lys Phe
            35                  40                  45

Thr Tyr Gln Gly Glu Glu Lys Gln Val Asp Ile Ser Lys Ile Lys Ser
    50                  55                  60

Val Trp Arg Arg Gly Gln Arg Ile Trp Phe Arg Tyr Asp Glu Gly Gly
65                  70                  75                  80

Gly Ala Trp Gly Ala Gly Lys Val Ser Glu Lys Asp Ala Pro Lys Glu
                85                  90                  95

Leu Leu Gln Met Leu Glu Lys Gln Gly Gly Gly Ser Gly Gly Gly
                100                 105                 110

Gly Ser Met Ala Thr Val Lys Phe Thr Tyr Gln Gly Glu Glu Lys Gln
                115                 120                 125

Val Asp Ile Ser Lys Ile Lys Ser Val Trp Arg Arg Gly Gln Arg Ile
            130                 135                 140

Trp Phe Arg Tyr Asp Glu Gly Gly Gly Ala Trp Gly Ala Gly Lys Val
145                 150                 155                 160

Ser Glu Lys Asp Ala Pro Lys Glu Leu Leu Gln Met Leu Glu Lys Gln
                165                 170                 175

Gly Gly Gly Gly Ser Gly Gly Gly Ser Met Ala Thr Val Lys Phe
                180                 185                 190

Thr Tyr Gln Gly Glu Glu Lys Gln Val Asp Ile Ser Lys Ile Lys Ser
            195                 200                 205

Val Trp Arg Arg Gly Gln Arg Ile Trp Phe Arg Tyr Asp Glu Gly Gly
        210                 215                 220

Gly Ala Trp Gly Ala Gly Lys Val Ser Glu Lys Asp Ala Pro Lys Glu
225                 230                 235                 240

Leu Leu Gln Met Leu Glu Lys Gln Gly Gly
                245                 250
```

```
<210> SEQ ID NO 65
<211> LENGTH: 371
<212> TYPE: PRT
<213> ORGANISM: Artificial Sequence
<220> FEATURE:
<223> OTHER INFORMATION: Synthetic Polypeptide

<400> SEQUENCE: 65

Met Gly Ser Ser His His His His His His Ser Ser Gly Leu Val Pro
1               5                   10                  15
```

Arg Gly Ser His Met Val Ile Ile Glu Leu Met Arg Arg Val Val Gly
                20                  25                  30

Leu Ala Gln Gly Ala Thr Ala Glu Val Ala Val Tyr Gly Asp Arg Asp
             35                  40                  45

Arg Asp Leu Ala Glu Arg Trp Cys Ala Asn Thr Gly Asn Thr Leu Val
 50                  55                  60

Arg Ala Asp Val Asp Gln Thr Gly Val Gly Thr Leu Val Arg Arg
 65                  70                  75                  80

Gly His Pro Pro Asp Pro Ala Ser Val Leu Gly Pro Asp Arg Leu Pro
                 85                  90                  95

Gly Val Arg Leu Trp Leu Tyr Thr Asn Phe His Cys Asn Leu Cys Cys
            100                 105                 110

Asp Tyr Cys Cys Val Ser Ser Pro Ser Thr Pro His Arg Glu Leu
            115                 120                 125

Gly Ala Glu Arg Ile Gly Arg Ile Val Gly Glu Ala Ala Arg Trp Gly
130                 135                 140

Val Arg Glu Leu Phe Leu Thr Gly Gly Glu Pro Phe Leu Leu Pro Asp
145                 150                 155                 160

Ile Asp Thr Ile Ile Ala Thr Cys Val Lys Gln Leu Pro Thr Thr Val
                165                 170                 175

Leu Thr Asn Gly Met Val Phe Lys Gly Arg Gly Arg Ala Leu Glu
            180                 185                 190

Ser Leu Pro Arg Gly Leu Ala Leu Gln Ile Ser Leu Asp Ser Ala Thr
            195                 200                 205

Pro Glu Leu His Asp Ala His Arg Gly Ala Gly Thr Trp Val Lys Ala
210                 215                 220

Val Ala Gly Ile Arg Leu Ala Leu Ser Leu Gly Phe Arg Val Arg Val
225                 230                 235                 240

Ala Ala Thr Val Ala Ser Pro Ala Pro Gly Glu Leu Thr Ala Phe His
                245                 250                 255

Asp Phe Leu Asp Gly Leu Gly Ile Ala Pro Gly Asp Gln Leu Val Arg
            260                 265                 270

Pro Ile Ala Leu Glu Gly Ala Ala Ser Gln Gly Val Ala Leu Thr Arg
            275                 280                 285

Glu Ser Leu Val Pro Glu Val Thr Val Thr Ala Asp Gly Val Tyr Trp
290                 295                 300

His Pro Val Ala Ala Thr Asp Glu Arg Ala Leu Val Thr Arg Thr Val
305                 310                 315                 320

Glu Pro Leu Thr Pro Ala Leu Asp Met Val Ser Arg Leu Phe Ala Glu
                325                 330                 335

Gln Trp Thr Arg Ala Ala Glu Gly Ala Ala Leu Phe Pro Cys Ala Gly
            340                 345                 350

Ser Met Ala Gly Gly Leu Asn Asp Ile Phe Glu Ala Gln Lys Ile Glu
            355                 360                 365

Trp His Glu
    370

<210> SEQ ID NO 66
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 66

Met Ala Thr Val Lys Phe Thr Tyr Gln Gly Glu Glu Lys Gln Val Asp
1               5                   10                  15

Ile Ser Lys Ile Lys His Val Arg Arg Trp Gly Gln Tyr Ile Ile Phe
                20                  25                  30

Ala Tyr Asp Glu Gly Gly Gly Ala Tyr Gly Gly Gly Trp Val Ser Glu
            35                  40                  45

Lys Asp Ala Pro Lys Glu Leu Leu Gln Met Leu Glu Lys Gln
    50                  55                  60

<210> SEQ ID NO 67
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 67

Met Ala Thr Val Lys Phe Thr Tyr Gln Gly Glu Glu Lys Gln Val Asp
1               5                   10                  15

Ile Ser Lys Ile Lys His Val Ile Arg Asn Gly Gln Tyr Ile Ile Phe
                20                  25                  30

Ala Tyr Asp Glu Gly Gly Gly Ala Tyr Gly Gly Gly Trp Val Ser Glu
            35                  40                  45

Lys Asp Ala Pro Lys Glu Leu Leu Gln Met Leu Glu Lys Gln
    50                  55                  60

<210> SEQ ID NO 68
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 68

Met Ala Thr Val Lys Phe Thr Tyr Gln Gly Glu Glu Lys Gln Val Asp
1               5                   10                  15

Ile Ser Lys Ile Lys His Val Ile Arg Asn Gly Gln Tyr Ile Ile Phe
                20                  25                  30

Ala Tyr Asp Glu Gly Gly Gly Ala Tyr Gly Gly Gly Trp Val Ser Glu
            35                  40                  45

Lys Asp Ala Pro Lys Glu Leu Leu Gln Met Leu Glu Lys Gln
    50                  55                  60

<210> SEQ ID NO 69
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 69

Met Ala Thr Val Lys Phe Thr Tyr Gln Gly Glu Glu Lys Gln Val Asp
1               5                   10                  15

Ile Ser Lys Ile Lys Asn Val Tyr Arg Trp Gly Gln Tyr Ile Ile Phe
                20                  25                  30

Ser Tyr Asp Glu Gly Gly Gly Ala Tyr Gly Trp Gly Trp Val Ser Glu
            35                  40                  45

Lys Asp Ala Pro Lys Glu Leu Leu Gln Met Leu Glu Lys Gln
    50                  55                  60

<210> SEQ ID NO 70
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 70

Met Ala Thr Val Lys Phe Thr Tyr Gln Gly Glu Glu Lys Gln Val Asp
1               5                   10                  15

Ile Ser Lys Ile Lys Tyr Val Arg Arg Tyr Gly Gln Tyr Ile Gly Phe
                20                  25                  30

Ile Tyr Asp Glu Gly Gly Gly Ala Trp Gly Lys Gly Tyr Val Ser Glu
            35                  40                  45

Lys Asp Ala Pro Lys Glu Leu Leu Gln Met Leu Glu Lys Gln
        50                  55                  60

<210> SEQ ID NO 71
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 71

Met Ala Thr Val Lys Phe Thr Tyr Gln Gly Glu Glu Lys Gln Val Asp
1               5                   10                  15

Ile Ser Lys Ile Lys Asp Val Trp Arg Trp Gly Gln Trp Ile Asp Phe
                20                  25                  30

Ile Tyr Asp Glu Gly Gly Gly Ala Asp Gly Trp Gly Arg Val Ser Glu
            35                  40                  45

Lys Asp Ala Pro Lys Glu Leu Leu Gln Met Leu Glu Lys Gln
        50                  55                  60

<210> SEQ ID NO 72
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 72

His Arg Trp Tyr Ile Ala Tyr Gly Trp
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 73

Arg Ala Tyr Tyr Ile Ala Tyr Ala Trp
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 74

```
His Ile Asn Tyr Ile Ala Tyr Gly Trp
1               5
```

<210> SEQ ID NO 75
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 75

```
Asn Tyr Trp Tyr Ile Ser Tyr Trp Trp
1               5
```

<210> SEQ ID NO 76
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 76

```
Tyr Arg Tyr Tyr Gly Ile Trp Lys Tyr
1               5
```

<210> SEQ ID NO 77
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 77

```
Asp Trp Trp Trp Asp Ile Asp Trp Arg
1               5
```

<210> SEQ ID NO 78
<211> LENGTH: 294
<212> TYPE: PRT
<213> ORGANISM: Artificial Sequence
<220> FEATURE:
<223> OTHER INFORMATION: Synthetic Polypeptide

<400> SEQUENCE: 78

```
Met Gly Ser Ser His His His His His Ser Ser Gly Leu Val Pro
1               5                   10                  15

Arg Gly Ser His Met Ser Gly Glu Thr Thr Arg Leu Thr Glu Pro Gln
                20                  25                  30

Leu Arg Glu Leu Ala Ala Arg Gly Ala Ala Glu Leu Asp Gly Ala Thr
            35                  40                  45

Ala Thr Asp Met Leu Arg Trp Thr Asp Glu Thr Phe Gly Asp Ile Gly
    50                  55                  60

Gly Ala Gly Gly Gly Val Ser Gly His Arg Gly Trp Thr Thr Cys Asn
65                  70                  75                  80

Tyr Val Val Ala Ser Asn Met Ala Asp Ala Val Leu Val Asp Leu Ala
                85                  90                  95

Ala Lys Val Arg Pro Gly Val Pro Val Ile Phe Leu Thr Gly Tyr
            100                 105                 110

His Phe Val Glu Thr Ile Gly Thr Arg Asp Ala Ile Glu Ser Val Tyr
        115                 120                 125

Asp Val Arg Val Leu Asn Val Thr Pro Glu His Thr Val Ala Glu Gln
    130                 135                 140
```

```
Asp Glu Leu Leu Gly Lys Asp Leu Phe Ala Arg Asn Pro His Glu Cys
145                 150                 155                 160

Cys Arg Leu Arg Lys Val Val Pro Leu Gly Lys Thr Leu Arg Gly Tyr
                165                 170                 175

Ser Ala Trp Val Thr Gly Leu Arg Arg Val Asp Ala Pro Thr Arg Ala
            180                 185                 190

Asn Ala Pro Leu Val Ser Phe Asp Glu Thr Phe Lys Leu Val Lys Val
                195                 200                 205

Asn Pro Leu Ala Ala Trp Thr Asp Gln Asp Val Gln Glu Tyr Ile Ala
            210                 215                 220

Asp Asn Asp Val Leu Val Asn Pro Leu Val Arg Glu Gly Tyr Pro Ser
225                 230                 235                 240

Ile Gly Cys Ala Pro Cys Thr Ala Lys Pro Ala Glu Gly Ala Asp Pro
                245                 250                 255

Arg Ser Gly Arg Trp Gln Gly Leu Ala Lys Thr Glu Cys Gly Leu His
            260                 265                 270

Ala Ser Gly Ser Met Ala Gly Leu Asn Asp Ile Phe Glu Ala Gln
                275                 280                 285

Lys Ile Glu Trp His Glu
    290
```

<210> SEQ ID NO 79
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 79

```
Met Ala Thr Val Lys Phe Thr Tyr Gln Gly Glu Glu Lys Gln Val Asp
1               5                   10                  15

Ile Ser Lys Ile Lys Arg Val Ile Arg Tyr Gly Gln Ala Ile Ala Phe
            20                  25                  30

Ala Tyr Asp Glu Gly Gly Gly Ala Arg Gly Tyr Gly Trp Val Ser Glu
        35                  40                  45

Lys Asp Ala Pro Lys Glu Leu Leu Gln Met Leu Glu Lys Gln
    50                  55                  60
```

<210> SEQ ID NO 80
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 80

```
Met Ala Thr Val Lys Phe Thr Tyr Gln Gly Glu Glu Lys Gln Val Asp
1               5                   10                  15

Ile Ser Lys Ile Lys Tyr Val Gly Arg Trp Gly Gln Asn Ile Gly Phe
            20                  25                  30

Ala Tyr Asp Glu Gly Gly Gly Ala Tyr Gly Tyr Gly Val Ser Glu
        35                  40                  45

Lys Asp Ala Pro Lys Glu Leu Leu Gln Met Leu Glu Lys Gln
    50                  55                  60
```

<210> SEQ ID NO 81
<211> LENGTH: 9
<212> TYPE: PRT

```
<213> ORGANISM: Artificial Sequence
<220> FEATURE:
<223> OTHER INFORMATION: Synthetic Polypeptide

<400> SEQUENCE: 81

Arg Ile Tyr Ala Ala Ala Arg Tyr Trp
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 82

Tyr Gly Trp Asn Gly Ala Tyr Tyr Gly
1               5

<210> SEQ ID NO 83
<211> LENGTH: 328
<212> TYPE: PRT
<213> ORGANISM: Artificial Sequence
<220> FEATURE:
<223> OTHER INFORMATION: Synthetic Polypeptide

<400> SEQUENCE: 83

Met Gly Ser Ser His His His His His Ser Gly Leu Val Pro
1               5                   10                  15

Arg Gly Ser His Met Val Ile Arg His Phe Leu Arg Asp Asp Leu
            20                  25                  30

Ser Pro Ala Glu Gln Ala Glu Val Leu Glu Leu Ala Ala Glu Leu Lys
        35                  40                  45

Lys Asp Pro Val Ser Arg Arg Pro Leu Gln Gly Pro Arg Gly Val Ala
    50                  55                  60

Val Ile Phe Asp Lys Asn Ser Thr Arg Thr Arg Phe Ser Phe Glu Leu
65                  70                  75                  80

Gly Ile Ala Gln Leu Gly Gly His Ala Val Val Asp Ser Gly Ser
                85                  90                  95

Thr Gln Leu Gly Arg Asp Glu Thr Leu Gln Asp Thr Ala Lys Val Leu
                100                 105                 110

Ser Arg Tyr Val Asp Ala Ile Val Trp Arg Thr Phe Gly Gln Glu Arg
            115                 120                 125

Leu Asp Ala Met Ala Ser Val Ala Thr Val Pro Val Ile Asn Ala Leu
130                 135                 140

Ser Asp Glu Phe His Pro Cys Gln Val Leu Ala Asp Leu Gln Thr Ile
145                 150                 155                 160

Ala Glu Arg Lys Gly Ala Leu Arg Gly Leu Arg Leu Ser Tyr Phe Gly
                165                 170                 175

Asp Gly Ala Asn Asn Met Ala His Ser Leu Leu Leu Gly Gly Val Thr
            180                 185                 190

Ala Gly Ile His Val Thr Val Ala Ala Pro Glu Gly Phe Leu Pro Asp
        195                 200                 205

Pro Ser Val Arg Ala Ala Ala Glu Arg Arg Ala Gln Asp Thr Gly Ala
    210                 215                 220

Ser Val Thr Val Thr Ala Asp Ala His Ala Ala Ala Gly Ala Asp
225                 230                 235                 240

Val Leu Val Thr Asp Thr Trp Thr Ser Met Gly Gln Glu Asn Asp Gly
                245                 250                 255
```

```
Leu Asp Arg Val Lys Pro Phe Arg Pro Phe Gln Leu Asn Ser Arg Leu
            260                 265                 270

Leu Ala Leu Ala Asp Ser Asp Ala Ile Val Leu His Cys Leu Pro Ala
        275                 280                 285

His Arg Gly Asp Glu Ile Thr Asp Ala Val Met Asp Gly Pro Ala Ser
        290                 295                 300

Ala Val Trp Asp Glu Ala Glu Asn Arg Leu His Ala Gln Lys Ala Leu
305                 310                 315                 320

Leu Val Trp Leu Leu Glu Arg Ser
                325

<210> SEQ ID NO 84
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 84

Met Ala Thr Val Lys Phe Thr Tyr Gln Gly Glu Glu Lys Gln Val Asp
1               5                   10                  15

Ile Ser Lys Ile Lys Ser Val Trp Arg Arg Gly Gln Arg Ile Trp Phe
            20                  25                  30

Arg Tyr Asp Glu Gly Gly Gly Ala Trp Gly Ala Gly Lys Val Ser Glu
        35                  40                  45

Lys Asp Ala Pro Lys Glu Leu Leu Gln Met Leu Glu Lys Gln
    50                  55                  60

<210> SEQ ID NO 85
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 85

Met Ala Thr Val Lys Phe Thr Tyr Gln Gly Glu Glu Lys Gln Val Asp
1               5                   10                  15

Ile Ser Lys Ile Lys Trp Val Arg Arg Tyr Gly Gln Tyr Ile Gly Phe
            20                  25                  30

Ser Tyr Asp Glu Gly Gly Gly Ala Trp Gly Lys Gly Tyr Val Ser Glu
        35                  40                  45

Lys Asp Ala Pro Lys Glu Leu Leu Gln Met Leu Glu Lys Gln
    50                  55                  60

<210> SEQ ID NO 86
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 86

Met Ala Thr Val Lys Phe Thr Tyr Gln Gly Glu Glu Lys Gln Val Asp
1               5                   10                  15

Ile Ser Lys Ile Lys His Val Trp Arg Arg Gly Gln Asn Ile Tyr Phe
            20                  25                  30

Arg Tyr Asp Glu Gly Gly Gly Ala Trp Gly Ala Gly Ala Val Ser Glu
        35                  40                  45
```

```
Lys Asp Ala Pro Lys Glu Leu Leu Gln Met Leu Glu Lys Gln
        50                  55                  60

<210> SEQ ID NO 87
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 87

Met Ala Thr Val Lys Phe Thr Tyr Gln Gly Glu Glu Lys Gln Val Asp
1               5                   10                  15

Ile Ser Lys Ile Lys Ser Val Lys Arg Asn Gly Gln Ser Ile Asp Phe
            20                  25                  30

Asp Tyr Asp Glu Gly Gly Gly Ala Ala Gly Glu Gly Lys Val Ser Glu
        35                  40                  45

Lys Asp Ala Pro Lys Glu Leu Leu Gln Met Leu Glu Lys Gln
    50                  55                  60

<210> SEQ ID NO 88
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 88

Met Ala Thr Val Lys Phe Thr Tyr Gln Gly Glu Glu Lys Gln Val Asp
1               5                   10                  15

Ile Ser Lys Ile Lys Gly Val Tyr Arg His Gly Gln Ser Ile Trp Phe
            20                  25                  30

Arg Tyr Asp Glu Gly Gly Gly Ala Trp Gly Trp Gly Ile Val Ser Glu
        35                  40                  45

Lys Asp Ala Pro Lys Glu Leu Leu Gln Met Leu Glu Lys Gln
    50                  55                  60

<210> SEQ ID NO 89
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 89

Met Ala Thr Val Lys Phe Thr Tyr Gln Gly Glu Glu Lys Gln Val Asp
1               5                   10                  15

Ile Ser Lys Ile Lys Ser Val His Arg Tyr Gly Gln Lys Ile Tyr Phe
            20                  25                  30

Asp Tyr Asp Glu Gly Gly Gly Ala Ile Gly Lys Gly His Val Ser Glu
        35                  40                  45

Lys Asp Ala Pro Lys Glu Leu Leu Gln Met Leu Glu Lys Gln
    50                  55                  60

<210> SEQ ID NO 90
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 90
```

```
Met Ala Thr Val Lys Phe Thr Tyr Gln Gly Glu Glu Lys Gln Val Asp
1               5                   10                  15

Ile Ser Lys Ile Lys Tyr Val Trp Arg His Gly Gln His Ile Ala Phe
                20                  25                  30

Arg Tyr Asp Glu Gly Gly Gly Ala His Gly Trp Gly Ser Val Ser Glu
            35                  40                  45

Lys Asp Ala Pro Lys Glu Leu Leu Gln Met Leu Glu Lys Gln
50                  55                  60
```

<210> SEQ ID NO 91
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 91

```
Met Ala Thr Val Lys Phe Thr Tyr Gln Gly Glu Glu Lys Gln Val Asp
1               5                   10                  15

Ile Ser Lys Ile Lys Asp Val Trp Arg His Gly Gln His Ile Ile Phe
                20                  25                  30

Ser Tyr Asp Glu Gly Gly Gly Ala Tyr Gly Ala Gly His Val Ser Glu
            35                  40                  45

Lys Asp Ala Pro Lys Glu Leu Leu Gln Met Leu Glu Lys Gln
50                  55                  60
```

<210> SEQ ID NO 92
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 92

```
Met Ala Thr Val Lys Phe Thr Tyr Gln Gly Glu Glu Lys Gln Val Asp
1               5                   10                  15

Ile Ser Lys Ile Lys Tyr Val Lys Arg Ile Gly Gln Tyr Ile Ser Phe
                20                  25                  30

Asn Tyr Asp Glu Gly Gly Gly Ala His Gly His Gly Ile Val Ser Glu
            35                  40                  45

Lys Asp Ala Pro Lys Glu Leu Leu Gln Met Leu Glu Lys Gln
50                  55                  60
```

<210> SEQ ID NO 93
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 93

```
Ser Trp Arg Arg Trp Arg Trp Ala Lys
1               5
```

<210> SEQ ID NO 94
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 94

Ser Trp Arg Arg Trp Arg Trp Ala Arg
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 95

Trp Arg Tyr Tyr Gly Ser Trp Lys Tyr
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 96

His Trp Arg Asn Tyr Arg Trp Ala Ala
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 97

Ser Lys Asn Ser Asp Asp Ala Glu Lys
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 98

Gly Tyr His Ser Trp Arg Trp Trp Ile
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 99

Ser His Tyr Lys Tyr Asp Ile Lys His
1               5

<210> SEQ ID NO 100
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 100

Tyr Trp His His Ala Arg His Trp Ser

```
1               5

<210> SEQ ID NO 101
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 101

Asp Trp His His Ile Ser Tyr Ala His
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 102

Tyr Lys Ile Tyr Ser Asn His His Ile
1               5

<210> SEQ ID NO 103
<211> LENGTH: 355
<212> TYPE: PRT
<213> ORGANISM: Artificial Sequence
<220> FEATURE:
<223> OTHER INFORMATION: Synthetic Polypeptide

<400> SEQUENCE: 103

Met Gly Ser Ser His His His His His Ser Ser Gly Leu Val Pro
1               5                   10                  15

Arg Gly Ser His Met Val Ala Arg Thr Asp Asp Asn Trp Asp Leu
                20                  25                  30

Thr Ser Ser Val Gly Val Thr Ala Thr Ile Val Ala Val Gly Arg Ala
            35                  40                  45

Leu Ala Thr Lys Asp Pro Arg Gly Leu Ile Asn Asp Pro Phe Ala Glu
        50                  55                  60

Pro Leu Val Arg Ala Val Gly Leu Asp Leu Phe Thr Lys Met Met Asp
65                  70                  75                  80

Gly Glu Leu Asp Met Ser Thr Ile Ala Asp Val Ser Pro Ala Val Ala
                85                  90                  95

Gln Ala Met Val Tyr Gly Asn Ala Val Arg Thr Lys Tyr Phe Asp Asp
                100                 105                 110

Tyr Leu Leu Asn Ala Thr Ala Gly Gly Ile Arg Gln Val Ala Ile Leu
            115                 120                 125

Ala Ser Gly Leu Asp Ser Arg Ala Tyr Arg Leu Pro Trp Pro Thr Arg
        130                 135                 140

Thr Val Val Tyr Glu Ile Asp Gln Pro Lys Val Met Glu Phe Lys Thr
145                 150                 155                 160

Thr Thr Leu Ala Asp Leu Gly Ala Glu Pro Ser Ala Ile Arg Arg Ala
                165                 170                 175

Val Pro Ile Asp Leu Arg Ala Asp Trp Pro Thr Ala Leu Gln Ala Ala
                180                 185                 190

Gly Phe Asp Ser Ala Ala Pro Thr Ala Trp Leu Ala Glu Gly Leu Leu
            195                 200                 205

Ile Tyr Leu Lys Pro Gln Thr Gln Asp Arg Leu Phe Asp Asn Ile Thr
        210                 215                 220
```

```
Ala Leu Ser Ala Pro Gly Ser Met Val Ala Thr Glu Phe Val Thr Gly
225                 230                 235                 240

Ile Ala Asp Phe Ser Ala Glu Arg Ala Arg Thr Ile Ser Asn Pro Phe
            245                 250                 255

Arg Cys His Gly Val Asp Val Asp Leu Ala Ser Leu Val Tyr Thr Gly
        260                 265                 270

Pro Arg Asn His Val Leu Asp Tyr Leu Ala Ala Lys Gly Trp Gln Pro
    275                 280                 285

Glu Gly Val Ser Leu Ala Glu Leu Phe Arg Arg Ser Gly Leu Asp Val
290                 295                 300

Arg Ala Ala Asp Asp Thr Ile Phe Ile Ser Gly Cys Leu Thr Asp
305                 310                 315                 320

His Ser Ser Ile Ser Pro Pro Thr Ala Ala Gly Trp Arg Glu Phe Gly
                325                 330                 335

Ser Met Ala Gly Gly Leu Asn Asp Ile Phe Glu Ala Gln Lys Ile Glu
            340                 345                 350

Trp His Glu
    355

<210> SEQ ID NO 104
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 104

Met Ala Thr Val Lys Phe Thr Tyr Gln Gly Glu Glu Lys Gln Val Asp
1               5                   10                  15

Ile Ser Lys Ile Lys Trp Val Tyr Arg Tyr Gly Gln Tyr Ile Ile Phe
            20                  25                  30

Gly Tyr Asp Glu Gly Gly Gly Ala Lys Gly Asn Gly Tyr Val Ser Glu
        35                  40                  45

Lys Asp Ala Pro Lys Glu Leu Leu Gln Met Leu Glu Lys Gln
    50                  55                  60

<210> SEQ ID NO 105
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 105

Met Ala Thr Val Lys Phe Thr Tyr Gln Gly Glu Glu Lys Gln Val Asp
1               5                   10                  15

Ile Ser Lys Ile Lys Trp Val Tyr Arg Trp Gly Gln Tyr Ile Ile Phe
            20                  25                  30

Ala Tyr Asp Glu Gly Gly Gly Ala Ala Gly Lys Gly Ser Val Ser Glu
        35                  40                  45

Lys Asp Ala Pro Lys Glu Leu Leu Gln Met Leu Glu Lys Gln
    50                  55                  60

<210> SEQ ID NO 106
<211> LENGTH: 62
<212> TYPE: PRT
<213> ORGANISM: Artificial Sequence
<220> FEATURE:
<223> OTHER INFORMATION: Synthetic Polypeptide
```

<400> SEQUENCE: 106

Met Ala Thr Val Lys Phe Thr Tyr Gln Gly Glu Glu Lys Gln Val Asp
1               5                   10                  15

Ile Ser Lys Ile Lys Arg Val Ile Arg Ala Gly Gln Ser Ile Ile Phe
            20                  25                  30

Ser Tyr Asp Glu Gly Gly Gly Ala Ile Gly His Gly Trp Val Ser Glu
        35                  40                  45

Lys Asp Ala Pro Lys Glu Leu Leu Gln Met Leu Glu Lys Gln
    50                  55                  60

<210> SEQ ID NO 107
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 107

Trp Tyr Tyr Tyr Ile Gly Lys Asn Tyr
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 108

Trp Tyr Trp Tyr Ile Ala Ala Lys Ser
1               5

<210> SEQ ID NO 109
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 109

Arg Ile Ala Ser Ile Ser Ile His Trp
1               5

<210> SEQ ID NO 110
<211> LENGTH: 254
<212> TYPE: PRT
<213> ORGANISM: Artificial Sequence
<220> FEATURE:
<223> OTHER INFORMATION: Synthetic Polypeptide

<400> SEQUENCE: 110

Met Gly Ser Ser His His His His His His Ser Ser Gly Leu Val Pro
1               5                   10                  15

Arg Gly Ser His Met Thr Leu Asn Leu Ser Val Asp Glu Val Leu Thr
            20                  25                  30

Thr Thr Arg Ser Val Arg Lys Arg Leu Asp Phe Asp Lys Pro Val Pro
        35                  40                  45

Arg Asp Val Leu Met Glu Cys Leu Glu Leu Ala Leu Gln Ala Pro Thr
    50                  55                  60

Gly Ser Asn Ser Gln Gly Trp Gln Trp Val Phe Val Glu Asp Ala Ala
65                  70                  75                  80

```
Lys Lys Lys Ala Ile Ala Asp Val Tyr Leu Ala Asn Ala Arg Gly Tyr
                85                  90                  95

Leu Ser Gly Pro Ala Pro Glu Tyr Pro Asp Gly Asp Thr Arg Gly Glu
            100                 105                 110

Arg Met Gly Arg Val Arg Asp Ser Ala Thr Tyr Leu Ala Glu His Met
        115                 120                 125

His Arg Ala Pro Val Leu Leu Ile Pro Cys Leu Lys Gly Arg Glu Asp
    130                 135                 140

Glu Ser Ala Val Gly Gly Val Ser Phe Trp Ala Ser Leu Phe Pro Ala
145                 150                 155                 160

Val Trp Ser Phe Cys Leu Ala Leu Arg Ser Arg Gly Leu Gly Ser Cys
                165                 170                 175

Trp Thr Thr Leu His Leu Leu Asp Asn Gly Glu His Lys Val Ala Asp
            180                 185                 190

Val Leu Gly Ile Pro Tyr Asp Glu Tyr Ser Gln Gly Leu Leu Pro
        195                 200                 205

Ile Ala Tyr Thr Gln Gly Ile Asp Phe Arg Pro Ala Lys Arg Leu Pro
    210                 215                 220

Ala Glu Ser Val Thr His Trp Asn Gly Trp Gly Ser Met Ala Gly Gly
225                 230                 235                 240

Leu Asn Asp Ile Phe Glu Ala Gln Lys Ile Glu Trp His Glu
                245                 250

<210> SEQ ID NO 111
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 111

Met Ala Thr Val Lys Phe Thr Tyr Gln Gly Glu Glu Lys Gln Val Asp
1               5                   10                  15

Ile Ser Lys Ile Lys Tyr Val Tyr Arg Trp Gly Gln Arg Ile Trp Phe
            20                  25                  30

Arg Tyr Asp Glu Gly Gly Gly Ala Ile Gly Arg Gly Arg Val Ser Glu
        35                  40                  45

Lys Asp Ala Pro Lys Glu Leu Leu Gln Met Leu Glu Lys Gln
    50                  55                  60

<210> SEQ ID NO 112
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 112

Tyr Tyr Trp Arg Trp Arg Ile Arg Arg
1               5

<210> SEQ ID NO 113
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 113

Tyr Tyr Trp Arg Trp Arg Ser Tyr Arg
```

<210> SEQ ID NO 114
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 114

Met Ala Thr Val Lys Phe Thr Tyr Gln Gly Glu Glu Lys Gln Val Asp
1               5                   10                  15
Ile Ser Lys Ile Lys Trp Val Ile Arg Tyr Gly Gln Lys Ile Ala Phe
            20                  25                  30
Gly Tyr Asp Glu Gly Gly Gly Ala Lys Gly Ala Gly Ala Val Ser Glu
        35                  40                  45
Lys Asp Ala Pro Lys Glu Leu Leu Gln Met Leu Glu Lys Gln
    50                  55                  60

<210> SEQ ID NO 115
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 115

Met Ala Thr Val Lys Phe Thr Tyr Gln Gly Glu Glu Lys Gln Val Asp
1               5                   10                  15
Ile Ser Lys Ile Lys Lys Val Trp Arg Tyr Gly Gln Trp Ile Tyr Phe
            20                  25                  30
Ile Tyr Asp Glu Gly Gly Gly Ala Lys Gly Arg Gly Trp Val Ser Glu
        35                  40                  45
Lys Asp Ala Pro Lys Glu Leu Leu Gln Met Leu Glu Lys Gln
    50                  55                  60

<210> SEQ ID NO 116
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 116

Trp Ile Tyr Lys Ala Gly Lys Ala Ala
1               5

<210> SEQ ID NO 117
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 117

Lys Trp Tyr Trp Tyr Ile Lys Arg Trp
1               5

<210> SEQ ID NO 118
<211> LENGTH: 208
<212> TYPE: PRT
<213> ORGANISM: Artificial Sequence
<220> FEATURE:
<223> OTHER INFORMATION: Synthetic Polypeptide

<400> SEQUENCE: 118

```
Met Gly Ser Ser His His His His His Ser Ser Gly Leu Val Pro
1               5                   10                  15

Arg Gly Ser His Met Ala Thr Val Lys Phe Thr Tyr Gln Gly Glu Glu
                20                  25                  30

Lys Gln Val Asp Ile Ser Lys Ile Lys Ile Val Ala Arg Asp Gly Gln
            35                  40                  45

Tyr Ile Asp Phe Lys Tyr Asp Glu Gly Gly Ala Tyr Gly Tyr Gly
    50                  55                  60

Trp Val Ser Glu Lys Asp Ala Pro Lys Glu Leu Leu Gln Met Leu Glu
65                  70                  75                  80

Lys Gln Gly Ser Ala Gly Pro Gly Ala Asn Pro Pro Gly Thr Thr Thr
                85                  90                  95

Thr Ser Arg Pro Ala Thr Thr Gly Ser Ser Pro Gly Pro Gln Ala
            100                 105                 110

Cys Ser Ser Val Trp Gly Gln Cys Gly Gly Gln Asn Trp Ser Gly Pro
                115                 120                 125

Thr Cys Cys Ala Ser Gly Ser Thr Cys Val Tyr Ser Asn Asp Tyr Tyr
130                 135                 140

Ser Gln Cys Leu Pro Gly Ala Asn Pro Pro Gly Thr Thr Thr Thr Ser
145                 150                 155                 160

Arg Pro Ala Thr Thr Thr Gly Ser Ser Pro Gly Pro Thr Gln Ser His
                165                 170                 175

Tyr Gly Gln Cys Gly Gly Ile Gly Tyr Ser Gly Pro Thr Val Cys Ala
                180                 185                 190

Ser Gly Thr Thr Cys Gln Val Leu Asn Pro Tyr Tyr Ser Gln Cys Leu
            195                 200                 205
```

<210> SEQ ID NO 119
<211> LENGTH: 258
<212> TYPE: PRT
<213> ORGANISM: Artificial Sequence
<220> FEATURE:
<223> OTHER INFORMATION: Synthetic Polypeptide

<400> SEQUENCE: 119

```
Met Gly Ser Ser His His His His His Ser Ser Gly Leu Val Pro
1               5                   10                  15

Arg Gly Ser His Met Ala Thr Val Lys Phe Thr Tyr Gln Gly Glu Glu
                20                  25                  30

Lys Gln Val Asp Ile Ser Lys Ile Lys Ile Val Ala Arg Asp Gly Gln
            35                  40                  45

Tyr Ile Asp Phe Lys Tyr Asp Glu Gly Gly Ala Tyr Gly Tyr Gly
    50                  55                  60

Trp Val Ser Glu Lys Asp Ala Pro Lys Glu Leu Leu Gln Met Leu Glu
65                  70                  75                  80

Lys Gln Gly Ser Gly Gly Gly Ser Gly Gly Ser Gly Gly
                85                  90                  95

Gly Gly Ser Pro Val Ser Gly Asn Leu Lys Val Glu Phe Tyr Asn Ser
            100                 105                 110

Asn Pro Ser Asp Thr Thr Asn Ser Ile Asn Pro Gln Phe Lys Val Thr
                115                 120                 125

Asn Thr Gly Ser Ser Ala Ile Asp Leu Ser Lys Leu Thr Leu Arg Tyr
            130                 135                 140
```

```
Tyr Tyr Thr Val Asp Gly Gln Lys Asp Gln Thr Phe Trp Cys Asp His
145                 150                 155                 160

Ala Ala Ile Ile Gly Ser Asn Gly Ser Tyr Asn Gly Ile Thr Ser Asn
            165                 170                 175

Val Lys Gly Thr Phe Val Lys Met Ser Ser Ser Thr Asn Asn Ala Asp
        180                 185                 190

Thr Tyr Leu Glu Ile Ser Phe Thr Gly Gly Thr Leu Glu Pro Gly Ala
    195                 200                 205

His Val Gln Ile Gln Gly Arg Phe Ala Lys Asn Asp Trp Ser Asn Tyr
210                 215                 220

Thr Gln Ser Asn Asp Tyr Ser Phe Lys Ser Ala Ser Gln Phe Val Glu
225                 230                 235                 240

Trp Asp Gln Val Thr Ala Tyr Leu Asn Gly Val Leu Val Trp Gly Lys
                245                 250                 255

Glu Pro

<210> SEQ ID NO 120
<211> LENGTH: 330
<212> TYPE: PRT
<213> ORGANISM: Artificial Sequence
<220> FEATURE:
<223> OTHER INFORMATION: Synthetic Polypeptide

<400> SEQUENCE: 120

Met Gly Ser Ser His His His His His His Ser Ser Gly Leu Val Pro
1               5                   10                  15

Arg Gly Ser His Met Ala Thr Val Lys Phe Thr Tyr Gln Gly Glu Glu
            20                  25                  30

Lys Gln Val Asp Ile Ser Lys Ile Lys Ile Val Ala Arg Asp Gly Gln
        35                  40                  45

Tyr Ile Asp Phe Lys Tyr Asp Glu Gly Gly Gly Ala Tyr Gly Tyr Gly
    50                  55                  60

Trp Val Ser Glu Lys Asp Ala Pro Lys Glu Leu Leu Gln Met Leu Glu
65                  70                  75                  80

Lys Gln Gly Gly Gly Ser Gly Gly Gly Gly Ser Met Ala Thr Val
            85                  90                  95

Lys Phe Thr Tyr Gln Gly Glu Glu Lys Gln Val Asp Ile Ser Lys Ile
            100                 105                 110

Lys Ile Val Ala Arg Asp Gly Gln Tyr Ile Asp Phe Lys Tyr Asp Glu
        115                 120                 125

Gly Gly Gly Ala Tyr Gly Tyr Gly Trp Val Ser Glu Lys Asp Ala Pro
130                 135                 140

Lys Glu Leu Leu Gln Met Leu Glu Lys Gln Gly Ser Gly Gly Gly Gly
145                 150                 155                 160

Ser Gly Gly Gly Gly Ser Gly Gly Gly Gly Ser Pro Val Ser Gly Asn
            165                 170                 175

Leu Lys Val Glu Phe Tyr Asn Ser Asn Pro Ser Asp Thr Thr Asn Ser
        180                 185                 190

Ile Asn Pro Gln Phe Lys Val Thr Asn Thr Gly Ser Ser Ala Ile Asp
    195                 200                 205

Leu Ser Lys Leu Thr Leu Arg Tyr Tyr Tyr Thr Val Asp Gly Gln Lys
210                 215                 220

Asp Gln Thr Phe Trp Cys Asp His Ala Ala Ile Ile Gly Ser Asn Gly
225                 230                 235                 240

Ser Tyr Asn Gly Ile Thr Ser Asn Val Lys Gly Thr Phe Val Lys Met
```

```
                    245                 250                 255
Ser Ser Ser Thr Asn Asn Ala Asp Thr Tyr Leu Glu Ile Ser Phe Thr
                260                 265                 270

Gly Gly Thr Leu Glu Pro Gly Ala His Val Gln Ile Gln Gly Arg Phe
            275                 280                 285

Ala Lys Asn Asp Trp Ser Asn Tyr Thr Gln Ser Asn Asp Tyr Ser Phe
        290                 295                 300

Lys Ser Ala Ser Gln Phe Val Glu Trp Asp Gln Val Thr Ala Tyr Leu
305                 310                 315                 320

Asn Gly Val Leu Val Trp Gly Lys Glu Pro
                325                 330

<210> SEQ ID NO 121
<211> LENGTH: 402
<212> TYPE: PRT
<213> ORGANISM: Artificial Sequence
<220> FEATURE:
<223> OTHER INFORMATION: Synthetic Polypeptide

<400> SEQUENCE: 121

Met Gly Ser Ser His His His His His His Ser Ser Gly Leu Val Pro
1               5                   10                  15

Arg Gly Ser His Met Ala Thr Val Lys Phe Thr Tyr Gln Gly Glu Glu
            20                  25                  30

Lys Gln Val Asp Ile Ser Lys Ile Lys Ile Val Ala Arg Asp Gly Gln
        35                  40                  45

Tyr Ile Asp Phe Lys Tyr Asp Glu Gly Gly Ala Tyr Gly Tyr Gly
    50                  55                  60

Trp Val Ser Glu Lys Asp Ala Pro Lys Glu Leu Leu Gln Met Leu Glu
65                  70                  75                  80

Lys Gln Gly Gly Gly Ser Gly Gly Gly Ser Met Ala Thr Val
            85                  90                  95

Lys Phe Thr Tyr Gln Gly Glu Glu Lys Gln Val Asp Ile Ser Lys Ile
                100                 105                 110

Lys Ile Val Ala Arg Asp Gly Gln Tyr Ile Asp Phe Lys Tyr Asp Glu
            115                 120                 125

Gly Gly Gly Ala Tyr Gly Tyr Gly Trp Val Ser Glu Lys Asp Ala Pro
        130                 135                 140

Lys Glu Leu Leu Gln Met Leu Glu Lys Gln Gly Gly Gly Ser Gly
145                 150                 155                 160

Gly Gly Gly Ser Met Ala Thr Val Lys Phe Thr Tyr Gln Gly Glu Glu
                165                 170                 175

Lys Gln Val Asp Ile Ser Lys Ile Lys Ile Val Ala Arg Asp Gly Gln
            180                 185                 190

Tyr Ile Asp Phe Lys Tyr Asp Glu Gly Gly Ala Tyr Gly Tyr Gly
        195                 200                 205

Trp Val Ser Glu Lys Asp Ala Pro Lys Glu Leu Leu Gln Met Leu Glu
    210                 215                 220

Lys Gln Gly Ser Gly Gly Gly Ser Gly Gly Gly Ser Gly Gly
225                 230                 235                 240

Gly Gly Ser Pro Val Ser Gly Asn Leu Lys Val Glu Phe Tyr Asn Ser
                245                 250                 255

Asn Pro Ser Asp Thr Thr Asn Ser Ile Asn Pro Gln Phe Lys Val Thr
            260                 265                 270

Asn Thr Gly Ser Ser Ala Ile Asp Leu Ser Lys Leu Thr Leu Arg Tyr
```

```
                275                 280                 285
Tyr Tyr Thr Val Asp Gly Gln Lys Asp Gln Thr Phe Trp Cys Asp His
    290                 295                 300

Ala Ala Ile Ile Gly Ser Asn Gly Ser Tyr Asn Gly Ile Thr Ser Asn
305                 310                 315                 320

Val Lys Gly Thr Phe Val Lys Met Ser Ser Thr Asn Asn Ala Asp
                325                 330                 335

Thr Tyr Leu Glu Ile Ser Phe Thr Gly Gly Thr Leu Glu Pro Gly Ala
            340                 345                 350

His Val Gln Ile Gln Gly Arg Phe Ala Lys Asn Asp Trp Ser Asn Tyr
        355                 360                 365

Thr Gln Ser Asn Asp Tyr Ser Phe Lys Ser Ala Ser Gln Phe Val Glu
    370                 375                 380

Trp Asp Gln Val Thr Ala Tyr Leu Asn Gly Val Leu Val Trp Gly Lys
385                 390                 395                 400

Glu Pro

<210> SEQ ID NO 122
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 122

Lys Gly Val Tyr Arg His Gly Gln Ser Ile Trp Phe Arg Tyr Asp Glu
1               5                   10                  15

Gly Gly Gly Ala Trp Gly Trp Gly Ile
            20                  25

<210> SEQ ID NO 123
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 123

Lys Tyr Val Lys Arg Ile Gly Gln Tyr Ile Ser Phe Asn Tyr Asp Glu
1               5                   10                  15

Gly Gly Gly Ala His Gly His Gly Ile
            20                  25

<210> SEQ ID NO 124
<211> LENGTH: 367
<212> TYPE: PRT
<213> ORGANISM: Artificial Sequence
<220> FEATURE:
<223> OTHER INFORMATION: Synthetic Polypeptide

<400> SEQUENCE: 124

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60
```

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ser Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr
        355                 360                 365

<210> SEQ ID NO 125
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 125

Gly Gly Gly Gly Ser Gly Gly Gly Ser Gly Gly Gly Gly Ser
1               5                   10                  15

<210> SEQ ID NO 126
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 126

Gly Gly Gly Gly Gly Gly
1               5

<210> SEQ ID NO 127
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 127

Gly Gly Gly Gly Gly Gly Gly Gly
1               5

<210> SEQ ID NO 128
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 128

Glu Ala Ala Ala Lys Glu Ala Ala Ala Lys Glu Ala Ala Ala Lys
1               5                   10                  15

<210> SEQ ID NO 129
<211> LENGTH: 46
<212> TYPE: PRT
<213> ORGANISM: Artificial Sequence
<220> FEATURE:
<223> OTHER INFORMATION: Synthetic Polypeptide

<400> SEQUENCE: 129

Ala Glu Ala Ala Ala Lys Glu Ala Ala Ala Lys Glu Ala Ala Ala Lys
1               5                   10                  15

Glu Ala Ala Ala Lys Ala Leu Glu Glu Ala Ala Ala Lys Glu Ala
            20                  25                  30

Ala Ala Lys Glu Ala Ala Ala Lys Glu Ala Ala Ala Lys Ala
        35                  40                  45

<210> SEQ ID NO 130
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 130

Pro Ala Pro Ala Pro
1               5

<210> SEQ ID NO 131
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 131

Val Ser Gln Thr Ser Lys Leu Thr Arg Ala Glu Thr Val Phe Pro Asp
1               5                   10                  15

Val

<210> SEQ ID NO 132

```
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 132

Arg Val Leu Ala Glu Ala
1               5

<210> SEQ ID NO 133
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 133

Glu Asp Val Val Cys Cys Ser Met Ser Tyr
1               5                   10

<210> SEQ ID NO 134
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 134

Gly Gly Ile Glu Gly Arg Gly Ser
1               5

<210> SEQ ID NO 135
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 135

Gly Phe Leu Gly
1
```

UNITED STATES PATENT AND TRADEMARK OFFICE
CERTIFICATE OF CORRECTION

PATENT NO. : 11,740,236 B2
APPLICATION NO. : 16/158506
DATED : August 29, 2023
INVENTOR(S) : Hadley Sikes Johnson et al.

It is certified that error appears in the above-identified patent and that said Letters Patent is hereby corrected as shown below:

In the Specification

At Column 1, Lines 11-16, the section entitled "GOVERNMENT SUPPORT" should be removed.

Signed and Sealed this
Twenty-eighth Day of November, 2023

Katherine Kelly Vidal
*Director of the United States Patent and Trademark Office*